US008637737B2

(12) United States Patent
Van Roggen et al.

(10) Patent No.: US 8,637,737 B2
(45) Date of Patent: Jan. 28, 2014

(54) ENGINEERING OF BOLTING RESISTANCE IN SUGAR BEET BY MEANS OF THE TRANSGENIC EXPRESSION OF THE BEET HOMOLOGUE OF FLOWERING TIME CONTROL GENE FT

(75) Inventors: Petronella Maria Van Roggen, Landskrona (SE); Johannes Jacobus Ludgerus Gielen, Bouloc (FR); Pierre Pin, Malmo (SE); Signe Irene Elisabet Wremert Weich, Landskrona (SE)

(73) Assignee: Syngenta Participations AG, Basel (CH)

( * ) Notice: Subject to any disclaimer, the term of this patent is extended or adjusted under 35 U.S.C. 154(b) by 175 days.

(21) Appl. No.: 13/061,948

(22) PCT Filed: Sep. 1, 2009

(86) PCT No.: PCT/EP2009/006319
§ 371 (c)(1),
(2), (4) Date: Mar. 2, 2011

(87) PCT Pub. No.: WO2010/025888
PCT Pub. Date: Mar. 11, 2010

(65) Prior Publication Data
US 2011/0231946 A1 Sep. 22, 2011

(30) Foreign Application Priority Data
Sep. 2, 2008 (EP) .................................... 08163495

(51) Int. Cl.
*C07K 14/415* (2006.01)
*C12N 15/00* (2006.01)
*A01H 5/00* (2006.01)
*C12N 15/82* (2006.01)

(52) U.S. Cl.
USPC ........ 800/290; 530/370; 435/320.1; 435/128; 800/298; 800/278

(58) Field of Classification Search
None
See application file for complete search history.

(56) References Cited

U.S. PATENT DOCUMENTS 6,225,530 B1 * 5/2001 Weigel et al. ................. 800/290
2006/0070141 A1 * 3/2006 Nielsen et al. ................ 800/287

FOREIGN PATENT DOCUMENTS

WO   WO 2004/067723 A2   8/2004
WO   WO 2004/101792 A1   11/2004

OTHER PUBLICATIONS

Chab et al, 2008, Planta, 228:929-940.*
Sévenier et al, 2002, J. Am. College of Nutrition, 21:199S-204S.*
EMBL Database Accession No. BG586296, submitted on Apr. 12, 2001.
EMBL Database Accession No. DX982373, submitted on Aug. 4, 2006.
UniProt Database Accession No. A8HR54, submitted on Dec. 4, 2007.
International Search Report mailed Feb. 16, 2011 for Parent Application No. PCT/EP2009/006319, filed Sep. 1, 2009.
Carmona, M.J. et al., "The FT/TFL1 Gene Family in Grapevine," *Plant Mol Biol*, Dec. 10, 2006, pp. 637-650, vol. 63, No. 5.
Hohmann, U., et al., "An EMS Mutagenesis Protocol for Sugar Beet and Isolation of Non-bolting Mutants," *Plant Breeding*, Aug. 2005, pp. 317-321, vol. 127, No. 4.
Sreekantan, L., and M.R. Thomas, "VvFT and VvMADS8, The Grapevine Homologues of the Floral Integrators FT and SOC1, Have Unique Expression Patterns in Grapevine and Hasten Flowering in *Arabidopsis*," *Functional Plant Biology*, 2006, pp. 1129-1139, vol. 33, No. 12.
EMBL Database Accession No. AB110613, submitted on Nov. 26, 2003.
EMBL Database Accession No. BD206241, submitted on Aug. 13, 2003.
EMBL Database Accession No. DQ871590, submitted on Mar. 13, 2007.
EMBL Database Accession No. EF445636, submitted on Apr. 19, 2007.
EMBL Database Accession No. EU128013, submitted on Oct. 15, 2007.
EMBL Database Accession No. EX956310, submitted on Nov. 7, 2007.
Partial International Search Report mailed Nov. 10, 2010 with Invitation to Pay Additional Fees for Parent Application No. PCT/EP2009/006319, filed Sep. 1, 2009.

* cited by examiner

*Primary Examiner* — Ashwin Mehta
*Assistant Examiner* — Jason Deveau Rosen
(74) *Attorney, Agent, or Firm* — Joshua L. Price

(57) ABSTRACT

This invention relates to the field of bolting and flowering time control in sugar beet, specifically to methods as well as nucleic acid molecules, chimeric constructs, and vectors for engineering bolting resistance in sugar beet by means of altering the expression of the *Beta vulgaris* homologues BvFT1 and BvFT2 of the FT gene. In particular, the present invention provides sugar beet plants having a phenotype of bolting resistance.

20 Claims, 22 Drawing Sheets

```
              251                                                 300
AtFT_mRNA    GGTTACTTATGGCCAAAGAGAGGTGACTAATGGCTTGGATCTAAGGCCTT
CiFT_mRNA    GATTACCTATTCAAACAAGGATGTTAATAATGGCCGTGAGCTCAAACCTT
OsHd3a_mRNA  GGTCACCTATGGCTCCAAGACCGTGTCCAATGGCTGCGAGCTCAAGCCGT
TaFT_mRNA    GGTGACCTTCGGGAACAGGACCGTGTCCAACGGCTGCGAGCTCAAGCCGT 301                                                 350
AtFT_mRNA    CTCAGGTTCAAAACAAGCCAAGAGTTGAGATTGGTGGAGAAGACCTCAGG
CiFT_mRNA    CTGAAGTTCTGACCAGCCTAGGGCTGAAATTGGTGGTGATGATCTTAGG
OsHd3a_mRNA  CCATGGTCACCCACCAGCCTAGGGTCGAGGTCGGCGGCAATGACATGAGG
TaFT_mRNA    CCATGGTCGCCCAGCAGCCCAGGGTTGAGGTGGGCGGCAATGAGATGAGG 351                                                 400
AtFT_mRNA    AACTTCTATACTTTGGTTATGGTGGATCCAGATGTTCCAAGTCCTAGCAA
CiFT_mRNA    ACATTTTATACTTTGGTAATGGTTGATCCTGATGCACCAAGCCCAAGTGA
OsHd3a_mRNA  ACATTCTACACCCTTGTGATGGTAGACCCAGATGCACCAAGCCCAAGTGA
TaFT_mRNA    ACCTTCTACACACTCGTGATGGTAGACCCAGATGCTCCAAGTCCAAGCGA 401                                                 450
AtFT_mRNA    CCCTCACCTCCGAGAATATCTCCATTGCTTGGTGACTGATATCCCTGCTA
CiFT_mRNA    CCCCAGCCTTAGGGAGTATTTGCATTGCTTGGTGACTGATATTCCAGCAA
OsHd3a_mRNA  CCCTAACCTTAGGGAGTATCTACATTGGTTGGTCACTGATATTCCTGGTA
TaFT_mRNA    TCCCAACCTTAGGGAGTATCTCCACTGCCTTGTGACAGATATCCCCGGTA 451                                                 500
AtFT_mRNA    CAACTGGAACAACCTTTGGCAATGAGATTGTGTGTTACGAAAATCCAAGT
CiFT_mRNA    CCACAGGGGCCAGCTTTGGCCAAGAGATTGTGAACTATGAAAGCCCTAGG
OsHd3a_mRNA  CTACTGCAGCGTCATTTGGGCAAGAGGTGATGTGCTACGAGAGCCCAAGG
TaFT_mRNA    CAACTGGTGCGTCGTTCGGGCAGGAGGTGATGTGCTACGAGAGCCCTCGT 501                                                 550
AtFT_mRNA    CCCACTGCAGGAATTCATCGTGTCGTGTTTATATTGTTTCGACAGCTTGG
CiFT_mRNA    CCAACGATGGGGATTCACAGGTTTGTCTTTGTGTTGTTCCGGCAACTTGG
OsHd3a_mRNA  CCAACCATGGGGATCCACCGGCTGGTGTTCGTGCTGTTCCAGCAGCTGGG
TaFT_mRNA    CCGACCATGGGGATCCACCGCTTCGTGCTCGTACTCTTCCAGCAGCTCGG 551                                                 600
AtFT_mRNA    CAGGCAAACAGTGTATGCACCAGGGTGGCGCCAGAACTTCAACACTCGCG
CiFT_mRNA    GAGGCAGACTGTTTATGCACCAGGGTGGCGTCAGAACTTCAGCACGAGGG
OsHd3a_mRNA  GCGTCAGACAGTGTACGCGCCCGGGTGGCGTCAGAACTTCAACACCAAGG
TaFT_mRNA    GCGGCAGACGGTGTACGCCCCGGGTGGCGCCAGAACTTCAACACCAGGG 601                                                 650
AtFT_mRNA    AGTTTGCTGAGATCTACAATCTCGGCCTTCCCGTGGCCGCAGTTTTCTAC
CiFT_mRNA    ATTTTGCTGAGCTTTACAATCTGGGACCTCCGGTGGCCGCTGTCTACTTC
OsHd3a_mRNA  ACTTCGCCGAGCTCTACAACCTCGGCTCGCCGGTCGCCGCCGTCTACTTC
TaFT_mRNA    ACTTCGCCGAGCTCTACAACCTCGGCCCGCCTGTTGCCGCCGTCTACTTC
```

Figure 1

```
Identities = 126/175 (72%), Positives = 144/175 (82%)

AtFT    1 M---S-INIRDPLIVSRVVGDVLDPFNRSITLKVTYGQREVTNGLDLRPSQVQNKPRVEIGGEDLRNFY  65
BvFT1   1 MPRTSASAPRDPLVLGGVIGDVLEPFERSVTLKISFNNRNVNNGGSFRPSQVVNQPRVEVGGDDLRTCY  69

AtFT   66 TLVMVDPDVPSPSNPHLREYLHWLVTDIPATTGTTFGNEIVCYENPSPTAGIHRVVFILFRQLGRQTVY 134
BvFT1  70 TLVMVDPDAPSPSNPHQREYLHWLVTDIPGTTSASFGELIVYYENPRPSTGIERFVFALFRQLGRQTVN 138

AtFT  135 APGWRQNFNTREFAEIYNLGLPVAAVFYNCQRESGCGGRRL 175
BvFT1 139 APQQRQNFNTRDFAELYNLGLFVAAVYFNCQREGGCGGRRF 179
```

Figure 4

```
Identities = 132/175 (75%), Positives = 154/175 (88%)

AtFT    1   MSINIRDPLIVSRVVGDVLDPFNRSITLKVTYGQREVTNGLDLRPSQVQNKPRVEIGGEDLRNFY   65
BvFT2   1   MPRAPRDPLVVGRVIGDVLDPFSRTVNLRVSYSNRDVNNGCELRPSQVVNQPRVEVGGDDLRTFY   65

AtFT   66   TLVMVDPDVPSPSNPHLREYLHWLVTDIPATTGTTFGNEIVCYENPSPTAGIHRVVFILFRQLGR  130
BvFT2  66   TLVMVDPDAPSPSNPHLREYLHWLVTDIPGTTGASFGQEVVCYENPRPSVGIHRFILVLFRQLGR  130

AtFT  131   QTVYAPGWRQNFNTREFAEIYNLGLPVAAVFYNCQRESGCGGRRL  175
BvFT2 131   QTVYAPGWRQNFNTRDFAELYNLGLPVAAVYFNCQREGSSGGRRL  175
```

Figure 5

ENGINEERING OF BOLTING RESISTANCE IN SUGAR BEET BY MEANS OF THE TRANSGENIC EXPRESSION OF THE BEET HOMOLOGUE OF FLOWERING TIME CONTROL GENE FT

FIELD OF THE INVENTION

This invention relates to the field of bolting and flowering control in sugar beet, specifically to genes conferring bolting resistance, to methods for engineering bolting resistance in sugar beet and transgenic sugar beet plants showing delayed bolting. In particular, the present invention relates to the modulation of the vernalization response in sugar beet by means of altering the expression of the *Beta* homologues BvFT1 and BvFT2 of the FT gene.

BACKGROUND OF THE INVENTION

Sugar beet has been cultivated for thousands of years as a sweets source, but its potential as a source of sugar was not discovered until the 18$^{th}$ century. The cultivated sugar beet (*Beta vulgaris* ssp. *vulgaris* L.) is a biennial plant belonging to the Chenopodiaceae. Its usual life cycle is completed in two years. In the first year a leaf rosette and a large succulent root is developed, which serves as a reserve for energy in the form of sucrose. For this reason it is farmed as an annual. In the second year shoot elongation (bolting) and flower formation starts after a period of low temperature and flowers and seeds are produced. If there happens to be prolonged cool periods in the first year, the seed stalk can already sprout. This genetically determined thermal induction leads to a phenomenon called bolting. Cropping the beet for sugar extraction cuts the biennial cycle in half, whilst the sucrose is at its peak.

Traditionally, there exist two methods for cropping sugar beet, spring and autumn cropping, which are practiced in the southern, milder climate or in northern latitudes, respectively. Both rely on varieties with different degrees of natural bolting resistance. Bolting resistance influences temperature, length and irradiation limits tolerable for seed stalk induction and is a key trait in sugar beet breeding. To allow for complete control of bolting and flowering, by either blocking vernalization, devernalizing vernalized plants or suppressing flower or viable seed production, would allow the sugar beet crop to be sown in autumn in northern latitudes without the risk of bolting and flowering in the following season. This shift from a spring into a winter crop would permit growers to drill their crop in autumn and to harvest the next summer. A comparison of winter cultivars to spring cultivars in crops like wheat and oilseed rape has shown that winter cultivars consistently yield higher than spring crops. The result would be an improvement of the economic viability and profitability of the crop. A further advantage would be the possibility to combine the growing of spring and winter crops, which would result in an extension of the harvest campaign by starting two to three months earlier, thus allowing for the improved capitalization on investments in equipment and infrastructure necessary for sugar beet harvesting, transport and processing. This extension of the sugar beet processing campaign would address one demand of the sugar industry.

The cold-induced vernalization as an obligate part of the complete sugar beet life cycle induces bolting of the plants. Vernalization and its effect on biennial sugar beet have been described in detail (e.g., JAGGARD et al., 1983). Sugar beet responds to temperatures between 3 and 12° C. Several weeks of 3 to 12° C. are required for the beet to start bolting. The ITB Bolting Model shows that in France, vernalization occurs up to 90 days (13 weeks) after drilling. Seventeen days of 7° C. is the critical number during these 90 days to initiate bolting. The likelihood of bolting is increased in relationship to the number of days on which the maximum temperature does not exceed 12° C. This can lead to loss of yield when the early sowing method is applied, as 1% bolters in a crop have been estimated to reduce sugar yield by 0.4-0.7%.

The knowledge about the vernalization response as the most important factor of flower induction has led to the development of bolting resistant sugar beet varieties which were made available to sugar beet farmers. However, cultivation of present sugar beet in central Europe over winter (i.e., as winter crop) to meet the demand of the sugar industry is currently not possible. Even with the cultivation of the higher yielding winter beet there are still major problems due to bolting incidents. The vernalization inducted by the exposure to the cold temperatures during winter still results in bolting and yield loss as currently no plants or methods are available for predictably delaying sugar beet vernalization.

For the foregoing reasons, it is highly desirable to develop non-bolting winter beet in which bolting resistance is engineered, e.g. by transgenic means, in order to modulate the vernalization response to confer resistance against or significantly delay of bolting after cold-induction. There is thus a need for nucleotide sequences of genes involved in the vernalization response and transgenic means making use of said gene sequences for modulating the vernalization response of sugar beet. The present invention now provides such nucleotide sequences and such transgenic means.

Functional analysis in the model organism *Arabidopsis thaliana* has distinguished four distinct flowering pathways (LEVY and DEAN, 1998). These four pathways can be assigned to environmental stimuli, such as photoperiodic and vernalization promotion pathways, or inherent developmental signals, e.g. autonomous promotion and floral repression pathways. In some species the timing of flowering is primarily influenced by environmental factors, such as photoperiod, light quality/quantity, vernalization and water or nutrient availability. Other species are influenced less by exogenous signals and rely more on endogenous ones, such as plant size or number of nodes.

One locus of interest is the FLOWERING LOCUS T (FT) discovered in naturally occurring late-flowering ecotypes of *Arabidopsis* (KOORNEEF et al., 1991). FT is a small protein of 23 KD and is homologous to phosphatidylethanolamine-binding proteins, which are also called RAF kinase inhibitor proteins (KARDAILSKY et al., 1999; KOBAYASHI et al., 1999).

The present inventors now have identified orthologues of the FT genes in sugar beet. Engineering of the expression of these genes has lead to a modulation of the vernalization response in sugar beet and to sugar beet plants in which the vernalization response is delayed or suppressed.

SUMMARY OF THE INVENTION

The present invention includes nucleotide sequences from sugar beet FT genes and methods for modulating sugar beet vernalization response by suppressing or upregulating the expression of these FT gene expression in sugar beet.

In one aspect the present invention relates to nucleic acid sequences, preferably to isolated nucleic acid sequences, which have a sequence identity of at least 70% to a nucleic acid sequence selected from the group of nucleic acid sequences as set forth in any of SEQ ID NOs: 5, 6, 8, or 9, or the complement thereof, to nucleic acid sequences which comprise at least 15 consecutive nucleotides of a nucleic acid sequence selected from the group of nucleic acid sequences as set forth in any of SEQ ID NOs: 5, 6, 8, or 9, or the complement thereof, or to nucleotide sequences which hybridizes under stringent conditions to a nucleic acid sequence selected from the group of nucleic acid sequences as set forth in any of SEQ ID NOs: 5, 6, 8, or 9, or the complement thereof.

In a preferred embodiment the nucleic acid sequence of the present invention comprises a nucleic acid sequence as set forth in any of SEQ ID NOs: 5, 6, 8, or 9.

According to another aspect, the present invention further provides polypeptides, preferably isolated polypeptides, which are encoded by the nucleic acid sequences of the present invention described hereinbefore. In a preferred embodiment the polypeptide of the present invention has an amino acid sequence selected from the group of amino acid sequences as depicted in SEQ ID NOs: 7 or 10.

In yet another aspect of the present invention chimeric constructs are provided which comprise a nucleic acid sequence of the present invention as described hereinbefore under the control of regulatory elements, preferably under the control of regulatory elements functional in plants.

In one preferred embodiment, the chimeric construct of the present invention further comprises a selection marker gene which allows discrimination between transformed and non-transformed plant material in a selection process.

In a further preferred embodiment the chimeric construct of the present invention is provided either for transgenic downregulation or suppression of expression of the endogenous BvFT2 gene in sugar beet, or for transgenic upregulation of expression of the endogenous BvFT1 gene in sugar beet.

In one aspect the present invention is related to chimeric constructs provided for transgenic downregulation or suppression of expression of the endogenous BvFT2 gene in sugar beet.

In a preferred embodiment of that aspect the chimeric construct of the present invention is a chimeric construct with which downregulation or suppression is achieved by a means selected from either dsRNA, antisense suppression or co-suppression.

In yet another preferred embodiment the chimeric construct of the present invention comprises a heterologous DNA which codes for a first RNA strand and a second RNA strand and which, when transcribed, yields a first RNA nucleotide sequence and a second RNA nucleotide sequence, wherein said first RNA strand is sufficiently complimentary to at least a portion of a RNA strand of the endogenous BvFT2 gene in sugar beet to hybridize or anneal to the RNA strand produced by said endogenous BvFT2 gene so as to cause downregulation or suppression of the expression of the endogenous BvFT2 gene, and wherein said first RNA nucleotide sequence and said second RNA nucleotide sequence form a double stranded RNA, wherein the double stranded RNA upon expression in a sugar beet plant participate in RNA interference of expression of said endogenous BvFT2 gene thereby causing downregulation or suppression of expression of the endogenous BvFT2 gene.

In one further embodiment the chimeric construct of the present invention as described hereinbefore comprises an inverted repeat, preferably operatively linked to a constitutive promoter, which when transcribed, forms a double stranded RNA molecule in a sugar beet plant cell comprising said first and second RNA strands, wherein said double stranded RNA molecule triggers BvFT2 silencing.

In a further preferred embodiment the chimeric construct of the present invention comprises a heterologous DNA which encodes a nucleic acid sequence either having sequence identity of at least 70% to a nucleic acid sequence of the present invention set forth as SEQ ID NOs: 8 or 9, or comprising at least 15 consecutive nucleotides of a nucleic acid sequence of the present invention set forth as SEQ ID NOs: 8 or 9, or hybridizes under stringent conditions to a nucleic acid sequence of the present invention set forth as SEQ ID NOs: 8 or 9.

In one embodiment, the chimeric construct of the present invention comprises a heterologous DNA obtainable from a 0.27 Kb cDNA fragment consisting of exon 4 of the BvFT2 gene in a PCR reaction using forward primer HiNK6382 with the nucleotide sequence 5'-CTATGGATCCGCATT-TAATAAAATCTCTTTCAATG-3' (SEQ ID NO: 44) and reverse primer HiNK6384 with the nucleotide sequence 5'-GTAGAAGCAGAAACTTACCTGCCAA-GAAGTTGTCTGCTATG-3' (SEQ ID NO: 45).

In a further embodiment the chimeric construct of the present invention comprises a heterologous DNA as depicted by nucleotides 8747 to 9046 of SEQ ID NO: 33.

In yet another embodiment the heterologous DNA comprised in the chimeric construct of the present invention is inserted between a promoter and a terminator, wherein said heterologous DNA is obtainable by a) amplifying a 0.27 Kb cDNA fragment derived from exon 4 of the BvFT2 gene in a PCR reaction using forward primer HiNK6382 with the nucleotide sequence 5'-CTATG-GATCCGCATTTAATAAAATCTCTTTCAATG-3' (SEQ ID NO: 44) and reverse primer HiNK6384 with the nucleotide sequence 5'-GTAGAAGCAGAAACTTACCTGC-CAAGAAGTTGTCTGCTATG-3' (SEQ ID NO: 45) and sugar beet cDNA as template, wherein the sugar beet cDNA was obtained from total RNA extracted from sugar beet leaves in a reverse transcriptase reaction using the 3' RACE ADAPTER with the nucleotide sequence 5'-GCGAGCACAGAATTAATACGACTCACTATAGGT-12VN-3' (SEQ ID NO: 35) as a primer;

b) by amplifying a 0.19 Kb fragment comprising the ST-LS1 intron and flanking splicing sites using forward primer HiNK6383 with the nucleotide sequence 5'-CATAGCA-GACAACTTCTTGGCAGGTAAGTTTCTGCTTCTAC-3' (SEQ ID NO: 46) and reverse primer HiNK529 with the nucleotide sequence 5'-ATCCAACCGCGGACCTGCA-CATCAACAA-3' (SEQ ID NO: 40) and potato DNA containing the potato St-LS1 intron as template;

c) fusing the amplification products obtained in steps a) and b) to each other by means of a second round of PCR using primers HiNK6382 and HiNK529 and using a mix of both amplification products as template, yielding a fusion product of 0.47 Kb in length;

d) amplifying the 0.27 Kb BvFT2 fragment a second time, using forward primer HiNK6385 with the nucleotide sequence 5'-TAAATCCGCGGGCCAAGAAGTTGTCT-GCTATG-3' (SEQ ID NO: 47) and reverse primer HiNK6386 with the nucleotide sequence 5'-CTATTTGTC-GACGCATTTAATAAAATCTCTTTC-3' (SEQ ID NO: 48) and the sugar beet cDNA as obtained in subsection a) above as template;

e) fusing both fragments at the Sac II restriction sites to create an inverted repeat for the BvFT2 sequence separated by the intron from the potato ST-LS1 gene.

In a further embodiment of this aspect the chimeric construct of the present invention comprises a sequence as depicted by the nucleotide sequence set forth as SEQ ID NO: 332.

In a further aspect the present invention is related to chimeric constructs provided for transgenic upregulation of expression of the endogenous BvFT1 gene in sugar beet.

In one embodiment of this aspect the chimeric construct of the present invention is a chimeric construct for transgenic upregulation of expression of the endogenous BvFT1 gene comprising a nucleotide sequence encoding the BvFT1 gene or parts of it, wherein said nucleotide sequence encoding the BvFT1 gene or parts of it has a nucleotide sequence which either has a sequence identity of at least 70% to or hybridizes under stringent conditions to a nucleic acid sequence of the present invention set forth as SEQ ID NOs: 5 or 6, wherein said nucleotide sequence encoding the BvFT1 gene or parts of it is operably linked to regulatory sequences such that upon expression in a plant upregulation of expression of the endogenous BvFT1 gene is caused.

In a further preferred embodiment the nucleotide sequence encoding the BvFT1 gene comprised in the chimeric construct of the present invention has a nucleotide sequence as set forth in SEQ ID NO: 6.

In another preferred embodiment the chimeric construct of the present invention as described hereinbefore comprises a nucleotide sequence as depicted by nucleotides 2076 to 2615 of SEQ ID NO: 34.

In yet another preferred embodiment the chimeric construct of the present invention as described hereinbefore comprises the nucleotide sequence as depicted in SEQ ID NO: 34.

In a further preferred embodiment the heterologous DNA comprised in the chimeric construct of the present invention is operatively linked to a constitutive promoter, preferably a Ubi3 promoter from *Arabidopsis*.

A further aspect of the present invention relates to a plant transformation vector and/or a plant expression vector comprising the chimeric construct of the present invention as described hereinbefore.

In one preferred embodiment of this aspect the plant transformation vector of the present invention is a RNAi expression vector comprising the chimeric construct of the present invention as described hereinbefore, and/or a plant expression vector comprising the chimeric construct of the present invention.

In another preferred embodiment the RNAi expression vector of the present invention comprises the chimeric construct having the nucleotide sequence as set forth in SEQ ID NO: 33.

In yet another preferred embodiment the expression vector of the present invention comprises the chimeric construct having the nucleotide sequence as set forth in SEQ ID NO: 34.

In yet another aspect of the present invention a transgenic sugar beet plant is provided in which the expression of the endogenous BvFT1 gene and/or BvFT2 gene is modulated, or cells, tissues or seeds thereof, wherein the expression of the endogenous BvFT2 gene is downregulated or suppressed in said transgenic sugar beet plant, and/or wherein expression of the endogenous BvFT1 gene is upregulated in said transgenic sugar beet plant.

One preferred embodiment of this aspect provides transgenic sugar beet plant, or cells, tissues or seeds thereof, in which the expression of the endogenous BvFT2 gene is down-regulated or suppressed by a method selected from the group consisting of dsRNA, antisense suppression, or co-suppression.

In a further embodiment the transgenic sugar beet plant of the present invention, or cells, tissues or seeds thereof, comprise a chimeric construct of the present invention or a nucleic acid sequence of the present invention, wherein said transgenic sugar beet plant, or cells, tissues or seeds thereof expressing the dsRNA are bolting resistant and exhibit a phenotype of delayed bolting, preferably a non-bolting phenotype.

In another preferred embodiment the transgenic sugar beet plant of the present invention, or cells, tissues or seeds thereof comprise a chimeric construct of the present invention or a nucleic acid sequence of the present invention, wherein in said transgenic sugar beet plant the endogenous BvFT1 is overexpressed and the plant exhibits a phenotype of delayed bolting, preferably a non-bolting phenotype.

In another preferred embodiment the transgenic sugar beet plant is produced from cells, tissues or seeds of the present invention and as described hereinabove.

Another preferred embodiment relates to a root or a progeny of a transgenic sugar beet plant of the present invention.

Another aspect of the present invention relates to a method of producing hybrid seeds from which sugar beet plants having a phenotype of bolting resistance can be grown, wherein the method comprises the steps of:

a. providing a sugar beet line having a phenotype of bolting resistance, particularly a transgenic sugar beet plant of the present invention as described hereinbefore as a first parent line;

b. providing as a second parent line a sugar beet line having a different genotype than the sugar beet line in step a);

wherein one of the parent lines of step a) or step b) is a male sterile cms line and wherein the other parent line is male fertile, and c. allowing the plants of the male fertile parent line to pollinate the flowers of the male sterile parent line, let the seed develop, and harvest the hybrid seed;

wherein the harvested hybrid seeds are seeds of a sugar beet hybrid plant having a phenotype of delayed bolting, preferably a non-bolting phenotype bolting resistance.

One embodiment of this aspect is a method of producing sugar beet hybrid seeds of the present invention, wherein the male sterile CMS sugar beet parent line is an inbred sugar beet line comprising a chimeric construct of the present invention as described hereinbefore.

One further preferred embodiment relates to hybrid seed of a sugar beet plant having a phenotype of delayed bolting, preferably a non-bolting phenotype.

In another preferred embodiment the hybrid seed of the present invention is produced by the method of producing sugar beet hybrid seeds of the present invention as described hereinbefore.

In yet another preferred embodiment a hybrid sugar beet plant having a phenotype of delayed bolting, preferably a non-bolting phenotype, is produced by growing the hybrid seed of the present invention as described hereinabove.

Another aspect of the present invention relates to plant parts selected from the group consisting of seeds, embryos, microspores, anthers, zygotes, protoplasts, cells, ovary, ovules, pollen, taproots, cotyledons, extracts or biological samples are provided, wherein said plant parts are derived from the transgenic sugar beet plant, or cells, tissues or seeds thereof of the present invention as described hereinabove or from hybrid seed of the present invention as described hereinabove or from hybrid sugar beet plants of the present invention as described hereinabove.

In yet a further aspect the present invention relates to the use of a nucleic acid sequence or a chimeric construct of the present invention as described hereinabove or fragments thereof for the transformation of sugar beet plant cells.

In one embodiment, a method of transforming sugar beet plant cells is provided comprising the use of a nucleic acid sequence of the present invention as described hereinabove or a chimeric construct of the present invention or a vector of the present invention as described hereinabove.

Another embodiment of the present invention relates to the use of the transgenic sugar beet plant of the present invention, of the hybrid sugar beet plant of the present invention, or of the plant parts of the present invention in a method selected from the group comprising of methods of sugar production, methods of aerobic fermentation and methods of anaerobic fermentation, particularly in a method of sugar production.

In a preferred embodiment a method for producing sugar is provided wherein the sugar beet plant, or cells or tissues thereof of the present invention as described hereinabove are processed to produce sugar.

One further aspect of the present invention relates to sugar produced from the sugar beet plant, or cells or tissues thereof of the present invention.

BRIEF DESCRIPTION OF THE FIGURES AND THE SEQUENCES

FIGURES:

FIG. 1 is a sequence alignment between the mRNA of the FT orthologues from *Arabidopsis* (AtFT, accession No. NM_105222), *Citrus* (CiFT, accession No. AB027456), wheat (TaFT, accession No. AY705794) and rice (OsHd3a, accession No. NM_001063395). The position of the degenerate primers HiNK581 (SEQ ID No. 1) and HiNK860 (SEQ ID No. 2) are boxed.

FIG. 4 shows an amino acid sequence comparison between BvFT1 and AtFT proteins. Conserved amino acids are in dark grey, weakly similar in light grey and non-similar in white.

FIG. 5 shows an amino acid sequence comparison between BvFT2 and AtFT proteins. Conserved amino acids are in dark grey, weakly similar in light grey and non-similar in white.

Figure 6:
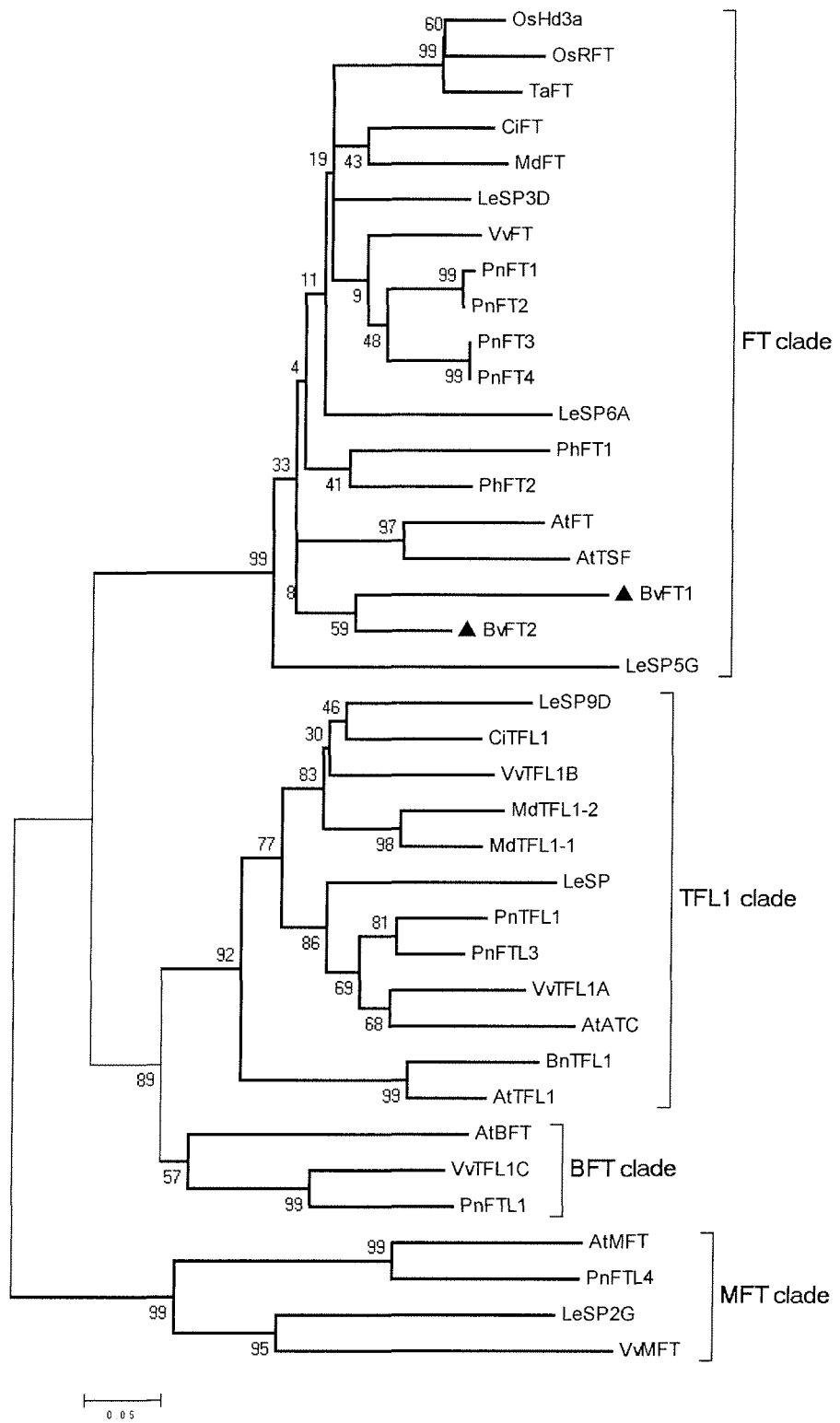

FIG. 6 shows the phylogenetic analysis of multiple members in the FT gene family from several plant species including the FT homologues from sugar beet. The tree was constructed by the Neighbor-Joining method including *Beta vulgaris* BvFT1 and BvFT2, *Arabidopsis thaliana* (FT, accession No. NP_176726; TFL1, accession No. NP_196004; MFT, accession No. NP_173250; ATC, accession No. NP_180324; TSF, accession No. NP_193770 and BFT, accession No. NP_201010), grapevine (VvFT, accession No. ABI99465; VvTFL1A, accession No. ABI99466; VvTFL1B, accession No. ABI99467; VvTFL1C, accession No. abi99468; and VvMFT, accession No. ABI99469), citrus (CiFT, accession No. BAA77836; and CiTFL1, accession No. AAR04683), apple (MdFT, accession No. BAD08340; MdTFL1-1, accession No. BAD10961; and MdTFL1-2, accession No. BAD10967), Pharbitis (PhFT1, accession No. ABW73562; and PhFT2, accession No. ABW73563), tomato (SP, accession No. AAC26161; SP2G, accession No. AAO31791; SP3D, accession No. AAO31792; SP5G, accession No. AAO31793; SP6A, accession No. AAO31794; and SP9D, accession No. AAO31795), wheat (TaFT, accession No. ABK32205), rice (OsHd3a, accession No. NP_001056860; and OsRFT, accession No. BAF92712), *Brassica napus* (BnTFL1, accession No. BAA33415) and poplar (PnFTL1, accession No. BAD08339; PnTFL1, accession No. BAD22599; PnFTL3, accession No. BAD22601; PnFTL4, accession No. BAD22677; PnFT1, accession No. BAD01612; PnFT2, accession No. BAD01561; PnFT3, accession No. BAD02371; and PnFT4, accession No. BAG12904). The unrooted dendrograms were generated from the alignment of the amino acid sequences using the ClustalW program, and the phylogenetic tree was displayed by the MEGA4 software package (TAMURA et al., 2007). Bootstraps values for 1000 re-samplings are shown on each branch. The scale indicates the average number of substitutions per site. The *Beta vulgaris* FT homologues are marked with a triangle.

Figure 7:
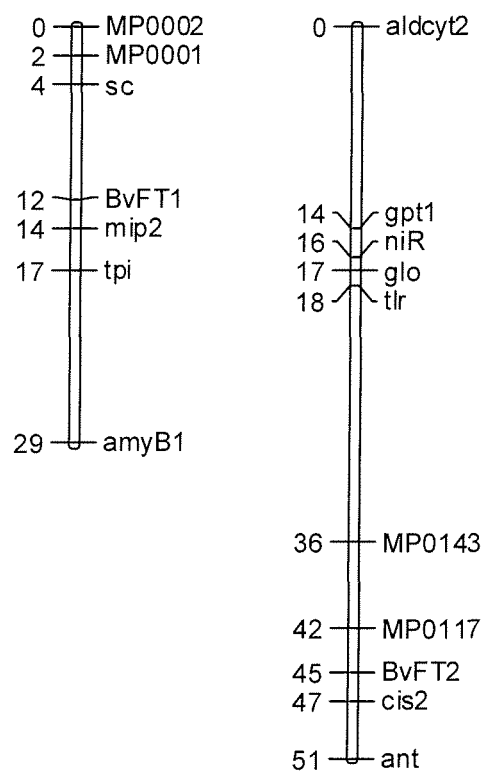

FIG. 7 shows genetic maps of sugar beet chromosomes IX and IV. Markers are given at the right side of the chromosome; the cumulative genetic distance is indicated at the left side. The genetic maps were constructed using the JoinMap 3.0 software. The genetic positions of BvFT1 and BvFT2, respectively, are highlighted.

Figure 8:
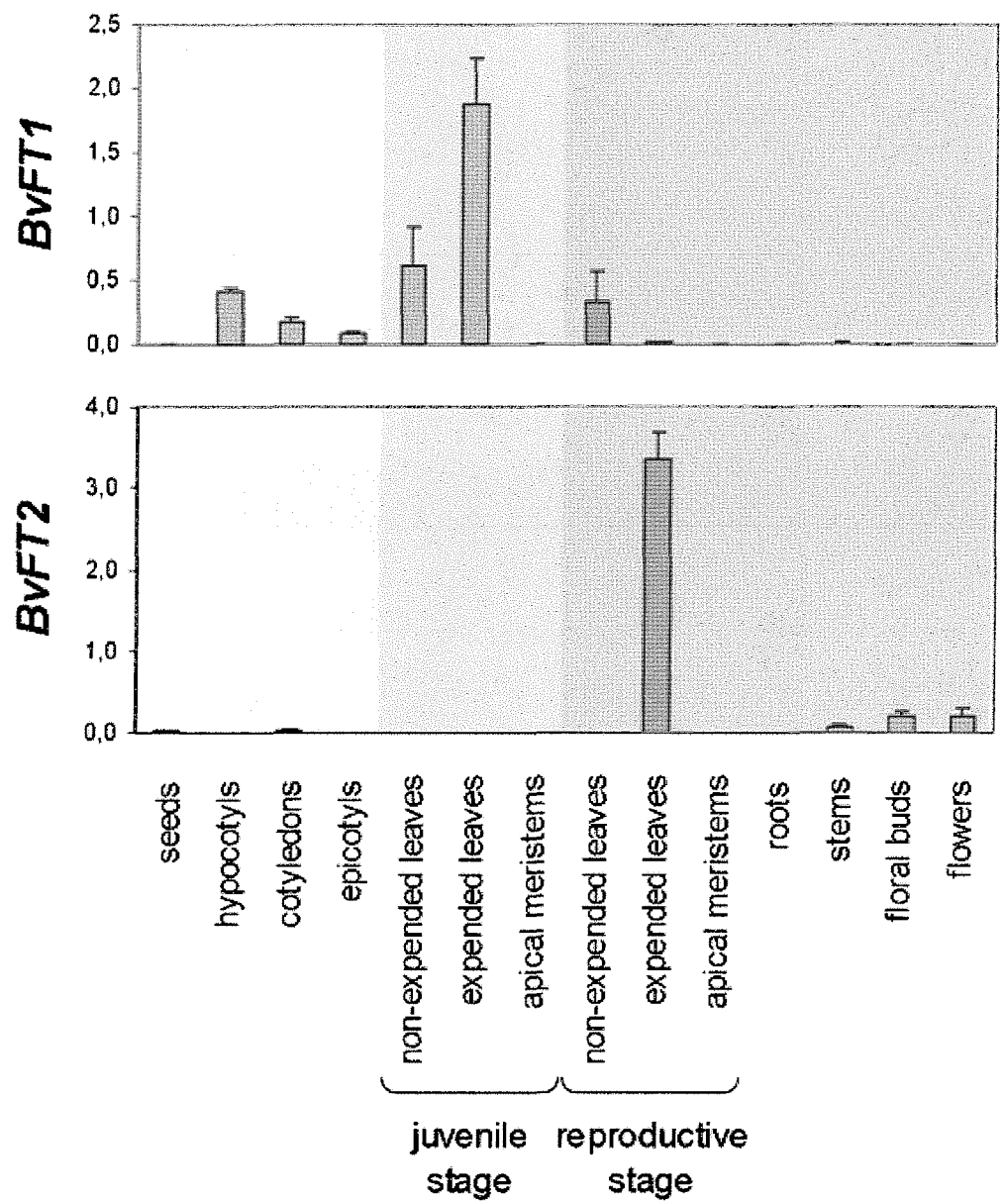

FIG. 8 shows the relative expression of BvFT1 and BvFT2 genes in various organs of biennial sugar beet plants. Samples were harvested from biennial sugar beet plants grown under LD conditions (16 hours light/8 hours dark) at a temperature of 18° C. Levels of detected amplicons were normalized by reference to amplified products that correspond to the beta isocitrate dehydrogenase (BvICDH) gene. Data points represent mean value of three biological replicates.

Figure 9:
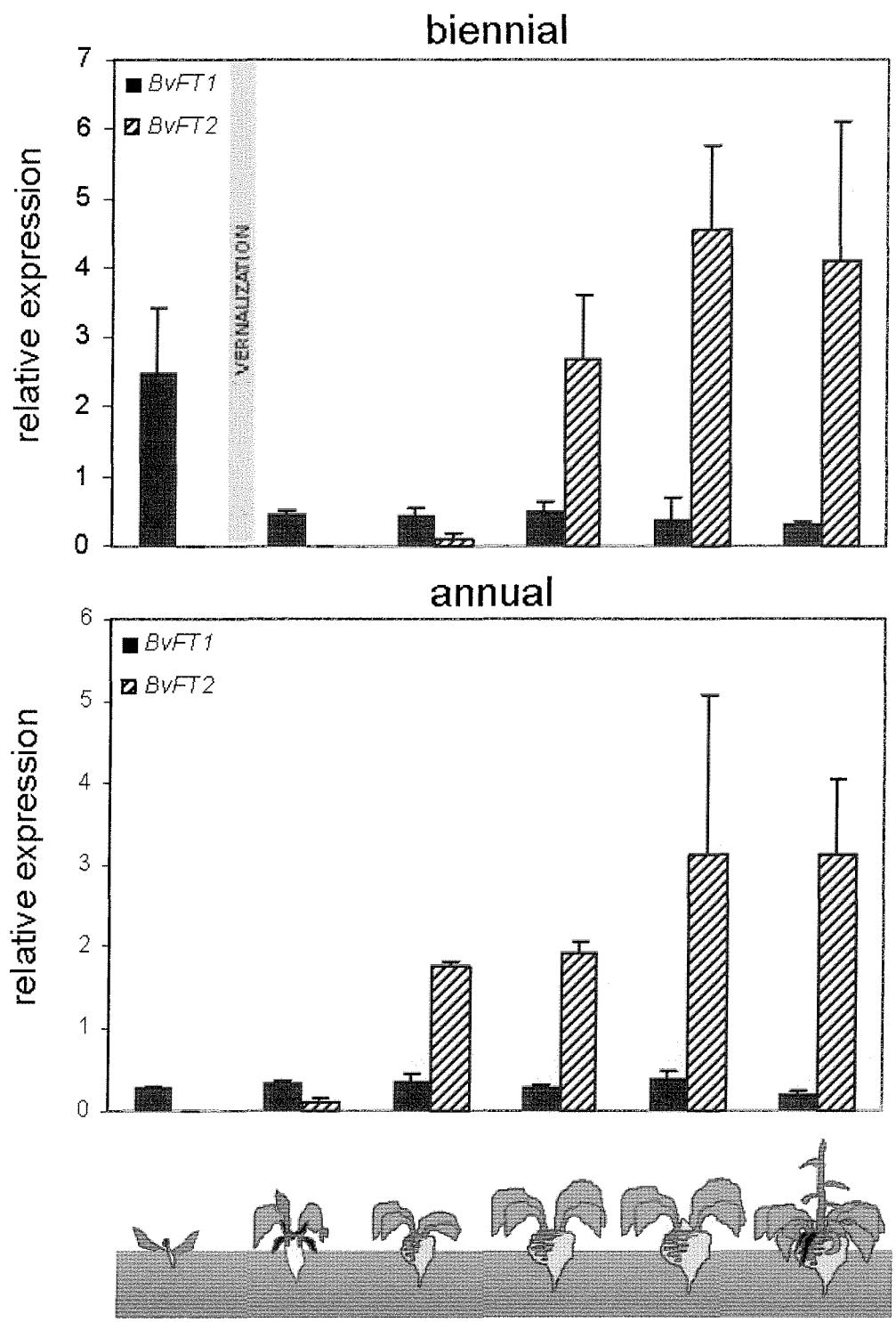

FIG. 9 depicts the relative gene expression levels of BvFT1 and BvFT2 across different developmental stages of biennial and annual sugar beet. The dashed bar represents the vernalization period. Levels of detected amplicons for BvFT1 and BvFT2 were normalized by referencing to amplification products that correspond to the beta isocitrate dehydrogenase (BvICDH1) gene that was used as internal calibrator genes (see Example 3). Data points represent the mean value of two biological replicates.

Figure 10:
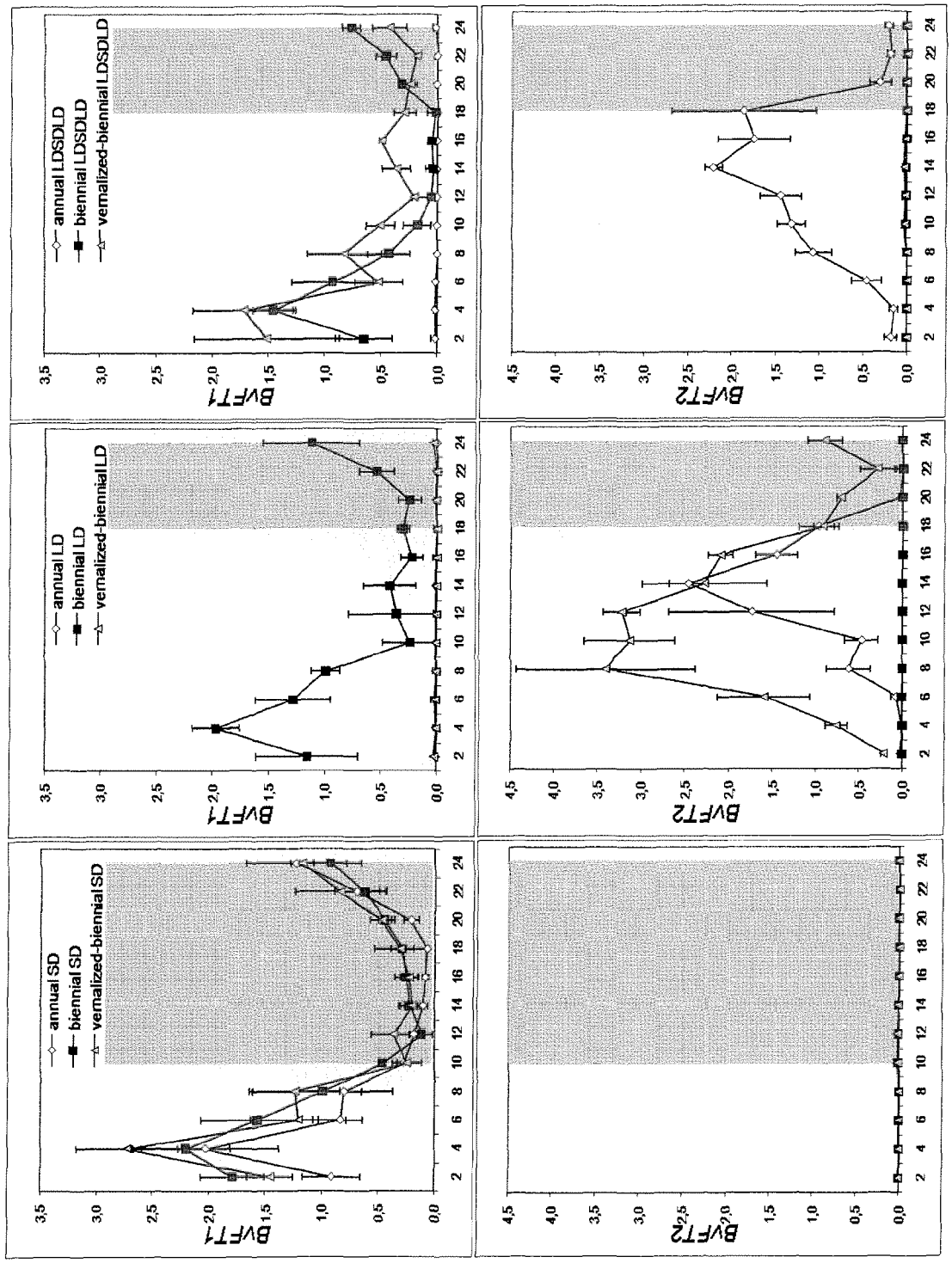

FIG. 10 depicts the diurnal oscillation of BvFT1 and BvFT2 genes in annual, biennial and vernalized biennial plants. The transcripts from leaf tissues sampled every 2 hours across a period of 24 hours were quantified by quantitative PCR. Three independent experiments were undertaken under either SD conditions (10 hours light/14 hours dark), LD conditions (18 hours light/6 hours dark) or SDLD conditions, wherein the plants were grown for one week under SD conditions followed by a transfer to LD conditions. Levels of detected amplicons were normalized by referencing to amplification products that correspond to the BvICDH1 gene that was used as internal calibrator gene. Data points represent mean value of three biological replicates.

Figure 11:
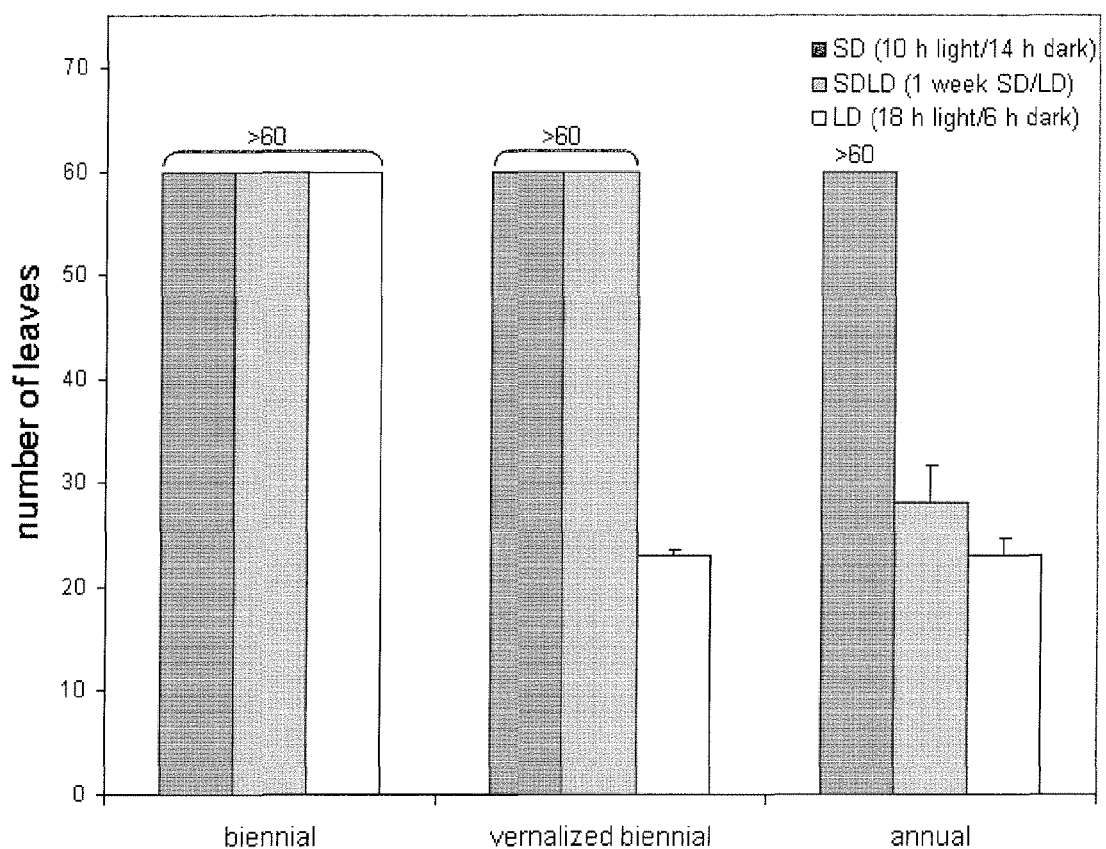

FIG. 11 depicts the bolting time of annual, biennial and vernalized-biennial sugar beet plants grown under different photoperiods. SD conditions consisted of 10 hours light/14 hours dark. LD condition s consisted of 18 hours light/6 hours dark. The bolting time was measured based on the total leaf number from 6 independent plants.

Figure 12:
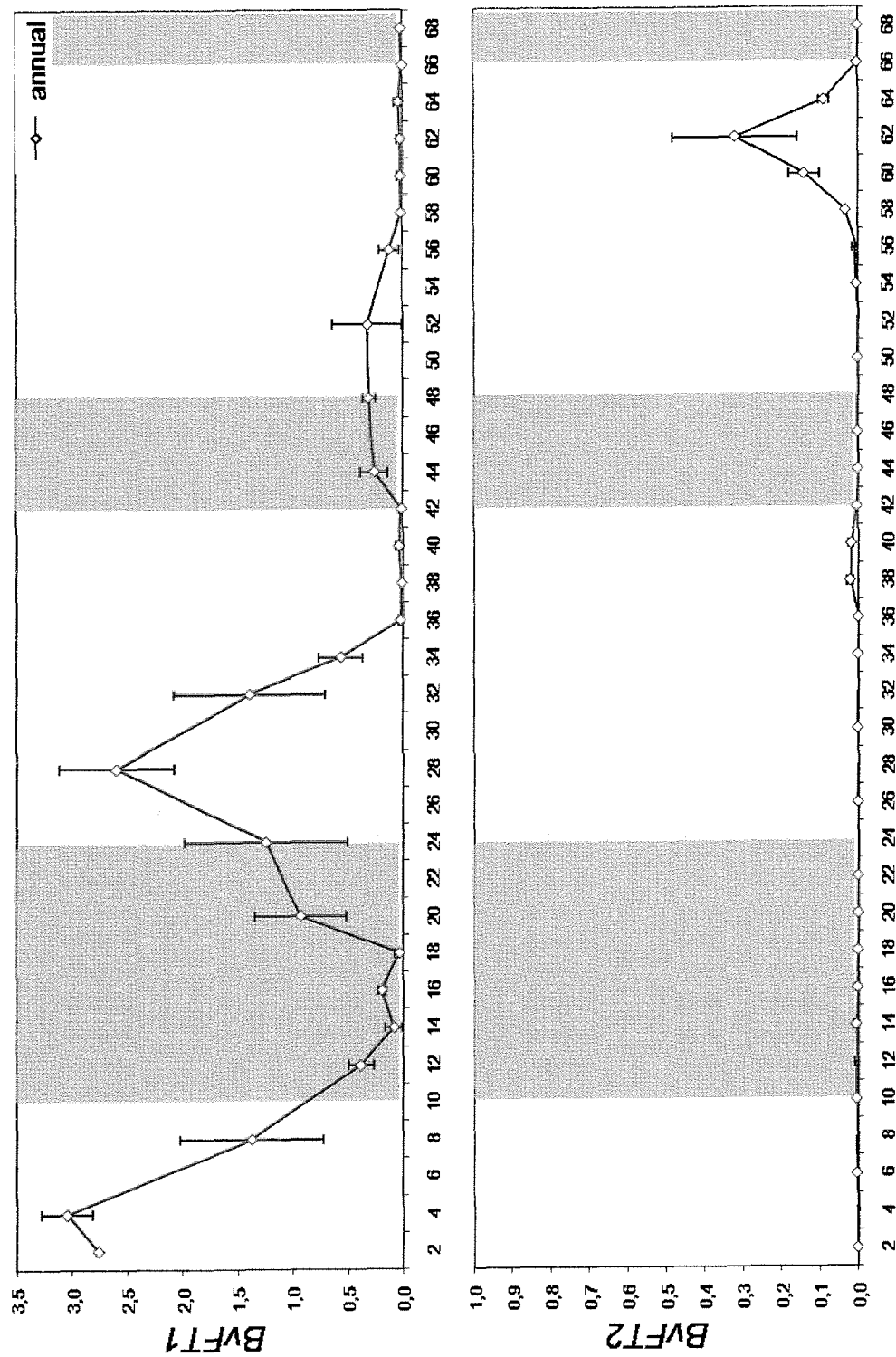

FIG. 12 shows the relative expression of BvFT1 and BvFT2 in annual plants across a period of 72 hours. The first 24 hours consisted of 10 hours light/14 hours dark followed by 48 hours where the illuminated period was changed to 18 hours light/6 hours dark. Levels of detected amplicons were normalized by reference to amplified products that correspond to the BvICDH gene. Data points represent mean value of three biological.

Figure 13:
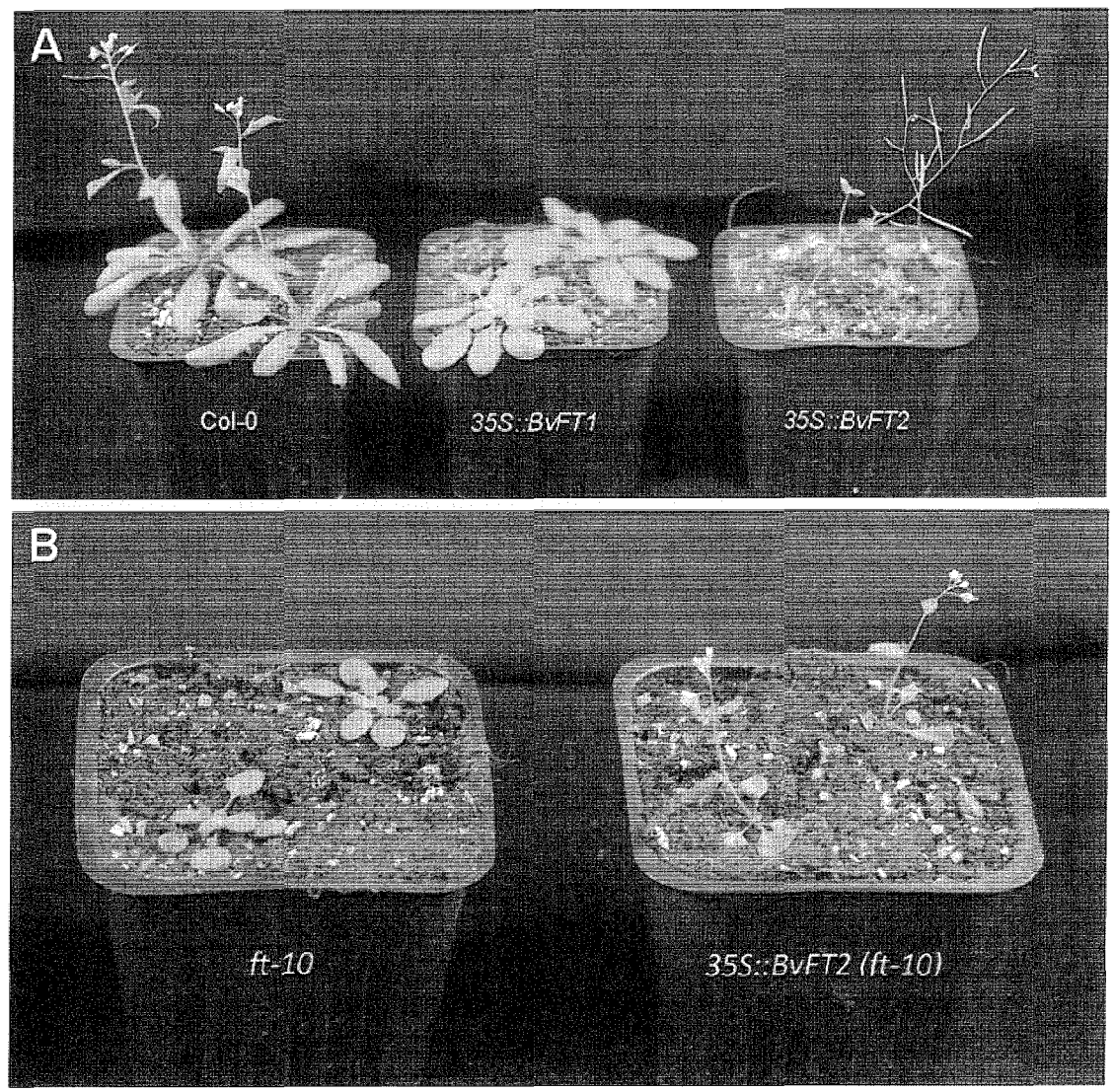

FIG. 13 depicts the effect of ectopic expression of the genes BvFT1 and BvFT2 on the flowering time in *Arabidopsis*. (A)—phenotype of 30 days old wild type (Col-0) *Arabidopsis* plants and of transgenic *Arabidopsis* plants expressing BvFT1 and BvFT2 grown under in LD conditions. (B)— phenotype of 20 days old ft-10 mutants and transgenic ft-10 mutants expressing BvFT2 grown under LD conditions (16 hours light/8 hours dark).

Figure 14:
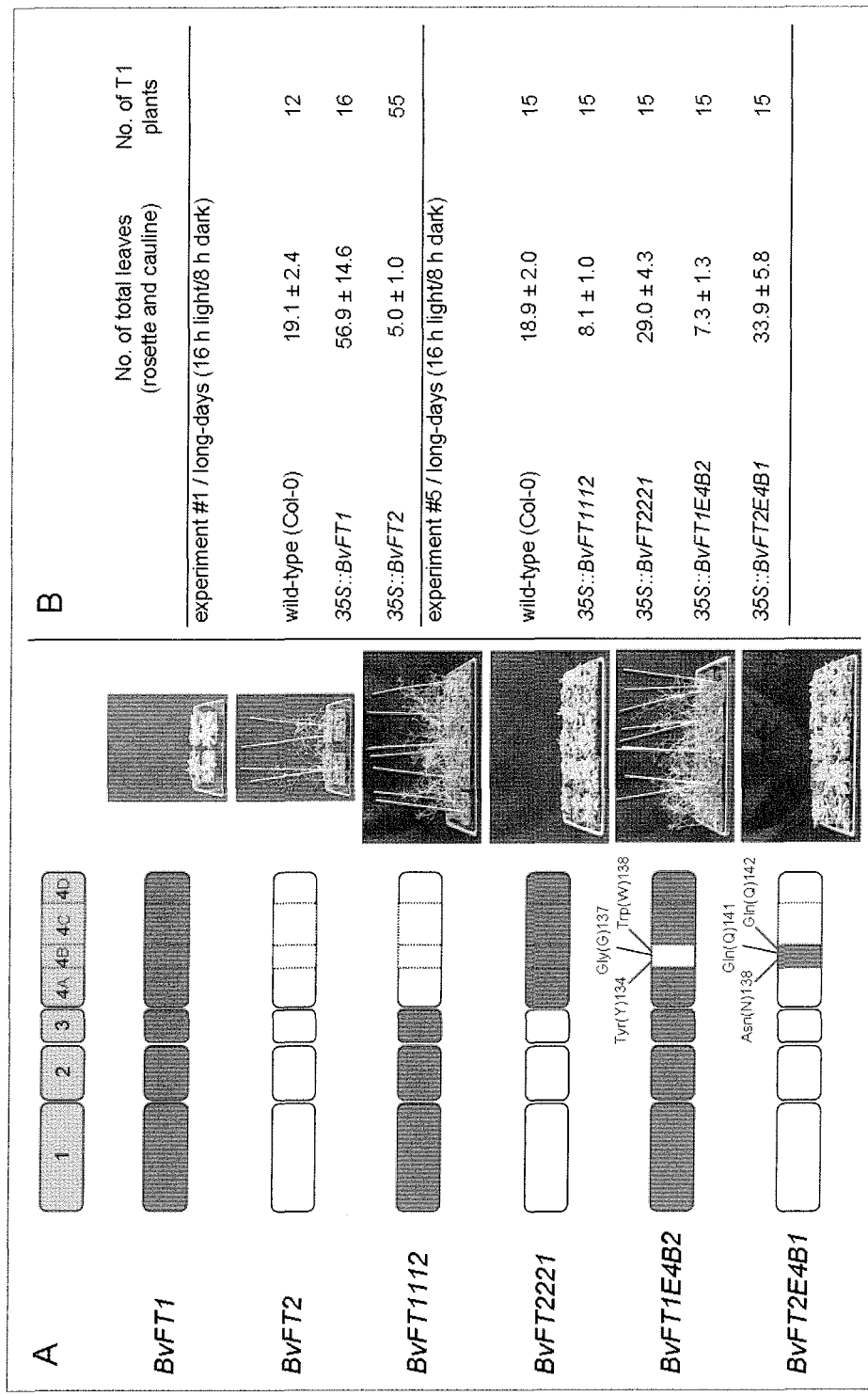

FIG. 14 depicts the mapping of the BvFT1 and BvFT2 specific activity to the segment B of the exon 4 which encodes for the external loop of the PEBP proteins. (A)—structure of the different chimeras used in this study and their effect on flowering time in *Arabidopsis*. Exonic part of BvFT1 and BvFT2 are shown as black and white rounded rectangles, respectively. BvFT1112 (SEQ ID No. 29) denotes chimera in which exon 1, 2 and 3 are from BvFT1 and exon 4 is from BvFT2. BvFT2221 (SEQ ID No. 30) denotes chimera in which exon 1, 2 and 3 are from BvFT2, and exon 4 is from BvFT1. BvFT1E4B2 (SEQ ID No. 31) denotes a chimera based on BvFT1 in which segment B of exon 4 is derived from BvFT2. BvFT2E4B1 (SEQ ID No. 32) denotes a chimera based on BvFT2 in which segment B of exon 4 is derived from BvFT1. (B)—flowering times of *Arabidopsis* plants expressing BvFT1, BvFT2 or BvFT1/BvFT2 chimeras. T1 plants were grown under LD conditions. The number of leaves is presented as the average of at least 15 independent T1 plants±SD.

Figure 15:
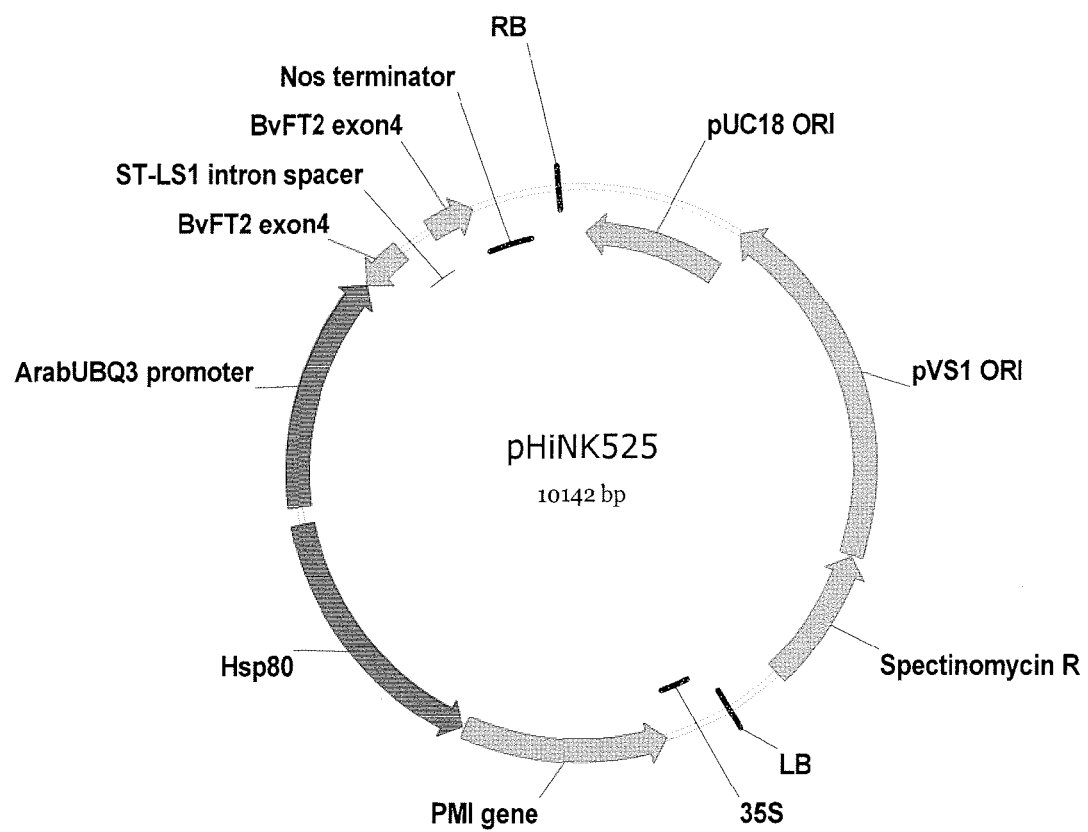

FIG. 15 shows the plasmid map of binary vector pHiNK525 (SEQ ID No. 33), carrying the RNAi gene cassette for BvFT2 under the control of the constitutive UBQ3 promoter from *Arabidopsis* in combination with the PMI selectable marker.

Figure 16:
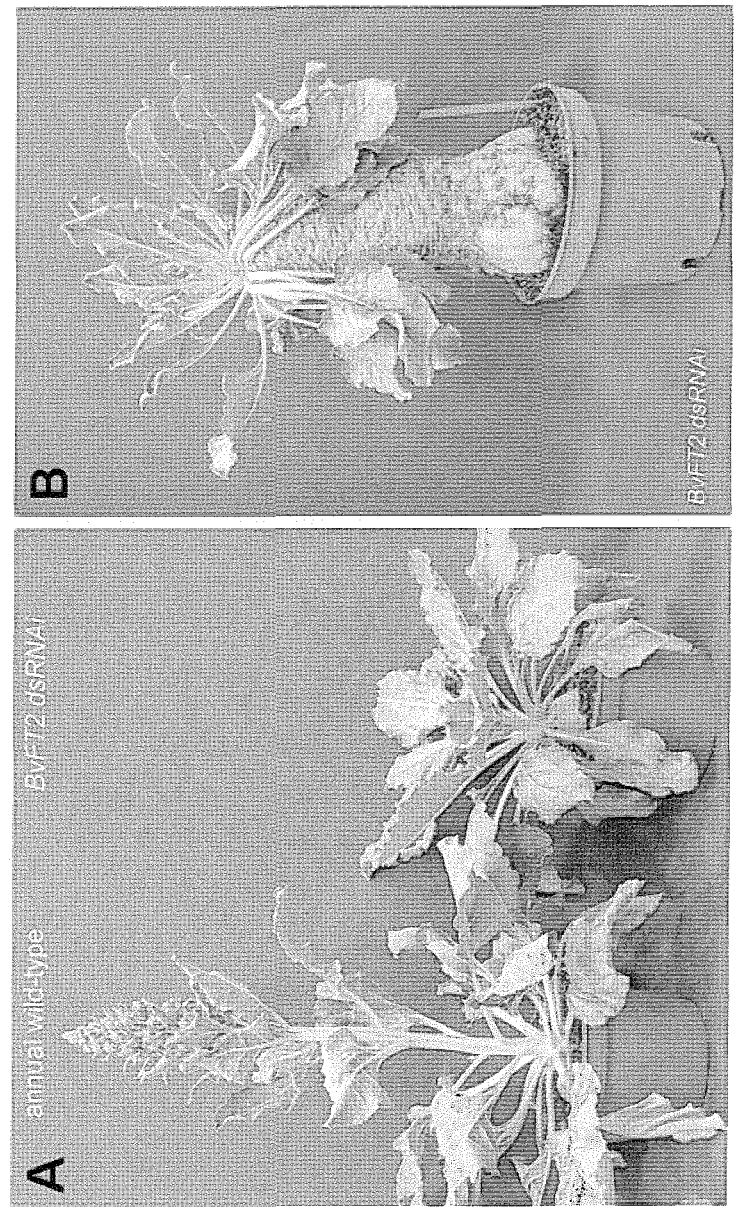

FIG. 16 shows the effect of suppression of the BvFT2 gene on the bolting time in T0 annual sugar beet grown under bolting inductive conditions (18° C.; 18 hours light/6 hours dark). (A)—phenotype of non-transgenic annual line and transgenic BvFT2 dsRNAi annual plant. (B)—phenotype of a non-bolting, 400 days old transgenic BvFT2 dsRNAi annual plant.

Figure 17:

FIG. 17 depicts the effect of suppression of the BvFT2 gene on the bolting time in T1 annual sugar beet grown under bolting inductive conditions (18° C.; 18 hours light/6 hours dark). The three bolting plants to the left are non-transgenic (NT) plants, whereas the three non-bolting plants to the right are BvFT2 dsRNAi plants (event 2A). The picture was taken on day 36 of the experiment.

Figure 18:
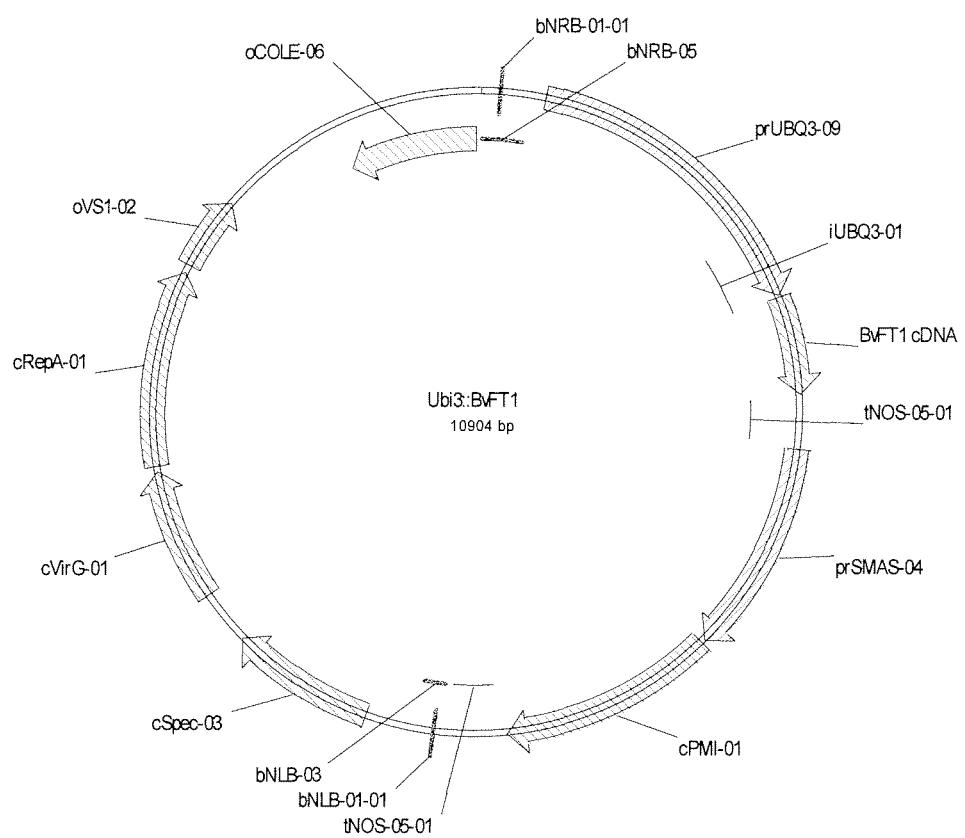

FIG. 18 depicts the plasmid map of binary vector Ubi3:: BvFT1 (SEQ ID No. 34), carrying the Ubi3::BvFT1 gene cassette for BvFT1 in combination with the PMI selectable marker gene under the control of the superMAS promoter.

Figure 19:
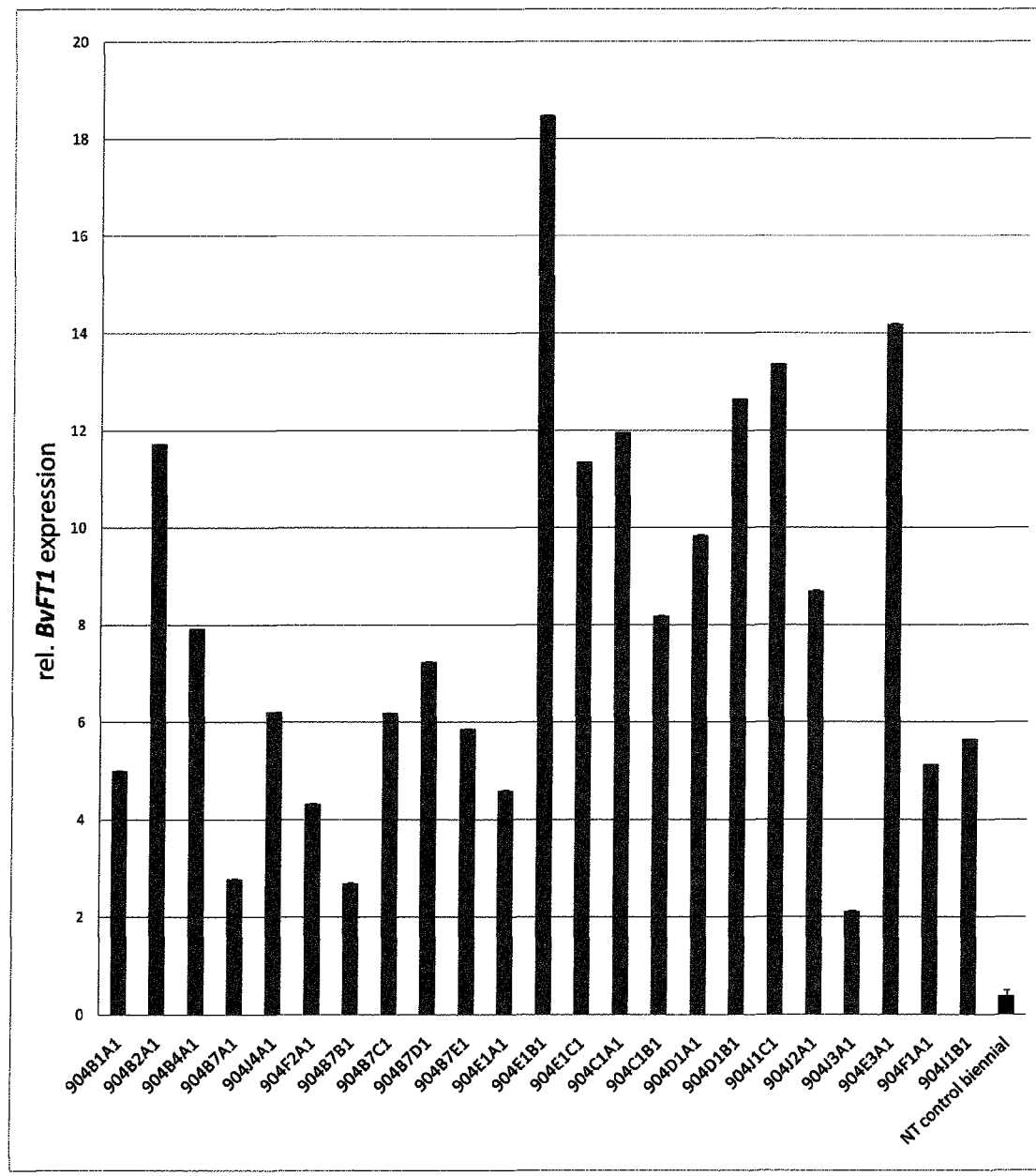

FIG. 19 shows the relative expression of BvFT1 in PMI-positive T0 shoots carrying the Ubi3::BvFT1 gene cassette. Levels of detected amplicons were normalized by reference to amplified products that correspond to the BvICDH gene. The data for the non-transgenic control T0 plant represent the mean value of three biological replicates.

Figure 20:
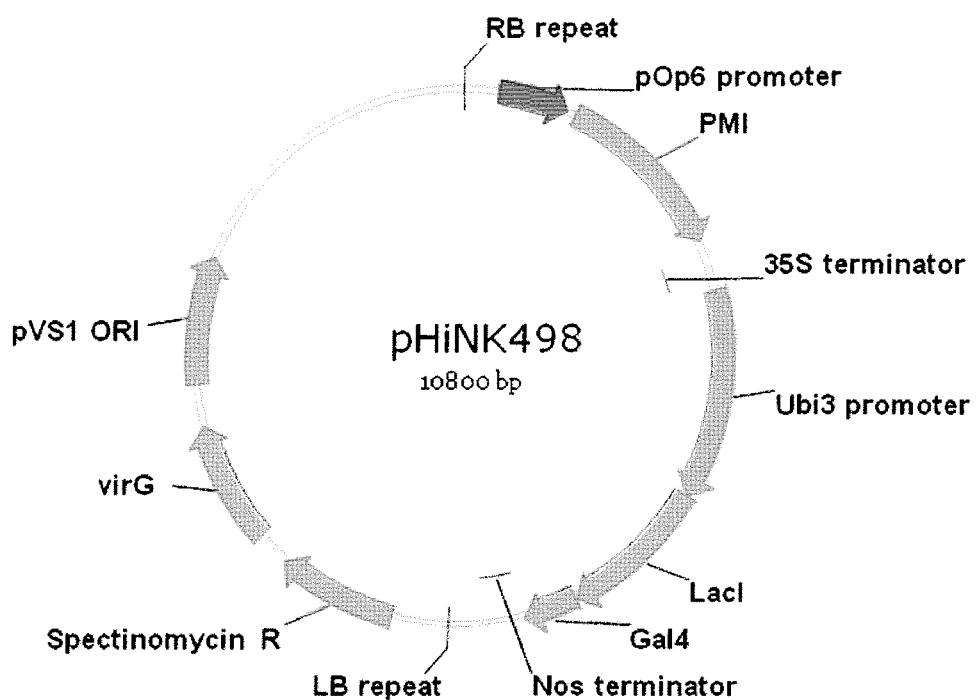

FIG. 20 shows the plasmid map of binary vector pHiNK498 (SEQ ID No. 53), carrying the PMI selectable marker gene downstream of the pOp6 promoter and combined with the gene cassette for the constitutive expression of LhG4Ato under to the control of the Ubi3 promoter from *Arabidopsis*.

Figure 21:
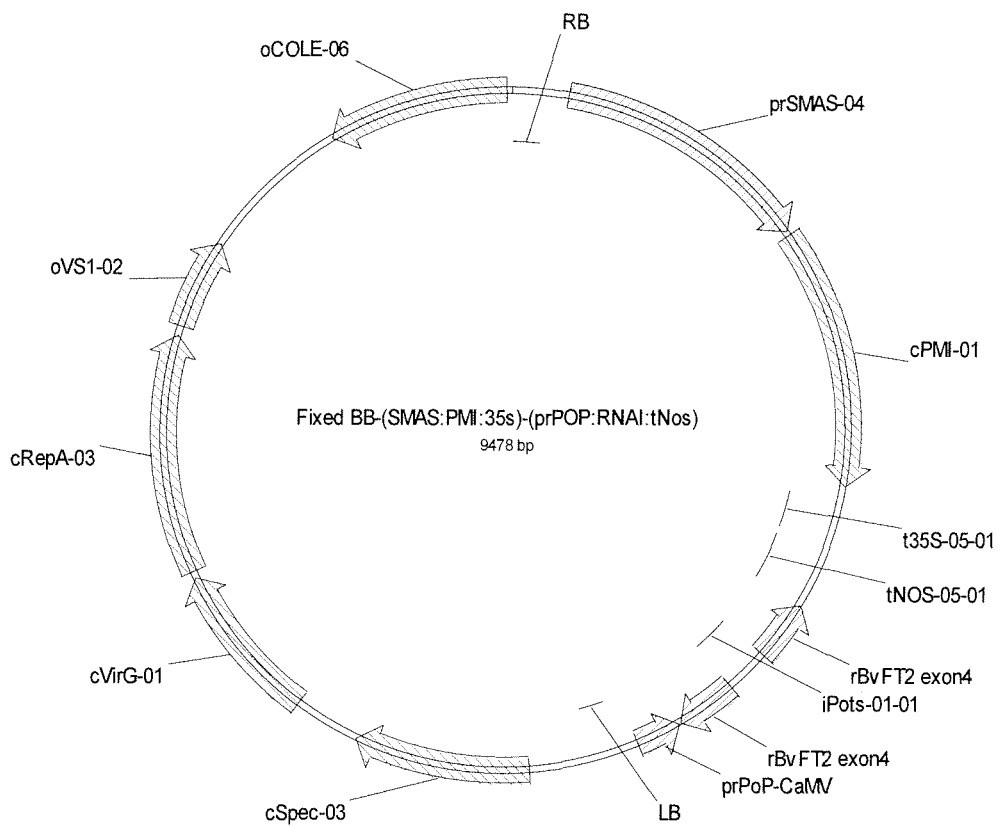

FIG. 21 shows the plasmid map of binary vector (SEQ ID No. 54), carrying the inverted repeat as present at pHiNK525 (see Example 7) downstream of the pOp6 promoter fragment and combined with the PMI selectable marker gene under the control of the SuperMAS promoter.

Figure 22:
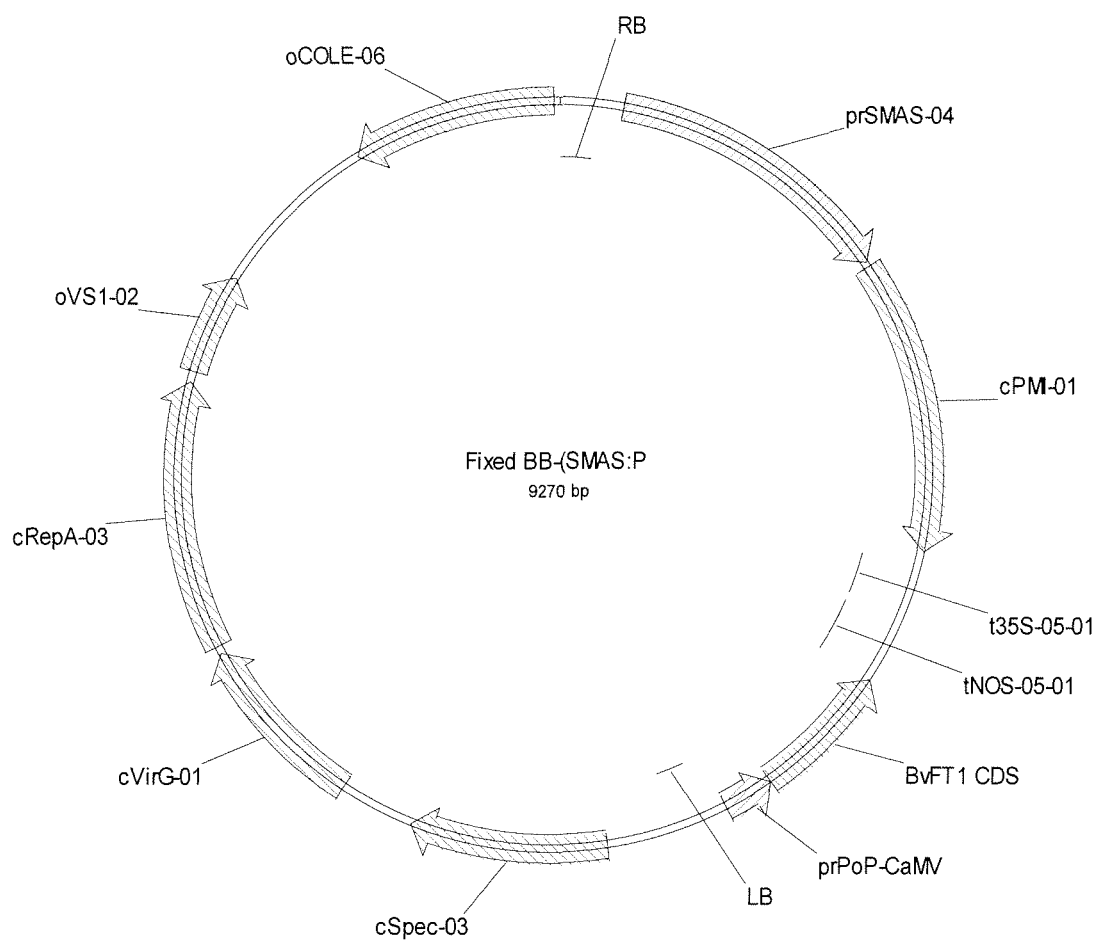

FIG. 22 shows the plasmid map of binary vector (SEQ ID No. 55), carrying the full-length coding region of BvFT1 downstream of the pOp6 promoter fragment and combined with the PMI selectable marker gene under the control of the SuperMAS promoter.

SEQUENCES

SEQ ID No: 1 depicts the nucleotide sequence of degenerate primer HiNK581.

SEQ ID No: 2 depicts the nucleotide sequence of degenerate primer HiNK860.

SEQ ID No: 3 represents the fragment of the sugar beet FT1 gene (referred to as BvFT1 fragment) obtained from a PCR reaction using the degenerate primers as described in Example 1.

SEQ ID No: 4 represents the fragment of the sugar beet FT2 gene (referred to as BvFT2 fragment) obtained from a PCR reaction using the degenerate primers as described in Example 1.

SEQ ID No: 5 represents the genomic sequence of the sugar beet FT1 gene obtained from the sequencing of BAC SBA066-G04.

SEQ ID No: 6 represents the corresponding coding sequence of the sugar beet FT1 gene as depicted in SEQ ID No: 5.

SEQ ID No: 7 represents the protein sequence of the protein encoded by the coding sequence of the sugar beet FT1 as depicted in SEQ ID NO: 6.

SEQ ID No: 8 represents the genomic sequence of the sugar beet FT2 gene obtained from the sequencing of BAC SBA077-N02.

SEQ ID No: 9 represents the corresponding coding sequence of the sugar beet FT2 gene as depicted in SEQ ID NO: 8.

SEQ ID No: 10 represents the protein sequence of the protein encoded by the coding sequence of the sugar beet FT2 as depicted in SEQ ID NO: 9.

SEQ ID No: 11 depicts the nucleotide sequence of the forward primer SELA3770 for BvFT1.

SEQ ID No: 12 depicts the nucleotide sequence of the reverse primer SELA3771 for BvFT1.

SEQ ID No: 13 depicts the nucleotide sequence of the forward primer SELA3776 for BvFT2.

SEQ ID No: 14 depicts the nucleotide sequence of the reverse primer SELA3777 for BvFT2.

SEQ ID No: 15 depicts the nucleotide sequence of the forward primer SELA 4259 for FT1(T1).

SEQ ID No: 16 depicts the nucleotide sequence of the reverse primer SELA4260 for FT1(T1).

SEQ ID No: 17 depicts the nucleotide sequence of SELA4261 probe #1 for FT1(T1).

SEQ ID No: 18 depicts the nucleotide sequence of SELA4262 probe #2 for FT1(T1).

SEQ ID No: 19 depicts the nucleotide sequence of forward primer SELA4263 for FT2(T1).

SEQ ID No: 20 depicts the nucleotide sequence of reverse primer SELA4264 for FT2(T1).

SEQ ID No: 21 depicts the nucleotide sequence of SELA4265 probe #1 for FT2(T1).

SEQ ID No: 22 depicts the nucleotide sequence of SELA4266 probe #2 for FT2(T1).

SEQ ID No: 23 depicts the nucleotide sequence of the forward primer SELA3730 for BvFT1.

SEQ ID No: 24 depicts the nucleotide sequence of the reverse primer SELA3731 for BvFT1.

SEQ ID No: 25 depicts the nucleotide sequence of the forward primer SELA3732 for BvFT2.

SEQ ID No: 26 depicts the nucleotide sequence of the reverse primer SELA3733 for BvFT2.

SEQ ID No: 27 depicts the nucleotide sequence of the forward primer SELA3724 for the beta isocitrate dehydrogenase gene BvICDH1.

SEQ ID No: 28 depicts the nucleotide sequence of the reverse primer SELA3725 for the beta isocitrate dehydrogenase gene BvICDH1.

SEQ ID No: 29 depicts the sequence of the gene chimera referred to as BvFT1112.

SEQ ID No: 30 depicts the sequence of the gene chimera referred to as BvFT2221.

SEQ ID No: 31 depicts the sequence of the gene chimera referred to as BvFT1E4B2.

SEQ ID No: 32 depicts the sequence of the gene chimera referred to as BvFT2E4B1.

SEQ ID No: 33 depicts the nucleotide sequence of binary vector pHiNK525 that carries an expression cassette comprising an inverted repeat of exon 4 of the BvFT2 gene.

SEQ ID No: 34 depicts the nucleotide sequence of binary vector 17602 (Ubi3::BvFT1) that carries an expression cassette comprising the coding sequence of BvFT1 under the control of a constitutive promoter.

SEQ ID No: 35 depicts the nucleotide sequence of the 3' RACE ADAPTER used in the reverse transcriptase reaction.

SEQ ID No: 36 depicts the nucleotide sequence of the 3' RACE Outer Primer.

SEQ ID No: 37 depicts the nucleotide sequence of the 3' RACE Inner Primer.

SEQ ID No: 38 depicts the nucleotide sequence of the forward primer HiNK6371 for BvFT1.

SEQ ID No: 39 depicts the nucleotide sequence of the reverse primer HiNK6372 for BvFT1.

SEQ ID No: 40 depicts the nucleotide sequence of primer HiNK529.

SEQ ID No: 41 depicts the nucleotide sequence of primer HiNK6373 for BvFT1.

SEQ ID No: 42 depicts the nucleotide sequence of primer HiNK6374 for BvFT1.

SEQ ID No: 43 depicts the nucleotide sequence of primer HiNK6375 for BvFT1.

SEQ ID No: 44 depicts the nucleotide sequence of primer HiNK6382 for BvFT2.

SEQ ID No: 45 depicts the nucleotide sequence of primer HiNK6384 for BvFT2.

SEQ ID No: 46 depicts the nucleotide sequence of primer HiNK6383 for BvFT2.

SEQ ID No: 47 depicts the nucleotide sequence of primer HiNK6385 for BvFT2.

SEQ ID No: 48 depicts the nucleotide sequence of primer HiNK6386 for BvFT2.

SEQ ID No: 49 depicts the amino acid sequence of the amino acid motif "KPRVEIGG" located at exon 1 (amino acid residues 51 to 58) of the *Arabidopsis* FT gene.

SEQ ID No: 50 depicts the amino acid sequence of the amino acid motif "LVTDIPATT" (amino acid residues 89 to 98) at exon 3 immediately downstream of the splicing site of intron 2 of the *Arabidopsis* FT gene.

SEQ ID No: 51 depicts the nucleotide sequence of primer SELA267 for PMI.

SEQ ID No: 52 depicts the nucleotide sequence of primer SELA 268 for PMI.

SEQ ID No: 53 depicts the nucleotide sequence of binary vector pHiNK498 that carries an expression cassette comprising the PMI selectable marker gene downstream of the pOp6 promoter and combined with the gene cassette for the constitutive expression of LhG4Ato under to the control of the Ubi3 promoter from *Arabidopsis*.

SEQ ID No: 54 depicts the nucleotide sequence of binary vector that carries an expression cassette comprising the inverted repeat as present at pHiNK525 (see Example 7) downstream of the pOp6 promoter fragment and combined with the PMI selectable marker gene under the control of the SuperMAS promoter.

SEQ ID No: 55 depicts the nucleotide sequence of binary vector that carries an expression cassette comprising the full-length coding region of BvFT1 downstream of the pOp6 promoter fragment and combined with the PMI selectable marker gene under the control of the SuperMAS promoter.

Definitions

The technical terms and expressions used within the scope of this application are generally to be given the meaning commonly applied to them in the pertinent art of plant breeding and cultivation if not otherwise indicated herein below.

As used in this specification and the appended claims, the singular forms "a", "an", and "the" include plural references unless the context clearly dictates otherwise. Thus, for example, reference to "a plant" includes one or more plants, and reference to "a cell" includes mixtures of cells, tissues, and the like.

"Sugar beet" refers to all species and subspecies within the genus *Beta* as well as all kinds of cultivated beets of *Beta vulgaris*. Cultivated beets have been separated into four groups: leaf beet, garden beet, fodder beet and sugar beet. "Sugar beet" refers also to all cultivated beets including those grown for other purposes than the production of sugar, such as ethanol, plastics or other industrial products. In particular, "Sugar beet" refers to fodder beet and sugar beet, but especially to sugar beet. This term also includes sugar beet plants adapted for growth in tropical or subtropical regions.

An "annual sugar beet" refers to a sugar beet plant that takes two years to complete its biological lifecycle. A "biennial sugar beet" refers to a sugar beet plant that germinates, flowers, and dies in one year "Bolting" refers to the transition from the vegetative rosette stage to the inflorescence or reproductive growth stage.

"Engineering of bolting resistance" in the context of the present invention refers to the modulation of the expression of the FT genes of *Beta vulgaris* in sugar beet by means of genetic engineering. Such engineered sugar beet plants show a phenotype of bolting resistance in which the bolting reaction in response to vernalization is delayed or completely suppressed. Sugar beet plants that are bolting resistant are also non-flowering (or flowering resistant), as without bolting of the plant normally no flowers are developed.

"Delay of bolting reaction" or short "delay of bolting" as used herein has to be understood as a modulation of the natural bolting reaction of sugar beet plants in response to vernalization. In sugar beet plants with delayed bolting (i.e., plants with bolting resistance), stem elongation as the first visible step of bolting starts later than in normal plants. The bolting reaction can be delayed by just a few days (i.e., by, for example, 5, 6, 7, 8, 9, 10, 11, 12, 13 or 14 days) and up to several weeks (i.e., by 2, 3, 4, 5, 6, 7, or 8 weeks) or several months (i.e., 1, 2, 3, 5, or 6 months). Delay of bolting can also result in a complete suppression of the bolting response; such plants do not bolt after vernalization and exhibit a non-bolting phenotype in which the vegetative growth continuous.

"Vernalization" refers to the process by which floral induction in some plants is promoted by exposing the plants to chilling for a certain period of time.

As used herein, the phrase "phenotypic trait" refers to the appearance or other detectable characteristic of an individual, resulting from the interaction of its genome with the environment.

"Phenotype" is understood within the scope of the invention to refer to a distinguishable characteristic(s) of a genetically controlled trait.

A "coding sequence" is a nucleic acid sequence that is transcribed into RNA, such as mRNA, rRNA, tRNA, snRNA, sense RNA or antisense RNA. Preferably the RNA is then translated in an organism to produce a protein. It may constitute an "uninterrupted coding sequence", i.e., lacking an intron, such as in a cDNA, or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

A "gene" is a defined region that is located within a genome and that, besides the aforementioned coding nucleic acid sequence, comprises other, primarily regulatory, nucleic acid sequences responsible for the control of the expression, that is to say the transcription and translation, of the coding portion. A gene may also comprise other 5' and 3' untranslated sequences and termination sequences. Further elements that may be present are, for example, introns.

The term "gene of interest" refers to any gene which, when transferred to a plant, confers upon the plant a desired characteristic or phenotype, such as, for example, antibiotic resistance, virus resistance, insect resistance, disease resistance, or resistance to other pests, herbicide tolerance, improved nutritional value, improved performance in an industrial process or altered reproductive capability.

"Genotype" as used herein is the genetic material inherited from parent sugar beet plants not all of which is necessarily expressed in the descendant sugar beet plants. The genotype refers to the heterologous genetic material transformed into the genome of a plant as well as the genetic material flanking an inserted sequence.

The term "polynucleotide" thus refers to a polymer of DNA or RNA. The term "nucleic acid" refers to deoxyribonucleotides or ribonucleotides and polymers thereof which can be single- or double-stranded, optionally containing synthetic, non-natural or altered nucleotide bases capable of incorporation into DNA or RNA polymers, composed of monomers (nucleotides) containing a sugar, phosphate and a base which is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (BATZER et al., 1991; OHTSUKA et al., 1985; ROSSOLINI et al., 1994). A "nucleic acid fragment" is a fraction of a given nucleic acid molecule. In higher plants, deoxyribonucleic acid (DNA) is the genetic material while ribonucleic acid (RNA) is involved in the transfer of information contained within DNA into proteins. The term "nucleotide sequence" or "nucleic acid sequence" refers to a polymer of DNA or RNA which can be single or double-stranded, optionally containing synthetic, non-natural or altered nucleotide bases capable of incorporation into DNA or RNA polymers. The terms "nucleic acid" or "nucleic acid sequence" may also be used interchangeably with gene, cDNA, DNA and RNA encoded by a gene.

The term "isolated", when used in the context of the nucleic acid molecules of the present invention, refers to a nucleic acid sequence that is identified within and isolated/separated from its chromosomal nucleic acid sequence context within the respective source organism. An isolated nucleic acid is not a nucleic acid as it occurs in its natural context, if it indeed has a naturally occurring counterpart. In contrast, non-isolated nucleic acids are nucleic acids such as DNA and RNA, which are found in the state they exist in nature. For example, a given DNA sequence (e.g., a gene) is found on the host cell chromosome in proximity to neighboring genes. The isolated nucleic acid sequence may be present in single-stranded or double-stranded form. Alternatively, it may contain both the sense and antisense strands (i.e., the nucleic acid sequence may be double-stranded). In a preferred embodiment, the nucleic acid molecules of the present invention are understood to be isolated.

The term "heterologous" when used in reference to a gene or nucleic acid refers to a gene encoding a factor that is not in its natural environment (i.e., has been altered by the hand of man). For example, a heterologous gene may include a gene from one species introduced into another species. A heterologous gene may also include a gene native to an organism that has been altered in some way (e.g., mutated, added in multiple copies, linked to a non-native promoter or enhancer sequence, etc.). Heterologous genes further may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). In one aspect of the invention, heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed). Further, a "heterologous" nucleotide sequence is a nucleotide sequence not naturally associated with a host cell into which it is introduced, including non-naturally occurring multiple copies of a naturally occurring nucleic acid sequence.

A "homologous" nucleotide sequence is a nucleotide sequence naturally associated with a host cell into which it is introduced.

The term "chimeric construct" as used herein refers to construct of two or more nucleic acid sequences of different origin assembled into a single nucleic acid molecule. The term chimeric construct refers to any construct that contains (1) DNA sequences, including regulatory and coding sequences that are not found together in nature (i.e., at least one of nucleotide sequences is heterologous with respect to at least one of its other nucleotide sequences), or (2) sequences encoding parts of proteins not naturally adjoined, or (3) parts of promoters that are not naturally adjoined. Further, a chimeric construct may comprise regulatory sequences and coding sequences that are derived from different sources, or comprise regulatory sequences and coding sequences derived from the same source, but arranged in a manner different from that found in nature. In a preferred aspect of the present invention the chimeric construct comprises an expression cassette comprising a nucleic acid sequence of the present invention under the control of regulatory elements, particularly under the control of regulatory elements functional in plants.

"Expression cassette" as used herein means a nucleic acid molecule capable of directing expression of a particular nucleotide sequence or sequences in an appropriate host cell, comprising a promoter operably linked to the nucleotide sequence or sequences of interest which is/are operably linked to termination signals. It also typically comprises sequences required for proper translation of the nucleotide sequence(s). The expression cassette may also comprise sequences not necessary in the direct expression of a nucleotide sequence of interest but which are present due to convenient restriction sites for removal of the cassette from an expression vector. The expression cassette comprising the nucleotide sequence(s) of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e. the particular nucleic acid sequence of the expression cassette does not occur naturally in the host cell and must have been introduced into the host cell or an ancestor of the host cell by a transformation process known in the art. The expression of the nucleotide sequence(s) in the expression cassette is generally under the control of a promoter. In the case of a multicellular organism, such as a plant, the promoter can also be specific to a particular tissue, or organ, or stage of development. An expression cassette, or fragment thereof, can also be referred to as "inserted sequence" or "insertion sequence" when transformed into a plant.

The terms "protein," "peptide" and "polypeptide" are used interchangeably herein.

The term "promoter" refers to a nucleotide sequence, usually upstream (5') of its coding sequence, which controls the expression of the coding sequence by providing the recognition for RNA polymerase and other factors required for proper transcription.

"Constitutive promoter" refers to a promoter that is able to express the open reading frame (ORF) that it controls in all or nearly all of the plant tissues during all or nearly all developmental stages of the plant (referred to as "constitutive expression"). Each of the transcription-activating elements do not exhibit an absolute tissue-specificity, but mediate transcriptional activation in most plant parts at a level of ≥1% of the level reached in the part of the plant in which transcription is most active.

"Regulated promoter" refers to promoters that direct gene expression not constitutively, but in a temporally- and/or spatially-regulated manner, and includes both tissue-specific and inducible promoters. It includes natural and synthetic sequences as well as sequences which may be a combination of synthetic and natural sequences. Different promoters may direct the expression of a gene in different tissues or cell types, or at different stages of development, or in response to different environmental conditions.

"Tissue-specific promoter" refers to regulated promoters that are not expressed in all plant cells but only in one or more cell types in specific organs (such as leaves or seeds), specific tissues (such as embryo or cotyledon), or specific cell types (such as leaf parenchyma or seed storage cells). These also include promoters that are temporally regulated, such as in early or late embryogenesis, during fruit ripening in developing seeds or fruit, in fully differentiated leaf, or at the onset of senescence.

"Inducible promoter" refers to those regulated promoters that can be turned on in one or more cell types by an external stimulus, such as a chemical, light, hormone, stress, or a pathogen.

"Operably linked" refers to the association of nucleic acid sequences on a single nucleic acid fragment so that the function of one affects the function of the other. For example, a promoter is operably linked with a coding sequence or functional RNA when it is capable of affecting the expression of that coding sequence or functional RNA (i.e., that the coding sequence or functional RNA is under the transcriptional control of the promoter). Coding sequences in sense or antisense orientation can be operably linked to regulatory sequences.

"Primers" as used herein are isolated nucleic acids that are capable of becoming annealed to a complementary target DNA strand by nucleic acid hybridization to form a hybrid between the primer and the target DNA strand, then becoming extended along the target DNA strand by a polymerase, such as DNA polymerase. Primer pairs or sets can be used for amplification of a nucleic acid molecule, for example, by the polymerase chain reaction (PCR) or other conventional nucleic acid amplification methods.

"PCR" or "Polymerase chain reaction" is understood within the scope of the invention to refer to a method of producing relatively large amounts of specific regions of DNA, thereby making possible various analyses that are based on those regions.

"PCR primer" or "primer" is understood within the scope of the invention to refer to short fragments of isolated single-stranded DNA used in the PCR amplification of specific regions of DNA. They are annealed to a complimentary target DNA strand by nucleic acid hybridization to form a hybrid between the primer and the target DNA strand, and are then extended along the target DNA strand by a polymerase, such as DNA polymerase. Primer pairs or sets can be used for amplification of a nucleic acid molecule, for example, by the polymerase chain reaction (PCR) or other conventional nucleic-acid amplification methods. Primers are generally between 10 and 15 nucleotides or more in length. Primers can also be at least 20 nucleotides or more in length, or at least 25 nucleotides or more, or at least 30 nucleotides or more in length. Such primers hybridize specifically to a target sequence under high stringency hybridization conditions. Primers according to the present invention may have complete sequence complementarity with the target sequence. It is to be understood that the length of the primers of the present invention can be any numerical value between the values specified herein. Thus, primers being generally between 10 and 15 nucleotides or more in length encompass primer having a length of 10, 11, 12, 13, 14, or 15 nucleotides, whereas the expression "at least 20 nucleotides" further includes primer having a length of 16, 17, 18, 19, or nucleotides. The same applies to the expressions "at least 25 nucleotides or more" and "at least 30 nucleotides or more in length".

As used herein, the term "amplified" means the construction of multiple copies of a nucleic acid molecule or multiple copies complementary to the nucleic acid molecule using at least one of the nucleic acid molecules as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology: Principles and Applications, PERSING et al., Ed., American Society for Microbiology, Washington, D.C. (1993). The product of amplification is termed an amplicon.

A "probe" is an isolated nucleic acid to which is attached a conventional detectable label or reporter molecule, such as a radioactive isotope, ligand, chemiluminescent agent, fluorescent label or enzyme. Such a probe is complimentary to a strand of a target nucleic acid. Probes according to the present invention include not only deoxyribonucleic or ribonucleic acids but also polyamides and other probe materials that bind specifically to a target DNA sequence and can be used to detect the presence of that target DNA sequence.

Primers and probes are generally between 10 and 15 nucleotides or more in length. Primers and probes can also be at least 20 nucleotides or more in length, or at least 25 nucleotides or more, or at least 30 nucleotides or more in length. Such primers and probes hybridize specifically to a target sequence under stringent hybridization conditions. Primers and probes according to the present invention may have complete sequence complementarity with the target sequence, although probes differing from the target sequence and which retain the ability to hybridize to target sequences may be designed by conventional methods. It is to be understood that the length of the primers and probes of the present invention can be any numerical value between the values specified herein. Thus, primers and probes being generally between 10 and 15 nucleotides or more in length encompass primer and probes having a length of 10, 11, 12, 13, 14, or 15 nucleotides, whereas the expression "at least 20 nucleotides" further includes primer and probes having a length of 16, 17, 18, 19, or nucleotides. The same applies to the expressions "at least 25 nucleotides or more" and "at least 30 nucleotides or more in length".

Substantially identical or homologous in the context of two nucleic acid or protein sequences refers to two or more sequences or subsequences that have at least 60%, preferably at least 80%, more preferably at least 90%, even more preferably at least 95%, and most preferably at least 99% nucleotide or amino acid residue identity, when compared and aligned for maximum correspondence, as measured using one of the sequence comparison algorithms mentioned below or by visual inspection. In particular, the substantial identity exists over a region of the sequences that is at least about 50 residues in length, more particularly over a region of at least about 100 residues, and especially the sequences are substantially identical over at least about 150 residues. In a specific embodiment, the sequences are substantially identical over the entire length of the coding regions. Furthermore, substantially identical nucleic acid or protein sequences perform substantially the same function.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of SMITH & WATERMAN (1981), by the homology alignment algorithm of NEEDLEMAN & WUNSCH (1970), by the search for similarity method of PEARSON & LIPMAN (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, AUSUBEL et al., infra). One example of an algorithm that is suitable for determining percent sequence identity and sequence similarity is the BLAST algorithm, which is described in ALTSCHUL et al. (1990).

Another indication that two nucleic acid sequences are substantially identical is that the two molecules hybridize to each other under stringent hybridization conditions.

"Stringent hybridization conditions" and "stringent hybridization wash conditions" in the context of nucleic acid hybridization experiments, such as Southern and Northern hybridizations, are sequence dependent, and are different under different environmental parameters. Longer sequences hybridize specifically at higher temperatures. An extensive guide to the hybridization of nucleic acids is found in TIJSSEN (1993). In the context of the present invention the term "hybridize" refers to conventional hybridization conditions, preferably to hybridization conditions at which 5×SSPE, 1% SDS, 1×Denhardts solution is used as a solution and/or hybridization temperatures are between 35° C. and 70° C., preferably 65° C. After hybridization, washing is preferably carried out first with 2×SSC, 1% SDS and subsequently with 0.2×SSC at temperatures between 35° C. and 75° C., particularly between 45° C. and 65° C., but especially at 59° C. (regarding the definition of SSPE, SSC and Denhardt's solution see Sambrook et al.). High stringency hybridization conditions as for instance described in Sambrook et al, loc. cit., are particularly preferred. Particularly preferred stringent hybridization conditions are for instance present if hybridization and washing occur at 65° C. as indicated above. Non-stringent hybridization conditions for instance with hybridization and washing carried out at 45° C. are less preferred and at 35° C. even less.

A further indication that two nucleic acid sequences or proteins are substantially identical is that the protein encoded by the first nucleic acid is immunologically cross reactive with, or specifically binds to, the protein encoded by the second nucleic acid. Thus, a protein is typically substantially identical to a second protein, for example, where the two proteins differ only by conservative substitutions.

"Transformation" is a process for introducing heterologous nucleic acid into a host cell or organism. In particular, "transformation" means the stable integration of a DNA molecule into the genome of an organism of interest.

"Transformed/transgenic/recombinant" refers to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

The term transgenic "event" refers to a recombinant plant produced by transformation and regeneration of a single plant cell with heterologous DNA, for example, an expression cassette that includes a gene of interest. The term "event" refers to the original transformant and/or progeny of the transformant that include the heterologous DNA. The term "event" also refers to progeny produced by a sexual outcross between the transformant and another sugar beet line. Even after repeated backcrossing to a recurrent parent, the inserted DNA and the flanking DNA from the transformed parent is present in the progeny of the cross at the same chromosomal location. Normally, transformation of plant tissue produces multiple events, each of which represent insertion of a DNA construct into a different location in the genome of a plant cell. Based on the expression of the transgene or other desirable characteristics, a particular event is selected.

A "transgene" refers to a gene introduced into the genome of an organism by genetic manipulation in order to alter its genotype. Transgenes may include, for example, genes that are either heterologous or homologous to the genes of a particular plant to be transformed. Additionally, transgenes may comprise native genes inserted into a non-native organism, or chimeric genes.

As used herein, gene or trait "stacking" is combining desired genes or traits into one transgenic plant line. Plant breeders stack transgenic traits by making crosses between parents that each have a desired trait and then identifying offspring that have both of these desired traits (so-called "breeding stacks"). Another way to stack genes is by transferring two or more genes into the cell nucleus of a plant at the same time during transformation. Another way to stack genes is by re-transforming a transgenic plant with another gene of interest. For example, gene stacking can be used to combine two different insect resistance traits, an insect resistance trait and a disease resistance trait, or a herbicide resistance trait (such as, for example, Bt11). The use of a selectable marker in addition to a gene of interest would also be considered gene stacking.

A "transgenic plant" is a plant having one or more plant cells that contain an expression vector.

A "plant" is any plant at any stage of development, particularly a seed plant.

The term "cultivated" with respect to plants means any plant of the respective species that are commercially grown for their production. The term "cultivated plant" includes those plants which has been brought into cultivation and have been selectively bred for growing purposes. Cultivated plants exclude those wild-type species which comprise the trait of the present invention as a natural trait and/or part of their natural genetics.

A "plant cell" is a structural and physiological unit of a plant comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, anthers, ovaries, zygotes, seeds, cuttings, cell or tissue cultures, or any other part or product of a plant. This also includes callus or callus tissue as well as extracts (such as extracts from taproots) or samples. Generally, the term "plant material" refers to a relatively unprocessed plant material, having intact plant cells.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

The terms "messenger RNA" or "mRNA" refer to RNA that does not comprise introns and that can be translated into a protein by the cell.

"cDNA" refers to a single-stranded or a double-stranded DNA that is complementary to and derived from mRNA.

The term "expression" when used with reference to a nucleic acid sequence, such as a gene, ORF or portion thereof, or a transgene in plants, refers to the process of converting genetic information encoded in a gene into RNA (e.g., mRNA, rRNA, tRNA, or snRNA) through "transcription" of the gene (i.e., via the enzymatic action of an RNA polymerase), and into protein where applicable (e.g. if a gene encodes a protein), through "translation" of mRNA. Gene expression can be regulated at many stages in the process. For example, in the case of antisense or dsRNA constructs, respectively, expression may refer to the transcription of the antisense RNA only or the dsRNA only. In addition, expression refers to the transcription and stable accumulation of sense (mRNA) or functional RNA. Expression may also refer to the production of protein.

"Downregulation" refers to the level of expression in transgenic cells or organisms that is lower than the levels of expression in normal or untransformed (non-transgenic) cells or organisms. In particular, "downregulation" refers to a decrease in the level of protein and/or mRNA product from a target gene in the range of between 20% and 100%, particularly of between 40% and 80%, more particularly of between 50% and 90%, even more particularly of between 60% and 95%, but especially of between 75% and 98% and up to 100%. "Suppression" refers to the absence of protein and/or mRNA product from a target gene (i.e., complete downregulation of expression of a target gene). The consequences of inhibition can be confirmed by examination of the outward properties of the cell or organism or by biochemical and gene expression detection techniques known to those skilled in the art. For example, downregulation and/or suppression of FT gene expression is indicated by an absence or delay of the vernalization response in a growing sugar beet plant.

"Overexpression" or "upregulation" refers to the level of expression in transgenic cells or organisms that exceeds levels of expression in normal or untransformed (non-transgenic) cells or organisms. In particular, "overexpression" or "upregulation" refers to an increase in the level of protein and/or mRNA product from a target gene in the range of between 20% and 100%, particularly of between 40% and 80%, more particularly of between 50% and 90%, even more particularly of between 60% and 95%, but especially of between 75% and 98% and up to 100%.

The term "co-suppression" refers to a transgenic approach for silencing gene expression also referred to as "sense downregulation". In this approach expression of the gene of interest is inhibited by expression of a transgenic sequence having homology to the gene of interest through the interaction of native and transgenic mRNA.

The term "tilling" (or "TILLING" for "Targeting-Induced Local Lesions IN Genomes") refers to a non-transgenic approach for the generation of null or knockout alleles of a certain gene of interest (McCallum et al., 2000).

"Antisense inhibition" refers to the production of antisense RNA transcripts capable of suppressing the expression of protein from an endogenous gene or a transgene.

"Gene silencing" refers to homology-dependent suppression of genes, transgenes, or endogenous nuclear genes. Gene silencing may be transcriptional, when the suppression is due to decreased transcription of the affected genes, or posttranscriptional, when the suppression is due to increased turnover (degradation) of RNA species homologous to the affected genes. Gene silencing includes virus-induced gene silencing.

"RNA interference" (RNAi) refers to the process of sequence-specific posttranscriptional gene silencing in plants and animals mediated by short interfering RNAs (siRNAs) involving dsRNA. Various terms such as siRNA, target RNA molecule, dicer or ribonuclease III enzyme are concepts known to those skilled in the art and full descriptions of these terms and other concepts pertinent to RNAi can be found in the literature. For reference, several terms pertinent to RNAi are defined below. However, it is understood that any particular hypothesis describing the mechanisms of RNAi are not necessary to practice the present invention.

"dsRNA" or "double-stranded RNA" is RNA with two complementary strands, which directs the sequence-specific degradation of mRNA through a process known as RNA interference (RNAi). dsRNA is cut into siRNAs interfering with the expression of a specific gene.

"Inverted repeat" refers to a nucleotide sequence found at two sites on the same nucleic acid sequence, but in opposite orientation.

The term "siRNAs" refers to so-called short interfering RNAs. In some embodiments, siRNAs comprise a duplex, or double-stranded region, of a length of about 21-23 nucleotides; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "target RNA molecule" refers to an RNA molecule to which at least one strand of the short double-stranded region of a siRNA is homologous or complementary. Typically, when such homology or complementary is about 100%, the siRNA is able to silence or inhibit expression of the target RNA molecule. Although it is believed that processed mRNA is a target of siRNA, the present invention is not limited to any particular hypothesis, and such hypotheses are not necessary to practice the present invention. Thus, it is contemplated that other RNA molecules may also be targets of siRNA. Such RNA target molecules include unprocessed mRNA, ribosomal RNA, and viral RNA genomes. It is not necessary that there is 100% homology between the target RNA molecule and the dsRNA over the whole length of the dsRNA, but the hairpins of the dsRNA should comprise stretches of at least 21 nucleotides, preferably of at least 23 nucleotides, more preferred of at least 50 nucleotides, even more preferred of at least 500 nucleotides, most preferred of at least 700 nucleotides, and up to 1000 nucleotides having at least 95%, preferred 100% homology between the target RNA molecule.

The "RNA-inducing silencing complex" (RISC) mediates cleavage of single-stranded RNA having sequence complementary to the antisense strands of siRNA duplex. Cleavage of the target RNA takes place in the middle of the region of complementary to the antisense strand of the siRNA duplex (ELBASHIR et al., 2001).

The term "sufficient complementary" means that a first or a second strand sequence of RNA introduced into a plant cell is capable of hybridizing or annealing sufficiently to the RNA produced by a target gene (mRNA) under conditions found in the cytoplasm of said plant cell, such that suppression of the expression of the target gene is triggered. For example, the sequence of the first or second strand sequence of RNA that binds to the mRNA produced by the target gene is at least 50% identical to the corresponding mRNA sequence of the target gene, more desirably at least 70% identical, yet more desirable is at least 90% identical and even more desirable is at least 95% identical.

It is to be understood that the percentage of identity between the sequence of the first or second strand sequence of RNA and the mRNA produced by the target gene, which is in the range of between at least 70% identity and at least 95% identity, can be any numerical value within this range.

"Fermentation" as used herein refers to the process of transforming an organic molecule into another molecule using a microorganism. If not indicated otherwise the term "fermentation" includes anaerobic and aerobic fermentation.

The term "biofuel" as used herein refers to any biofuel produced by aerobic or anaerobic fermentation of plant material. A non-limiting example of a biofuel obtained by aerobic fermentation is bioethanol. Biofuels that can be obtained by anaerobic fermentation include, but are not limited to biogas and/or biodiesel. Methods of aerobic and/or anaerobic fermentation are known to the person skilled in the art.

The term "sugar" refers to fermentable monosaccharides disaccharides, and trisaccharides, particularly to mono- and disaccharides. Thus, in the present invention sugars include, but are not limited to, sucrose, fructose, glucose, galactose, maltose, lactose, and mannose.

The term "bioplastic" refers to plastic produced from a biological source. "Biological source" in this context covers both plastic produced directly in transgenic plants and plastic produced from biomass, such as, for example, vegetable oil, starch or sugar by chemical processes either in chemical plants or in microorganism. The term "bioplastic" includes, but is not limited to starch based plastics, polylactic acid (PLA) plastics, poly-3-hydrobutyrate (PHB), polyamide 11 (PA 11), bio-derived polyethylene and bioplastics produced in genetically modified organisms (such as bacteria or plants).

DETAILED DESCRIPTION OF THE INVENTION

The present invention discloses nucleotide sequences of FT genes of sugar beet (also referred to as *Beta* FT genes) involved in the vernalization response of sugar beet as well as transgenic sugar beet plants and methods for modulating sugar beet bolting resistance by suppressing FT gene expression in sugar beet.

The cultivated sugar beet (*Beta vulgaris* ssp. *vulgaris* L.) is a biennial plant which forms a storage root and a leaf rosette in the first year. Shoot elongation (bolting) and flower formation starts after a period of low temperature. This cold-induced vernalization that leads to bolting of the plants is an obligate part of the complete sugar beet life cycle. Details on vernalization and its effect on biennial sugar beet have been described in the literature (e.g., JAGGARD et al., 1983).

However, details on the genetic basis of the vernalization response and bolting in sugar beet are mainly still missing. In particular, the genes as the key players in the vernalization response in sugar beet have not yet been identified so far.

Functional analysis conducted in the model organism *Arabidopsis thaliana* has allowed to distinguish four distinct flowering pathways (LEVY & DEAN, 1998). These four pathways can be assigned to environmental stimuli, such as photoperiodic and vernalization promotion pathways, or inherent developmental signals, e.g. autonomous promotion and floral repression pathways. In some species the timing of flowering is primarily influenced by environmental factors, such as photoperiod, light quality/quantity, vernalization and water or nutrient availability. One locus of interest that has been identified in *Arabidopsis* is the FLOWERING LOCUS T (FT). This locus was discovered in naturally occurring late-flowering ecotypes of *Arabidopsis* (KOORNEEF et al., 1991). FT is a small protein of 23 KD and is homologous to phosphatidylethanolamine-binding proteins, which are also called RAF kinase inhibitor proteins (KARDAILSKY et al., 1999; KOBAYASHI et al., 1999).

In an attempt to identify genes being involved in bolting in sugar beet in response to vernalization, the present inventors concentrated on identifying the orthologue of the FT gene of *Arabidopsis* in sugar beet. Conserved nucleotide sequences in the cDNA sequences of the FT orthologues of *Arabidopsis* (AtFT), *Citrus* (CiFT), wheat (TaFT), and rice (OsHd3a) were identified by aligning these sequences (FIG. 1). Using degenerated primers targeting the conserved amino acid sequence motif "KPRVEIGG" located at exon 1 (amino acid residues 51 to 58) according to the sequence of the FT protein from *Arabidopsis* as well as exon 3 immediately downstream of the splicing site of intron 2 targeting amino acid sequence motif "LVTDIPATT" (amino acid residues 89 to 98) two nucleotide fragments were amplified in a PCR reaction using total RNA extracted from sugar beet leaves as a template (see Example 1). Subsequent sequence analysis of the amplification fragments revealed two BvFT homologues having different sequences. These homologues are referred to as BvFT1 fragment (SEQ ID NO: 3) and BvFT2 fragment (SEQ ID NO: 4), respectively. Both share strong sequence homology to the FT protein from *Arabidopsis* (FIGS. 4 and 5).

Figure 2:
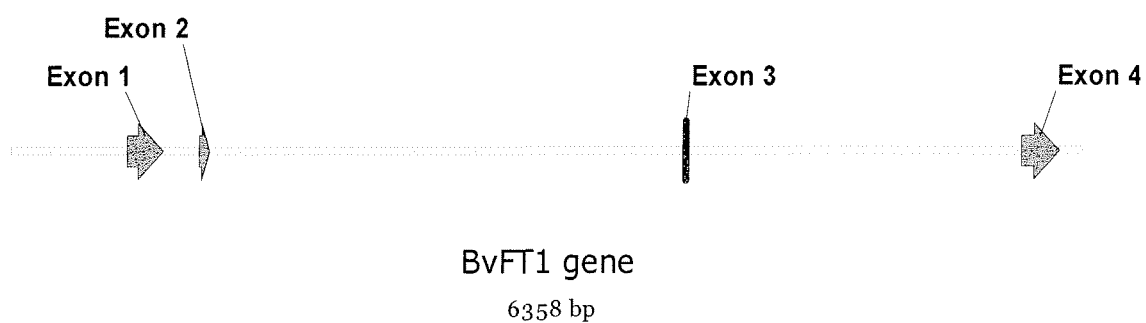
FIG. 2 is a schematic representation of the BvFT1 gene structure.
Figure 3:
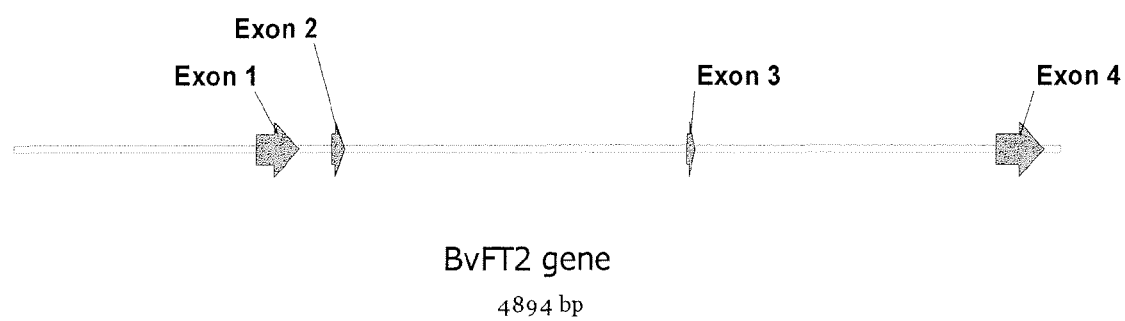
FIG. 3 is a schematic representation of the BvFT2 gene structure.

Based on both the BvFT1 fragment and the BvFT2 fragment, respectively, BAC clones were identified comprising these sequences and were sequenced (see Example 1). Based on the alignment of the genomic sequences to both cDNA fragments and on sequence homology to the FT gene from *Arabidopsis*, the putative gene structure of the *Beta* FT genes comprising introns and exons was predicted (FIGS. 2 and 3). The coding sequence and amino acid sequence of BvFT1 are shown as SEQ ID NOs: 6 and 7, respectively. The coding sequence and amino acid sequence of BvFT2 are set forth as SEQ ID NOs: 9 and 10, respectively. Alignment of the full-length amino acid sequences of BvFT1 and BvFT2 to the protein sequence of the FT from *Arabidopsis* further confirmed the strong sequence homology of 72% identity and 82% similarity (for BvFT1) and 75% identity and 88% similarity (for BvFT2), respectively (FIGS. 4 and 5; Example 1).

Expression analysis surprisingly showed opposite expression patterns of these two genes in sugar beet plant leaves across different developmental stages in biennial and annual sugar beet plants (see Example 3). BvFT1 transcripts were readily detected in leaves of early vegetative stages in biennial plants, but expression levels dropped after vernalization and remained low throughout the transition from vegetative to reproductive phases, whereas expression of the BvFT2 gene increased dramatically prior to the first visible signs of bolting. This increase in expression of BvFT2 observed prior to bolting time is very similar to the expression profile of the FT gene in *Arabidopsis*, which suggest that BvFT2 is in fact the sugar beet orthologue of the FT gene of *Arabidopsis*. An analysis of expression of these genes across the diurnal cycle with different photoperiods (see Example 4) further supported this suggestion.

On the other hand, expression studies in *Arabidopsis* plants overexpressing the coding regions of BvFT1 (see Example 5) surprisingly showed that BvFT1 rather acts like AtTFL1 (RATCLIFFE et al., 1998), an inhibitor of flowering in *Arabidopsis*. This illustrates the fact that BvFT1 surprisingly acts more like a repressor than a promoter of flowering despite its clustering into the FT-like clade in the phylogeny tree of the FT gene family (FIG. 6). Ectopic expression of BvFT2 in *Arabidopsis* on the other hand resulted in an extreme early-flowering phenotype. These opposite functions of BvFT1 and BvFT2 as shown, i.e. repression of flowering conferred by BvFT1 versus promotion of flowering conferred by BvFT2, is consistent with their opposing expression profiles surprisingly found in sugar beet as described above.

The present inventors could show that both FT genes from sugar beet have expression profiles that are actively regulated depending on the developmental stage of the plant with very contrasting expression profiles and further play a key role in the vernalization response in sugar beet. Both genes can thus be used for engineering bolting resistance in sugar beet plants by delaying or suppressing the vernalization response.

In a first aspect the present invention relates to nucleic acid sequences of the FT genes of *Beta vulgaris*, which have a sequence identity of at least 70% to a nucleic acid sequence selected from the group of nucleic acid sequences as set forth in any of SEQ ID NOs: 5, 6, 8, or 9, or which comprise at least 15 consecutive nucleotides of a nucleic acid sequence selected from the group of nucleic acid sequences as set forth in any of SEQ ID NOs: 5, 6, 8, or 9, or which hybridize under stringent conditions to a nucleic acid sequence selected from the group of nucleic acid sequences as set forth in any of SEQ ID NOs: 5, 6, 8, or 9.

Preferably the nucleic acid sequence of the present invention is an isolated nucleic acid.

In a preferred embodiment the nucleic acid sequences of the present invention have a sequence identity of at least 70%, preferably of at least 80%, more preferred of at least 85%, even more preferred of at least 90%, even more preferred of at least 95%, and most preferred of at least 98% to a nucleic acid sequence selected from the group of nucleic acid sequences as set forth in any of SEQ ID NOs: 5, 6, 8, or 9.

With regard to sequence identity it is understood that throughout the present invention all individual numerical values, which fall into a range as claimed should likewise be covered by the present invention. For example, the expression "at least 70%" as mentioned herein before thus also covers 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, whereas the expression "at least 80%" as mentioned herein before also covers 81%, 82%, 83%, 84%, 85%, 86%, 87%, 88%, 89%, 90%, 91%, 92%, 93%, 94%, 95%, 96%, 97%, 98%, 99%. The same applies to the expressions "at least 85%", "at least 90%", "at least 95%", and "at least 98%".

In a preferred embodiment the nucleic acids sequences of the present invention comprise at least 20, preferably at least 25, more preferred at least 35, even more preferred at least 50, yet more preferred at least 75, and most preferred at least 100 contiguous nucleotides of a nucleic acid sequence selected from the group of nucleic acid sequences as set forth in any one of SEQ ID NOs: 5, 6, 8, or 9. It is to be understood that throughout the present invention the term "at least x nucleotides" encompasses nucleic acid molecules having any numerical value starting with x and above. For example, the term "at least 15 nucleotides" is intended to encompass nucleic acid molecules having 15, 16, 17, 18, 19, 20, and more nucleotides present in a nucleic acid sequence as set forth in any one of SEQ ID NOs: 5, 6, 8, or 9. Similarly, the term "at least 20 nucleotides" is intended to encompass nucleic acid molecules having 21, 22, 23, 24, 25, 26, and more nucleotides present in a nucleic acid sequence as set forth in any one of SEQ ID NOs: 5, 6, 8, or 9. The same applies to the other ranges mentioned hereinabove.

In a further preferred embodiment, the nucleic acid sequence of the present invention described hereinbefore hybridizes under stringent conditions, more preferred under highly stringent conditions to a nucleic acid sequence selected from the group of nucleic acid sequences as set forth in any one of SEQ ID NOs: 5, 6, 8, or 9.

In a further preferred embodiment of this aspect, the nucleic acid sequence of the present invention comprises a nucleic acid sequence as set forth in any of SEQ ID NOs: 5, 6, 8, or 9 and the complements thereof.

The nucleic acid sequences of the present invention including any corresponding anti-sense constructs can be operably linked to any promoter that is functional within the plant host including the promoter sequences described herein below or mutants thereof.

The invention further provides polypeptides which are encoded by the nucleic acid sequences of the present invention described hereinbefore.

In a preferred embodiment of this aspect the polypeptide of the present invention have an amino acid sequence selected from the group of amino acid sequences as depicted in SEQ ID NOs: 7 or 10.

Modulation of expression of the nucleic acids of the present invention results in bolting resistance in sugar beet, particularly when expressed in a transgenic plant such as a transgenic sugar beet plant (see, e.g., Examples 7 and 8).

In a further aspect, the nucleotide sequences of the present invention may thus be used in a transgenic approach for producing transgenic sugar beet plants comprising said polynucleotides stably integrated into the sugar beet genome. In particular, upon expression from the genome, the expression product can be used to confer bolting resistance by modulating the vernalization response of the sugar beet plant. Based on the contrasting expression profile as mentioned above this can be achieved by either suppressing or down-regulating expression of the BvFT2 gene or by upregulating expression of the BvFT1 gene, or a combination of both.

In one aspect the nucleic acid sequences of the present invention are assembled into chimeric constructs which contain the nucleic acid sequence to be expressed in the transgenic plant under the control of regulatory elements, preferably under the control of regulatory elements functional in plants. Methods for assembling such chimeric constructs are well known to the person skilled in the art. The chimeric constructs of the present invention are a nucleic acid sequence capable of directing expression of a particular nucleotide sequence (i.e., the nucleotide sequences of the present invention) in an appropriate host cell, like a plant cell.

Expression of the nucleotide sequences comprised in the chimeric constructs of the present invention in sugar beet leads to modulation of expression of BvFT1 and/or BvFT2 thus conferring bolting resistance by delaying or suppressing the vernalization response.

In the chimeric constructs of the present invention, the nucleic acids are preferably comprised in expression cassettes comprising regulatory elements for expression of the nucleotide sequences in a host cell capable of expressing the nucleotide sequences. Such regulatory elements usually comprise promoter and termination signals and preferably also comprise elements allowing efficient translation of polypeptides encoded by the nucleic acids of the present invention.

The chimeric constructs of the present invention comprising the nucleic acids of the present invention are capable of replication in particular host cells, preferably as extrachromosomal molecules, and are therefore used to amplify the nucleic acids of this invention in the host cells. In yet another embodiment, such chimeric constructs are viral vectors and are used for replication of the nucleotide sequences in particular host cells, e.g. plant cells. Recombinant vectors are also used for transformation of the nucleotide sequences of this invention into host cells, whereby the nucleotide sequences are stably integrated into the DNA of a transgenic host.

In one preferred embodiment, the chimeric construct of the present invention further comprises a selection marker gene which allows discrimination between transformed and non-transformed plant material in a selection process. Marker genes that can be used for selection purposes and their application are known to the person skilled in the art.

In one aspect the chimeric construct of the present invention is provided for transgenic downregulation or suppression of expression of the endogenous BvFT2 gene in sugar beet.

The downregulation or suppression of expression of BvFT2 leads to a delay of the vernalization response in a growing sugar beet plant or causes the sugar beet plant to develop a non-bolting phenotype, which means that the sugar beet plant does no longer respond to a typical vernalization period of 18 weeks by bolting and subsequent flowering, but to the contrary continue vegetative growth (non-bolting) and develop a normal taproot. Plants expressing said delayed vernalization response or said non-bolting phenotype can be easily identified and selected by applying a phenotypic analysis experiment employing standardized growth conditions.

The invention comprises various strategies for reducing the expression, amount, activity and/or function of the endogenous BvFT2 gene in sugar beet. The skilled worker appreciates the fact that a number of various methods are available in order to influence the expression, amount, activity and/or function of genes in a plant in the desired way. Examples which may be mentioned but which are not limiting are:

"Sense" Suppression

Alteration of the expression of a gene in a plant (i.e., the BvFT2 gene in sugar beet), preferably reduction of its expression, is obtained by "sense" suppression (referenced in e.g., JORGENSEN et al. (1996) *Plant Mol. Biol.* 31, 957-973). In this case, the entirety or a portion of a nucleotide sequence of the present invention is comprised in a DNA molecule. The DNA molecule is preferably operatively linked to a promoter functional in a cell comprising the target gene, preferably a plant cell, and introduced into the cell, in which the nucleotide sequence is expressible. The nucleotide sequence is inserted in the DNA molecule in the "sense orientation", meaning that the coding strand of the nucleotide sequence can be transcribed. In a preferred embodiment, the nucleotide sequence is fully translatable and all the genetic information comprised in the nucleotide sequence, or portion thereof, is translated into a polypeptide. In another preferred embodiment, the nucleotide sequence is partially translatable and a short peptide is translated. In a preferred embodiment, this is achieved by inserting at least one premature stop codon in the nucleotide sequence, which brings translation to a halt. In another more preferred embodiment, the nucleotide sequence is transcribed but no translation product is being made. This is usually achieved by removing the start codon, e.g., the "ATG", of the polypeptide encoded by the nucleotide sequence. In a further preferred embodiment, the DNA molecule comprising the nucleotide sequence, or a portion thereof, is stably integrated in the genome of the plant cell. In another preferred embodiment, the DNA molecule comprising the nucleotide sequence, or a portion thereof, is comprised in an extrachromosomally replicating molecule.

In transgenic plants containing one of the DNA molecules described immediately above, the expression of the nucleotide sequence corresponding to the nucleotide sequence comprised in the DNA molecule is preferably reduced. Preferably, the nucleotide sequence in the DNA molecule is at least 80% identical to the nucleotide sequence the expression of which is reduced, more preferably it is at least 90% identical, yet more preferably at least 95% identical, and most preferably at least 99% identical.

"Anti-Sense" Suppression

In another preferred embodiment, the alteration of the expression of gene in a plant (i.e., the BvFT2 gene in sugar beet), preferably the reduction of its expression is obtained by "anti-sense" suppression. The entirety or a portion of a nucleotide sequence of the present invention is comprised in a DNA molecule. The DNA molecule is preferably operatively linked to a promoter functional in a plant cell, and introduced in a plant cell, in which the nucleotide sequence is expressible. The nucleotide sequence is inserted in the DNA molecule in the "anti-sense orientation", meaning that the reverse complement (also called sometimes non-coding strand) of the nucleotide sequence can be transcribed. In a preferred embodiment, the DNA molecule comprising the nucleotide sequence, or a portion thereof, is stably integrated in the genome of the plant cell. In another preferred embodiment the DNA molecule comprising the nucleotide sequence, or a portion thereof, is comprised in an extrachromosomally replicating molecule. Several publications describing this approach are cited for further illustration (GREEN et al., *Ann. Rev. Biochem.* 55:569-597 (1986); VAN DER KROL et al., *Antisense Nuc. Acids & Proteins*, pp. 125-141 (1991); ABEL et al., *Proc. Natl. Acad. Sci.* USA 86:6949-6952 (1989); ECKER et al., *Proc. Natl. Acad. Sci.* USA 83:5372-5376 (1986)).

In transgenic plants containing one of the DNA molecules described immediately above, the expression of the nucleotide sequence corresponding to the nucleotide sequence comprised in the DNA molecule is preferably reduced. Preferably, the nucleotide sequence in the DNA molecule is at least 80% identical to the nucleotide sequence the expression of which is reduced, more preferably it is at least 90% identical, yet more preferably at least 95% identical, and most preferably at least 99% identical.

Homologous Recombination

In another preferred embodiment, at least one genomic copy corresponding to a nucleotide sequence of the present invention is modified in the genome of the plant by homologous recombination as further illustrated in PASZKOWSKI et al., *EMBO Journal* 7:4021-26 (1988). This technique uses the property of homologous sequences to recognize each other and to exchange nucleotide sequences between each by a process known in the art as homologous recombination. Homologous recombination can occur between the chromosomal copy of a nucleotide sequence in a cell and an incoming copy of the nucleotide sequence introduced in the cell by transformation. Specific modifications are thus accurately introduced in the chromosomal copy of the nucleotide sequence. In one embodiment, the regulatory elements of the respective plant gene (i.e., the BvFT2 gene in sugar beet) are modified. Such regulatory elements are easily obtainable by screening a genomic library using the nucleotide sequence of the present invention, or a portion thereof, as a probe. The existing regulatory elements are replaced by different regulatory elements, thus altering expression of the nucleotide sequence, or they are mutated or deleted, thus abolishing the expression of the nucleotide sequence. In another embodiment, the nucleotide sequence is modified by deletion of a part of the nucleotide sequence or the entire nucleotide sequence, or by mutation. Expression of a mutated polypeptide in a plant cell is also contemplated in the present invention. More recent refinements of this technique to disrupt endogenous plant genes have been described (KEMPIN et al., *Nature* 389:802-803 (1997) and MIAO & LAM, *Plant J.*, 7:359-365 (1995). The skilled worker knows numerous possible processes for the modification of genomic sequences in a targeted manner. These include, in particular, processes such as the generation of knockout mutants by means of targeted homologous recombination, for example, by generating stop codons, shifts in the reading frame etc. (HOHN & PUCHTA (1999) *Proc Natl Acad Sci USA* 96:8321-8323) or the targeted deletion or inversion of sequences by means of, for example, sequence-specific recombinases or nucleases. In another preferred embodiment, a mutation in the chromosomal copy of a nucleotide sequence is introduced by transforming a cell with a chimeric oligonucleotide composed of a contiguous stretch of RNA and DNA residues in a duplex conformation with double hairpin caps on the ends. An additional feature of the oligonucleotide is for example the presence of 2'-O-methylation at the RNA residues. The RNA/DNA sequence is designed to align with the sequence of a chromosomal copy of a nucleotide sequence of the present invention and to contain the desired nucleotide change. For example, this technique is further illustrated in U.S. Pat. No. 5,501,967 and ZHU et al. (1999) *Proc. Natl. Acad. Sci.* USA 96: 8768-8773.

Ribozymes

In a further embodiment, the RNA coding for a polypeptide of the present invention is cleaved by a catalytic RNA, or ribozyme, specific for such RNA. The ribozyme is expressed in transgenic plants and results in reduced amounts of RNA coding for the polypeptide of the present invention in plant cells, thus leading to reduced amounts of polypeptide accumulated in the cells. This method is further illustrated in U.S. Pat. No. 4,987,071.

Dominant-Negative Mutants

In another preferred embodiment, the activity of the polypeptide encoded by the nucleotide sequences of this invention is changed. This is achieved by expression of dominant negative mutants of the proteins in transgenic plants, leading to the loss of activity of the endogenous protein.

Aptamers

In a further embodiment, the activity of polypeptide of the present invention is inhibited by expressing in transgenic plants nucleic acid ligands, so-called aptamers, which specifically bind to the protein. Aptamers are preferentially obtained by the SELEX (Systematic Evolution of Ligands by EXponential Enrichment) method. In the SELEX method, a candidate mixture of single stranded nucleic acids having regions of randomized sequence is contacted with the protein and those nucleic acids having an increased affinity to the target are partitioned from the remainder of the candidate mixture. The partitioned nucleic acids are amplified to yield a ligand enriched mixture. After several iterations a nucleic acid with optimal affinity to the polypeptide is obtained and is used for expression in transgenic plants. This method is further illustrated in U.S. Pat. No. 5,270,163.

Zinc Finger Proteins

A zinc finger protein that binds a nucleotide sequence of the present invention or to its regulatory region is also used to alter expression of the nucleotide sequence. Preferably, transcription of the nucleotide sequence is reduced or increased. Zinc finger proteins are for example described in BEERLI et al. (1998) *PNAS* 95:14628-14633., or in WO 95/19431, WO 98/54311, or WO 96/06166, all incorporated herein by reference in their entirety.

In a preferred embodiment transgenic downregulation or suppression of expression of the endogenous BvFT2 of sugar beet is achieved by a method selected from either dsRNA, antisense suppression or co-suppression.

Alteration of the expression of a plant gene of interest (e.g., BvFT2 in sugar beet) is also obtained by dsRNA interference (RNAi). The process of gene regulation by means of double-stranded RNA ("double-stranded RNA interference"; dsRNAi) has been described many times for animal and plant organisms (e.g., MATZKE et al. (2000) *Plant Mol Biol* 43:401-415; FIRE et al. (1998) *Nature* 391:806-811; WO 99/32619; WO 99/53050; WO 00/68374; WO 00/44914; WO 00/44895; WO 00/49035; WO 00/63364, all incorporated herein by reference in their entirety.). The processes and methods described in the references indicated are hereby explicitly referred to dsRNAi processes are based on the phenomenon that simultaneously introducing the complementary strand and contour strand of a gene transcript suppresses expression of the corresponding gene in a highly efficient manner. As currently understood, the dsRNA are processed by Dicer by cutting the dsRNA into short interfering RNA (siRNA). Preferably, the phenotype caused is very similar to that of a corresponding knockout mutant (WATERHOUSE et al. (1998) *Proc Natl Acad Sci USA* 95:13959-64). The dsRNAi process has proved to be particularly efficient and advantageous in reducing marker protein expression. Interfering with sugar beet BvFT2 gene mRNA expression results in suppression or delay of the sugar beet vernalization response. A delay in the vernalization response results in the sugar beet plant continuing its vegetative growth and to develop a normal taproot.

Within the scope of the invention, double-stranded RNA (dsRNA) molecule means preferably one or more ribonucleic acid sequences which, owing to complementary sequences, are theoretically (e.g., according to the base pair rules by Watson and Crick) and/or actually (e.g., owing to hybridization experiments in vitro and/or in vivo) capable of forming double-stranded RNA structures. The skilled worker is aware of the fact that the formation of double-stranded RNA structures represents a state of equilibrium. Preferably, the ratio of double-stranded molecules to corresponding dissociated forms is at least 1 to 10, preferably 1:1, particularly preferably 5:1, most preferably 10:1.

In one aspect the present invention thus further relates to double-stranded RNA molecules which, when introduced into a sugar beet plant (or into a cell, tissue, organ or propagation material derived therefrom) cause the reduction of expression of at least the endogenous BvFT2. The double-stranded RNA molecule for reducing expression of at least the endogenous BvFT2 here preferably comprises (a) a "sense" RNA strand comprising at least one ribonucleotide sequence which is essentially identical to at least a part of the "sense" RNA transcript of at least the endogenous BvFT2, and (b) an "antisense" RNA strand which is essentially, preferably fully, complementary to the RNA sense strand under (a).

"Essentially identical" means that the dsRNA sequence may also have insertions, deletions and also individual point mutations in comparison with the target gene sequence and nevertheless causes an efficient reduction in expression. The homology (as defined herein below) between the "sense" strand of an inhibitory dsRNA and at least one part of the "sense" RNA transcript of a target gene nucleic acid sequence (or between the "antisense" strand of the complementary strand of a nucleic acid sequence of a target gene) is preferably at least 75%, preferably at least 80%, very particularly preferably at least 90%, most preferably 100%.

A 100% sequence identity between dsRNA and a marker protein gene transcript is not absolutely necessary in order to cause an efficient reduction in target gene expression. Consequently, the process is advantageously tolerant toward sequence deviations as may be present due to genetic mutations, polymorphisms or evolutionary divergences. Thus it is possible, for example, using the dsRNA which has been generated starting from the sequence of the target gene of the first organism, to suppress target gene expression in a second organism. For this purpose, the dsRNA preferably includes sequence regions of the target gene transcripts which correspond to conserved regions.

Said conserved regions may be readily derived from sequence comparisons.

Alternatively, an "essentially identical" dsRNA may also be defined as a nucleic acid sequence capable of hybridizing with part of a target gene transcript.

"Essentially complementary" means that the "antisense" RNA strand may also have insertions, deletions and also individual point mutations in comparison with the complement of this "sense" RNA strand. The homology between the "antisense" RNA strand and the complement of the "sense" RNA strand is preferably at least 80%, preferably at least 90%, very particularly preferably at least 95%, most preferably 100%.

"Part of the "sense" RNA transcript" of a nucleic acid sequence of a target gene means fragments of an RNA or mRNA transcribed or transcribable from a nucleic acid sequence of a target gene. In this context, the fragments have a sequence length of preferably at least 20 bases, preferably at least 50 bases, particularly preferably at least 100 bases, very particularly preferably at least 200 bases, most preferably at least 500 bases. The complete transcribable RNA or mRNA is also included. Included are also sequences such as those which may be transcribed under artificial conditions from regions of a target gene which are otherwise, under natural conditions, not transcribed, such as promoter regions, for example.

The dsRNA may consist of one or more strands of polyribonucleotides. Naturally, in order to achieve the same purpose, it is also possible to introduce a plurality of individual dsRNA molecules which comprise in each case one of the above-defined ribonucleotide sequence sections into the cell or the organism. The double-stranded dsRNA structure may be formed starting from two complementary, separate RNA strands or, preferably, starting from a single, self-complementary RNA strand. In this case, the "sense" RNA strand and the "antisense" RNA strand are preferably connected covalently to one another in the form of an inverted "repeat".

As described in WO 99/53050, for example, the dsRNA may also comprise a hairpin structure by connecting the "sense" and the "antisense" strands by a connecting sequence ("linker"; for example an intron). Preference is given to the self-complementary dsRNA structures, since they require only the expression of an RNA sequence and always comprise the complementary RNA strands in an equimolar ratio. The connecting sequence may is preferably an intron (e.g., an intron of the potato ST-LS1 gene; VANCANNEYT et al. (1990)).

The nucleic acid sequence coding for a dsRNA may include further elements such as, for example, transcription termination signals or polyadenylation signals.

Bringing together, if intended, the two strands of the dsRNA in a cell or plant may be achieved by way of example in the following way: (a) transformation of the cell or plant with a vector comprising both expression cassettes, (b) cotransformation of the cell or plant with two vectors, one of which comprises the expression cassettes containing the "sense" strand and the other one of which comprises the expression cassettes containing the "antisense" strand. The formation of the RNA duplex may be initiated either outside or inside the cell.

The dsRNA may be synthesized either in vivo or in vitro. For this purpose, a DNA sequence coding for a dsRNA may be inserted into an expression cassette under the control of at least one genetic control element (such as, for example, a promoter). A polyadenylation is not necessary and neither need any elements for initiating a translation be present. Preference is given to the expression cassette for the dsRNA targeting the target gene being present on the transformation construct or the transformation vector. For this purpose, the expression cassettes coding for the "antisense" strand and/or the "sense" strand of a dsRNA targeting the target gene or for the self-complementary strand of the dsRNA are preferably inserted into a transformation vector and introduced into the plant cell by using the processes described below. A stable insertion into the genome may be advantageous for the process of the invention but is not absolutely necessary. Since a dsRNA causes a long-term effect, transient expression is also sufficient in many cases. The dsRNA may also be part of the RNA to be expressed by the nucleic acid sequence to be inserted by fusing it, for example, to the 3'-untranslated part of said RNA.

The dsRNA may be introduced in an amount which makes possible at least one copy per cell. Higher amounts (e.g. at least 5, 10, 100, 500 or 1000 copies per cell) may, if appropriate, cause a more efficient reduction.

In one preferred embodiment the chimeric construct of the present invention comprises a heterologous DNA which codes for a first RNA strand and a second RNA strand and which, when transcribed, yields a first RNA nucleotide sequence and a second RNA nucleotide sequence, wherein said first RNA strand is sufficiently complimentary to at least a portion of a RNA strand of the endogenous BvFT2 gene in sugar beet to hybridize or anneal to the RNA strand produced by said endogenous BvFT2 gene so as to cause downregulation or suppression of the expression of the endogenous BvFT2 gene, and wherein said first RNA nucleotide sequence and said second RNA nucleotide sequence form a double stranded RNA, wherein the double stranded RNA upon expression in a sugar beet plant participate in RNA interference of expression of said endogenous BvFT2 gene thereby causing downregulation or suppression of expression of the endogenous BvFT2 gene.

In a specific embodiment of the invention, a chimeric construct is provided comprising an inverted repeat, which, when transcribed in the sugar beet cell, forms a double stranded RNA molecule in said sugar beet plant cell comprising said first and second RNA strands, wherein said double stranded RNA molecule triggers BvFT2 silencing. In a further preferred embodiment the inverted repeat is preferably operatively linked to a constitutive promoter.

In another embodiment of the invention, the first or second RNA strand sequences encoded by the heterologous DNA comprised in the chimeric construct of the present invention are sufficiently complementary or identical to a nucleotide sequence of RNA produced by the BvFT2 gene to trigger RNA silencing. The term "sufficient complementary" means that the first or second RNA strand sequences are capable of hybridizing or annealing sufficiently to the RNA produced by the endogenous BvFT2 gene (mRNA) under conditions found in the cytoplasm, such that RNAi is triggered which leads to a suppression of the expression of the endogenous BvFT2 gene. This suppression of the BvFT2 gene causes the sugar beet plant to develop a non-bolting phenotype which means that the sugar beet plant does no longer respond to a typical vernalization period of 18 weeks by bolting and subsequent flowering, but to the contrary continue vegetative growth (non-bolting) and develop a normal taproot.

In one embodiment, the chimeric construct of the invention includes heterologous DNA encoding a nucleic acid strand that is sufficiently complementary or identical to at least a portion of the BvFT2 gene. It is known that if the siRNA strand is identical, the target mRNA is cut into useless RNA fragments. However, if the pairing is less than identical, the RISC complex binds to the mRNA and is capable of blocking ribosome movement along the native mRNA, but is not capable of cutting the mRNA into small fragments. Nevertheless, in either case, expression of the gene from which the mRNA is transcribed is silenced and thus no protein encoded by the target gene (e.g., BvFT2) is formed. The present invention, therefore, further includes one strand of the siRNA that is sufficiently complementary or identical to a corresponding sequence of the mRNA transcribed from the endogenous BvFT2 gene whose expression is altered. For example, the strand of the siRNA that binds to the mRNA is preferably at least 50% identical to the corresponding mRNA sequence of the endogenous BvFT2 gene, more preferably at least 70% identical, yet more preferably at least 80% identical, even more preferably at least 90% identical and most preferably at least 95% identical.

It is to be understood that the percentage of identity between the one strand of the siRNA that is sufficiently complementary or identical to a corresponding sequence of the mRNA transcribed from the endogenous BvFT2 gene whose expression is altered and the mRNA produced by the endogenous BvFT2 gene, which is in the range of between at least 50% identity and at least 95% identity, can be any numerical value within this range.

It is known that RNA sequences with insertions, deletions, and single point mutations relative to the target sequence are also effective for target gene expression suppression. Sequence identity between the siRNA molecule and the target gene transcription product (for example, the target gene mRNA) may be optimized by alignment algorithms known in the art and calculating the percent similarity between the nucleotide sequences. Alternatively, the siRNA molecule of the present invention may be identified not by its sequence similarity to the target molecule, but by its capability to hybridize to and silence expression of the target sequence.

In a further preferred embodiment of the present invention, the chimeric construct comprises a heterologous DNA which encodes a nucleic acid sequence either having sequence identity of at least 70% to a nucleic acid sequence of the present invention set forth as SEQ ID NOs: 8 or 9, or comprising at least 15 consecutive nucleotides of a nucleic acid sequence of the present invention set forth as SEQ ID NOs: 8 or 9, or hybridizes under stringent conditions to a nucleic acid sequence of the present invention set forth as SEQ ID NOs: 8 or 9.

In further embodiments, the sequence identity between the nucleic acid sequence encoded by the heterologous DNA comprised in the chimeric construct of the present invention is preferably at least 80%, yet more preferably at least 85%, even more preferably at least 90% identical and most preferably at least 95%.

In one embodiment of the invention, the chimeric construct comprises a heterologous DNA encoding a first RNA nucleotide sequence that is between 18 and 30 nucleotides in length and a second RNA nucleotide sequence that hybridizes to the first sequence under biological conditions, such as those conditions found in the cell, particularly in the cytoplasm and/or the nucleus of the cell. Said first RNA molecule has a degree of complementarity to a portion of RNA of the endogenous BvFT2 gene of sugar beet which allows said first RNA strand to hybridize or to anneal to the portion of said BvFT2 gene such as to result in the suppression of the expression of the endogenous BvFT2 gene.

In yet another embodiment of the invention, the chimeric construct comprises a heterologous DNA encoding a first RNA nucleotide sequence that is between 21 and 25 nucleotides in length and a second RNA strand that hybridizes to the first sequence under biological conditions, such as those conditions found cell, particularly in the cytoplasm and/or the nucleus of the cell. Said first RNA molecule has a degree of complementarity to a portion of RNA of the endogenous BvFT2 gene of sugar beet which allows said first RNA strand to hybridize or to anneal to the portion of said BvFT2 gene such as to result in the suppression of the expression of the endogenous BvFT2 gene.

In yet another embodiment of the invention, the chimeric construct comprises a heterologous DNA encoding a first RNA nucleotide sequence that is between 21 and 23 nucleotides in length and a second RNA strand that hybridizes to the first sequence under biological conditions, such as those conditions found cell, particularly in the cytoplasm and/or the nucleus of the cell. Said first RNA molecule has a degree of complementarity to a portion of RNA of the endogenous BvFT2 gene of sugar beet which allows said first RNA strand to hybridize or to anneal to the portion of said BvFT2 gene such as to result in the suppression of the expression of the endogenous BvFT2 gene Generally, the invention includes chimeric constructs of any length, provided that the heterologous DNA comprised in the chimeric construct plays a role in triggering RNA interference of the sugar beet BvFT2 gene mRNA.

In another embodiment, the invention relates to a chimeric construct as described herein before comprising a heterologous DNA obtainable from a 0.27 Kb cDNA fragment consisting of exon 4 of the BvFT2 gene as described hereinbefore in a PCR reaction using forward primer HiNK6382 with the nucleotide sequence 5'-CTATGGATCCGCATT-TAATAAAATCTCTTTCAATG-3' (SEQ ID NO: 44) and reverse primer HiNK6384 with the nucleotide sequence 5'-GTAGAAGCAGAAACTTACCTGCCAA-GAAGTTGTCTGCTATG-3' (SEQ ID NO: 45). This embodiment is further outlines in Example 7.

In this specific embodiment of the invention the chimeric construct preferably comprises a heterologous DNA as depicted by nucleotides 8747 to 9046 of SEQ ID NO: 33.

In one embodiment, the invention relates to a chimeric construct of the present invention as described herein before for BvFT2, wherein said heterologous DNA comprised in said chimeric construct is inserted between a promoter and terminator, wherein said heterologous DNA is obtainable by a. amplifying a 0.27 Kb cDNA fragment derived from exon 4 of the BvFT2 gene in a PCR reaction using forward primer HiNK6382 with the nucleotide sequence 5'-CTATG-GATCCGCATTTAATAAAATCTCTTTCAATG-3' (SEQ ID NO: 44) and reverse primer HiNK6384 with the nucleotide sequence 5'-GTAGAAGCAGAAACTTACCTGC-CAAGAAGTTGTCTGCTATG-3' (SEQ ID NO: 45) and sugar beet cDNA as template, wherein the sugar beet cDNA was obtained from total RNA extracted from sugar beet leaves in a reverse transcriptase reaction using the 3' RACE ADAPTER with the nucleotide sequence 5'-GCGAGCACAGAATTAATACGACTCACTATAGGT12VN23' (SEQ ID NO: 33) as a primer;

b. by amplifying a 0.19 Kb fragment comprising the ST-LS1 intron and flanking splicing sites using forward primer HiNK6383 with the nucleotide sequence 5'-CATAGCA-GACAACTTCTTGGCAGGTAAGTTTCTGCTTCTAC-3' (SEQ ID NO: 46) and reverse primer HiNK529 with the nucleotide sequence 5'-ATCCAACCGCGGACCTGCA-CATCAACAA3' (SEQ ID NO: 40) and potato DNA containing the potato St-LS1 intron as template;

c. fusing the amplification products obtained in steps a) and b) to each other by means of a second round of PCR using primers HiNK6382 and HiNK529 and using a mix of both amplification products as template, yielding a fusion product of 0.47 Kb in length;

d. amplifying the 0.27 Kb BvFT2 fragment a second time, using forward primer HiNK6385 with the nucleotide sequence 5'-TAAATCCGCGGGCCAAGAAGTTGTCT-GCTATG-3' (SEQ ID NO: 47) and reverse primer HiNK6386 with the nucleotide sequence 5'-CTATTTGTC-GACGCATTTAATAAAATCTCTTTC-3' (SEQ ID NO: 48) and the sugar beet cDNA obtained in subsection a) above as template;

e. fusing both fragments at the Sac II restriction sites to create an inverted repeat for the BvFT2 sequence separated by the intron from the potato ST-LS1 gene.

Details on the assembly of this preferred embodiment of the present invention are outlines in Example 7 below. The intron sequence of the ST-LS1 gene is easily obtainable from potato DNA by methods known to the person skilled in the art. The Sac II restriction sites used for the assembly of the heterologous DNA are introduced by using the specific primers outlined above.

In a specific embodiment, a chimeric construct of the present invention for BvFT2 silencing is provided comprising a sequence as depicted by the nucleotide sequence of SEQ ID NO: 33.

In further specific embodiments of the present invention, the inverted repeat comprised in the chimeric construct is operatively linked to a constitutive promoter, particularly a CaMV promoter.

In addition to the use of coding sequences for the suppression of gene expression by means of post-transcriptional gene silencing (PTGS) or RNAi as described hereinabove, the use of non-coding sequence, especially promoter sequences, has been reported for the downregulation of gene expression. Transgenic expression of dsRNA containing promoter sequences triggers de novo methylation of the target promoter region and the concomitant silencing that promoter, a process also known as transcriptional gene silencing (TGS) (METTE et al., 2000; SIJEN et al., 2001; HEILERSIG et al., 2006). The assembly of promoter fragments into gene cassettes for their antisense, sense or dsRNA expression accordingly proved successful in downregulating the transcription of the cognate gene in several plant species. People skilled in the art will appreciate that the sequences of the promoter regions of both BvFT1 and BvFT2 as disclosed in SEQ ID No: 5 and SEQ ID No: 8, respectively, can likewise be exploited for the construction of chimveric constructs and the subsequent transcriptional gene silencing of the corresponding BvFT homologue.

Yet an alternative strategy for the suppression of the expression of BvFT2 is the use of artificial miRNA as originally described by SCHWAB et al., (2006) and ALVAREZ et al., (2006). Artificial microRNAs (amiRNAs) are single-stranded 21mer RNAs, which are not normally found in plants and which are processed from endogenous miRNA precursors. Their sequences are designed according to the determinants of plant miRNA target selection, such that the 21mer specifically silences its intended target gene, i.e. BvFT2 in the present invention. More details on the use and design of artificial miRNA as tool, for example, for the suppression of BvFT2 in sugar beer, are provided by OSSOWSKI et al., (2008) with reference to the website of the Web MicroRNA Designer wmd3.weigelworld.org/cgi-bin/webapp.cgi).

Further (non-limiting) examples for strategies for reducing the expression, amount, activity and/or function of the endogenous BvFT2 gene in sugar beet covered by the present invention are the following:

Insertion of a DNA Molecule (Insertional Mutagenesis)

In another preferred embodiment, a DNA molecule is inserted into a chromosomal copy of a nucleotide sequence of the present invention, or into a regulatory region thereof. Preferably, such DNA molecule comprises a transposable element capable of transposition in a plant cell, such as, e.g., Ac/Ds, Em/Spm, mutator. Alternatively, the DNA molecule comprises a T-DNA border of an *Agrobacterium* T-DNA. The DNA molecule may also comprise a recombinase or integrase recognition site which can be used to remove part of the DNA molecule from the chromosome of the plant cell. Methods of insertional mutagenesis using T-DNA, transposons, oligonucleotides or other methods known to those skilled in the art are also encompassed. Methods of using T-DNA and transposon for insertional mutagenesis are described in WINKLER et al. (1989) *Methods Mol. Biol.* 82:129-136 and MARTIENSSEN (1998) *PNAS* 95:2021-2026, incorporated herein by reference in their entireties. Further suitable methods are the introduction of nonsense mutations into endogenous target genes, for example, by means of introducing RNA/DNA oligonucleotides into the plant (ZHU et al. (2000) *Nat Biotechnol* 18(5): 555-558). Point mutations may also be generated by means of DNA-RNA hybrids which are also known as "chimeraplasty" (COLE-STRAUSS et al. (1999) *Nucl Acids Res* 27(5):1323-1330; KMIEC (1999) *Gene therapy American Scientist* 87(3):240-247).

Deletion Mutagenesis

In yet another embodiment, a mutation of a nucleic acid molecule of the present invention is created in the genomic copy of the sequence in the cell or plant by deletion of a portion of the nucleotide sequence or regulator sequence. Methods of deletion mutagenesis are known to those skilled in the art. See, for example, MIAO et al. (1995) *Plant J.* 7:359. The activity or amount of the expression of a target gene may also be reduced by a targeted deletion in the target gene, for example by sequence-specific induction of DNA double-strand breaks at a recognition sequence for specific induction of DNA double-strand breaks in or close to the nucleic acid sequence of the target gene.

In yet another embodiment, this deletion is created at random in a large population of plants by chemical mutagenesis or irradiation and a plant with a deletion in a gene of the present invention is isolated by forward or reverse genetics. Irradiation with fast neutrons or gamma rays is known to cause deletion mutations in plants (SILVERSTONE et al. (1998) *Plant Cell,* 10:155-169; BRUGGEMANN et al. (1996) *Plant J.,* 10:755-760; REDEI &a KONCZ in Methods in *Arabidopsis* Research, World Scientific Press (1992), pp. 16-82). Deletion mutations in a gene of the present invention can be recovered in a reverse genetics strategy using PCR with pooled sets of genomic DNAs as has been shown in *C. elegans* (LIU et al., (1999), *Genome Research,* 9:859-867.). A forward genetics strategy would involve mutagenesis of a line displaying PTGS followed by screening the M2 progeny for the absence of PTGS. Among these mutants would be expected to be some that disrupt a gene of the present invention. This could be assessed by Southern blot or PCR for a gene of the present invention with genomic DNA from these mutants.

In addition to the processes for the introduction of mutations mentioned above people skilled in the art will appreciate that numerous techniques for mutagenesis are available for the generation of null or knockout alleles of a gene of interest. The methods can be categorized by their physical properties and by their mutagenic effects. Gamma irradiation and fast neutron irradiation cause chromosome breakage often resulting in translocations and deletions while ethylmethanesulfonate (EMS) is highly efficient for inducing transitions by alkylation of guanine bases. The Targeting-Induced Local Lesions IN Genomes (TILLING) strategy relies on large populations of mutagenized plants which are screened for point mutations within a given sequence (MCCALLUM et al., 2000). During recent years TILLING projects have been successfully been launched for several major crop species, including sugar beet (HOHMANN et al., 2005). With the cloning and sequence analysis of a gene of interest (e.g., the BvFT2 genes of the present invention), targeted mutagenesis approaches such as TILLING now become feasible as source for mutant alleles of these genes.

In still another embodiment, the expression of the nucleotide sequence of the present invention is altered in every cell of a plant. This is for example obtained though homologous recombination or by insertion in the chromosome. This is also for example obtained by expressing a sense or antisense RNA, zinc finger protein or ribozyme under the control of a promoter capable of expressing the sense or antisense RNA, zinc finger protein or ribozyme in every cell of a plant. Constructs for expression of the sense or antisense RNA, zinc finger protein or ribozyme, or for overexpression of a nucleotide sequence of the present invention, are prepared and transformed into a plant cell according to the teachings of the present invention, e.g., as described infra.

A combined application is also conceivable. Further methods are known to the skilled worker and may comprise hindering or stopping the processing of the target gene, the transport of the protein encoded by the target gene or of its mRNA, the inhibition of ribosome attachment, the inhibition of RNA splicing, the induction of an enzyme degrading target gene RNA and/or the inhibition of translational elongation or termination.

In one further aspect the chimeric construct of the present invention is provided for transgenic transgenic upregulation of expression of the endogenous BvFT1 gene in sugar beet.

The upregulation of expression of the endogenous BvFT1 gene leads to a delay of the vernalization response in a growing sugar beet plant or causes the sugar beet plant to develop a non-bolting phenotype, which means that the sugar beet plant does no longer respond to a typical vernalization period of 18 weeks by bolting and subsequent flowering, but to the contrary continue vegetative growth (non-bolting) and develop a normal taproot. Plants expressing said delayed vernalization response or said non-bolting phenotype can be easily identified and selected by applying a phenotypic analysis experiment employing standardized growth conditions.

The invention comprises various strategies for increasing the expression, amount, activity and/or function of the endogenous BvFT1 gene in sugar beet. The skilled worker appreciates the fact that a number of various methods are available in order to upregulate expression of a target gene in plants or otherwise influence the amount, activity and/or function of genes in a plant in the desired way. In this context it has to be noted that the term "upregulation" is to be construed as including overexpression.

In one embodiment of this aspect the chimeric construct of the present invention for transgenic upregulation of expression of the endogenous BvFT1 gene comprises a nucleotide sequence encoding the BvFT1 gene or parts of it, wherein said nucleotide sequence encoding the BvFT1 gene or parts of it has a nucleotide sequence which either has a sequence identity of at least 70% to or hybridizes under stringent conditions to a nucleic acid sequence of the present invention set forth as SEQ ID NOs: 5 or 6, wherein said nucleotide sequence encoding the BvFT1 gene or parts of it is operably linked to regulatory sequences such that upon expression in a plant upregulation of expression of the endogenous BvFT1 gene is caused.

In further embodiments, the sequence identity between the nucleic acid sequence encoding the BvFT1 gene or parts of it comprised in the chimeric construct of the present invention and the nucleic acid sequence of the present invention set forth as SEQ ID NOs: 5 or 6 is preferably at least 80%, yet more preferably at least 85%, even more preferably at least 90% identical and most preferably at least 95%.

In another preferred embodiment the of the present invention is the coding sequence of the BvFT1 gene of sugar beet as set forth in SEQ ID NO: 6. Said nucleotide sequence encoding the BvFT1 gene comprised in the chimeric construct is also represented by nucleotides 2076 to 2615 of SEQ ID NO: 34.

In yet another preferred embodiment the chimeric construct of the present invention for transgenic upregulation of expression of the endogenous BvFT1 gene as described hereinbefore comprises the nucleotide sequence as depicted in SEQ ID NO: 34.

Preferably the heterologous DNA comprised in the chimeric construct of the present invention for transgenic upregulation of expression of the endogenous BvFT1 gene is operatively linked to a constitutive promoter, preferably a Ubi3 promoter from *Arabidopsis*.

Obtaining sufficient levels of transgene expression in the appropriate plant tissues is an important aspect in the production of genetically engineered crops. Expression of heterologous DNA sequences in a plant host is dependent upon the presence of an operably linked promoter that is functional within the plant host. Choice of the promoter sequence will determine when and where within the organism the heterologous DNA sequence is expressed.

Different promoters may direct the expression of a gene in different tissues or cell types, or at different stages of development, or in response to different environmental conditions. New promoters of various types useful in plant cells are constantly being discovered, numerous examples may be found in the compilation by Okamuro et al. (1989). Typical regulated promoters useful in plants include, but are not limited to safener-inducible promoters, promoters derived from the tetracycline-inducible system, promoters derived from salicylate-inducible systems, promoters derived from alcohol-inducible systems, promoters derived from glucocorticoid-inducible system, promoters derived from pathogen-inducible systems, and promoters derived from ecdysone-inducible systems. For example, a plant promoter fragment may be employed which will direct expression of the gene in all tissue; of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill. Such genes include for example, the AP2 gene, ACT11 from *Arabidopsis* (HUANG et al. (1996) *Plant Mol. Biol.* 33:125-139), Cat3 from *Arabidopsis* (GenBank No. U43147, ZHONG et al., (1996) *Mol. Gen. Genet.* 251:196-203), the gene encoding stearoyl-acyl carrier protein desaturase from *Brassica napus* (Genbank No. X74782, SOLOCOMBE et al. (1994) Plant Physiol. 104:1167-1176), GPc1 from maize (GenBank No. X15596, MARTINEZ et al. (1989) J. Mol. Biol 208:551-565), and Gpc2 from maize (GenBank No. U45855, MANJUNATH et al. (1997) Plant Mol. Biol. 33:97-112).

Alternatively, the plant promoter may direct expression of the nucleic acid molecules or chimeric constructs of the present invention in a specific tissue or may be otherwise under more precise environmental or developmental control. Examples of environmental conditions that may affect transcription by inducible promoters include anaerobic conditions, elevated temperature, or the presence of light. Such promoters are referred to here as "inducible" or "tissue-specific" promoters. One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

Examples of promoters under developmental control include promoters that initiate transcription only (or primarily only) in certain tissues, such as fruit, ovules, seeds, or flowers. As used herein a seed-specific or preferential promoter is one which directs expression specifically or preferentially in seed tissues, such promoters may be, for example, ovule-specific, embryo-specific, endosperm-specific, integument-specific, seed coat-specific, or some combination thereof. Examples include a promoter from the ovule-specific BEL1 gene described in REISER et al. (1995) (*Cell* 83:735-742; GenBank No. U39944). Other suitable seed specific promoters are derived from the following genes: MAC1 from maize (SHERIDAN et al. (1996) *Genetics* 142:1009-1020 (1996), Cat3 from maize (GenBank No. L05934, ABLER et al. (1993) *Plant Mol. Biol.* 22:10131-1038, the gene encoding oleosin 18 kD from maize (GenBank No, J05212, LEE et al. (1994) *Plant Mol. Biol.* 26:1981-1987), vivparous-1 from *Arabidopsis* (Genbank No. U93215), the gene encoding oleosin from *Arabidopsis* (Genbank No. Z17657), Atmyc1 from *Arabidopsis* (URAO et al. (1996) *Plant Mol. Biol.* 32:571-576, the 2s seed storage protein gene family from *Arabidopsis* (CONCEICAO et al. (1994) *Plant* 5:493-505), the gene encoding oleosin 20 kD from *Brassica napus* (GenBank No. M63985), napA from *Brassica napus* (GenBank No. J02798, JOSEFSSON et al. (1987) *JBL* 26:12196-1301), the napin gene family from *Brassica napus* (SJODAHL et al. (1995) *Planta* 197:264-271), the gene encoding the 2S storage protein from *Brassica napus* (DASGUPTA et al. (1993) *Gene* 133:301-302), the genes encoding oleosin A (Genbank No. U09118) and oleosin B (Genbank No. U09119) from soybean and the gene encoding low molecular weight sulphur rich protein from soybean (CHOI et al. (1995) *Mol Gen, Genet.* 246:266-268).

The term "promoter" further includes a minimal promoter that is a short DNA sequence comprised of a TATA box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors which control the effectiveness of transcription initiation in response to physiological or developmental conditions. The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative. Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

Alternatively, particular sequences which provide the promoter with desirable expression characteristics, or the promoter with expression enhancement activity, could be identified and these or similar sequences introduced into the sequences via mutation. It is further contemplated that one could mutagenize these sequences in order to enhance their expression of transgenes in a particular species.

Furthermore, it is contemplated that promoters combining elements from more than one promoter may be useful. For example, U.S. Pat. No. 5,491,288 discloses combining a Cauliflower Mosaic Virus (CaMV) promoter with a histone promoter. Thus, the elements from the promoters disclosed herein may be combined with elements from other promoters.

A variety of 5' and 3' transcriptional regulatory sequences are available for use in the present invention. Transcriptional terminators are responsible for the termination of transcription and correct mRNA polyadenylation. The 3' nontranslated regulatory DNA sequence preferably includes from about 50 to about 1,000, more preferably about 100 to about 1,000, nucleotide base pairs and contains plant transcriptional and translational termination sequences. Appropriate transcriptional terminators and those which are known to function in plants include the CaMV 35S terminator, the tml terminator, the nopaline synthase terminator, the pea rbcS E9 terminator, the terminator for the T7 transcript from the octopine synthase gene of *Agrobacterium tumefaciens*, and the 3' end of the protease inhibitor I or II genes from potato or tomato, although other 3' elements known to those of skill in the art can also be employed. Alternatively, one also could use a gamma coixin, oleosin 3 or other terminator from the genus *Coix*. Preferred 3' elements include those from the nopaline synthase gene of *Agrobacterium tumefaciens* (BEVAN et al., 1983), the terminator for the T7 transcript from the octopine synthase gene of *Agrobacterium tumefaciens*, and the 3' end of the protease inhibitor I or II genes from potato or tomato.

As the DNA sequence between the transcription initiation site and the start of the coding sequence, i.e., the untranslated leader sequence, can influence gene expression, one may also wish to employ a particular leader sequence. Preferred leader sequences are contemplated to include those which include sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will be most preferred.

Other sequences that have been found to enhance gene expression in transgenic plants include intron sequences (e.g., from Adh1, bronze1, actin1, actin 2 (WO 00/760067), or the sucrose synthase intron) and viral leader sequences (e.g., from TMV, MCMV and AMV). For example, a number of non-translated leader sequences derived from viruses are known to enhance expression. Specifically, leader sequences from Tobacco Mosaic Virus (TMV), Maize Chlorotic Mottle Virus (MCMV), and Alfalfa Mosaic Virus (AMV) have been shown to be effective in enhancing expression (e.g., GALLIE et al., 1987; SKUZESKI et al., 1990). Other leaders known in the art include but are not limited to: Picornavirus leaders, for example, EMCV leader (Encephalomyocarditis 5 non-coding region) (ELROY-STEIN et al., 1989); Potyvirus leaders, for example, TEV leader (Tobacco Etch Virus); MDMV leader (Maize Dwarf Mosaic Virus); Human immunoglobulin heavy-chain binding protein (BiP) leader, (MACEJAK et al., 1991); Untranslated leader from the coat protein mRNA of alfalfa mosaic virus (AMV RNA 4), (JOBLING et al., 1987; Tobacco mosaic virus leader (TMV), (GALLIE et al., 1989; and Maize Chlorotic Mottle Virus leader (MCMV) (LOMMEL et al., 1991. See also, DELLA-CIOPPA et al., 1987.

Regulatory elements such as Adh intron 1 (CALLIS et al., 1987), sucrose synthase intron (VASIL et al., 1989) or TMV omega element (GALLIE et al., 1989), may further be included where desired.

Examples of enhancers include elements from the CaMV 35S promoter, octopine synthase genes (ELLIS et al., 1987), the rice actin I gene, the maize alcohol dehydrogenase gene (CALLIS et al., 1987), the maize shrunken I gene (VASIL et al., 1989), TMV Omega element (GALLIE et al., 1989) and promoters from non-plant eukaryotes (e.g., yeast; MA et al., 1988).

Once completed, the chimeric constructs of the present invention comprising an expression cassette (e.g., an RNAi cassette for BvFT2) may be mobilized into a suitable vector for plant transformation, such as, for example, a binary vector, which may then be mobilized to sugar beet using one of the well known transformation techniques such as, for example, *Agrobacterium*-mediated transformation.

In further aspect the present invention thus provides a plant transformation vector and/or a plant expression vector comprising the nucleic acids of the present invention and/or the chimeric construct of the present invention described above.

In such vectors, the nucleic acids are preferably comprised in expression cassettes comprising regulatory elements for expression of the nucleotide sequences in a host cell capable of expressing the nucleotide sequences. Such regulatory elements usually comprise promoter and termination signals and preferably also comprise elements allowing efficient translation of polypeptides encoded by the nucleic acids of the present invention.

In yet another embodiment, such vectors are viral vectors and are used for replication of the nucleotide sequences in particular host cells, e.g. in plant cells.

Recombinant vectors are also used for transformation of the nucleotide sequences of this invention into host cells, whereby the nucleotide sequences are stably integrated into the DNA of a transgenic host.

It is particularly preferred to use the binary type vectors of Ti and Ri plasmids of *Agrobacterium* spp. Ti-derived vectors transform a wide variety of higher plants, including monocotyledonous and dicotyledonous plants, such as sugar beet, soybean, cotton, rape, tobacco, and rice (PACCIOTTI et al., 1985: BYRNE et al., 1987; SUKHAPINDA et al., 1987; LORZ et al., 1985; POTRYKUS, 1985; PARK et al., 1985: HIEI et al., 1994). The use of T-DNA to transform plant cells has received extensive study and is amply described (EP 120516; HOEKEMA, 1985; KNAUF, et al., 1983; and AN et al., 1985). For introduction into plants, the chimeric constructs of the invention can be inserted into binary vectors as described in the examples.

In one preferred embodiment of this aspect the plant transformation vector is a RNAi expression vector comprising the chimeric construct of the present invention as described hereinbefore. Preferably the RNAi expression vector comprises the chimeric construct having the nucleotide sequence as set forth in SEQ ID NO: 33. The plasmid map of this RNAi expression map is depicted in FIG. 15.

In a further embodiment the plant transformation vector is a plant expression vector comprising the chimeric construct of the present invention. Preferably the expression vector comprises the chimeric construct having the nucleotide sequence as set forth in SEQ ID NO: 34. The plasmid map of this RNAi expression map is depicted in FIG. 18.

Those skilled in the art will appreciate that the plant transformation vector or the plant expression vector of the present invention can also comprise more than one chimeric constructs. By employing such a plant transformation vector or plant expression vector, more than one nucleotide sequences can be introduced into the plant. Thus, for example, within the same vector two or more chimeric constructs for upregulation of expression of one or more genes can be inserted (one or more of those being, for example, the chimeric construct of the present invention for the modulation of expression of BvFT1). In another embodiment two or more chimeric constructs for downregulation or suppression of expression of one or more genes can be inserted (one or more of those, for example, being the chimeric construct of the present invention for the modulation of expression of BvFT2). Chimeric constructs for upregulation of expression of certain gene(s) (such as, for example, BvFT1) and chimeric constructs for downregulation of expression of certain gene(s) (such as, for example, BvFT2) can also be introduced into the same vector. The chimeric constructs of the present can further be stacked with chimeric constructs modulating expression of other genes influencing the flowering response in sugar beet. This is outlined in more detail below.

As shown in the context of the present invention, modulating or controlling the expression levels of the *Beta* FT homologues allows for the engineering of bolting resistance. However, bolting resistant sugar beet will not produce seed as due to the lack of bolting no flowers are developed. In order to be able to maintain, multiply and commercialize the bolting resistant sugar beet plants of the present invention, the modulation of expression of the *Beta* FT homologues, either by overexpression of BvFT1 and/or downregulation of expression of BvFT2, needs to be conditional or latent. The skilled person is aware of system to control expression of a transgene, such as, but not limited to the use of activator systems based on inducible promoters, or targeted recombination. Further, two-component trans-activation systems have been described in the past for the conditional control of gene expression in plants. In these system chimeric transcription factors recognize their cognate promoters to drive the transcription of the downstream gene (GUYER et al., 1998; MOORE et al., 1998). The application of the pOp6/LhG4 system for the conditional control of expression of chimeric constructs of the present invention in sugar beet described in detail in Example 8 below. The pOp6/LhG4 system comprises a chimeric transcription factor, LhG4, in which transcription activation domain II of Gal4 is fused to a high-affinity DNA-binding mutant of the lac repressor. This activates transcription from promoters such as pOp6 that carries six copies of an optimized lac operator sequence upstream of a minimal CaMV 35S promoter (RUTHERFORD et al., 2005). With the purpose of facilitating the generation and selection of transgenic events in which the pOp6/LhG4 trans-activation system is functional, the PMI selectable marker gene was cloned downstream of the pOp6 promoter and combined with the gene cassette for the constitutive expression of LhG4Ato (RUTHERFORD et al., 2005) under to the control of the Ubi3 promoter from *Arabidopsis* (NORRIS et al., 1993) on one and the same T-DNA. The second genetic element for the conditional expression of the *Beta* FT homologues consists of the gene cassette for one or both BvFT genes under the control of the pOp6 promoter. Transformation of these two binary vectors into sugar beet and the subsequent crossing of the obtained events to an 'activator' event expressing the LhG4 hybrid transcription factor results in the transcription of the BvFT chimeric constructs of the present invention conferring bolting resistance in a controlled manner. For commercial application both genetic elements are typically present in the homozygous state in one or the other parental lines used for the production of hybrid seeds. Upon crossing the male and female parental lines the resulting hybrid seed inherits a copy of both genetic elements in the heterozygous state leading to the successful trans-activation of the BvFT chimeric constructs of the present invention and to a bolting resistant commercial hybrid.

In further preferred embodiments, the present invention thus provides vectors for the genetic control of expression of the chimeric constructs of the present invention. Non-limiting examples of such vectors described in Example 9 and are further set forth as SEQ ID Nos: 53, 54, and 54 and are also shown in FIGS. 20, 21, and 22. The present invention further provides transgenic sugar beet plants comprising one or both vectors needed for transactivation control of the expression of the chimeric constructs of the present invention. Preferably the vectors needed for transactivation control are vectors belonging to the pOp/LhG4 or pOp6/LhG4 transactivation system. In another preferred embodiment the present invention provides hybrid sugar beet plants of the present invention in which the expression of the chimeric constructs of the present invention is controlled by use of a transactivation system, preferably the pOp/LhG4 or pOp6/LhG4 transactivation system.

Transgenic plants (or plant cells, or plant explants, or plant tissues) incorporating and expressing the nucleic acid sequences or chimeric constructs of the present invention can be produced by a variety of well established techniques. Following construction of the chimeric construct of the invention comprising a nucleic acid sequence according to the invention and as described herein before, standard techniques can be used to introduce the chimeric construct into a plant, a plant cell, a plant explant or a plant tissue of interest. Optionally, the plant cell, explant or tissue can be regenerated to produce a transgenic plant.

Transformation and regeneration of sugar beet plant cells is now routine, and the selection of the most appropriate transformation technique will be determined by the practitioner. Suitable methods can include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumefaciens* mediated transformation. Transformation of plants can be undertaken with a single DNA molecule or multiple DNA molecules (i.e., co-transformation), and both these techniques are suitable for use with the chimeric constructs of the present invention. Numerous transformation vectors are available for plant transformation, and the expression cassettes of this invention can be used in conjunction with any such vectors. The selection of vector will depend upon the preferred transformation technique and the target species for transformation.

A variety of techniques are available and known to those skilled in the art for introduction of constructs into a plant cell host. These techniques generally include transformation with DNA employing *Agrobacterium tumefaciens* or *Agrobacterium rhizogenes* as the transforming agent, liposomes, PEG precipitation, electroporation, DNA injection, direct DNA uptake, microprojectile bombardment, particle acceleration, and the like (See, for example, EP 295959 and EP 138341) (see below). However, cells other than plant cells may be transformed with expression vectors containing a nucleic acid sequence or the chimeric construct of the invention. The general descriptions of plant expression vectors and reporter genes, and *Agrobacterium* and *Agrobacterium*-mediated gene transfer, can be found in GRUBER et al. (1993).

Expression vectors containing a nucleic acid sequence or a chimeric construct according to the invention can be introduced into protoplasts or into intact tissues or isolated cells. Preferably expression vectors are introduced into intact tissue. General methods of culturing plant tissues are provided, for example, by MAKI et al., (1993); and by PHILLIPS et al. (1988). Preferably, expression vectors are introduced into sugar beet or other plant tissues using a direct gene transfer method such as microprojectile-mediated delivery, DNA injection, electroporation and the like. More preferably expression vectors are introduced into plant tissues using the microprojectile media delivery with the biolistic device. See, for example, TOMES et al. (1995).

The main focus of the present invention is on transformation of sugar beet. The experimental procedures for the transformation of sugar beet are well known to those skilled in the art such as that disclosed by CHANG et al. (2002) using sugar beet meristems as explant material or as described by JOERSBO et al. (1998).

The experimental procedure for the transformation of annual and biennial sugar beet of genotype G018 with the chimeric constructs of the present invention was basically the multiple shoot protocol as described in International Patent Application WO 02/14523 using sugar beet meristematic tissues as explant material and mannose-6-phosphate as selective agent together with the phosphomannose isomerase (PMI) gene as selectable marker as described in International Patent Application WO 94/20627 (as shown in Examples 7 and 8). Transgenic shoots are checked for expression of the selection marker such as, for example, PMI activity (JOERSBO et al. 1998). Positive shoots and non-transgenic controls are rooted and transferred to the greenhouse for an acclimatization period of two weeks minimum at 18° C. prior to the vernalization treatment. Once well-established, the transgenic plants are exposed to the vernalization treatment. Plants are subsequently repotted into to larger pots (2 liter), and monitored for bolting (see, e.g., Example 7).

Additionally, to confirm that the trait of interest is due to expression of the introduced nucleic acid sequence of the present invention under, expression levels or activity of the gene of interest (i.e., either BvFT1 or BvFT2, or both) can be determined by analyzing mRNA expression using Northern blots, RT-PCR or microarrays, or protein expression using immunoblots or Western blots or gel shift assays.

The invention thus includes a transgenic sugar beet plant or cells, tissues or seeds thereof, in which the expression of the endogenous BvFT1 gene and/or BvFT2 gene is modulated, more specifically in which expression of the endogenous BvFT2 gene is downregulated or suppressed or in which expression of the endogenous BvFT1 gene is upregulated, or in which both the expression of the endogenous BvFT2 gene is downregulated or suppressed and expression of the endogenous BvFT1 gene is upregulated.

With regard to BvFT2, downregulation of expression of the endogenous BvFT2 gene in sugar beet leads to a delay of the vernalization response in a growing sugar beet plant or causes the sugar beet plant to develop a non-bolting phenotype, which means that the sugar beet plant does no longer respond to a typical vernalization period of 18 weeks by bolting and subsequent flowering, but to the contrary continue vegetative growth (non-bolting) and develop a normal taproot. Plants expressing said delayed vernalization response or said non-bolting phenotype can be easily identified and selected by applying a phenotypic analysis experiment employing standardized growth conditions.

In one preferred embodiment of this aspect transgenic sugar beet plant, or cells, tissues or seeds thereof are provided, in which the expression of the endogenous BvFT2 gene is down-regulated or suppressed by either dsRNA, antisense suppression, or co-suppression, preferably by dsRNA.

Thus, in a preferred embodiment transgenic sugar beet plant of the present invention, or cells, tissues or seeds thereof, comprising a chimeric construct of the present invention or a nucleic acid sequence of the present invention are provided, wherein said transgenic sugar beet plant, or cells, tissues or seeds thereof express the dsRNA of the present invention and are bolting resistant exhibiting a phenotype of delayed bolting, preferably a non-bolting phenotype.

In a further embodiment, a transgenic sugar beet plant of the present invention, or cells, tissues or seeds thereof is provided, wherein the heterologous DNA introduced into said plant is obtainable from a 0.27 Kb cDNA fragment consisting of exon 4 of the BvFT2 gene as described hereinbefore in a PCR reaction using forward primer HiNK6382 with the nucleotide sequence 5'-CTATGGATCCGCATT-TAATAAAATCTCTTTCAATG-3' (SEQ ID NO: 44) and reverse primer HiNK6384 with the nucleotide sequence 5'-GTAGAAGCAGAAACTTACCTGCCAA-GAAGTTGTCTGCTATG-3' (SEQ ID NO: 45).

In a further specific embodiment the transgenic sugar beet plant of the present invention, or cells, tissues or seeds thereof comprises a heterologous DNA as depicted by nucleotides 8747 to 9046 of SEQ ID NO: 33.

In still another specific embodiment the transgenic sugar beet plant of the present invention, or cells, tissues or seeds thereof comprises a heterologous gene construct, which includes an inverted repeat, which when transcribed, forms a double stranded RNA molecule in said plant cell comprising said first and second RNA strands, wherein said double stranded RNA molecule triggers BvFT2 gene silencing.

In a specific embodiment of the invention, a transgenic sugar beet plant, or cells, tissues or seeds thereof, is provided which comprises a heterologous DNA for BvFT2 inserted between a promoter and terminator, which heterologous DNA is obtainable by a. amplifying a 0.27 Kb cDNA fragment derived from exon 4 of the BvFT2 gene in a PCR reaction using forward primer HiNK6382 with the nucleotide sequence 5'-CTATG-GATCCGCATTTAATAAAATCTCTTTCAATG-3' (SEQ ID NO: 44) and reverse primer HiNK6384 with the nucleotide sequence 5'-GTAGAAGCAGAAACTTACCTGC-CAAGAAGTTGTCTGCTATG-3' (SEQ ID NO: 45) and sugar beet cDNA as template, wherein the sugar beet cDNA was obtained from total RNA extracted from sugar beet leaves in a reverse transcriptase reaction using the 3' RACE ADAPTER with the nucleotide sequence 5'-GCGAGCACAGAATTAATACGACTCACTATAGG-T12VN-3' (SEQ ID NO: 35) as a primer;
b. by amplifying a 0.19 Kb fragment comprising the ST-LS1 intron and flanking splicing sites using forward primer HiNK6383 with the nucleotide sequence 5'-CATAGCA-GACAACTTCTTGGCAGGTAAGTTTCTGCTTCTAC-3' (SEQ ID NO: 46) and reverse primer HiNK529 with the nucleotide sequence 5'-ATCCAACCGCGGACCTGCA-CATCAACAA-3' (SEQ ID NO: 40) and potato DNA containing the potato St-LS1 intron as template;
c. fusing the amplification products obtained in steps a) and b) to each other by means of a second round of PCR using primers HiNK6382 and HiNK529 and using a mix of both amplification products as template, yielding a fusion product of 0.47 Kb in length;
d. amplifying the 0.27 Kb BvFT2 fragment a second time, using forward primer HiNK6385 with the nucleotide sequence 5'-TAAATCCGCGGGCCAAGAAGTTGTCT-GCTATG-3' (SEQ ID NO: 47) and reverse primer HiNK6386 with the nucleotide sequence 5'-CTATTTGTC-GACGCATTTAATAAAATCTCTTTC-3' (SEQ ID NO: 48) and the sugar beet cDNA as described in subsection a) above as template;
e. fusing both fragments at the Sac II restriction sites to create an inverted repeat for the BvFT2 sequence separated by the intron from the potato ST-LS1 gene.

In another specific embodiment the transgenic sugar beet plant, or cells, tissues or seeds thereof, according to the invention comprises a heterologous gene construct for BvFT2, wherein said gene construct preferably comprises an expression cassette depicted by nucleotides 7388 to 9779 of SEQ ID NO: 32.

In another specific embodiment of the invention, a transgenic sugar beet plant, or cells, tissues or seeds thereof, is provided comprising an expression cassette according to the invention and as described herein before.

In addition to dsRNA the other strategies for reducing the expression, amount, activity and/or function of the endogenous BvFT2 gene in sugar beet outlines above can also be employed.

With regard to BvFT1, upregulation of expression of the endogenous BvFT1 gene in sugar beet leads to a delay of the vernalization response in a growing sugar beet plant or causes the sugar beet plant to develop a non-bolting phenotype, which means that the sugar beet plant does no longer respond to a typical vernalization period of 18 weeks by bolting and subsequent flowering, but to the contrary continue vegetative growth (non-bolting) and develop a normal taproot. Plants expressing said delayed vernalization response or said non-bolting phenotype can be easily identified and selected by applying a phenotypic analysis experiment employing standardized growth conditions.

In one preferred embodiment of this aspect transgenic sugar beet plant, or cells, tissues or seeds thereof are provided, in which the expression of the endogenous BvFT1 gene is upregulated.

Thus, in a preferred embodiment transgenic sugar beet plant of the present invention, or cells, tissues or seeds thereof, comprising a chimeric construct of the present invention or a nucleic acid sequence of the present invention are provided, wherein in said transgenic sugar beet plant the endogenous BvFT1 is overexpressed and the plant exhibits a phenotype of delayed bolting, preferably a non-bolting phenotype.

Preferably, the nucleotide sequence encoding the BvFT1 gene introduced into the sugar beet plants for upregulating expression of BvFT1 has a nucleotide sequence as set forth as SEQ ID NO: 6.

In another preferred embodiment the chimeric construct introduced into the sugar beet plants for upregulating expression of BvFT1 comprises a nucleotide sequence as depicted by nucleotides 2076 to 2615 of SEQ ID NO: 34. Preferably, said chimeric construct comprises the nucleotide sequence as depicted in SEQ ID NO: 34.

In one embodiment the transgenic, expression of one or more further genes involved in the flowering response is modulated in addition to down-regulating expression of the endogenous BvFT2 or up-regulating expression of the endogenous BvFT1 resulting in a synergistic effect with regard to delaying the vernalization response in a growing sugar beet plant or conferring a non-bolting phenotype. Examples of such further genes are outlined in more detail below.

It is to be understood that the transgenic plants of the present invention or its progeny as well as the hybrid sugar beet plants of the present invention (see below) can also be "cultivated" plants commercially grown for their production. The term "cultivated plant" includes those plants which has been brought into cultivation and have been selectively bred for growing purposes. Cultivated plants exclude those wild-type species which comprise the trait of the present invention as a natural trait and/or part of their natural genetics In a further embodiment the present invention also includes a transgenic sugar beet plant derived from cells, tissues or seeds according to the invention and as described herein before.

These transgenic sugar beet plants derived from cells, tissues or seeds according to the invention have a non-bolting phenotype, which means that the sugar beet plant does no longer respond to a typical vernalization period of 18 weeks by bolting and subsequent flowering, but to the contrary continue vegetative growth (non-bolting) and develop a normal taproot.

In a further embodiment the present invention is directed to a root of a transgenic sugar beet plant of the present invention. In particular, the root is a taproot harvested from a transgenic sugar beet plant of the present invention.

In yet a further embodiment the present invention is directed to progeny of a transgenic sugar beet plant of the present invention. In this context the term "progeny" refers to the descendant(s) of a particular cross like, for example, the F1, the F2, or any subsequent generation. Typically, progeny result from breeding of two individuals, although the progeny can also result from selfing of the sugar beet (i.e., the same plant acts as the donor of both male and female gametes). The term progeny also includes sugar beet grown from seeds obtained from transgenic sugar beet plants of the present invention.

More specifically, the present invention also includes a progeny plant derived from a transgenic sugar beet plant according to the invention and as described herein before having a non-bolting phenotype, which means that the progeny sugar beet plant does no longer respond to a typical vernalization period of 18 weeks by bolting and subsequent flowering, but to the contrary continue vegetative growth (non-bolting) and develop a normal taproot.

Once a vector or a chimeric construct according to the present invention and as described herein before comprising a nucleic acid sequence of the present invention has been transformed into a particular plant species, it may be propagated in that species or moved into other varieties of the same species, particularly including commercial varieties, using traditional breeding techniques.

The genetic properties engineered into the transgenic plants described above are passed on by sexual reproduction or vegetative growth and can thus be maintained and propagated in progeny plants. Generally said maintenance and propagation make use of known agricultural methods developed to fit specific purposes such as tilling, sowing or harvesting. Specialized processes such as hydroponics or greenhouse technologies can also be applied.

One skilled in the art will recognize that the transgenic genotype of the present invention can be introgressed by breeding into other plant lines (preferably sugar beet plant lines) comprising different transgenic or non-transgenic genotypes. This different transgenic or non-transgenic genotype could be any genotype, but a genotype comprising at least one trait of interest is preferred. For example, a sugar beet inbred comprising the transgenic genotype of the present invention can be crossed with a sugar beet inbred line comprising the transgenic genotype of an event resistant to a virus known to infect sugar beet plants. The resulting seed and progeny plants will have the trait of delayed bolting and the resistance traits in stacked form. For example, a sugar beet inbred with the transgenic genotype of the present invention can be crossed with a sugar beet inbred comprising herbicide resistance, like, for example, the transgenic genotype of the glyphosate resistant H7-1 event (European patent application EP-A1-1597373, herein incorporated by reference). The resulting seed and progeny plants would have both the resistance trait and the trait of delayed bolting. In general, traits like herbicide resistance, disease resistance or resistance against viruses (i.e., viruses like, for example, BNYVV in either transgenic from or from conventional sources (like Holly or C48) or viruses other than BNYVV) can be used for stacking with transgenic genotype of the present invention. It will be further recognized that other combinations or stacks can be made with the transgenic genotype of the invention and thus these examples should not be viewed as limiting.

The transgenic genotype of the present invention can be introgressed in any sugar beet inbred or hybrid using art recognized breeding techniques. The goal of plant breeding is to combine in a single variety or hybrid various desirable traits in order to develop plants with improved properties. For field crops, these traits may include resistance to insects and diseases (e.g., derived from conventional sources including, but not limited to Holly and C48), tolerance to herbicides, tolerance to heat and drought, greater yield, and better agronomic quality. With mechanical harvesting of many crops, uniformity of plant characteristics such as germination and taproot establishment, growth rate, maturity, and root size, is important.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

Plant breeding techniques known in the art and used in a sugar beet plant breeding program include, but are not limited to, recurrent selection, backcrossing, pedigree breeding, restriction length polymorphism enhanced selection, genetic marker enhanced selection and transformation. The development of sugar beet hybrids in a sugar beet plant breeding program requires, in general, the development of homozygous inbred lines, the crossing of these lines, and the evaluation of the crosses. Pedigree breeding and recurrent selection breeding methods are used to develop inbred lines from breeding populations. Sugar beet plant breeding programs combine the genetic backgrounds from two or more inbred lines or various other germplasm sources into breeding pools from which new inbred lines are developed by selfing and selection of desired phenotypes. The new inbreds are crossed with other inbred lines and the hybrids from these crosses are evaluated to determine which of those have commercial potential. Plant breeding and hybrid development, as practiced in a sugar beet plant-breeding program, are expensive and time-consuming processes.

Pedigree breeding starts with the crossing of two genotypes, each of which may have one or more desirable characteristics that is lacking in the other or which complements the other. If the two original parents do not provide all the desired characteristics, other sources can be included into the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: F1→F2; F2→F3; F3→F4; F4→F5; etc.

Recurrent selection breeding, backcrossing for example, can be used to improve an inbred line and a hybrid that is made using those inbreds. Backcrossing can be used to transfer a specific desirable trait from one inbred or source to an inbred that lacks that trait. This can be accomplished, for example, by first crossing a superior inbred (recurrent parent) to a donor inbred (non-recurrent parent), that carries the appropriate gene(s) for the trait in question. The progeny of this cross is then mated back to the superior recurrent parent followed by selection in the resultant progeny for the desired trait to be transferred from the non-recurrent parent.

Elite inbred lines, that is, pure breeding, homozygous inbred lines, can also be used as starting materials for breeding or source populations from which to develop other inbred lines. These inbred lines derived from elite inbred lines can be developed using the pedigree breeding and recurrent selection breeding methods described earlier. As an example, when backcross breeding is used to create these derived lines in a sugar beet plant-breeding program, elite inbreds can be used as a parental line or starting material or source population and can serve as either the donor or recurrent parent.

A single cross hybrid results from the cross of two inbred lines, each of which has a genotype that complements the genotype of the other. The hybrid progeny of the first generation is designated F1. In the development of commercial hybrids in a sugar beet plant-breeding program, only the F1 hybrid plants are sought. Preferred F1 hybrids are more vigorous than their inbred parents. This hybrid vigor, or heterosis, can be manifested in many polygenic traits, including increased vegetative growth and increased yield.

The development of a sugar beet hybrid in a sugar beet plant breeding program involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrid progeny (F1). During the inbreeding process in sugar beet, the vigor of the lines decreases. Vigor is restored when two different inbred lines are crossed to produce the hybrid progeny (F1). An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained.

A single cross hybrid is produced when two inbred lines are crossed to produce the F1 progeny. A double cross hybrid is produced from four inbred lines crossed in pairs (A×B and C×D) and then the two F1 hybrids are crossed again (A×B)× (C×D). A three-way cross hybrid is produced from three inbred lines where two of the inbred lines are crossed (A×B) and then the resulting F1 hybrid is crossed with the third inbred (A×B)×C. Much of the hybrid vigor exhibited by F1 hybrids is lost in the next generation (F2). Consequently, seed from hybrids is not used for planting stock.

In hybrid seed production it is preferred to eliminate or inactivate pollen production by the female parent. Incomplete removal or inactivation of the pollen provides the potential for self-pollination. This inadvertently self-pollinated seed may be unintentionally harvested and packaged with hybrid seed. Once the seed is planted, it is possible to identify and select these self-pollinated plants. These self-pollinated plants will be genetically equivalent to the female inbred line used to produce the hybrid. Typically these self-pollinated plants can be identified and selected due to their decreased vigor. Female selfs are identified by their less vigorous appearance for vegetative and/or reproductive characteristics. Identification of these self-pollinated lines can also be accomplished through molecular marker analyses.

However, simple and efficient pollination control systems exist which ensure utilizing heterosis by excluding self-pollination in commercial hybrid seed production. If one of the parents is a self-incompatible (SI), cytoplasmic male sterile (CMS) or nuclear male sterile (NMS) plant that is not able to self-pollinate or is incapable of producing pollen, only cross pollination will occur. By eliminating the pollen of one parental variety in a cross, a plant breeder is assured of obtaining hybrid seed of uniform quality, provided that the parents are of uniform quality and the breeder conducts a single cross. Cytoplasmic male sterility (CMS) is a maternally inherited phenomenon, the genetic determinants of which are located in the genome of the cytoplasmic organelles, the mitochondria. Such plants are severely impaired in their ability to produce functional pollen grains. Restorer genes for CMS systems are dominant nuclear genes, which suppress male sterile effects of the cytoplasm. The expression of male sterility in CMS plants is the result of incompatibility between recessive nuclear gene and male sterile specific cytoplasmic genome.

In a preferred embodiment, a CMS system is applied for production of the hybrid sugar beet plants of the present invention. In such a system a male sterile CMS line is used as female parent that is pollinated by a male fertile line used as male parent. The trait of bolting resistance according to the present invention can be present in both the CMS male sterile (female) parent line or the male fertile (male) parent line or even both. Preferably, the trait of delayed bolting is kept on the male sterile side in order to avoid GM contaminations via the pollen containing the trait shed by the male parent. Further, in such a system one or both parents can transgenic plants.

In another aspect, the present invention thus provides a method for producing hybrid seeds from which sugar beet plants with a phenotype of bolting resistance can be grown. Said method comprise the steps of: (a) providing a sugar beet line having a phenotype of bolting resistance, particularly a transgenic sugar beet plant of the present invention as described hereinbefore as a first parent line, (b) providing a second sugar beet line having a different genotype as a second parent line, wherein one of the parent lines used in step a) or step b) is a male sterile cms line and wherein the other parent line is male fertile. The next step of said method is (c) allowing the plants of the male fertile parent line to pollinate the flowers of the male sterile parent line, let the seed develop, and harvest the hybrid seed, wherein the harvested hybrid seeds are seeds of a sugar beet hybrid plant having a phenotype of delayed bolting, preferably a phenotype of bolting resistance.

In general, the second parent line used for the hybrid production can also be a sugar beet plant line having the phenotype of bolting resistance like, for example, a sugar beet plant of the present invention. Preferably, the first parent line and the second parent line employed in the production of the hybrid seed are based on genetically diverse backgrounds. Genetic distance can be measured by the use of molecular markers as described for example in KNAAK (1996). However, the second parent line could also be a sugar beet inbred comprising another trait of interest like, for example but not limited to herbicide (e.g., glyphosate) resistance (e.g., containing the H7-1 event as described in the European patent application EP-A1-1597373, herein incorporated by reference). The resulting hybrid seed will contain the stacked traits of delayed bolting and glyphosate resistance.

In an embodiment of this aspect, the first or the second parental line is an inbred sugar beet line comprising a nucleic acid or a chimeric construct or a vector of the present invention. In a further embodiment of this aspect, the other parental line is selected from the group consisting of (a) an inbred sugar beet plant line resistant to at least one virus affecting sugar beet, such as, for example, Beet necrotic yellow vein virus (BNYVV) from either transgenic or conventional sources (like Holly or C48); (b) an inbred sugar beet plant line resistant to at least one herbicide; (c) an inbred sugar beet plant line having resistant to at least one disease; and (d) an inbred sugar beet plant line showing bolting resistance (like, for example, the transgenic sugar beet plant of the present invention). Examples of common viruses and diseases affecting sugar beet and sources for resistance against these viruses or diseases for stacking with transgenic genotype of the present invention in the hybrid seed are known to the person skilled in the art. Further, herbicides used on sugar beet and sources of resistance against these herbicides are also known to the person skilled in the art. It will be further recognized that other combinations or stacks can be made with the transgenic genotype of the invention and thus these examples should not be viewed as limiting.

In one embodiment of this aspect, the male sterile CMS sugar beet parent line used in the method of producing sugar beet hybrid seeds of the present invention is an inbred sugar beet line comprising a nucleic acid sequence, a chimeric construct and/or a vector of the present invention as described hereinbefore.

As is readily apparent to one skilled in the art, the foregoing are only some of the various ways by which the inbred of the present invention can be obtained by those looking to introgress the transgenic genotype of the invention into other sugar beet lines. Other means are available and known to the person skilled in the art, and the above examples are illustrative only.

Another preferred embodiment of the present invention relates to hybrid seed of a sugar beet plant having a phenotype of delayed bolting, preferably a non-bolting phenotype. In one aspect of the present invention said hybrid seed is produced by the method for producing sugar beet hybrid seed of sugar beet plants having a phenotype of delayed bolting of the present invention described above. Such methods are known to the person skilled in the art. In yet another aspect of the present invention a hybrid sugar beet plant having a phenotype of delayed bolting, preferably a non-bolting phenotype, is provided that is produced by growing the hybrid seed of the present invention. Preferably, this hybrid plant is not bolting at all, i.e. shows complete suppression of the vernalization response and is thus bolting resistance.

A further aspect of the present invention relates to a part of the sugar beet plant of the present invention. Preferably said plant part is selected from the group comprising seeds, embryos, microspores, anthers, zygotes, protoplasts, cells, ovary, ovules, pollen, taproots, cotyledons, or other reproductive or vegetative parts or extracts or samples. All these plant parts including extracts or biological samples are derived from the transgenic sugar beet plant, or cells, tissues or seeds thereof of the present invention or from hybrid seeds or hybrid plants of the present invention which are all as described hereinabove.

Another aspect relates to roots or progeny of the transgenic sugar beet plants or the hybrid sugar beet plants of the present invention.

In one further aspect, the present invention relates to the use of a nucleic acid sequence of the present invention as described hereinabove or fragments thereof for the transformation of sugar beet plant cells. In another embodiment the present invention relates to the use of a chimeric construct or a vector of the present invention as described hereinabove for the transformation of sugar beet plant cells.

In one further embodiment, a method of transforming sugar beet plant cells is provided, in which said method comprises the use of a nucleic acid sequence, or of a chimeric construct, or of a vector of the present invention. Methods of transforming sugar beet are described in detail above and are also known to the person skilled in the art. An example of a method for transforming sugar beet plant cells is further provided in Examples 7 and 8 herein below.

In yet another embodiment of the invention, a method of gene silencing is provided that includes separately introducing into a plant cell a sense RNA fragment of the endogenous BvFT2 gene, and an antisense RNA fragment of the same gene, wherein the sense RNA fragment and the antisense RNA are capable of forming a double-stranded RNA molecule, wherein the expression of the endogenous BvFT2 gene in the cell is altered. In a preferred embodiment, the RNA fragments are comprised in two different RNA molecules.

In another preferred embodiment, the RNA fragments are mixed before being introduced into the cell under conditions allowing them to form a double-stranded RNA molecule.

In another preferred embodiment, the RNA fragments are introduced into said cell sequentially. In yet another embodiment, the RNA fragments are comprised in one RNA molecule. In such case, the RNA molecule is preferably capable of folding such that said RNA fragments comprised therein form a double stranded RNA molecule. Various methods of using sense and antisense RNA fragments to silence a target gene are described in the published International Patent Application WO99/61631.

The present invention further provides for a method of introducing into a plant cell a dsRNA molecule comprises of sense and antisense fragments of a target gene mRNA.

In one embodiment, the present invention is directed to a method of down-regulating or suppressing the expression of the endogenous BvFT2 gene of a sugar beet plant cell, wherein in said method a nucleic acid sequence, a chimeric construct, or a vector according to the present invention comprising a nucleic acid sequence derived from the sequence of BvFT2 is introduced into said plant cell. Upon expression of the nucleic acid sequence, chimeric construct, or vector according to the present invention in said plant cell downregulation or suppression of the expression of the endogenous BvFT2 gene is caused. This downregulation or suppression of expression of the endogenous BvFT2 gene leads to a delay of the vernalization response in a growing sugar beet plant or causes the sugar beet plant to develop a non-bolting phenotype, which means that the sugar beet plant does no longer respond to a typical vernalization period of 18 weeks by bolting and subsequent flowering, but to the contrary continue vegetative growth (non-bolting) and develop a normal taproot.

In yet another embodiment of the invention, a method of upregulating expression of the endogenous BvFT1 in sugar beet is provided, in which a nucleic acid sequence, a chimeric construct, or a vector according to the present invention comprising a nucleic acid sequence derived from the sequence of BvFT1 is introduced into a sugar beet plant cell, such that upon expression of said nucleic acid sequence, chimeric construct, or vector in said plant cell upregulation of expression of the endogenous BvFT1 gene is caused. This upregulation of expression of the endogenous BvFT1 gene leads to a delay of the vernalization response in a growing sugar beet plant or causes the sugar beet plant to develop a non-bolting phenotype, which means that the sugar beet plant does no longer respond to a typical vernalization period of 18 weeks by bolting and subsequent flowering, but to the contrary continue vegetative growth (non-bolting) and develop a normal taproot.

In another aspect, the invention further relates to a method of producing a transgenic sugar beet plant according to the invention and as described herein before comprising:
a) transforming a sugar beet cell with an chimeric construct or a vector according to the invention and as described herein before;
b) identifying a sugar beet cell containing the heterologous DNA,
c) regenerating a transgenic plant from said plant cell identified in step b),
d) identifying a sugar beet plant exhibiting a delay of the vernalization response or a complete suppression of the vernalization response resulting in a non bolting (NB) phenotype,
e) optionally confirming the presence of the heterologous DNA in the plant cell genome introduced in step a).

The chimeric construct used in step (a) is preferably either the RNAi expression vector of the present invention containing the chimeric construct for downregulation or suppression of expression of the endogenous BvFT2 gene, or the expression vector of the present invention containing the chimeric construct for upregulation of expression of the endogenous BvFT1 gene both described above. In another preferred embodiment the vector used in step (a) contains a chimeric construct for downregulation or suppression of expression of the endogenous BvFT2 gene and a chimeric construct for upregulation of expression of the endogenous BvFT1 gene.

The invention also includes a method of suppressing the expression of the endogenous BvFT2 gene in a sugar beet plant cell, comprising introducing into the plant cell a first RNA fragment according to the present invention and as described hereinabove that is sufficiently identical or complementary to a portion of the endogenous BvFT2 gene, a second RNA fragment that is sufficiently complementary to the first RNA fragment, to result in the suppression of the expression of the endogenous BvFT2 gene, wherein the first and second RNA fragments form a double stranded RNA molecule in the plant cell, wherein the double stranded RNA molecule suppresses by siRNA mediated silencing the expression of the BvFT2 gene.

The invention also includes a method of suppressing the expression of the endogenous BvFT2 gene in a sugar beet plant, comprising:
a) introducing into a sugar beet plant cell a first RNA strand according to the present invention;
b) growing said plant cell into a first plant;
c) introducing into a second sugar beet plant cell a second RNA strand, wherein said first RNA strand is sufficiently complimentary to at least a portion of a RNA strand produced by said endogenous BvFT2 gene to hybridize or anneal to the RNA produced by the BvFT2 gene such as to cause suppression of the expression of the endogenous BvFT2 gene and said first RNA strand and said second RNA strand are capable of forming a double stranded RNA;
d) growing said second sugar beet plant cell into a second plant;
e) crossing said first plant with said second plant to produce seed; and
f) growing a plant from said seed, wherein said first and second RNA strands form double stranded RNA which participates in RNA interference of expression of said endogenous BvFT2 gene.

According to another aspect of the invention, methods of detecting the presence of a nucleic acid sequence or a chimeric construct of the present invention in a biological sample are provided. Such methods comprise: (a) contacting the sample comprising DNA with a pair of primers that, when used in a nucleic-acid amplification reaction with genomic DNA from a sugar beet carrying a nucleic acid sequence or a chimeric construct of the present invention, produces an amplicon that is diagnostic for a sugar beet of the present invention; (b) performing a nucleic acid amplification reaction, thereby producing the amplicon; and (c) detecting the amplicon. Detection of the amplicon can be conducted by any means well known in the art including but not limited to fluorescent, chemiluminescent, radiological, immunological, or otherwise. In the case in which hybridization is intended to be used as a means for amplification of a particular sequence to produce an amplicon, the production and detection by any means well known in the art of the amplicon is intended to be indicative of the intended hybridization to the target sequence where one probe or primer is utilized, or sequences where two or more probes or primers are utilized.

The present invention includes the use of the transgenic sugar beet plants, or of the hybrid sugar beet plant, or of the plant parts of the present invention in a method selected from the group comprising of methods of sugar production, methods of aerobic fermentation and methods of anaerobic fermentation. The transgenic sugar beet plants or the hybrid sugar beet plant or the plant parts of the present invention are preferably used in a method of sugar production.

The method of the present invention for producing sugar can be any conventional method for producing sugar known to person skilled in the art. In a preferred embodiment a method for producing sugar is provided wherein the sugar beet plant, or cells or tissues thereof of the present invention as described hereinabove are processed to produce sugar. Further, the present invention provides sugar that is produced by the method of producing sugar of the present invention.

Another embodiment of the present invention relates to the use of the transgenic sugar beet plant of the present invention, of the hybrid sugar beet plant of the present invention, or of the plant parts of the present invention in a method of aerobic or anaerobic fermentation. Methods of aerobic or anaerobic fermentation are known to the person skilled in the art.

For example, "fermentation" can refer to aerobic transforming sugars or other molecules from plant material, such as the plant material of the present invention, to produce alcohols (e.g., ethanol, methanol, butanol); organic acids (e.g., citric acid, acetic acid, itaconic acid, lactic acid, gluconic acid); ketones (e.g., acetone), amino acids (e.g., glutamic acid); gases (e.g., $H_2$ and $CO_2$), antibiotics (e.g., penicillin and tetracycline); enzymes; vitamins (e.g., riboflavin, $B_{12}$, beta-carotene); and/or hormones. Fermentation includes fermentations used in the consumable alcohol industry (e.g., beer and wine). Fermentation also includes anaerobic fermentations, for example, for the production of biofuels. Fermenting can be accomplished by any organism suitable for use in a desired fermentation step, including, but not limited to, bacteria, fungi, archaea, and protists. Suitable fermenting organisms include those that can convert mono-, di-, and trisaccharides, especially glucose and maltose, or any other biomass-derived molecule, directly or indirectly to the desired fermentation product (e.g., ethanol, butanol, etc.). Suitable fermenting organisms also include those which can convert non-sugar molecules to desired fermentation products. Such organisms and fermentation methods are known to the person skilled in the art.

Another preferred aspect relates to a method for producing one or more biofuel(s) selected from the group comprising ethanol, biogas and/or biodiesel, by processing a transgenic sugar beet plant of the present invention, or cells or tissues, or a biological sample or an extract thereof to produce the one or more biofuel(s).

The term "biofuel", as used herein, refers to a fuel that is derived from biomass, i.e., a living or recently living biological organism, such as a plant or an animal waste. Biofuels include, but are not limited to, biodiesel, biohydrogen, biogas, biomass-derived dimethylfuran (DMF), and the like. In particular, the term "biofuel" can be used to refer to plant-derived alcohols, such as ethanol, methanol, propanol, or butanol, which can be denatured, if desired prior to use. The term "biofuel" can also be used to refer to fuel mixtures comprising plant-derived fuels, such as alcohol/gasoline mixtures (i.e., gasohols). Gasohols can comprise any desired percentage of plant-derived alcohol (i.e., about 10%, 15%, 20%, 25%, 30%, 35%, 40%, 45%, 50%, 55%, 60%, 65%, 70%, 75%, 80%, 85%, 90%, or 95% plant-derived alcohol). For example, one useful biofuel-based mixture is E85, which comprises 85% ethanol and 15% gasoline. The biofuel can be any biofuel produced by aerobic or anaerobic fermentation of plant material. A non-limiting example of a biofuel obtained by aerobic fermentation is bioethanol. Biofuels that can be obtained by anaerobic fermentation include, but are not limited to biogas and/or biodiesel. Methods of aerobic and/or anaerobic fermentation are known to the person skilled in the art. Further encompassed by the present invention are biofuels selected from the group comprising ethanol, biogas and/or biodiesel as produced by the method for producing one or more biofuel(s) or the present invention.

The present invention includes other industrial applications such as the production of antibodies or bioplastic in the transgenic sugar beet plants of the present invention. Further, transgenic sugar beet plants of the present invention or parts thereof can be also be used without further processing, such as, for example, as cattle feed.

In a further specific aspect, the present invention relates to a transgenic sugar beet plant, in which the expression of one or more further genes gene involved in flowering control has been modulated in addition to a modulation of expression of the endogenous sugar beet genes BvFT1 and/or BvFT2.

In a more specific embodiment said one or more further gene involved in flowering control is selected from the group of genes comprising AGL20 (AGAMOUS-LIKE 20), VRN1 (REDUCED VERNALIZATION RESPONSE 1), VRN2 (REDUCED VERNALIZATION RESPONSE 2), VIN3 (VERNALIZATION INSENSITIVE 3), CONSTANS, GIGANTEA, FPF1 (FLOWERING PROMOTING FACTOR 1), SVP (SHORT VEGETATIVE PHASE), and AGL24 (AGAMOUS-LIKE 24), FLC (FLOWERING LOCUS C), FRIGIDA, and TFL1 (TERMINAL FLOWER 1).

Dependent on the function of the one or more further gene involved in flowering control the expression of said one or more gene needs to be either upregulated or suppressed in order to be effect a modulating the bolting response of the transgenic sugar beet resulting in a phenotype of delayed bolting, preferably a non-bolting phenotype. It will be obvious for the person skilled in the art on the basis of the gene function of this one or more further gene involved in flowering control if overexpression or suppression is required for a particular gene. For example, when AGL20 is used it is obvious that the expression of AGL20 needs to be suppressed, whereas the expression of FLC gene needs to be upregulated (see, for example, published International Patent Application WO07/122,086). In one embodiment, the introduction into the genome of a sugar beet plant of two or more genes of the same type is contemplated. "Of the same type" in this context refers to genes the expression of which has to be modulated in the same manner (i.e., upregulation compared to downregulation)

Thus, in a further aspect the present invention provides a method of downregulating or suppressing expression of the endogenous BvFT2 gene as described hereinabove, further comprising modulating the expression in the sugar beet plant cell of at least one further gene involved in flowering control.

In a preferred embodiment of this aspect the further at least one gene involved in flowering control is selected from the group consisting of AGL20, VRN1, VRN2, VIN3, CONSTANS, GIGANTEA, FPF1, SVP, and AGL24, in which case the expression of these genes in the sugar beet plant needs to be down-regulated or suppressed in order to confer bolting resistance. In a further preferred embodiment of this aspect the further at least one gene involved in flowering control is selected from the group consisting of FLC, FRIGIDA, BvFT1, and TFL1, in which case the expression of these genes in the sugar beet plant needs to be upregulated in order to confer bolting resistance.

In a further aspect the present invention provides a method of upregulating of expression of the endogenous BvFT1 gene as described hereinabove, further comprising modulating the expression in the sugar beet plant cell of at least one further gene involved in flowering control.

In a preferred embodiment of this aspect the further at least one gene involved in flowering control is selected from the group consisting of AGL20, VRN1, VRN2, VIN3, CONSTANS, GIGANTEA, FPF1, SVP1, AGL24, and BvFT2, in which case the expression of these genes in the sugar beet plant needs to be down-regulated or suppressed in order to confer bolting resistance. In a further preferred embodiment of this aspect the further at least one gene involved in flowering control is selected from the group consisting of FLC, FRIGIDA, and TFL1, in which case the expression of these genes in the sugar beet plant needs to be upregulated in order to confer bolting resistance.

Preferably, modulation of expression of one or more further gene involved in flowering control in addition to modulation of expression of the endogenous BvFT1 and/or BvFT2 leads to a synergistic delay of the vernalization response in said sugar beet plant.

In still another specific aspect, the invention relates to a transgenic sugar beet plant as described herein before in which the expression of one or more other genes gene involved in flowering control has been modulated in addition to a modulation of the endogenous sugar beet genes BvFT1 and/or BvFT2, which plant is obtainable by a cross of two parent plants wherein the first heterologous gene construct for modulating expression of BvFT1 and/or BvFT2 is contributed by one parent, and wherein the second heterologous gene construct for modulating expression of said one or more other genes gene involved in flowering control is contributed by the other parent, wherein at least one of the parent plants does not exhibit a non bolting (NB) phenotype.

In a preferred embodiment both heterologous genes constructs are comprised in the same vector and are transformed into a sugar beet plant simultaneously by a method of transforming sugar beet plant cells as described above.

In a further embodiment, the transgenic sugar beet plant as described herein before in which the expression of one or more other genes gene involved in flowering control has been modulated in addition to a modulation of the endogenous sugar beet genes BvFT1 and/or BvFT2 is obtained by a method of sequential transformation comprising the steps of:

a) transforming a sugar beet cell with a first chimeric construct comprising a heterologous DNA, wherein said heterologous DNA is derived from a gene involved in flowering control and is operably linked to regulatory sequences and/or an expression cassette according to the invention and as described herein before comprising a heterologous gene construct capable of upregulating or down-regulating expression of said endogenous gene involved in flowering control;

b) identifying a sugar beet cell containing the heterologous DNA;

c) transforming the sugar beet cell identified in step b) with a second first chimeric construct comprising a heterologous DNA, wherein said heterologous DNA is derived from a gene involved in flowering control and is operably linked to regulatory sequences or with an expression cassette according to the invention and as described herein before comprising a heterologous gene construct capable of upregulating or downregulating expression of said endogenous gene involved in flowering control and identifying a sugar beet cell containing both the introduced heterologous DNAs;

d) regenerating a transgenic plant from said plant cell identified in step b);

e) identifying a sugar beet plant exhibiting a delay of the vernalization response or a complete suppression of the vernalization response resulting in a non bolting (NB) phenotype;

f) optionally confirming the presence of the heterologous DNAs in the plant cell genome introduced in step a) and, optionally, step c).

Preferably the first and second chimeric construct comprise a different heterologous DNA derived from a different gene involved in flowering control.

In a specific embodiment, the method of producing a transgenic sugar beet plant comprises crossing of two parent plants wherein the first chimeric construct is contributed by parent 1 represented by a sugar beet plant comprising a gene involved in flowering control according to the invention and as described herein before selected from the group of genes comprising AGL20 (AGAMOUS-LIKE 20), VRN1 (RE- DUCED VERNALIZATION RESPONSE 1), VRN2 (REDUCED VERNALIZATION RESPONSE 2), VIN3 (VERNALIZATION INSENSITIVE 3), CONSTANS, GIGANTEA, FPF1 (FLOWERING PROMOTING FACTOR 1), SVP (SHORT VEGETATIVE PHASE), and AGL24 (AGAMOUS-LIKE 24), FLC (FLOWERING LOCUS C), FRIGIDA, and TFL1 (TERMINAL FLOWER 1), preferably the AGL20 or FLC gene, and the second chimeric construct is contributed by parent 2 represented by a sugar beet plant comprising a chimeric construct of the present invention capable of modulating expression of the endogenous BvFT1 gene and/or the endogenous BvFT2 gene according to the invention and as described herein before. The plant obtained by said method, i.e. resulting from said cross, particularly a plant that contains the chimeric constructs contributed by both parent 1 and parent 2 is a plant exhibiting the delayed vernalization response or non-bolting phenotype.

In a specific embodiment, the invention relates to a method of producing a transgenic sugar beet plant, wherein at least one of the parent plants does not exhibit a non bolting (NB) phenotype.

Further preferred embodiments relate to roots, progeny, or seeds (like, for example hybrid seed) derived from said transgenic sugar beet plant as described herein before in which the expression of one or more other genes gene involved in flowering control has been modulated in addition to a modulation of the endogenous sugar beet genes BvFT1 and/or BvFT2.

Further preferred embodiments relate to sugar or biofuel derived from said transgenic sugar beet plants, plant parts, cells or root thereof.

The present invention further includes the use of the transgenic sugar beet plants in which the expression of one or more other genes gene involved in flowering control has been modulated in addition to a modulation of the endogenous sugar beet genes BvFT1 and/or BvFT2, or of the plant parts of the present invention in a method selected from the group comprising of methods of sugar production, methods of aerobic fermentation and methods of anaerobic fermentation. The one or more other genes gene involved in flowering control is preferably selected from the group consisting of AGL20 (AGAMOUS-LIKE 20), VRN1 (REDUCED VERNALIZATION RESPONSE 1), VRN2 (REDUCED VERNALIZATION RESPONSE 2), VIN3 (VERNALIZATION INSENSITIVE 3), CONSTANS, GIGANTEA, FPF1 (FLOWERING PROMOTING FACTOR 1), SVP (SHORT VEGETATIVE PHASE), and AGL24 (AGAMOUS-LIKE 24), FLC (FLOWERING LOCUS C), FRIGIDA, and TFL1 (TERMINAL FLOWER 1) as described above.

In a preferred embodiment a method for producing sugar is provided wherein the sugar beet plant in which the expression of one or more other genes gene involved in flowering control has been modulated in addition to a modulation of the endogenous sugar beet genes BvFT1 and/or BvFT2, or cells or tissues thereof of the present invention as described hereinabove are processed to produce sugar. The one or more other genes gene involved in flowering control is preferably selected from the group consisting of AGL20 (AGAMOUS-LIKE 20), VRN1 (REDUCED VERNALIZATION RESPONSE 1), VRN2 (REDUCED VERNALIZATION RESPONSE 2), VIN3 (VERNALIZATION INSENSITIVE 3), CONSTANS, GIGANTEA, FPF1 (FLOWERING PROMOTING FACTOR 1), SVP (SHORT VEGETATIVE PHASE), and AGL24 (AGAMOUS-LIKE 24), FLC (FLOWERING LOCUS C), FRIGIDA, and TFL1 (TERMINAL FLOWER 1) as described above.

Further, the present invention provides sugar that is produced by the method of producing sugar of the present invention.

Another embodiment of the present invention relates to the use of the transgenic sugar beet plant of the present invention in which the expression of one or more other genes gene involved in flowering control has been modulated in addition to a modulation of the endogenous sugar beet genes BvFT1 and/or BvFT2, of the plant parts of the present invention in a method of aerobic or anaerobic fermentation. Methods of aerobic or anaerobic fermentation are known to the person skilled in the art. The one or more other genes gene involved in flowering control is preferably selected from the group consisting of AGL20 (AGAMOUS-LIKE 20), VRN1 (REDUCED VERNALIZATION RESPONSE 1), VRN2 (REDUCED VERNALIZATION RESPONSE 2), VIN3 (VERNALIZATION INSENSITIVE 3), CONSTANS, GIGANTEA, FPF1 (FLOWERING PROMOTING FACTOR 1), SVP (SHORT VEGETATIVE PHASE), and AGL24 (AGAMOUS-LIKE 24), FLC (FLOWERING LOCUS C), FRIGIDA, and TFL1 (TERMINAL FLOWER 1) as described above.

Another preferred aspect relates to a method for producing one or more biofuel(s) selected from the group comprising ethanol, biogas and/or biodiesel, by processing a transgenic sugar beet plant of the present invention in which the expression of one or more other genes gene involved in flowering control has been modulated in addition to a modulation of the endogenous sugar beet genes BvFT1 and/or BvFT2, or cells or tissues, or a biological sample or an extract thereof to produce the one or more biofuel(s). The one or more other genes gene involved in flowering control is preferably selected from the group consisting of AGL20 (AGAMOUS-LIKE 20), VRN1 (REDUCED VERNALIZATION RESPONSE 1), VRN2 (REDUCED VERNALIZATION RESPONSE 2), VIN3 (VERNALIZATION INSENSITIVE 3), CONSTANS, GIGANTEA, FPF1 (FLOWERING PROMOTING FACTOR 1), SVP (SHORT VEGETATIVE PHASE), and AGL24 (AGAMOUS-LIKE 24), FLC (FLOWERING LOCUS C), FRIGIDA, and TFL1 (TERMINAL FLOWER 1) as described above.

The present invention includes other industrial applications such as the production of antibodies or bioplastic in the transgenic sugar beet plants of the present invention. Further, transgenic sugar beet plants of the present invention or parts thereof can be also be used without further processing, such as, for example, as cattle feed.

EXAMPLES

The following examples provide illustrative embodiments. In light of the present disclosure and the general level of skill in the art, those of skill will appreciate that the following Examples are intended to be exemplary only and that numerous changes, modifications, and alterations can be employed without departing from the scope of the presently claimed subject matter.

Example 1

Cloning of the *Beta* FT Homologues and Analysis of their Evolutionary Relationship In order to amplify and clone the FT homologues from sugar beet (also referred to as BvFT homologues), degenerate primers were designed against the conserved nucleotide sequences when aligning the cDNA of the FT orthologs from

*Arabidopsis* (AtFT, accession No. NM_105222), *Citrus* (CiFT, accession No. AB027456), wheat (TaFT, accession No. AY705794), and rice (OsHd3a, accession No. NM_001063395) (FIG. 1). The combination of primers HiNK581 and HiNK860 revealed most successful as described herein below.

Degenerate primer HiNK581 (5'-ACCAGCCNAGRG-TYGARATHGGYGG-3', SEQ ID NO: 1) targets the conserved amino acid sequence motif "KPRVEIGG" located at exon 1 (amino acid residues 51 to 58) according to the sequence of the FT protein from *Arabidopsis*; primer HiNK860 (5'-GGYTGGTSACNGAYATYCCNGCNAC-NAC-3', SEQ ID NO: 2) hybridizes to exon 3 immediately downstream of the splicing site of intron 2 and targets amino acid sequence motif "LVTDIPATT" (amino acid residues 89 to 98).

Total RNA was extracted from sugar beet leaves using the RNeasy Plant Mini kit from Qiagen and converted into cDNA using the FirstChoice® RLM-RACE kit from Ambion, Inc. Experimental conditions were essentially as described by the 3' RLM-RACE protocol supplied with the kit using the 3' RACE adapter (5'-GCGAGCACAGAATTAATACGACTCACTATAGGT12VN-3'; SEQ ID NO: 35) as primer in the reverse transcriptase reaction. The putative BvFT homologues were subsequently amplified starting from the cDNA reaction as initial template in two successive rounds of PCR using the 3' RACE Outer Primer (5'-GCGAGCACAGAATTAATACGACT-3'; SEQ ID NO: 36) in combination with degenerate primer HiNK581 followed by the combination of the 3' RACE Inner Primer (5'-CGCGGATCCGAATTAATACGACTCACTATAGG-3'; SEQ ID NO: 37) with degenerate primer HiNK860 in typical PCR reactions. The thus obtained amplification fragments measured approximately 0.3 Kb in size as expected according to the sequence of the FT orthologs from heterologous species. The PCR products were excised, purified, cloned and sequenced applying routine procedures known to people skilled in the art. Subsequent sequence analysis revealed two homologues, but different sequences referred to as BvFT1 and BvFT2 (shown as SEQ ID NOs: 3 and 4, respectively), that both shared strong sequence homology to the FT protein from *Arabidopsis* (AtFT, accession No. NP_176726).

In order to recover the full-length genomic sequence of both FT homologues from sugar beet, a sugar beet BAC library was screened by means of PCR using primers designed to each FT homologue. The library was developed from the biennial commercial cultivar H20 and calculated to represent 6 genome equivalents with an average insert size of 120 Kb (McGrath et al., 2004). DNA pools for this library are distributed by Amplicon Express, Pullman Wash. The PCR conditions for the screening of the DNA pools were as follows: primary denaturation at 95° C. for 5 min followed by 35 amplification cycles of 30 seconds at 95° C., 30 seconds at 60° C. and 30 seconds at 72° C. and followed by 5 min at 72° C. PCR experiments were run at a GeneAMP® PCR System 9700 instrument from Applied Biosystems Inc. using Platinum® Taq DNA polymerase and the corresponding reaction mix from Invitrogen Corporation as recommended by the supplier. Subsequent screenings of the DNA pools for the presence of either BvFT fragment according to the supplier's instructions resulted in the positive identification of BAC SBA066_G04 for BvFT1 and SBA077_N02 for BvFT2. Both BACs were sent to MWG Biotech AG, Germany, for Sanger sequence analysis starting from the already available cDNA fragments.

Based on the alignment of the genomic sequences to both cDNA fragments and on sequence homology to the FT gene from *Arabidopsis*, the putative gene structure of the *Beta* FT genes comprising introns and exons was predicted as shown schematically in FIGS. 2 and 3. Based on this prediction, the genomic sequence for BvFT1 spans the entire gene with 0.7 Kb of sequence upstream of the ATG start codon (SEQ ID NO: 5). The corresponding coding sequence and amino acid sequence of BvFT1 are shown under SEQ ID NOs: 6 and 7, respectively. The genomic sequence for BvFT2 spans the entire gene with 1.1 Kb of sequence upstream of the ATG start codon (SEQ ID NO: 8). The corresponding coding sequence and amino acid sequence of BvFT2 are set forth as SEQ ID NOs: 9 and 10, respectively. Alignment of the full-length amino acid sequences of BvFT1 and BvFT2 to the protein sequence of the FT from *Arabidopsis* further confirmed the strong sequence homology: BvFT1 showed 72% identity and 82% similarity using the BLOSUM62 matrix, BvFT2 75% identity and 88% similarity (FIGS. 4 and 5). Moreover, when aligning BvFT1 and BvFT2 proteins to a large collection of FT family members from different species and converting the alignment into a phylogenetic tree according to the Neighbor-Joining method (Saitou and Nei, 1987), both BvFT1 and BvFT2 cluster in the FT-like clade (FIG. 6).

Example 2

Mapping of BvFT1 and BvFT2

Primer pairs SELA3770 (SEQ ID NO: 11) and SELA3771 (SEQ ID NO: 12), as well as SELA3776 (SEQ ID NO: 13) and SELA3777 (SEQ ID NO: 14) targeting BvFT1 and BvFT2, respectively, were used to amplify and to sequence a genomic fragment consisting of the entire exon 1, intron 1 and exon 2 for each gene across a set of 16 sugar beet lines. For BvFT1, five haplotypes or alleles were distinguished by eleven SNPs and one INDEL, for BvFT2 two alleles were characterized by only two SNPs (see Table 1).

TABLE 1

Sequence polymorphisms observed between sugar beet lines for both BvFT1 and BvFT2. The numbering of the polymorphic nucleotide positions is according to SEQ ID NOs: 5 and 8, respectively.

| | allele1 | allele2 | allele3 | allele4 | allele5 |
|---|---|---|---|---|---|
| BvFT1 (position SEQ ID No. 5) | | | | | |
| 659 | A | T | A | A | A |
| 708 | G | G | A | G | G |

TABLE 1-continued

Sequence polymorphisms observed between sugar beet lines for both BvFT1 and BvFT2. The numbering of the polymorphic nucleotide positions is according to SEQ ID NOs: 5 and 8, respectively.

| | allele1 | allele2 | allele3 | allele4 | allele5 |
|---|---|---|---|---|---|
| 758 | G | C | G | G | G |
| 760 | G | G | A | G | G |
| 800 | — | — | — | A | — |
| 801 | — | — | — | A | — |
| 802 | — | — | — | T | — |
| 864 | T | T | C | T | T |
| 935 | C | C | C | C | G |
| 980 | T | T | G | T | G |
| 1042 | G | G | G | C | G |
| 1055 | A | A | T | A | A |
| 1070 | A | A | A | A | T |
| 1119 | A | A | T | A | A |
| BvFT2 (position SEQ ID No. 8) | | | | | |
| 1508 | G | A | | | |
| 1558 | A | G | | | |

In order to map BvFT1 and BvFT2, two assays were developed targeting the SNP at position #935 (SEQ ID NO: 5) for BvFT1 and the SNP at position #1508 (SEQ ID NO: 8) for BvFT2 using the EndPoint TaqMan® technology. Table 2 summarizes the nucleotide sequences of the primers and probes designed for the two assays, called FT1(T1) and FT2 (T1). The reactions further consisted of the TaqMan® Universal PCR Master Mix, No AmpErase® UNG (2×) from Applied Biosystems Inc. according to the manufacturer's recommendations. The PCR amplification was performed as follows: 95° C. for 10 min followed by 40 cycles of 95° C. for 15 sec and 60° C. for 1 min, using a Real Time PCR 7500 System instrument. Endpoint measurement was performed using the Sequence Detection System software.

TABLE 2

Nucleotide sequences of primers and probes designed for and used in the TaqMan assays FT1(T1) and FT2(T1) targeting BvFT1 and BvFT2, respectively.

| Precursor name | SEQ ID No. | sequence 5' to 3' | chem-istry in 5' | chem-istry in 3' | direction | assay | target | allele |
|---|---|---|---|---|---|---|---|---|
| SELA4259 | 15 | AGTTTCTTTTTATGGGTATCAAACACTAGA— | — | — | reverse | FT1(T1) | #935 | — |
| SELA4260 | 16 | CCTTGGTAAGTCCATTGATTAAGATTG | — | — | forward | FT1(T1) | #935 | — |
| SELA4261 | 17 | ACAATGCACGAATAAT | FAM | MGB | reverse | FT1(T1) | #935 | 1, 2, 3 and 4 |
| SELA4262 | 18 | ACAATGCACCAATAAT | VIC | MGB | reverse | FT1(T1) | #935 | 5 |
| SELA4263 | 19 | GTAGGTTATGGTGGACCCAGATG | — | — | forward | FT2(T1) | #1508 | — |
| SELA4264 | 20 | TCACCAGTGTAAATATTCCCTCAAGT | — | — | reverse | FT2(T1) | #1508 | — |
| SELA4265 | 21 | TCCGAGCCCAAGTAA | FAM | MGB | forward | FT2(T1) | #1508 | 1 |
| SELA4266 | 22 | CTCCAAGCCCAAGTAA | VIC | MGB | forward | FT2(T1) | #1508 | 2 |

Using the above described TaqMan assays, the BvFT1 and BvFT2 gene were mapped in a F3 population of 284 individuals derived from a cross between two sugar beet parental lines polymorphic for both SNPs at positions #935 and #1508 representing BvFT1 and BvFT2, respectively. This population was previously genotyped with a set of public SNP markers (SCHNEIDER et al., 1999; SCHNEIDER et al., 2002). Using the JoinMap 3.0 software for genetic mapping known to people skilled in the art, BvFT1 and BvFT2 were mapped at chromosome IX and chromosome IV, respectively (FIG. 7).

Example 3

Gene Expression Analysis of the BvFT Homologues

For an analysis of the expression patterns of the *Beta* FT homologues, plants tissues consisting of seeds, seedlings, vegetative and reproductive organs from biennial plants were sampled. Plants were grown in chambers at a constant temperature of 18° C. and a photoperiod of 18 hours light/6 hours dark (LDs). The expression levels of the FT homologues in these tissues were analyzed by means of quantitative PCR (qPCR).

Total RNA was isolated using the RNAqueous®-4PCR Kit commercialized by Ambion, basically following the supplier's instructions. The RNA samples were converted to cDNA using the RETROscript® Kit (Ambion) starting from 1 μg of total RNA as template. The expression of both BvFT1 and BvFT2 was measured using the Power SYBR® Green PCR Master Mix (Applied Biosystems Inc) on a Real Time PCR 7500 System instrument. The PCR conditions were as follows: primary denaturation at 95° C. for 10 min followed by 40 amplification cycles of 15 seconds at 95° C. and 1 min at 60° C. The nucleotide sequences of the forward and reverse primers specific for BvFT1 and BvFT2 were as follows: 5'-CACAAGTGCATCATTTGGAGAAG-3' (SEQ ID NO: 23) and 5'-TTCCCAATTGCCGAAACAA-3' (SEQ ID NO: 24) for BvFT1, and 5'-GGGAATATTTACACTGGTTGGT-GACT-3' (SEQ ID NO: 25) and 5'-TCCAACTGATGGTCT-TGGATTTT-3' (SEQ ID NO: 26) for BvFT2. The isocitrate dehydrogenase (BvICDH) gene was used as reference gene for normalizing the expression of BvFT1 and BvFT2. The primer sequences designed for BvICDH (AF173666) was 5'-CACACCAGATGAAGGCCGT-3' (SEQ ID NO: 27) and 5'-CCCTGAAGACCGTGCCAT-3' (SEQ ID NO: 28). Expression levels were calculated as the average of three biological replicates and each qPCR reaction was repeated three times. Data were analysed using the Sequence Detection System software (Applied Biosystems Inc.) and the GenEx software (MultiD Analyses).

BvFT1 was highly expressed in leave tips of juvenile-stage plants, but its transcription was barely detectable in the reproductive-stage plants (FIG. 8). In contrast to BvFT1, BvFT2 was found to be mainly expressed in expended leaves of reproductive-stage plants.

The expression level of both BvFT1 and BvFT2 was also analyzed in leaves harvested across different developmental stages in biennial and annual sugar beet plants. Plants were grown in controlled environment chambers at a constant temperature of 18° C. and a photoperiod of 18 hours light/6 hours dark (LDs). The growth of biennial plants was interrupted by a vernalization period of 14 weeks with a temperature set at 5° C. and a photoperiod set at 12 hours light/12 hours dark. Leaves were sampled in the middle of the day every week throughout the growing period before and after the vernalization treatment. The last sampling was performed on plants showing an advanced stem elongation of about 10 cm, which marks the switch to the reproductive stage (FIG. 9).

BvFT1 transcripts were readily detected in leaves of early vegetative stages in biennial plants, but expression levels dropped after vernalization and remained low throughout the transition from vegetative to reproductive phases. In contrast, BvFT2 expression was barely detectable in the juvenile-stage biennial plants and increased dramatically prior to the first visible signs of bolting. Surprisingly, BvFT1 was expressed at very low levels at the juvenile stage in annual plants and remained low, whereas BvFT2 expression increased to substantial levels prior to the first visual signs of bolting as observed in biennial plants. These observations show that expression of both BvFT1 and BvFT2 is actively regulated depending on the developmental stage of the plant, but with very contrasting expression profiles. The increase in expression of BvFT2 observed in annual and biennial plants prior to bolting time is very similar to the expression profile of the FT gene in *Arabidopsis*, which suggest that BvFT2 is the true FT ortholog.

Example 4

The Effect of Photoperiod on BvFT1 and BvFT2 Expression

To further investigate the regulation of BvFT1 and BvFT2 and their role in controlling flowering time, expression analysis was performed on leaf samples in annual, biennial and vernalized biennial sugar beet plants across the diurnal cycle with different photoperiods. Three experiments were independently undertaken where plants were grown at a constant temperature of 18° C. either under SD (10 hours light/14 hours dark), LD (18 hours light/6 hours dark) or LDSDLD conditions, respectively. LDSDLD conditions mean that plants were initially grown under LD conditions, were transferred for one week to SD conditions and subsequently transferred back to LD conditions (FIG. 10). Plants were monitored for bolting time (FIG. 11) and gene expression analysis was performed by means of qPCR as described above in Example 3. Under SD conditions, BvFT2 was hardly detectable in the three classes of plants (i.e., in annual, biennial and vernalized biennial sugar beet plants), whereas BvFT1 showed a clear peak of expression 4 h after dawn. The amplitude of the oscillations of BvFT1 expression was equally high in all plants. In contrast to SD conditions, BvFT2 showed a diurnal oscillation under LD conditions in annual and vernalized-biennial plants quite similar to that of AtFT with a peak of expression at the end of the day, further suggesting that BvFT2 is likely to the true FT ortholog in *Beta*. BvFT1 was also found to be expressed and regulated under LD conditions, but the amplitude dropped substantially in annual and vernalized biennial plants. The contrasting expression profiles observed between BvFT1 and BvFT2 were found to be associated with the flowering time. Indeed, under SD conditions when plants show high expression levels BvFT1 and low expression levels of BvFT2, none of the plants progressed to bolting, whereas under LD conditions when BvFT2 is the predominantly expressed FT homologue, annual and vernalized-biennial plants switched to flowering. If plants were grown under SD conditions prior to transfer to LD conditions it was surprising that only the annual plants bolted without notable changes in the expression levels of BvFT1 and BvFT2. In contrast, vernalized biennial plants showed a setback of the BvFT1 and BvFT2 expression levels to those observed in non-vernalized biennial plants, which was associated with continuous vegetative growth.

Altogether, these data confirm that vernalization is required by biennial plants to be able to bolt, but that LDs are essential to trigger the final switch post vernalization. We here show that variations in the photoperiod such as a single pass to SDs for one week was enough to reverse the competence of the biennial plants to flower acquired during vernalization. To evaluate how fast the induction of BvFT2 expression occurs under LD conditions, we continued to explore the expression of BvFT2 in annual plants which seem to respond to LDs even after a single passage to SDs. Annual plants were grown in SDs (10 hours light/14 hours dark) for ten days prior to shifting day-length conditions to LDs (18 hours light/6 hours dark) by expending the light period on day eleven. We measured the expression of BvFT1 and BvFT2 over 72 hours. BvFT2 was found to be induced within 24 hours upon day-length extension (FIG. 12), which was also found to be associated with a decrease in BvFT1 expression. Therefore, a single 24 hours exposure to LDs was enough to down-regulate the expression of BvFT1 and to promote the up-regulation of BvFT2. These observations suggest that expression of BvFT1 and BvFT2 are mutually exclusive and that the expression of BvFT2 is prevented as long as BvFT1 is expressed, suggesting a negative feedback loop between the two genes.

Example 5

Characterization of the Molecular Function of BvFT1 and BvFT2 in *Arabidopsis*

To assess the functionality of the BvFT homologues, the coding regions of the cDNA of both BvFT1 and BvFT2 were assembled into gene cassettes under the control of the constitutive CaMV 35S promoter that were subsequently transformed into *Arabidopsis*.

The synthesis of the coding regions for both BvFT1 and BvFT2 as represented by SEQ ID NOs: 6 and 9, respectively, flanked by the Gateway attB flags, was subcontracted to Millegen SA in Toulouse, France. The obtained cDNA fragments were subsequently introduced into the pDONR201 donor vector by means of homologous BP recombination using the Gateway® cloning system (Gateway® BP Clonase Enzyme Mix) following the protocol recommended by the supplier. The recombinant vectors were transformed to *Escherichia coli* strain DH5a by means of electroporation and screened for successful recombination using standard procedures known to people skilled in the art. The gene cassettes of the pDONR201-BvFT1 and pDONR201-BvFT2 entry vectors were subsequently introduced into the pB7WG2D destination vector via the homologous LR recombination using the Gateway® cloning system (Gateway® LR Clonase Enzyme Mix) following the protocol recommended by the supplier. In addition to the BvFT cassettes, the thus obtained binary vectors carried the bar gene under the control of the nos promoter that allows for selection for glufosinate resistance. Upon transfer of the binary vectors into *Agrobacterium tumefaciens* strain GWF3101-pMP90KR by electroporation, the T-DNAs were transformed into flowering *Arabidopsis* plants by means of the floral dipping method essentially as described by CLOUGH & BENT (1998). Both, wild type (Col-0) as well as the ft-10 mutant (which is deficient for FT and which shows a characteristic late-flowering phenotype under classic long-day conditions consisting of 16 hours light/8 hours dark) were used as acceptor in the floral dipping experiments. Seeds harvested on the 'dipped' plants were germinated and seedlings treated with Basta™ in order to select for transgenic plants. Basta™ resistant plants were repotted and subsequently monitored for flowering using non-transgenic seedlings as control.

Ectopic expression of BvFT2 resulted in an extreme early-flowering phenotype in *Arabidopsis* (Col-0) with an average of 5.0 leaves formed at the time of the floral transition (FIG. 13 and Table 3). The late-flowering phenotype of the ft-10 mutant was fully complemented by the expression of BvFT2 suggesting that BvFT2 is indeed the FT ortholog in sugar beet. In contrast, transgenic events expressing BvFT1 displayed a very late-flowering phenotype with an average of 56.9 and 74.3 leaves, respectively, in wild-type Col-0 and ft-10 mutant plants at the time of flowering (FIG. 13 and Table 3). In addition to the late-flowering phenotype several morphological aberrations were observed in the transgenic *Arabidopsis* plants expressing BvFT1 such as lack of petals and formation of inflorescence structures. In general, floral organs on *Arabidopsis* plants expressing BvFT1 exhibited an intermediate morphology between flowers and inflorescences not subtended by bracts. All these features were previously observed in *Arabidopsis* plants overexpressing AtTFL1 (RATCLIFFE et al., 1998), a well-known inhibitor of flowering, which further illustrates the fact that BvFT1 acts more like a repressor than a promoter of flowering despite its clustering into the FT-like clade in the phylogeny tree of the FT gene family (FIG. 6). The opposite function of BvFT1 and BvFT2 as revealed by the overexpression experiments in *Arabidopsis*, i.e. repression of flowering conferred by BvFT1 versus promotion of flowering conferred by BvFT2, is consistent with their expression profiles that likewise are contrasting in sugar beet as described in Examples 3 and 4.

TABLE 3

Effect of ectopic expression of BvFT1 and BvFT2 in *Arabidopsis* wild type (Col-0) and *Arabidopsis* ft-10 mutant plants on flowering time. A flowering promoting effect (as conferred by BvFT2) is indicated by low numbers of leaves at the time of flowering, a flowering repressing phenotype (as conferred by BvFT1) is indicated by a high number of leaves at the time of flowering.

|  | number of leaves | number of analyzed independent T1 plant |
| --- | --- | --- |
| Wild type (Col-0) | 17.0 ± 1.6 | 18 |
| 35S::BvFT1 | 56.9 ± 14.6 | 16 |
| 35S::BvFT2 | 5.0 ± 1.0 | 55 |
| ft-10 | 50.6 ± 9.3 | 12 |
| 35S::BvFT1 (ft-10) | 74.3 ± 5.0 | 18 |
| 35S::BvFT2 (ft-10) | 5.5 ± 1.3 | 33 |

Example 6

Mapping of BvFT1- and BvFT2-Specific Activity to the B Segment of Exon 4

To further investigate the cause for the opposite function of BvFT1 and BvFT2, we transformed *Arabidopsis* (Col-0) with chimaeras of BvFT1 and BvFT2 in an attempt to map the regions conferring BvFT1- or BvFT2-like protein activity in vivo. These experiments are based on the studies performed by HANZAWA et al. (2005) and Am et al. (2006) that allowed for the identification of the relevant protein motifs that discriminate between FT- and TFL1-like activities in *Arabidopsis*. Since these studies demonstrated the critical role of the fourth exon in the antagonistic activities between FT and TFL1 genes (AHN et al., 2006), this region was expected to be also a determinant for the activities of BvFT1 and BvFT2. It was therefore decided to first swap the entire exon 4 between the BvFT1 and BvFT2 genes. The two corresponding chimeric genes were called BvFT1112 (SEQ ID NO: 29) and BvFT2221 (SEQ ID NO: 30), indicating that in the first case exons 1, 2 and 3 are from BvFT1, and exon 4 from BvFT2, and that in the second case exons 1, 2 and 3 are from BvFT2, and exon 4 from BvFT1. The activity of the chimeric BvFT genes was analyzed by counting the number of leaves in at least 15 independent T1 transformants (FIG. 14). Transgenic *Arabidopsis* plants expressing BvFT2221 flowered much later than the wild-type, although not quite as late as 35S::BvFT1 overexpressors. In contrast, transgenic BvFT1112 *Arabidopsis* plants did not display the late-flowering phenotype observed previously in the transgenic 35S::BvFT1 plants, and flowered much earlier than the wild-type *Arabidopsis* plants with an average of 8.1 leaves.

Because of the strong effect of exon 4 observed for the comparison of both BvFT1 to BvFT2, and AtFT to AtTFL1, respectively, a second set of chimeric genes, called BvFT1E4B2 (SEQ ID NO: 31) and BvFT2E4B1 (SEQ ID NO: 32), were generated by swapping only region B of exon 4 which was found to be highly variable in TFL1 orthologs but almost invariant in FT orthologs (ARN et al., 2006). In this region, BvFT1 and BvFT2 proteins differ only by three amino-acids (FIG. 14) that could lead to changes within the adjacent external loop of the anion-binding pocket of the BvFT1 and BvFT2 proteins, which might well contribute to the opposite biological function observed between the two proteins. Transgenic BvFT2E4B1 plants showed a similar late-flowering phenotype as the transgenic BvFT2221 plants, while overexpression of BvFT1E4B2 promoted an early phenotype with on average 7.3 leaves formed at the time of the floral transition. Consequently, the BvFT1 protein carrying the external loop domain of the FT2 protein basically becomes as effective in accelerating flowering as the authentic BvFT2 protein and vice versa, the BvFT2 protein carrying the external loop domain of the FT1 basically becomes as an effective suppressor of flowering as the authentic BvFT1. These results demonstrate that the external loop region of FT-like proteins that corresponds to the B segment of exon 4 is critical for the protein function and a difference of only three amino acid substitutions as observed between BvFT1 and BvFT2 are sufficient to convert a promoter of flowering into a repressor of flowering in *Beta* and vice versa.

Example 7

Transgenic Suppression of BvFT2 Confers Bolting Resistance in Beets

In order to explore the feasibility of engineering bolting resistance in sugar beet by down-regulating BvFT2, transgenic sugar beet plants were generated carrying an RNAi cassette derived from BvFT2 in both an annual and biennial background. By means of a strategy known as 'recombinant-PCR' (HIGUCHI, 1990), a 0.27 Kb cDNA fragment of FT homologue BvFT2 primarily consisting of exon 4 was fused to the second intron from the potato StLS1 gene (ECKES et al., 1986; VANCANNEYT et al., 1990). BvFT1 and BvFT2 show sufficient sequence variation across exon 4 to guarantee the specific silencing of BvFT2 without affecting BvFT1. The BvFT2 fragment was amplified from cDNA (previously synthesized from total RNA obtained from biennial sugar beet leaves as described in Example 1) using primers HiNK6382 (5'-CTAT GGATCCGCATTTAATAAAATCTCTTTCAATG-3' (SEQ ID NO: 44) and HiNK6384 (5'-_GTAGAAGCAG_ _AAACTTACCT_ GCCAAGAAGTTGTCTGCT-ATG-3', SEQ ID NO: 45), the first carrying a short linker to add a BamH I restriction site, the latter carrying a tail of 17 nucleotides complementary to the 5' end of the StLS1 intron (linkers and tails are underlined hereinafter). The 0.19 Kb fragment comprising the StLS1 intron and flanking splicing sites was amplified from potato DNA containing the StLS1 intron, using primers HiNK6383 (5'-_CATAGCAGAC_ _AACTTCTGGC_ AGGTAAG-TTTCTGCTTCTAC-3', SEQ ID NO: 46) and HiNK529 (5'-ATCCAA CCGCGGACCTGCACATCAACAA-3', SEQ ID NO: 40), with HiNK529 carrying a linker including the recognition sequence of Sac II and HiNK6382 carrying a tail of 22 nucleotides identical to the 5' extremity of the 0.27 Kb BvFT2 fragment. As a consequence of the added tails, primers HiNK6384 and HiNK6383 as well as their cognate amplification products are complementary to each other over a length of 39 nucleotides. By virtue of this overlap both amplification products were fused to each other by means of a second round of PCR using primers HiNK6382 and HiNK529 and using a mix of both amplification products as template, yielding a fusion product of 0.47 Kb in length between the BvFT2 fragment in antisense orientation upstream of the StLS1 intron fragment. The 0.27 Kb BvFT2 fragment was amplified a second time, now using primers HiNK6385 (5'-TAAATCCGCGGGCCAAGAA-GTTGTCTGCTATG-3', SEQ ID NO: 47) and HiNK6386 (5'-CTATTTGTCGACGCATTTAATAAAATCTCTTTC-3', SEQ ID NO: 48) that target the same sequence at BvFT2 as HiNK6382 and HiNK6384, respectively, but that carry different linkers; HiNK6385 and HiNK6386 both carry 5' linkers to add a Sac II and a Sal I recognition sequence, respectively. Both fragments were fused at the Sac II restriction sites to create an inverted repeat for the BvFT2 sequence separated by the intron from the potato StLS1 gene. The inverted repeat of the BvFT2 fragment was separated by the second intron from the potato StLS1 gene to stabilize the RNAi cassette, but also to improve the efficiency of the RNAi silencing (SMITH et al., 2000; WANG and WATERHOUSE, 2001). The thus obtained inverted repeat of approximately 0.73 Kb was subsequently introduced between the UBQ3 promoter from *Arabidopsis* (NORRIS et al., 1993) and the nos terminator from *Agrobacterium tumefaciens* as a BamH I-Sal I fragment. Subsequently, the gene cassette was transferred as a 2.4 Kb Asc I-Pac I fragment onto the T-DNA of the proprietary binary transformation vector pVictorHiNK, yielding pHiNK525. The plasmid map of the binary vector carrying the RNAi gene cassette for BvFT2 in combination with the PMI selectable marker gene under the control of the hsp80 promoter from *Brassica* (BRUNKE and WILSON, 1993-EP0559603) is shown in FIG. 15; the sequence of the binary vector pHiNK525 is set forth as SEQ ID NO: 33. The experimental procedure for the transformation of annual and biennial sugar beet of genotype G018 with the RNAi cassette was basically the multiple shoot protocol as described in International Patent Application WO 02/14523 using sugar beet meristematic tissues as explant material and mannose-6-phosphate as selective agent together with the phosphomannose isomerase (PMI) gene as selectable marker as described in International Patent Application WO 94/20627. Primary transformants are referred to as T0 plants; subsequent generations are referred to as T1, T2, T$_n$ plants. Upon delivery to the greenhouse, PMI-positive T0 shoots and non-transgenic controls were rooted first in small pots with soil and grown under enhanced CO$_2$ conditions for two weeks. Rooted plants were subsequently transferred to Ø 12 cm (0.7 liter) pots and placed and transferred to the biochamber for an acclimatization period of two weeks minimum at 18° C. (18 hours artificial light; 18° C. day+night temperature) prior to vernalization.

Biennial transgenic and control plants were vernalized during a period of 14-16 weeks at a constant temperature of 6° C. and at a photoperiod of 12 hours light/12 hours dark. Prior to applying bolting-inductive conditions, the vernalized plants were slowly acclimatized for two weeks in climate chambers by stepwise increasing the temperature from 10 to 18° C. Plants were subsequently repotted into to larger pots (2 liter), and monitored for bolting while exposed to a constant temperature of 18° C. and a photoperiod of 18 hours light/6 hours dark. Bolting was monitored every 3 to 4 days and defined as the first visible elongation of the apical meristem. Delay in bolting was always scored in comparison to non-transgenic control plants that underwent the same regeneration and vernalization procedure.

Non-transgenic control plants as well as transgenic plants started bolting between three to four weeks post vernalization. However, contrary to controls plants that reached full reproductive growth, transgenic plants stopped bolting after a few centimeters of stem elongation and resumed vegetative growth (Table 4A). This phenomenon has also been described for devernalized sugar beet plants and is referred to as stunting.

Gene expression analysis was carried out by means of quantitative PCR in order to validate the silencing of the endogenous BvFT2 target gene as described in Example 3. Transgenic plants showed a range in silencing from 95 to 99% of the normal expression levels of BvFT2 in non-transgenic control plants (Table 4B). Despite several attempts of forcing the transgenic plants to flower and set seed (prolonged vernalization and/or treatment with gibberellic acids), the obtained biennial events failed to develop flower buds and to set seed.

Annual material does not require cold (winter) temperatures in order to initiate flower development. Therefore, the annual material was directly transferred to climate chambers and exposed to bolting inductive conditions (18° C. and a photoperiod of 18 hours light/6 hours dark) without vernalization. Non-transgenic annual plants started bolting three to four weeks after acclimatization and repotting, whereas 18 out of 24 annual events suppressing BvFT2 showed a very late-flowering phenotype with more than one month delay in bolting. Five events remained non-bolting for at least 2 month. One non-bolting clone plant was kept under bolting inductive conditions and has remained vegetative growth for at least 15 months (FIG. 16 and Table 4A). The non-bolting annual beets suppressed for BvFT2 developed tap roots, which is very unusual for an annual genetic background. Gene expression analysis demonstrated that silencing by at least 50% of endogenous BvFT2 is required for the transgenic plants to be delayed for at least 1 month. The non-bolting transgenic plants showed an almost complete gene silencing (>90%) of the endogenous BvFT2 gene (Table 4B).

Table 4: (A)—Delay of bolting in annual and biennial control (i.e. non-transgenic) and transgenic plants (i.e. plants in which expression of BvFT2 is suppressed). Delay in bolting was calculated for each individual clone plant by deducting its bolting date with the average bolting date of the control plants from the same delivery date. Delay in bolting of each event was defined by calculating the average delay in bolting of the total number clone plants (three to eight). <3w=delay less than 3 weeks (=21 days) compared to control plants; >4w=delay more than 4 weeks (=28 days) compared to control plants; NB=Non-bolting during the experiment; stunting=stem elongation (bolting) was suppressed and plants resumed vegetative growth. (B)—Table providing more details on the plants summarized in Table 4A. Gene silencing of the endogenous BvFT2 in leaf tips was calculated by means of quantitative PCR and in comparison to control plants at similar developmental stage. Event—the number in the event identifier refers to the original sugar beet explants; the letter refers to different events all originating from the same sugar beet explants; An/Bi=Annual/Biennial; No. of plants=number of plants per event; GM average days delayed=average delay of the clone plants of one event (when some clone plants started bolting, but other clone plants were still non-bolting (NB) at the end of the screen, the average delay in bolting for the event was calculated as a bolting delay of at least the average number of days; St.Dev=standard deviation

TABLE 4A

| Gene | | Total | no delay | <3 w | >4 w | NB | Stunting |
|---|---|---|---|---|---|---|---|
| BvFT2 dsRNAi | T0 Annual | 24 | 4 | 4 | 11 | 5 | |
| BvFT2 dsRNAi | T0 Biennial | 5 | | | | | 5 |

TABLE 4B

| Event | An/Bi | % BvFT2 silencing | No. of plants | GM Average days delayed | St. Dev | Conclusion |
|---|---|---|---|---|---|---|
| 1B | Bi | 95 | 3 | 8 | 5.0 | stunting |
| 1C | Bi | 98 | 5 | 9 | 2.8 | stunting |
| 1D | Bi | 99 | 3 | >30 | | stunting |
| 1E | Bi | 96 | 5 | 8 | 6.2 | stunting |
| 1F | Bi | 95 | 4 | 5 | 6.3 | stunting |
| 2A | An | 95 | 5 | NB | | NB |
| 2B | An | 98 | 7 | NB | | NB |
| 2C | An | 96 | 5 | NB | | NB |
| 2D | An | 99 | 7 | NB | | NB |
| 2E | An | 95 | 5 | NB | | NB |
| 3A | An | 95 | 6 | >31 | | >4 w |
| 3C | An | 0 | 5 | 9 | 6 | <3 w |
| 4A | An | 8 | 2 | 1 | 2 | 0 |
| 4B | An | 44 | 8 | 4 | 4 | 0 |
| 5A | An | 60 | 5 | >48 | | >4 w |
| 6A | An | 85 | 2 | 44 | 7 | >4 w |
| 7A | An | 74 | 7 | >42 | | >4 w |
| 7B | An | 84 | 3 | 44 | 11 | >4 w |
| 7C | An | 80 | 4 | >37 | | >4 w |
| 7D | An | 89 | 2 | 41 | 12 | >4 w |
| 7E | An | 91 | 3 | 50 | 10 | >4 w |
| 7F | An | 89 | 4 | 55 | 6 | >4 w |
| 8A | An | 91 | 3 | >87 | | >4 w |
| 8B | An | 0 | 5 | 14 | 20 | <3 w |
| 8C | An | 0 | 6 | 12 | 13 | <3 w |
| 9A | An | 0-42 | 7 | -1 | 4 | 0 |
| 9B | An | 0-44 | 5 | 0 | 5 | 0 |
| 10A | An | 0-73 | 3 | 17 | 2 | <3 w |
| 10B | An | 95 | 2 | >74 | | >4 w |

Treatment of annual events with vernalization and/or gibberellins was, however, successful to produce seed from the bolting resistant BvFT2 plants. As expected the T1 progeny segregated into transgenic and non-transgenic plants; transgenic plants were identified by means of PCR analysis. During the phenotypic screen transgenic and non-transgenic segregants were handled and grown in parallel. In such way, the bolting behavior of the transgenic plants could be directly compared to control plants in the same genetic background and under the same conditions. The phenotypic screen of the 2nd generation (T1) transformed clone plants started from seed. Transgenic and non-transgenic control plants were repotted and transferred to a biochamber with 18° C. and a photoperiod of at least 18 hours light and monitored for bolting as described for the T0 generation. The transgenic progeny plants derived from a delayed T0 event suppressing 60% of the endogenous BvFT2 showed a significant bolting delay of 8.7 days compared to the control plants, while the progeny derived from the event suppressing 95-99% of BvFT2 remained non-bolting for at least 10 weeks (actually the plants are non-bolting at the end of the experiment after 72 days) (FIG. 17 and Table 5). These T1 results demonstrated that the BvFT2 mediated bolting resistance was successfully transferred to the next generation.

TABLE 5

Bolting behavior of T1 sugar beet events suppressing BvFT2. Average bolting day = average number of days at which bolting has started; NB = Non-bolting during the 72 days of experiment. In order to carry out a Duncan's test, the non-bolting plants were given the value 75 days. Events with different Duncan groups are significantly different in bolting time; GM Average Days delayed = average delay of bolting in transgenic plants.

| Event | No. of plants | Average bolting day | Duncan Grouping | GM Average Days Delayed |
|-------|---------------|---------------------|-----------------|-------------------------|
| 2A    | 11            | 75                  | A               | >43.7                   |
| 2C    | 5             | 75                  | A               | >43.8                   |
| 5A    | 24            | 40                  | B               | 8.7                     |
| NT    | 24            | 31.3                | C               |                         |

Example 8

Transgenic Overexpression of BvFT1 Confers Bolting Resistance in Sugar Beets

In order to explore the feasibility of engineering bolting resistance in sugar beet by over-expressing BvFT1, transgenic sugar beet plants were generated carrying a gene cassette consisting of the coding sequence of BvFT1 (SEQ ID NO: 6) under the control of the constitutive Ubi3 promoter from *Arabidopsis* (NORRIS et al., 1993) in both an annual and biennial background. To this purpose the coding sequence of BvFT1 was synthesized at the gene synthesis service offered by GENEART Inc (www.geneart.com) as one single fragment of 0.56 Kb with a BamH I restriction site immediately upstream of the ATG start codon and a Sac I restriction site immediately downstream of the stop codon. The synthetic BvFT1 fragment was ligated in between the Ubi3 promoter fragment and the nos terminator fragment by means of the BamH I and Sac I restriction sites. The complete gene cassette of 2.6 Kb was subsequently transferred to the T-DNA of the proprietary transformation vector pVictorHiNK as a SanD I/Rsr II fragment at the Rsr II site next to the SuperMAS::PMI::nos selectable marker gene that was already present at the binary vector pVictorHiNK. The plasmid map of the binary vector 17603 carrying the gene cassettes for both the PMI selectable marker gene and the BvFT1 gene is shown in FIG. 18 and is set forth in SEQ ID NO: 34. Trans-formation of this vector into both annual and biennial sugar beet was achieved as described in Example 7.

In order to check BvFT1 overexpression in PMI-positive T0 shoots the amount of BvFT1 transcripts was quantified in primary leaf samples in transgenic and non-transgenic control T0 plants as described above in Example 3. Variation in expression level was observed between transgenic events, but in average all transgenic T0 plants showed an increased expression of BvFT1 compared to the non-transgenic control T0 plants (FIG. 19). This result shows that the Ubi3::BvFT1 gene cassette is functional and delivers a strong and constitutive expression of the flowering repressing gene BvFT1.

Upon rooting and acclimatization, biennial events were exposed to vernalization, repotted and monitored for bolting while growing to a constant temperature of 18° C. and a photoperiod of 18 hours light/6 hours dark as described in Example 7. Transgenic events obtained in the annual background were directly monitored for bolting. Biennial control plants started bolting 3 to 4 weeks post vernalization and annual controls 3 to 4 weeks after acclimatization and repotting. Transgenic plants over-expressing BvFT1 frequently showed a delay in bolting ranging from only few weeks to more than three months. A few events, both in the annual and biennial background, never started bolting under the conditions applied in the biochamber. Apart from the delay in bolting and flowering, transgenic plants developed normally and showed no phenotypic aberrations. In general, plants delayed in bolting showed a higher leaf number at the time of bolting as a result of the prolonged vegetative stage, and the most delayed plants developed taproots as typically observed for non-vernalized biennial plants.

Example 9

Trans-Activation Systems for the Conditional Expression of BvFT

As illustrated in the examples above, controlling the expression levels of the *Beta* FT homologues allows for the engineering of bolting resistance. In order to be able to maintain, multiply and commercialize such bolting resistant sugar beet plants, the overexpression and/or downregulation in the case of BvFT1 and BvFT2, respectively, needs to be conditional or latent. In this example the performance of the pOp6/LhG4 system for the conditional control of gene expression with respect to BvFT1 and BvFT2 in sugar beet was assessed. The pOp6/LhG4 system comprises a chimeric transcription factor, LhG4, in which transcription activation domain II of Gal4 is fused to a high-affinity DNA-binding mutant of the lac repressor. This activates transcription from promoters such as pOp6 that carries six copies of an optimized lac operator sequence upstream of a minimal CaMV 35S promoter (RUTHERFORD et al., 2005).

With the purpose of facilitating the generation and selection of transgenic events in which the pOp6/LhG4 transactivation system is functional, the PMI selectable marker gene was cloned downstream of the pOp6 promoter and combined with the gene cassette for the constitutive expression of LhG4Ato (RUTHERFORD et al., 2005) under to the control to the Ubi3 promoter from *Arabidopsis* (NORRIS et al., 1993) on one and the same T-DNA to yield pHiNK498. The plasmid map of this binary vector is shown in FIG. 20; the sequence of this vector is set forth as SEQ ID No: 53. When applying mannose as selective agent, the regeneration of PMI-positive events thus is subject to the successful trans-activation of the PMI gene by means of the pOp6/LhG4/pOp system. Apart from this conditional aspect concerning the PMI selection, the procedures for the transformation, selection and regeneration of transgenic sugar beet events were the same as described in the previous examples. In total the transformation of pHiNK498 delivered 62 independent events that showed PMI expression levels ranging from negative to extremely high. PMI expression was determined both by Real-time PCR (as described in Example 3) employing primer SELA267 as forward primer (5'-CCGGGTGAATCAGCGTTT-3'; SEQ ID NO: 51) and primer SELA268 as reverse primer (5'-GCCGTGGCCTTTGACAGT-3'; SEQ ID NO: 52) and the enzymatic assay as described by JOERSBO et al., 1998)

Up to 4 times the level of PMI enzymatic activity was found in the activator events compared to that in plants transgenic for constitutively expressed SuperMAS::PMI. Using the Real time PCR method, PMI expression levels could be found up to 35 times that found in the SuperMAS::PMI plants. The activator events were divided in four classes:

negative, low, medium and high expressers. Four independent events were selected for each of the classes low, medium and high for validating the hybrid trans-activation approach.

The second genetic element for the conditional expression of the Beta FT homologues consists of the gene cassette for one or both FT genes under the control of the pOp6 promoter. In the case of BvFT2 the inverted repeat as present at pHiNK525 (see Example 7) was cloned downstream of the pOp6 promoter fragment and combined with the PMI selectable marker gene under the control of the SuperMAS promoter (Ni et al., 1995). The plasmid map of this binary vector is shown in FIG. 21; the sequence of this vector is set forth as SEQ ID No: 54. Likewise, the full-length coding region of BvFT1 as present at binary vector 17603 (see Example 8) was also cloned downstream of the pOp6 promoter. The plasmid map of this binary vector is shown in FIG. 22; the sequence of this vector is set forth as SEQ ID No: 55. Transformation of these two binary vectors to sugar beet and the subsequent crossing of the obtained events to an 'activator' event of pHiNK498 expressing the LhG4 hybrid transcription factor results in the transcription of the respective BvFT gene cassette thereby providing bolting resistance. For commercial application both genetic elements are typically be present in the homozygous state in one or the other parental lines used for the production of hybrid seeds. Upon crossing the male and female parental lines the resulting hybrid seed will inherit a copy of both genetic elements in the heterozygous state leading to the successful trans-activation of the respective BvFT gene cassettes and to a bolting resistant commercial hybrid.

Example 10

Industrial Applications

The present invention further includes a method of obtaining biofuels and/or sugar from the sugar beet plant of the present invention, wherein the root of the sugar beet plant is the predominant source of biofuels and/or sugar. The sugar and the biofuels obtainable from the sugar beet plant and root of the sugar beet plant of the invention also fall within the scope of the present invention. Methods of extracted sugar and biofuels from sources such as sugar beet are very well known in the industry.

In summary, ethanol production includes first washing and then slicing the sugar beets followed by an extraction step. The extraction step produces two products: extracted sugar juice and the beet slices. The beet pulp is typically tried and pelletized and sold as animal feed. Thus, beet pulp and animal feed derived from the sugar beet plant and root of the invention are within the scope of the present invention. The sucrose fraction is typically washed, sterilized or otherwise treated to prevent microbial contamination. The sucrose fraction is then fermented. There are numerous fermentation methodologies known to those skilled in the art. In one embodiment and by way of example only, *Saccharomyces cerevisiae* is the organism that is used in the fermentation step. During the fermentation a large amount of $CO_2$ is produced. The $CO_2$ is used to manufacture beverages, fire extinguishers and in food processing. The product of fermentation, with an alcohol content of 8-15% by volume, is passed on to the distillation unit, where it is concentrated to 95%. A final dehydration step is required to remove the remaining water from the ethanol. Ethanol production is well known in the industry and various different methodologies can be used to produce the final ethanol fuel. Ethanol can also be produced by fermentation of sugar beet molasses, sugar juice, dry sugar beet powder and sugar. Biogas can also be produced from sugar beet using method commonly known in the industry. Biogas consists of methane, carbon dioxide and a small amount of $H_2S$ and ammonia and is produced during anaerobic fermentation of organic material. The fermentation process takes approximately 1 month. In most cases, the biogas is used for combined heat and power generation. The gas is burnt directly and produces heat that can be used for heating houses or generating power. It also can be used as fuel for vehicles.

Biodiesel can also be generated from sugar beet. Using Fischer-Tropsch synthesis, biogas can be converted to liquid fuel, FT-diesel. At present, the production from biomass is only at the pilot stage, and large-scale Fisher-Tropsch conversion installations using fossil fuels exclusively, most commonly natural gas. The advantage of FT-diesel is that its composition can be optimized for the combustion behavior of the motor. The fuel is free from sulfur and aromatic compounds and compared to ordinary diesel, the emissions contain 8% less nitrogen oxides, 30% less particulate matters, 30% less hydrocarbons (HC), 75% less carbon monoxide and 90% less polluting compounds.

References

Ahn, J. H., Miller, D., Winter, V. J., Banfield, M. J., Lee, J. H., Yoo, S. Y., Henz, S. R., Brady, R. L., and Weigel, D. (2006) A divergent external loop confers antagonistic activity on floral regulators FT and TFL1. EMBO Journal 25: 605-614.

Alvarez, J. P., Pekker, I., Goldshmidt, A., Blum, E., Amsellem, Z., and Eshed, Y. (2006) Endogenous and synthetic microRNAs stimulate simultaneous, efficient, and localized regulation of multiple targets in diverse species. Plant Cell 2006, 18: 1134-1151.

Altschul et al., (1990) Basic local alignment search tool, J. Mol. Biol. 215: 4-03-410.

Brunke, K. J., Wilson, S. L. (1993) *Brassica* hsp80 promoter. European Patent EP 0 559 603

Chang, Y.-F., Zhou, H., Dunder, E. M., Rouse, S. N., Gu, W., Boutreau, E. (2002) Methods for stable transformation of plants. International Patent Application WO 02/14523

Clough, S. J., Bent, A. F. (1998) Floral dip: a simplified method for *Agrobacterium*-mediated transformation of *Arabidopsis thaliana*. Plant J. December; 16(6): 735-43.

Crossway, A., et al. (1986) Integration of foreign DNA following microinjection of tobacco mesophyll protoplasts, Mol. Gen. Genet. 202, 179-185.

Eckes, P., Rosahl, S., Schell, J. and Willmitzer, L. (1986) Isolation and characterization of a light-inducible, organ-specific gene from potato and analysis of its expression after tagging and transfer into tobacco and potato shoots. Mol. Gen. Genet. 205, 14-22.

Elbashir, S. M., Lendeckel, W., Tuschl, T. (2001) RNA interference is mediated by 21 and 22 nucleotide RNAs, Genes Dev. 15, 188-200.

Hanzawa, Y., Money, T., and Bradley, D. (2005) A single amino acid converts a repressor to an activator of flowering. Proc. Natl. Acad. Sci. USA 102: 7748-7753.

Heilersig, B. H. J. B., Loonen, A. E. H. M., Janssen, E. M., Wolters, A.-M. A., and Visser, R. G. F. (2006) Efficiency of transcriptional gene silencing of GBSSI in potato depends on the promoter region that is used in an inverted repeat Molecular Genetics and Genomics 275: 437-449.

Higuchi, R. (1990) Recombinant PCR. In: PCR protocols, A guide to methods and application. Innis M A, Gelfand D H, Sninsky J J and White T J (Eds.), Academic Press Inc., San Diego. pp. 177-183.

Hohmann U, Jacobs, G. and Jung, C. (2005) An EMS mutagenesis protocol for sugar beet and isolation of non-bolting mutants. Plant Breeding 124: 317-321.

Holsters, M., de Waele, D., Depicker, A., Messens, E., van Montagu, M., and Schell, J. (1978) Transfection and transformation of *Agrobacterium tumefaciens*. Mol Gen Genetics 163: 20 181-187.

Hood, E. E., Helmer, G. L., Fraley, R. T., and Chilton, M.-D. (1986) The hypervirulence of *Agrobacterium tumefaciens* A281 is encoded in a region of pTiBo542 outside of T-DNA. J Bacteriology 168: 1291-1301.

Jaggard, K. W., Wickens, R., Webb, D. J. and Scott, R. K. (1983) Effects of sowing date on plant establishment and bolting and the influence of these factors on yields of sugar beet. Journal of Agricultureal Science, Cambridge, 101, 147-161.

Joersbo, M., Donaldson, I., Kreiberg, J., Petersen, S. G., Brunstedt, J. and Okkels, F. T. (1998) Analysis of mannose selection used for transformation of sugar beet. Mol. Breeding 4: 111-117.

Klein, T. M., et al. (1987) High-velocity microprojectiles for delivering nucleic acids into living cells, Nature 327, 70.

Kardailsky, I., Shukla, V. K., Ahn, J. H., Dagenais, N., Christensen, S. K., Nguyen, J. T., Chory, J., Harrison, M. J., Weigel, D. (1999) Activation tagging of the floral inducer FT. Science, 286: 1962-1965.

Kobayashi, Y., Kaya, H., Goto, K., Iwabuchi, M. and Araki, T. (1999) A pair of related genes with antagonistic roles in mediating flowering signals. Science, 286, 1960-1962.

Koornneef, M., Hanhart, C. J., van der Veen, J. H. (1991) A genetic and physiological analysis of the late flowering mutants in *Arabidopsis thaliana*. Mol. Gen. Genet. 229: 57-66.

Koornneef, M., Blankestijn-de Vries, H., Hanhart, C., Soppe, W. and Peeters, T. (1994) The phenotype of some late-flowering mutants is enhanced by a locus on chromosome 5 that is not effective in the Landsberg erecta wild-type. The Plant Journal 6: 91 1-919.

Krens, F. A. et al. (1982) In vitro transformation of plant protoplasts with Ti-plasmid DNA, Nature 296, 72-74.

Levy, Y. Y. and Dean, C. (1998) The Transition to Flowering. Plant Cell, 10:1973-1990.

McCallum C, Comai, L., Greene, E. and Henikoff, S. (2000) Targeted screening for induced mutations. Nature Biotechnol 18: 455-457.

McGrath, J. M., Shaw, R. S., de los Reyes, B. G., Weiland, J. J. (2004) Construction of a Sugar Beet BAC Library from a Hybrid with diverse Traits. Plant Mol Biol Rep 22: 23-28.

Guyer, D., Tuttle, A., Rouse, S., Volrath, S., Johnson, M., Potter, S., Gorlach, J., Goff, S., Crossland, L. and Ward, E. (1998) Activation of latent transgenes in *Arabidopsis* using a hybrid transcription factor. Genetics 149, 633-639.

Joersbo, M., Donaldson, I., Kreiberg, J., Petersen, S. G., Brunstedt, J. and Okkels, F. T. (1998) Analysis of mannose selection used for transformation of sugar beet. Mol. Breeding 4: 111-117.

Mette, M. F., Aufsatz, W., van Der Winden, J., Matzke, M. A., and Matzke, A. J. (2000) Transcriptional silencing and promoter methylation triggered by double-stranded RNA. EMBO J 19: 5194-5201.

Moore, I., Galweiler, L., Grosskopf, D., Schell, J. and Palme, K. (1998) A transcription activation system for regulated gene expression in transgenic plants. Pro. Natl Aca. Sci USA, 95, 376-381.

Negrutiu, I., et al. (1987) Hybrid genes in the analysis of transformation conditions, Plant Mol. Biol. 8, 363-373.

Needleman & Wunsch (1970) A general method applicable to the search for similarities in the amino acid sequence of two proteins, J. Mol. Biol. 48: 443.

Ni, M., Cui, D., Einstein, J., Narasimhulu, S., Vergara, C., Gelvin, S. (1995) Strength and tissue specificity of chimeric promoters derived from the octopine and mannopine synthase genes. Plant J 7: 661-676.

Norris, S. R., Meyer, S. E., and Callis, J. (1993) The intron of *Arabidopsis thaliana* polyubiquitin genes is conserved in location and is a quantitative determinant of chimeric gene expression. Plant Mol Biol 21: 895-906.

Ossowski, S., Schwab, R., Weigel, D. (2008) Gene silencing in plants using artificial microRNAs and other small RNAs The Plant Journal 53: 674-690.

Paienicova, L. et al. (2003) Molecular and phylogenetic analyses of the complete MADS-box transcription factor family in *Arabidopsis*: New openings to the MADS world. Plant Cell 15: 1538-1 551.

Pearson, W. R., Lipman, D. (1988) Improved tools for biological sequence comparison. Proc. Nat'l. Acad Sci. USA 85: 2444-2448.

Ratcliffe, O. J., Amaya, I., Vincent, C. A., Rothstein, S., Carpenter, R., Coen, E. S., and Bradley, D. J. (1998) A common mechanism controls the life cycle and architecture of plants. Development 125, 1609-1615.

Reeves, P. A., He, Y., Schmitz, R. J., Amasino, R. M., Panella, L. W. and Richards, C. M. (2006) Evolutionary conservation of the FLC-mediated vernalization response: evidence from the sugar beet (*Beta vulgaris*) Genetics: Published Articles Ahead of Print, published on Dec. 18, 2006 as 10.1534/genetics.106.069336

Rutherford, S., Brandizzi, F., Townley, H., Craft, J., Wang, Y., Jepson, I., Martinez, A., Moore, I. (2005) Improved transcriptional activators and their use in mis-expression traps in *Arabidopsis*. Plant J 43: 769-788.

Saitou, N., Nei, M. (1987) The neighbor-joining method: A new method for reconstructing phylogenetic trees. Molecular Biology and Evolution 4:406-425.

Schwab, R., Ossowski, S., Riester, M., Warthmann, N., and Weigel, D. (2006) Highly Specific Gene Silencing by Artificial MicroRNAs in *Arabidopsis* Plant Cell 18: 1121-1133.

Schneider, K., Schäfer-Pregl, R., Borchardt, C., and Salamini, F. (2002) Mapping QTLs for sucrose content, yield and quality in a sugar beet population fingerprinted by EST-related markers. Theor. Appl. Genet. 104:1107-1113.

Shillito, R. D., et al. (1985) High efficiency direct gene transfer to plants, Bio/Technol. 3, 1099-1102.

Sijen, T., Vijn, I., Rebocho, A., van Blokland, R., Roelofs, D. Mol, J. N. M., and Kooter, J. M. (2001) Transcriptional and posttranscriptional gene silencing are mechanistically related. Current Biology 11: 436-440.

Smith, T. F., Waterman, M. S. (1981) Identification of common molecular subsequences. J. Mol. Biol., 147, 195-197.

Smith, N. A., Singh, S. P., Wang, M. B., Stoutjesdijk, P. A., Green, A. G., and Waterhouse, P. M. (2000) Total silencing by intron-spliced hairpin RNAs. Nature 407: 319-320.

Tamura, K., Dudley, J., Nei, M., Kumar, S. (2007) MEGA4: Molecular Evolutionary Genetics Analysis (MEGA) software version 4.0. Molecular Biology and Evolution 24: 1596-1599.

Tijssen (1993) Laboratory Techniques in Biochemistry and Molecular Biology—Hybridization with Nucleic Acid Probes part I chapter 2 "Overview of principles of hybridization and the strategy of nucleic acid probe assays" Elsevier, N.Y.

Vancanneyt, G., Schmidt, R., O'Connor-Sanchez, A., Willmitzer, L. and Rocha-Sosa, M. (1990) Construction of an intron-containing marker gene: Splicing of the intron in transgenic plants and its use in monitoring early events in *Agrobacterium*-mediated plant transformation. Mol. Gen. Genet. 220: 245-250.

Wang, M. B. and Waterhouse, P. M. (2001) Application of gene silencing in plants. Curr. Opin. Plant Biol. 5:124-150.

SEQUENCE LISTING

```
<160> NUMBER OF SEQ ID NOS: 55

<210> SEQ ID NO 1
<211> LENGTH: 25
<212> TYPE: DNA
<213> ORGANISM: Artificial
<220> FEATURE:
<223> OTHER INFORMATION: degenerate primer targeting conserved amino
      acid sequences motif KPRVEIGG located at exon 1 (aa 51 to 58)
      according to Ft protein of Arabidopsis th.
<220> FEATURE:
<221> NAME/KEY: misc_feature
<222> LOCATION: (8)..(8)
<223> OTHER INFORMATION: N = any nucleotide (A, C, G, or T)
<220> FEATURE:
<221> NAME/KEY: misc_feature
<222> LOCATION: (11)..(11)
<223> OTHER INFORMATION: R = A or G
<220> FEATURE:
<221> NAME/KEY: misc_feature
<222> LOCATION: (14)..(14)
<223> OTHER INFORMATION: Y = C or T
<220> FEATURE:
<221> NAME/KEY: misc_feature
<222> LOCATION: (17)..(17)
<223> OTHER INFORMATION: R = A or G
<220> FEATURE:
<221> NAME/KEY: misc_feature
<222> LOCATION: (20)..(20)
<223> OTHER INFORMATION: H = A, C, or T, but not G
<220> FEATURE:
<221> NAME/KEY: misc_feature
<222> LOCATION: (23)..(23)
<223> OTHER INFORMATION: Y = C or T

<400> SEQUENCE: 1
accagccnag rgtygarath ggygg                                        25

<210> SEQ ID NO 2
<211> LENGTH: 28
<212> TYPE: DNA
<213> ORGANISM: Artificial
<220> FEATURE:
<223> OTHER INFORMATION: Oligonucleotide primer hybridizing to exon 3
      immediately downstream of the splicing site of intron 2 and
      targets amino acid sequence motif "LVTDIPATT" (amino acid residues
      89 to 98).
<220> FEATURE:
<221> NAME/KEY: misc_feature
<222> LOCATION: (3)..(3)
<223> OTHER INFORMATION: Y = C or T
<220> FEATURE:
<221> NAME/KEY: misc_feature
<222> LOCATION: (8)..(8)
<223> OTHER INFORMATION: S = G or C
<220> FEATURE:
<221> NAME/KEY: misc_feature
<222> LOCATION: (11)..(11)
<223> OTHER INFORMATION: N = any nucleotide (A, C, G or T)
<220> FEATURE:
<221> NAME/KEY: misc_feature
<222> LOCATION: (14)..(14)
<223> OTHER INFORMATION: Y = C or T
<220> FEATURE:
<221> NAME/KEY: misc_feature
<222> LOCATION: (17)..(17)
<223> OTHER INFORMATION: Y = C or T
```

```
<220> FEATURE:
<221> NAME/KEY: misc_feature
<222> LOCATION: (20)..(20)
<223> OTHER INFORMATION: N = any nucleotide (A, C, G or T)
<220> FEATURE:
<221> NAME/KEY: misc_feature
<222> LOCATION: (23)..(23)
<223> OTHER INFORMATION: N = any nucleotide (A, C, G or T)
<220> FEATURE:
<221> NAME/KEY: misc_feature
<222> LOCATION: (26)..(26)
<223> OTHER INFORMATION: N = any nucleotide (A, C, G or T)

<400> SEQUENCE: 2
ggytggtsac ngayatyccn gcnacnac                                          28

<210> SEQ ID NO 3
<211> LENGTH: 405
<212> TYPE: DNA
<213> ORGANISM: Beta vulgaris
<220> FEATURE:
<221> NAME/KEY: misc_feature
<222> LOCATION: (11)..(11)
<223> OTHER INFORMATION: N = any nucleotide (A, C, G or T)
<220> FEATURE:
<221> NAME/KEY: misc_feature
<222> LOCATION: (20)..(20)
<223> OTHER INFORMATION: N = any nucleotide (A, C, G or T)
<220> FEATURE:
<221> NAME/KEY: misc_feature
<222> LOCATION: (23)..(23)
<223> OTHER INFORMATION: N = any nucleotide (A, C, G or T)
<220> FEATURE:
<221> NAME/KEY: misc_feature
<222> LOCATION: (26)..(26)
<223> OTHER INFORMATION: N = any nucleotide (A, C, G or T)

<400> SEQUENCE: 3
ggytggtsac ngayatyccn gcnacnacaa gtgcatcatt tggagaagag attgtttact      60
atgaaaaccc acgaccctca acggggatac atcgatttgt atttgcattg tttcggcaat     120
tgggaaggca aactgtaaat gctccacaac aacgccaaaa ttttaataca agagactttg     180
ctgaactcta caatcttggc ttgcctgttg ctgctgtata tttcaattgc caaagggagg     240
gaggctgtgg tggaaggagg ttttagaatt ccaattccac ctctccattt caatgaactt     300
aacgcttgct aaaaataaac gtataacaat atcgttacaa ttgtagttgt tatcttatag     360
gtttgtaaat tgcgttctat tatcacatgg gttcactttt tcttt                     405

<210> SEQ ID NO 4
<211> LENGTH: 344
<212> TYPE: DNA
<213> ORGANISM: Beta vulgaris
<220> FEATURE:
<221> NAME/KEY: misc_feature
<222> LOCATION: (11)..(11)
<223> OTHER INFORMATION: N = any nucleotide (A, C, G or T)
<220> FEATURE:
<221> NAME/KEY: misc_feature
<222> LOCATION: (20)..(20)
<223> OTHER INFORMATION: N = any nucleotide (A, C, G or T)
<220> FEATURE:
<221> NAME/KEY: misc_feature
<222> LOCATION: (23)..(23)
<223> OTHER INFORMATION: N = any nucleotide (A, C, G or T)
<220> FEATURE:
<221> NAME/KEY: misc_feature
<222> LOCATION: (26)..(26)
<223> OTHER INFORMATION: N = any nucleotide (A, C, G or T)

<400> SEQUENCE: 4
ggytggtsac ngayatyccn gcnacnacag gtgcatcatt tggccaagaa gttgtctgct      60
```

| | |
|---|---:|
| atgaaaatcc aagaccatca gttggaatac atcgattcat acttgtgttg tttagacaat | 120 |
| tgggaagaca aactgtttat gcaccagggt ggcgtcaaaa cttcaacact agagattttg | 180 |
| ctgaacttta caaccttggt ttgcctgttg ctgctgtcta tttcaattgt cagagggaag | 240 |
| gaggctctgg tggaagaagg ttgtaaattt actacacttc tctttctttc tacattgaaa | 300 |
| gagattttat aaatgcaag tttatctgat gtcaaaaaaa aaaa | 344 |

<210> SEQ ID NO 5
<211> LENGTH: 6361
<212> TYPE: DNA
<213> ORGANISM: Beta vulgaris

<400> SEQUENCE: 5

| | |
|---|---:|
| aatccatcaa aaagaagaaa agaaaaggta ctttagaaag aaaaaacaaa aattattaaa | 60 |
| agagacggtc taattttaat ataaaagtag acctagtaac taaatggatt aaactagtca | 120 |
| cctaaagaaa ttaacctagt cattattagg ctaattctct ttttaatatt aggcttatca | 180 |
| ttgcctaatt ttaatttaaa agtaggcggt ctcttacaag ataaattcag gaaaaaaaaa | 240 |
| ggagctaatt tatgttcaca catgcaataa taattcctga aataaaacaa atggatagaa | 300 |
| gtagtaaata aagtttactt tttcaaattt gtatgtggag tgttttagct aagtttatga | 360 |
| gccgacctaa attcatctaa gaagaatcta accttggtcc actatattac ttttataattt | 420 |
| atgaaagtag gtggaccttg gtattttga tatgatcttg caattgtaa gaagttatgc | 480 |
| ctgaaaacta ccaagctagc tatagtttgc taaatgatgg tacgtgtatg aaacagaagc | 540 |
| tgtatataag tgttcattgg gatcacctgt tttggtgcgc aacttcttag atagtgaagt | 600 |
| attccttagc tttctagcta gctagctagc ttatctccta aagattagga tactattawt | 660 |
| tagttttagg tagctagata ttcttataat gcctagaaca tcagcaartg cgccaagaga | 720 |
| tccattagta ttaggtggag ttattggtga tgttttasar ccattcgaaa gatccgtcac | 780 |
| tctcaaaatc agctttaaca ataatagaaa tgttaataat ggaggagatt ttaggccatc | 840 |
| acaagttgtt aaccaaccta gggycgaagt cggaggtgat gacctttagga cttgctatac | 900 |
| cttggtaagt ccattgatta agattgttat tattsgtgca ttgtacttct agtgtttgat | 960 |
| acccataaaa agaaacttck ttctatacag tatgtactca tattaaaagt tgtacgactt | 1020 |
| cattaaatat ttcttatgtt astacttctt taatwttttg ttgattaaaw attcaattca | 1080 |
| tatgttaatg caatatacta ctatttaatt cataggtawt ggtagatcca gatgctccta | 1140 |
| gcccaagtaa cccgcatcaa agagagtact tgcactggta agtagatata tctttttttt | 1200 |
| ttttggact tcaagaaaac gtacaatagg taagtagata tatcaatmca atataattac | 1260 |
| agttgatctc atttttttt tattcggtaa tttackggtc caagtaggct caggccctca | 1320 |
| tgaattaggg ggtaggaagg ggatcccaat cgataaagaa acttccagag actggaaact | 1380 |
| gaggattat acctagaagc ataaatccac cacaaacacc ccaaatatgg agttgatgaa | 1440 |
| aatcaaactc ccgaccatga ggttgggagg tgggagctcc aaccattggg ctcccacatg | 1500 |
| attctctaaa gttgatctca ttaatctcta agaattatt ttatgagtac actttatta | 1560 |
| tatttatttc atccaaaaat ttagaaacta ataatttatt atcttcgagg catatgagtt | 1620 |
| caaataataa taaaaaaaag catattaaat cagtaacatt tatgatcttc ttagttttgc | 1680 |
| ctttgataca ataatagtcc tagtagttct cttatgcgag cgttgtattt gaaaattatg | 1740 |
| aagtggttaa ttagtgaccc tggatgtctg gatcgatttt caccttaaaa ggtattgaa | 1800 |
| gggaggcgtt ttgaagggca tctaaacttg tcacatgcta ttcgagataa atgcactatt | 1860 |

```
ggctccttgt taacaaaaaa aaaaatacgg ggttttattt tctagagcaa aagattttaa    1920
tgtctggact tccaatctca tacttgggtt gttttcacct gcgacattct aacttatata    1980
tttgacaaca caaatttttg tgtatcaata tttttaattg aaatttaata ttaaaaaaga    2040
catgcattag aattttccat tactagtcaa aaatatttcc tcaaaattat tatatgaata    2100
gtgtcaaaag tcaaaatatt gcaattcctt aaataaaaca aagtaagttt cagtttacac    2160
aacttgactt ataatttgca tacaatattc cacaaattga ccatatttaa ttattgtcat    2220
atcagcaaaa gattattgtt tataatcaag taggtttcaa tttgtatttt taaatatgaa    2280
ttttaataat tttattaata cataatttta tttgcttaag ggacgactat gcgtgctagc    2340
tttaatttaa ttatattcat tgtgtgccta atagttgcta ttcaaaacca tcatgttcat    2400
ttcttacaat caacaagaga tacatattaa ttcatgttaa tctgttatat agattttgca    2460
acttggaagc ataagagcat atattatata tactttatat ttgaggattc tgctttgtgg    2520
caatgaaaat ggtattagtc gtcatccatg attatacata tatagctata ctactggacc    2580
gagcatgaaa acctatatt cgaatttact tgaagattaa gataacatgc agtatgtaat     2640
tatcagtaag tatttcagct tatcaattat ttaatcaact tcccctttgtc atcttaatat   2700 ctcatacctg tgtacggact atatatgaac tgtacgatat atattgatat attactgcgt    2760
ctgcatggtc ccaattccca aagcaaggga ttagaccgca aaatcaaaga catgtcgcca    2820
atataattcc ttgaacatgt tacattggac tccttgtaat acaaggaaat tacatcttca    2880
gttacacctt tttcttttacc ctcatctcct cgggtatcat aaacccatta aaagttgaga   2940
tggtagagga gtggcatcaa ttcctatttt attttcctta gttttcagga tcaaattta    3000 tgagacacgt tgaggatttt tccttatcc tctcaagtgg gtctcattga tcttacctta    3060
aaaaaaatca ccaacccgtt acatactgag ctactttgt cagtagcaac aatcaagttt    3120
tttaagataa tattgttata ttccctctaa tttttattag agcaaagcta atagttgatt    3180
caaaatttcg gatcatcatc aattatttta atactttatc tttcttcaat gacattattt    3240
tattaagaag ttcatacttc atggagtaat tcctcatctt ttcctcctgc cttcatatat    3300
ttgtctcaga taagacatgt gtatataaaa agatactaaa atattgggac aatagtttaa    3360
taataatgaa ggataagatt ggtgccgtaa gttagggtag attctaatta acatctctct    3420
tatcatgtat tgtcaccta aagttacttg ggaaagttgt cacttgacaa tgtcaaattc     3480
ctaagacaga aaaaaaaaaa attaaactcg taaatgagat aagaattgaa aactaataat    3540
aaaaaaaaag tttataaaat tcttaataat ttctaatggt tcagctagtg aacgaataat    3600
aaaactactc acatacgtgt cgttacaact catcttattt ctcttcgcat taaaaacatg    3660
ttagtcattt tgtactctat tccaattcat tttccaaata tatgccccac atatttgtgt    3720
taattgacgg tactttttc tagatctcaa catcgtttct cattcccctt gaataaaact     3780
tccatgcccc actacatctt gttctttaaa tttttcttca aattattcta aatttttact    3840
ataatattat gtcaaattca taaccttaaa attcaacaaa gcttagtaat ccaattccaa    3900
tcttatttat gtacatagtt aattggctat atgaagtagt attttacttt gctaattggg    3960
ggaattgttg atttaattct tcttttgttt ggataaaatt aggttggtga ctgatattcc    4020
cggaaccaca agtgcatcat ttggtgagtt tccttaatgt tagactatta atactttttt    4080
aaggggtttt aatactccta gttcactact tcacctcccc ctcccttgta caagttcttc    4140
aaaaaataaa aaaaactgtt ggatgatgtt caatcctgtt gtagttttag atacaggctt    4200
tggaagatca gtatcattct tgcattttat ttctagagat cgcatgcacg tttgatttct    4260
```

```
cacctttttga tgtgttcctt acaagaataa tagaatatga atatatggtg catcccccaa    4320
atggaatttc tttgcgaaaa gtctaccggg cccaactgaa attaccgacg tctattacta    4380
ggaaaataac ttttgacatg tctcccaaga ccccaaggtt cttatttatt gtgccaatat    4440
ttcaacgcta aatatcaatt tgttttaagc atccagccat tttccaaagt gtggattatg    4500
cactagagtg tacaatgttt attgtgcatt caaaaagaac ataccattta tataaaagag    4560
tacgaacttt ttttcaacaat ttttcaactt taaaattgaa cacacgactt aaaattaaaa    4620
aatatgtaaa tctatatcta taaaataata taggttataa tgaaaagaac atatactaaa    4680
tgaacatcta tgcttaaggt aaaagaacat ataccttta aatttttattt gaaaaggagt    4740 ctttagttgc aaaattcaag gaaataaatt aaataatatt ttttttaaaa aaaattatgg    4800
acactaaaaa tgataaaatg atgtaattta aaagaggttg caccagttct acatgcactt    4860
gggtgcatgt acttatttgc gtccatttttc cgtgcaaggg atcttatgct caaaattaaa    4920
tgattgaatt gggtgtggca aaagttcaac caatgggaca acccaattca aacctacctc    4980
aaataagcta attagggctg ggattttttga cccattcaca ttaactcatt taattaaacg    5040
ggttaggttc aggttgacat tttcgatccc aaaatgacat gctttgactt tattaactta    5100
tacatataga aaattctcga ataatatatt gataaatcta aaatttggct ttagaaagta    5160
aaaatataac taaaacaagt cataattatt ataagaaact ctaaacatgc atacttgcac    5220
agtttacttg atcatttagc tttttaagaa aataattatt tttcactata tttataatta    5280
tgatcaaatg ggtttacggg taacccgttt attaaatagg tcgggtcaat attgtgtttt    5340
ccaacttatt tattaaatga gatagattcg aggtaaggga attttgatcc atttatttcc    5400
gattcgaaga tgaaccaacc caattggact tgattgtcag ccctagatac aatgtcatga    5460 atacccccatt tatgtaatca tatctggtaa taataacctc atatatatac attaacaata    5520
attgtctcta taatgttagt agtgcttgtc agttatacat aatctcatat tcaaattatt    5580
ttgcttatct gtacttatta gacctaatta atctttatta gaccttatta gaacttctat    5640
taacctgtta gaccttattt cctgagagtg tcagacctta ttttgctgaa ttgaacatat    5700
taaaccttat tacaccctat taatctgtat tagaccttat ctaaactttt tttttctgat    5760
aaggatgaaa aattaggtga acagaaaaga cacatattat taataaccca tctatacttg    5820
tcgatgaccc ttatacgttt taacatcact aataagatgt atgtggcata taagagtttg    5880
ttttattaat taatgatttt tagaatgggt gttgttcttg ttcttttttt taagccatga    5940
tcaagtcttt aactcttact actctcataa tataacatct cttacataca ttatataggaa   6000 gaagagattg tttactatga aaacccacga ccctcaacgg ggatacatcg atttgtatttt   6060 gcattgtttc ggcaattggg aaggcaaact gtaaatgctc cacaacaacg ccaaaattt    6120 aatacaagag actttgctga actctacaat cttggcttgc ctgttgctgc tgtatatttc   6180
aattgccaaa gggagggagg ctgtggtgga aggaggtttt agaattccaa ttccacctct   6240
ccatttcaat gaacttaacg cttgctaaaa ataaacgtat aacaatatcg ttacaattgt   6300
agttgttatc ttataggttt gtaaattgcg ttctattatc acatgggttc actttttctt   6360
t                                                                  6361
```

<210> SEQ ID NO 6
<211> LENGTH: 540
<212> TYPE: DNA
<213> ORGANISM: Beta vulgaris

<400> SEQUENCE: 6

-continued

```
atgcctagaa catcagcaag tgcgccaaga gatccattag tattaggtgg agttattggt      60
gatgttttag agccattcga aagatccgtc actctcaaaa tcagctttaa caatagaaat     120
gttaataatg gaggagattt taggccatca caagttgtta accaacctag ggtcgaagtc     180
ggaggtgatg accttaggac ttgctatacc ttggtaatgg tagatccaga tgctcctagc     240
ccaagtaacc cgcatcaaag agagtacttg cactggttgg tgactgatat tcccggaacc     300
acaagtgcat catttggaga agagattgtt tactatgaaa acccacgacc ctcaacgggg     360
atacatcgat ttgtatttgc attgtttcgg caattgggaa ggcaaactgt aaatgctcca     420
caacaacgcc aaaattttaa tacaagagac tttgctgaac tctacaatct tggcttgcct     480
gttgctgctg tatatttcaa ttgccaaagg gagggaggct gtggtggaag gaggttttag     540
```

<210> SEQ ID NO 7
<211> LENGTH: 179
<212> TYPE: PRT
<213> ORGANISM: Beta vulgaris

<400> SEQUENCE: 7

```
Met Pro Arg Thr Ser Ala Ser Ala Pro Arg Asp Pro Leu Val Leu Gly
1               5                   10                  15

Gly Val Ile Gly Asp Val Leu Glu Pro Phe Glu Arg Ser Val Thr Leu
            20                  25                  30

Lys Ile Ser Phe Asn Asn Arg Asn Val Asn Asn Gly Gly Asp Phe Arg
        35                  40                  45

Pro Ser Gln Val Val Asn Gln Pro Arg Val Glu Val Gly Gly Asp Asp
    50                  55                  60

Leu Arg Thr Cys Tyr Thr Leu Val Met Val Asp Pro Asp Ala Pro Ser
65                  70                  75                  80

Pro Ser Asn Pro His Gln Arg Glu Tyr Leu His Trp Leu Val Thr Asp
                85                  90                  95

Ile Pro Gly Thr Thr Ser Ala Ser Phe Gly Glu Glu Ile Val Tyr Tyr
            100                 105                 110

Glu Asn Pro Arg Pro Ser Thr Gly Ile His Arg Phe Val Phe Ala Leu
        115                 120                 125

Phe Arg Gln Leu Gly Arg Gln Thr Val Asn Ala Pro Gln Gln Arg Gln
    130                 135                 140

Asn Phe Asn Thr Arg Asp Phe Ala Glu Leu Tyr Asn Leu Gly Leu Pro
145                 150                 155                 160

Val Ala Ala Val Tyr Phe Asn Cys Gln Arg Glu Gly Gly Cys Gly Gly
                165                 170                 175

Arg Arg Phe
```

<210> SEQ ID NO 8
<211> LENGTH: 4893
<212> TYPE: DNA
<213> ORGANISM: Beta vulgaris

<400> SEQUENCE: 8

```
tttgtggtca aaccaaattt tcgtaaaggc gtgaatgcct tatattatga aacagagggc      60
gtaataaaca gtttgcatga gttttttttg ttttttttta tccacatgaa ccacgaaggc     120
agagtacaaa gtacaaagaa ggaaaggaag gaatttgaac atgtgaccta tcgttcacag     180
cacctcaatc ttaatcacta gaccaaaaca tccttggttc ttgcgcaaga aggttggcta     240
gaaatttttt gtaaaaacac tagccccgct cagttcataa tgagaatgtc gatgtcacca     300
```

```
aagggatatt aaatgaatgg aattgggata tggatggaat ataatgaaat agagccactt    360
tgaggttccc tatgaaatga ggcatggaag ggagccacta cgaaaaagtt ccgggagtta    420
cgaaggaagc ttcgagctca tattggtcat gaacccgatt actgagtcta ataagttcaa    480
ttgaaaagaa aaagtcttat gttctaaaag aactttttcgt gcggtttgca tgagttcata   540
gtccatataa tataatgcag gaatgaagtt ctcagttgat tcttccacac ccgtccctca    600 cccccctaggc cccaccttca ccccgccgaa aaaataaag aaaatccaac gttatttttc    660
ttagaaatga cagtttgata tagaaaggaa aaataataat aaaaaaaaaa agtgttggcg    720
ttttcatttt caacctcagt atgttggttt gccccaacaa gttctgaacc aattggcgat    780
gtaatcttat aagaagaatc taacgttggt ccattttgct tctacagttt tgaaagttag    840
gtgggcccca ttattatgtt gatcctagaa taattaattt tggtaggctg agaagaggaa    900
aaataaagaa caatgctaaa acaagtgaaa aaatatagtt gcaactcatg atgcaacatg    960
agatgcgatg aaatatgata gtaacttgag ctcacaactc tgtatataag tgctcatttg    1020
gacacttatt ttctacaatt tcctagtaac tcagcttagc ttcattcccg actttttttat 1080 aaaagtcagg acgatcaata tctatctatt tatctgtctg tctgtcgatc atgcctagag    1140
caccaagaga tccactagta gtaggtcgag ttatcgggga tgttttagat ccctttagta    1200
ggactgtgaa tctgagagtt agctatagca atagagatgt taataatgga tgtgaactta    1260
ggccctctca agttgttaac caaccaagag ttgaagttgg tggtgatgac cttagaactt    1320
tctacacctt ggtaagttgt gttttttttc tttctttctt tgcattttct atgtgtacat    1380
cttcttctaa catctaccat ttacattatt tcatcaatct ttttggtgaa ttatttgata    1440
ggtatccttg tgttaaatgc tgatttttt tttttgatat gtaggttatg gtggacccag     1500 atgctcccrag cccaagtaat ccacacttga gggaatattt acactggtga gtagatartt    1560
ttagtgattt tacctcttgt acttaggcct tgtttggttg tatataggaa gtcatacttc    1620
ctaggaagtt attttttcca tgtatttgaa attcctaaga agtgtaaaat tgtatttggt    1680
tgataatggg aagtagaaca tcccatggga agttctactt acctaggggg gcctaggtaa    1740
gtaacttcct ccattttgga ggaagtagaa cttcctagga agtgcaaatt cctatgattt    1800
tgtcaaccaa acaacttcat atacttctac tttctagaaa tttgtacttc ccatgatttg    1860
ttttatcaac caaacaacgc cttatataat aggttactta aactggttat catatgaaga    1920
atatgatgag ttcaaaagac gaggatgata atagcatagc ctatcactat actttgtgtt    1980
ttcaccacct tcttacacca acaaattaaa gttccttctt cttttgaggc ttggggggtgt   2040 ttggagttcc tttaacatcg tgctcctctt tagagcatcg ctgttttgca cttcctctgt    2100
tttttattac attgcaacat ttgactagtt acgggttttc aatacacatt ttttttgtcg    2160
tgatactcca cataaatgat gtttagaata tacaaatcgt aaaaaaatca acaagttcat    2220
cttacacgta tgttattagt ttagaatttg ttgcatgtat taaagtcga ggaaacagga     2280 tacatgtaac tattgcttgt acgtaatatc tagtttgttt tgtagaaata caaaatccat    2340
gtatgattgt tttaacaact gttgtttttac tgtttcaagc tcttaaaaga gatatcatgg   2400
atattagagc atatactcta tgtctgtaag tttgccgctt cgtgggagtg aaaatggaaa    2460
tatcttttca tgatagttac ttcatgacaa attatatacg actattgagt aataatatat    2520
tctgtttctt cactgattat tcctaggaac aaaagcacaa taaaacaaga tgatttatca    2580
aatcattgac tgattattat tgccaaacac ctggctctta catactagga ataatatcaa    2640
agacaatttt tttttaccgt aatcttatct tcttcctttt tttcatttc tagtacctta    2700
```

```
aagcaaggag aaaacttaaa ggaaagcttt gttctctatt atattgggca acatttttt    2760
caatttttaat cgttttttat tagtcgcaac aaaatcttta tatagtaggt tacttttct    2820
atattttct tcgcaaacag gttttttca agcattatat ctctcgcctc ttcacataag     2880
tctcttaaaa ttctcgtgtg ttatctagtt gtctcccatg ttgctactag aaatagacaa   2940
ctagttaacg tcaaacaagt tcatatcacg tcagattgtc aaccctcttc ttgtccatgc   3000
acgtgtcctt ctcttttct ccaaattatt ctgatttttt tttttaatc ttttatcatt    3060
tggtttgatg catgtactct caaagcttcc aatcgtttat attatcgttt gctaactgaa   3120
tgcaatttta tttgtttgtt ataaaggttg gtgactgata ttcctgggac cacaggtgca   3180
tcatttggtg agtctcccat ctaaatattc aaagttcatc aaacattgag ttttcctgtt   3240
gatacatttt cagatgcagt ttttagacac agtagtgtga aatatcagt taatacaaca   3300
taaattatta gtatatatct tatagactac atgcacatgt ggttttgttg aattctaatg   3360
ctgtctttat tggccattga agagcattgt tgctgcttat gacttaggct acgtacctgt   3420
ctttgatact cgttactcag actcttcatt ttacctcaat aatgcttcaa agatatataa   3480
acattcgaca atttacttta gaaccacatg cattatgtac gcaaaaagtt attcatgaaa   3540
tagccgaatc tgacacttga acccttacaa cgcttactga aaccaccgga agggaagtga   3600
aagaatggtg ggtgaagaga aattaggaaa gggtagttag tacttgtatg aaggaggaag   3660
gtttatcaac ttttttttttt tcctgtatga caaagaccac acaaatgaag aagggggtggg   3720
gtaacttttt ttcctcgtta aaccaaacaa tgaaattaat ttgactgtct tttcatgctt   3780
tattttgaa aaggagtac tctcaaatgc ttatcacgaa tagcattaac ttttgtcttc    3840
cctttgtagt ttccttagta aaatttgagg ttgtttttca gcttgttttg tagattataa   3900
ggaaaaacta cttagtgcaa gttagatatg ttaagcaaga aaacagattg gtaattccag   3960
ctcaaagttt tcatagaaca aatacatctg attacaaaac tacgtggcat gaaaaactgt   4020
tcatttctta tacaaatttt tatatatgat atatactact catctatgaa gaagtcagta   4080
cagttttcgt accaattcaa aatttgaaat gtaatagatg tgtcttgtcg atgtttattt   4140
ctttttttt ttacagtgac gactgacgag gatataagat tagaatatat gattctacga    4200
cagtatgaaa ggacaaaaat tagaatattg attcattttt atcgaaactg gacccaaaaa   4260
ttaaaaaatc gaattagtta tccttatcaa aggtggaccc aaaattttaa gaatgcgcca   4320
gtgcaccttt tgtgtattgc acaagtgggt ggcatcttta caaaaaacaa gaaaagatgc   4380
aaagctaaac aaagtctaac tcgatcaagt ctttacagtc accttatttt cctactaata   4440
tctacttaat tacacactat aacacagtaa ttatcatacc ttcatatccc tactttcttc   4500
agctatatgt ataaacaaag ttacataaaa ctagtaattt tgatttgaat actttcgcaa   4560
cattacacta ttttttttt tttgtgtgta ggccaagaag ttgtctgcta tgaaaatcca   4620
agaccatcag ttggaataca tcgattcata cttgtgttgt ttagacaatt gggaagacaa   4680
actgtttatg caccagggtg gcgtcaaaac ttcaacacta gagattttgc tgaactttac   4740
aaccttggtt tgcctgttgc tgctgtctat ttcaattgtc agagggaagg aggctctggt   4800
ggaagaaggt tgtaaattta ctacacttct ctttctttct acattgaaag agattttatt   4860
aaatgcaagt ttatctgatg tcaaaaaaaa aaa                                4893
```

<210> SEQ ID NO 9
<211> LENGTH: 528
<212> TYPE: DNA
<213> ORGANISM: Beta vulgaris -continued

```
<400> SEQUENCE: 9
atgcctagag caccaagaga tccactagta gtaggtcgag ttatcgggga tgttttagat      60 cccttagta ggactgtgaa tctgagagtt agctatagca atagagatgt taataatgga     120
tgtgaactta ggccctctca agttgttaac caaccaagag ttgaagttgg tggtgatgac    180
cttagaactt tctacacctt ggttatggtg gacccagatg ctccgagccc aagtaatcca   240
cacttgaggg aatatttaca ctggttggtg actgatattc ctgggaccac aggtgcatca   300
tttggccaag aagttgtctg ctatgaaaat ccaagaccat cagttggaat acatcgattc   360
atacttgtgt tgtttagaca attgggaaga caaactgttt atgcaccagg gtggcgtcaa    420
aacttcaaca ctagagattt tgctgaactt tacaaccttg gtttgcctgt tgytgctgtc    480
tatttcaatt gtcagaggga aggaggctct ggtggaagaa ggttgtaa                528

<210> SEQ ID NO 10
<211> LENGTH: 175
<212> TYPE: PRT
<213> ORGANISM: Beta vulgaris

<400> SEQUENCE: 10

Met Pro Arg Ala Pro Arg Asp Pro Leu Val Val Gly Arg Val Ile Gly
1               5                   10                  15

Asp Val Leu Asp Pro Phe Ser Arg Thr Val Asn Leu Arg Val Ser Tyr
            20                  25                  30

Ser Asn Arg Asp Val Asn Asn Gly Cys Glu Leu Arg Pro Ser Gln Val
        35                  40                  45

Val Asn Gln Pro Arg Val Glu Val Gly Gly Asp Asp Leu Arg Thr Phe
    50                  55                  60

Tyr Thr Leu Val Met Val Asp Pro Asp Ala Pro Ser Pro Ser Asn Pro
65                  70                  75                  80

His Leu Arg Glu Tyr Leu His Trp Leu Val Thr Asp Ile Pro Gly Thr
                85                  90                  95

Thr Gly Ala Ser Phe Gly Gln Glu Val Val Cys Tyr Glu Asn Pro Arg
            100                 105                 110

Pro Ser Val Gly Ile His Arg Phe Ile Leu Val Leu Phe Arg Gln Leu
        115                 120                 125

Gly Arg Gln Thr Val Tyr Ala Pro Gly Trp Arg Gln Asn Phe Asn Thr
    130                 135                 140

Arg Asp Phe Ala Glu Leu Tyr Asn Leu Gly Leu Pro Val Ala Ala Val
145                 150                 155                 160

Tyr Phe Asn Cys Gln Arg Glu Gly Gly Ser Gly Gly Arg Arg Leu
                165                 170                 175

<210> SEQ ID NO 11
<211> LENGTH: 32
<212> TYPE: DNA
<213> ORGANISM: Artificial
<220> FEATURE:
<223> OTHER INFORMATION: oligonucleotide primer

<400> SEQUENCE: 11
ttagatagtg aagtattcct tagctttcta gc                                  32

<210> SEQ ID NO 12
<211> LENGTH: 20
<212> TYPE: DNA
<213> ORGANISM: Artificial
<220> FEATURE:
<223> OTHER INFORMATION: oligonucleotide primer
```

-continued

<400> SEQUENCE: 12
tgagggcctg agcctacttg                                          20

<210> SEQ ID NO 13
<211> LENGTH: 29
<212> TYPE: DNA
<213> ORGANISM: Artificial
<220> FEATURE:
<223> OTHER INFORMATION: oligonucleotide primer

<400> SEQUENCE: 13
actctgtata taagtgctca tttggacac                                29

<210> SEQ ID NO 14
<211> LENGTH: 28
<212> TYPE: DNA
<213> ORGANISM: Artificial
<220> FEATURE:
<223> OTHER INFORMATION: oligonucleotide primer

<400> SEQUENCE: 14
cttaggaatt tcaaatacat ggaaaaaa                                 28

<210> SEQ ID NO 15
<211> LENGTH: 30
<212> TYPE: DNA
<213> ORGANISM: Artificial
<220> FEATURE:
<223> OTHER INFORMATION: oligonucleotide primer

<400> SEQUENCE: 15
agtttctttt tatgggtatc aaacactaga                               30

<210> SEQ ID NO 16
<211> LENGTH: 27
<212> TYPE: DNA
<213> ORGANISM: Artificial
<220> FEATURE:
<223> OTHER INFORMATION: oligonucleotide primer

<400> SEQUENCE: 16
ccttggtaag tccattgatt aagattg                                  27

<210> SEQ ID NO 17
<211> LENGTH: 16
<212> TYPE: DNA
<213> ORGANISM: Artificial
<220> FEATURE:
<223> OTHER INFORMATION: oligonucleotide sequence used as a probe

<400> SEQUENCE: 17
acaatgcacg aataat                                              16

<210> SEQ ID NO 18
<211> LENGTH: 16
<212> TYPE: DNA
<213> ORGANISM: Artificial
<220> FEATURE:
<223> OTHER INFORMATION: oligonucleotide sequence used as a probe

<400> SEQUENCE: 18
acaatgcacc aataat                                              16

<210> SEQ ID NO 19
<211> LENGTH: 23

```
<212> TYPE: DNA
<213> ORGANISM: Artificial
<220> FEATURE:
<223> OTHER INFORMATION: oligonucleotide primer

<400> SEQUENCE: 19
gtaggttatg gtggacccag atg                                              23

<210> SEQ ID NO 20
<211> LENGTH: 26
<212> TYPE: DNA
<213> ORGANISM: Artificial
<220> FEATURE:
<223> OTHER INFORMATION: oligonucleotide primer

<400> SEQUENCE: 20
tcaccagtgt aaatattccc tcaagt                                           26

<210> SEQ ID NO 21
<211> LENGTH: 15
<212> TYPE: DNA
<213> ORGANISM: Artificial
<220> FEATURE:
<223> OTHER INFORMATION: oligonucleotide sequence used as a probe

<400> SEQUENCE: 21
tccgagccca agtaa                                                       15

<210> SEQ ID NO 22
<211> LENGTH: 16
<212> TYPE: DNA
<213> ORGANISM: Artificial
<220> FEATURE:
<223> OTHER INFORMATION: oligonucleotide sequence used as a probe

<400> SEQUENCE: 22
ctccaagccc aagtaa                                                      16

<210> SEQ ID NO 23
<211> LENGTH: 23
<212> TYPE: DNA
<213> ORGANISM: Artificial
<220> FEATURE:
<223> OTHER INFORMATION: oligonucleotide primer

<400> SEQUENCE: 23
cacaagtgca tcatttggag aag                                              23

<210> SEQ ID NO 24
<211> LENGTH: 19
<212> TYPE: DNA
<213> ORGANISM: Artificial
<220> FEATURE:
<223> OTHER INFORMATION: oligonucleotide primer

<400> SEQUENCE: 24
ttcccaattg ccgaaacaa                                                   19

<210> SEQ ID NO 25
<211> LENGTH: 26
<212> TYPE: DNA
<213> ORGANISM: Artificial
<220> FEATURE:
<223> OTHER INFORMATION: oligonucleotide primer

<400> SEQUENCE: 25
gggaatattt acactggttg gtgact                                           26
```

<210> SEQ ID NO 26
<211> LENGTH: 23
<212> TYPE: DNA
<213> ORGANISM: Artificial
<220> FEATURE:
<223> OTHER INFORMATION: oligoncleotide primer

<400> SEQUENCE: 26
tccaactgat ggtcttggat ttt                                          23

<210> SEQ ID NO 27
<211> LENGTH: 19
<212> TYPE: DNA
<213> ORGANISM: Artificial
<220> FEATURE:
<223> OTHER INFORMATION: oligonucleotide primer

<400> SEQUENCE: 27
cacaccagat gaaggccgt                                               19

<210> SEQ ID NO 28
<211> LENGTH: 18
<212> TYPE: DNA
<213> ORGANISM: Artificial
<220> FEATURE:
<223> OTHER INFORMATION: oligonucleotide primer

<400> SEQUENCE: 28
ccctgaagac cgtgccat                                                18

<210> SEQ ID NO 29
<211> LENGTH: 540
<212> TYPE: DNA
<213> ORGANISM: Artificial
<220> FEATURE:
<223> OTHER INFORMATION: chimeric sequence consisting of sequences of
       the fourth codon of BvFT2

<400> SEQUENCE: 29
atgcctagaa catcagcaag tgcgccaaga gatccattag tattaggtgg agttattggt    60
gatgttttag agccattcga aagatccgtc actctcaaaa tcagctttaa caatagaaat   120
gttaataatg gaggagattt taggccatca caagttgtta accaacctag ggtcgaagtc 180
ggaggtgatg accttaggac ttgctatacc ttggtaatgg tagatccaga tgctcctagc 240
ccaagtaacc cgcatcaaag agagtacttg cactggttgg tgactgatat tcccggaacc 300
acaagtgcat catttggcca agaagttgtc tgctatgaaa atccaagacc atcagttgga 360
atacatcgat tcatacttgt gttgtttaga caattgggaa gacaaactgt ttatgcacca 420
gggtggcgtc aaaacttcaa cactagagat tttgctgaac tttacaacct tggtttgcct 480
gttgctgctg tctatttcaa ttgtcagagg gaaggaggct ctggtggaag aaggttgtaa 540

<210> SEQ ID NO 30
<211> LENGTH: 528
<212> TYPE: DNA
<213> ORGANISM: Artificial
<220> FEATURE:
<223> OTHER INFORMATION: chimeric sequence consisting of sequences of the fourth codon of BvFT2

<400> SEQUENCE: 30
atgcctagag caccaagaga tccactagta gtaggtcgag ttatcgggga tgttttagat 60
ccctttagta ggactgtgaa tctgagagtt agctatagca atagagatgt taataatgga 120

```
tgtgaactta ggccttctca agttgttaac caaccaagag ttgaagttgg tggtgatgac    180
cttagaactt tctacacctt ggttatggtg gacccagatg ctccgagccc aagtaatcca    240
cacttgaggg aatatttaca ctggttggtg actgatattc ctgggaccac aggtgcatca    300
tttggagaag agattgttta ctatgaaaac ccacgaccct caacggggat acatcgattt    360
gtatttgcat tgtttcggca attgggaagg caaactgtaa atgctccaca caacgccaa     420 aattttaata caagagactt tgctgaactc tacaatcttg gcttgcctgt tgctgctgta    480
tatttcaatt gccaaaggga gggaggctgt ggtggaagga ggttttag                 528
```

<210> SEQ ID NO 31
<211> LENGTH: 540
<212> TYPE: DNA
<213> ORGANISM: Artificial
<220> FEATURE:
<223> OTHER INFORMATION: chimeric sequence consisting of sequences of
      the fourth codon of BvFT

<400> SEQUENCE: 31

```
atgcctagaa catcagcaag tgcgccaaga gatccattag tattaggtgg agttattggt    60
gatgttttag agccattcga aagatccgtc actctcaaaa tcagctttaa caatagaaat   120
gttaataatg gaggagattt taggccatca caagttgtta accaacctag ggtcgaagtc   180
ggaggtgatg accttaggac ttgctatacc ttggtaatgg tagatccaga tgctcctagc   240
ccaagtaacc cgcatcaaag agagtacttg cactggttgg tgactgatat tcccggaacc   300 acaagtgcat exon 4 of BvFT2
<220> FEATURE:
<221> NAME/KEY: misc_feature
<222> LOCATION: (8747)..(9046)
<223> OTHER INFORMATION: heterologous DNA encoding inverted repeat of
      exon 4 of BvFT2 inserted into the vector

<400> SEQUENCE: 33

| | | | | | |
|---|---|---|---|---|---|
| attcctgtgg | ttggcatgca | catacaaatg | gacgaacgga | taaacctttt cacgcccttt | 60 |
| taaatatccg | attattctaa | taaacgctct | tttctcttag | gtttacccgc caatatatcc | 120 |
| tgtcaaacac | tgatagttta | aactgaaggc | gggaaacgac | aatctgatca tgagcggaga | 180 |
| attaagggag | tcacgttatg | accccgccg | atgacgcggg | acaagccgtt ttacgtttgg | 240 |
| aactgacaga | accgcaacgc | tgcaggaatt | ggccgcagcg | gccatttaaa tcaattgggc | 300 |
| gcgccgaatt | cgagctcggt | acccggggat | cctctagaga | tctagtaaca tagatgacac | 360 |
| cgcgcgcgat | aatttatcct | agtttgcgcg | ctatattttg | ttttctatcg cgtattaaat | 420 |
| gtataattgc | gggactctaa | tcataaaaac | ccatctcata | ataacgtca tgcattacat | 480 |
| gttaattatt | acatgcttaa | cgtaattcaa | cagaaattat | atgataatca tcgcaagacc | 540 |
| ggcaacagga | ttcaatctta | agaaacttta | ttgccaaatg | tttgaacgat ctgcaggtcg | 600 |
| acgcatttaa | taaatctct | ttcaatgtag | aaagaaagag | aagtgtagta aatttacaac | 660 |
| cttcttccac | cagagcctcc | ttccctctga | caattgaaat | agacagcagc aacaggcaaa | 720 |
| ccaaggttgt | aaagttcagc | aaaatctcta | gtgttgaagt | tttgacgcca ccctggtgca | 780 |
| taaacagttt | gtcttcccaa | ttgtctaaac | aacacaagta | tgaatcgatg tattccaact | 840 |
| gatggtcttg | gattttcata | gcagacaact | tcttggcccg | cggacctgca catcaacaaa | 900 |
| ttttggtcat | atattagaaa | agttataaat | taaaatatac | acacttataa actacagaaa | 960 |
| agcaattgct | atatactaca | ttcttttatt | ttgaaaaaaa | tatttgaaat attatattac | 1020 |
| tactaattaa | tgataattat | tatatatata | tcaaaggtag | aagcagaaac ttacctgcca | 1080 |
| agagttgtct | gctatgaaaa | tccaagacca | tcagttggaa | tacatcgatt catacttgtg | 1140 |
| ttgtttagac | aattgggaag | acaaactgtt | tatgcaccag | ggtggcgtca aaacttcaac | 1200 |
| actagagatt | ttgctgaact | ttacaacctt | ggtttgcctg | ttgctgctgt ctatttcaat | 1260 |
| tgtcagaggg | aaggaggctc | tggtggaaga | aggttgcaaa | tttactacac ttctcttct | 1320 |
| ttctacattg | aaagagattt | tattaaatgc | ggatccaaag | agagagtcgc gagagatttg | 1380 |
| cagagatcgc | tttaggcttt | gggagagatt | gaagagtcag | aaaaagacga aaggatgaat | 1440 |
| tattatcttc | cacacgaagg | tcttctttat | atcgcaaacc | aaaagcccaa aaccgtcttt | 1500 |
| tctattaatg | agaataaaat | atctttagcc | aaaacaaaaa | aaggaagata tcagttgagg | 1560 |
| attattatca | cgaaactaaa | ggaaggaatc | atatgatacg | tgtcatattt tccaccgtgc | 1620 |
| gttttttaaaa | gaccgactca | agtagagaca | tcctatggtg | gtggttggat taggtcatcc | 1680 |
| attacatctg | cttcactgac | atttttctat | ttttcttttt | gtatatactt ttcctcaaat | 1740 |
| aatttctttc | ttttctatag | aagaatttaa | tcaataagga | aaagttcaa aaaagattct | 1800 |
| ttccattaag | actatgtctt | ggttaaccca | acccattaag | aataagcaat cataatatat | 1860 |
| atagagaata | ctaatactat | atatgagatt | tttcttttaa | tttcatgttg attatgatag | 1920 |
| tttatcttct | tgatttaatt | tatcaatact | tggcataaaa | gattctaatc tactctaata | 1980 |
| aagaaaagaa | aaaaagtat | ctaccattga | ctaattaaaa | taaggaaact tatctaccaa | 2040 |
| atttgagtat | ttttagaac | aatcttttg | gtttaattcc | aaaactctaa acctaattgt | 2100 |
| tgggaaaaag | gacctaattt | ttaagaaaag | ttaataatta | gaagatctgt atgttttttt | 2160 |

```
tttgatccaa gttttattt cttttctctt tttttcatga taaaatctat gttttttag    2220 tctacaatta aagtaattgt tattattttc tttatctttt tttgttgttg ttgttaattc   2280
cctttttttt ttttaacag caacttctta aaaaaaaaaa cagttgggcc ttgaatttat    2340
ttcaggcctg cgttattaag cccagataat aactcaaaac aaaaaaaatg ttgaaccgga   2400
ataaacccgc gagattaaat gccggttttc aggtaacata aagaagaat atatgaggat    2460 tgaagaagta ttcaagaggc ggaacaattc acaagtccaa gagcttaaat ttctcctcac   2520
tcttctgcta cagactcgga actctttctc tttgctaaaa taagatgttc aggattttg    2580 ttgcccgaca attcatgtat ctcacactct ctctcttctc tgttcttact actctgttac   2640
attaccacca actcaagact ttcttccaca atggcgttta tgagacttgg ctccaaatcc   2700
ggacggatct ctagagtcga ccatggtgat cactgcaggc atgcaagctt cgtacgttaa   2760
ttaattcgaa tccggagcgg ccgcacgcgt gggcccgttt aaacctcgag actagcaagg   2820
gatctttggt tctcgcataa tcatgcgtaa gattttcatc tagatgtctt ctcagaaata   2880
tcacggcctt agccttttca tgagaggttg atatattgcc ttctcttatt gtttcgagta   2940
ttttctcgga atctagatga agctccatgt ttgtaaccca tgccgtgtag tttgtcccag   3000
ttacttccaa tgccggaaac tgaagtttct cgattttgc catttgtatt tctaaagaac    3060
ataaataaaa attattagaa tattattcat attaaaagaa accgtttaca ttgatcatgc   3120
aagcaattac aaggagaagc gatgtaaaga aaagtaaacc gatattcatc ctaaattctc   3180
ttggagtaaa ttctccaacg ataaaccat aaatagaaac acaaataaaa atggcacata    3240
aaaacaaaag tgcgcgaatc atctttcttg aaaaaaaaaa tcggaagaga gcgatttgaa   3300 attttgaga gaagatgaaa tattttggat gatgaaatgg agtgaaaatg agttgtattt    3360
atagatgaaa aacactgttc ataccgttg gagaaagggg aaattttgaa aaaattcctt    3420
tgtgaccgtt ggggttaaat cgagtgcact aaaaatcagt ctgagaatat cgtattaaac   3480
agtcaatcaa atctataaaa tttcataaaa gtaaaaatta tggcaatgaa atatttatgt   3540
tatgacaaca aatcatgcga cggctcagcc gatcaatgca gagtaataaa taaattatac   3600
ggcggctcgg ccgaccaatt aataataaac agaatataag gcggctcggc cgaccaataa   3660
ataataaaca gaatataagg cggctcggcc gaccattaat aaattaaatt attagtaaat   3720
aatataggcg gtattccggc cattataaca taatataaat aatagtagag gcggtatacc   3780
gaccattata acagggtata aatgatacaa ataaattta ccgaatcgca gagtgatcgt    3840
gctgataacg tgttatgaaa ataactgaaa ttttattata tcgcgggaat ttaaataagg   3900
gcaaaatttt atacccgtaa aaattataac actgaaagaa agtgtttatc tgagagagaa   3960
gggaagagtg aagtgtgttc ttgaaacgat cgaacttgat cgtatatata aagaaaaaat   4020
ctactgtgca aatagtgcag cgggccccac atcatttata atttcaactt atgcggcgct   4080
gtgttctctg actttcataa caaaattatg ttatttgttt taacacaaaa aagtagaaaa   4140
ttataaagaa gaagaaaata acacattgac caaaagaag taattagtt acaccccaag    4200 attattgggc ccaacttgtc tcaaactaac aagttaagca taatgatct cagaaggatc    4260 tagaaaccct ataacgtttg tgtatatata cgtaacttgt ctcttcacta cctcgcatct   4320
gctctctcta ttatcgtacc tccttgataa accctggatc tgcagggatc cccgatcatg   4380
caaaaactca ttaactcagt gcaaaactat gcctggggca gcaaacggc gttgactgaa    4440 ctttatggta tggaaaatcc gtccagccag ccgatggccg agctgtggat gggcgcacat   4500
ccgaaaagca gttcacgagt gcagaatgcc gccggagata tcgtttcact gcgtgatgtg   4560
```

```
attgagagtg ataaatcgac tctgctcgga gaggccgttg ccaaacgctt tggcgaactg    4620
cctttcctgt tcaaagtatt atgcgcagca cagccactct ccattcaggt tcatccaaac    4680
aaacacaatt ctgaaatcgg ttttgccaaa gaaaatgccg caggtatccc gatggatgcc    4740
gccgagcgta actataaaga tcctaaccac aagccggagc tggttttgc gctgacgcct     4800 ttccttgcga tgaacgcgtt tcgtgaattt ccgagattg tctccctact ccagccggtc     4860
gcaggtgcac atccggcgat tgctcacttt ttacaacagc ctgatgccga acgtttaagc    4920
gaactgttcg ccagcctgtt gaatatgcag ggtgaagaaa atcccgcgc gctggcgatt     4980 ttaaaatcgg ccctcgatag ccagcagggt gaaccgtggc aaacgattcg tttaatttct    5040
gaattttacc cggaagacag cggtctgttc tccccgctat tgctgaatgt ggtgaaattg    5100
aaccctggcg aagcgatgtt cctgttcgct gaaacaccgc acgcttacct gcaaggcgtg    5160
gcgctggaag tgatggcaaa ctccgataac gtgctgcgtg cgggtctgac gcctaaatac    5220
attgatattc cggaactggt tgccaatgtg aaattcgaag ccaaaccggc taaccagttg    5280
ttgacccagc cggtgaaaca aggtgcagaa ctggacttcc cgattccagt ggatgatttt    5340
gccttctcgc tgcatgacct tagtgataaa gaaaccacca ttagccagca gagtgccgcc    5400
attttgttct gcgtcgaagg cgatgcaacg ttgtggaaag ttctcagca gttacagctt     5460 aaaccgggtg aatcagcgtt tattgccgcc aacgaatcac cggtgactgt caaaggccac    5520
ggccgtttag cgcgtgttta caacaagctg taagagctta ctgaaaaaat taacatctct    5580
tgctaagctg ggagctcgtc gacgcatgcc cgctgaaatc accagtctct ctctacaaat    5640
ctatctctct ctataataat gtgtgagtag ttcccagata agggaattag ggttcttata    5700
gggtttcgct catgtgttga gcatataaga aacccttagt atgtatttgt atttgtaaaa    5760
tacttctatc aataaaattt ctaattccta aaaccaaaat ccaggggtac gatctcgaga    5820
gatctgctag ccctgcagga aatttaccgg tgcccgggcg ccagcatgg ccgtatccgc     5880 aatgtgttat taagttgtct aagcgtcaat ttgtttacac cacaatatat cctgccacca    5940
gccagccaac agctccccga ccggcagctc ggcacaaaat caccactcga tacaggcagc    6000
ccatcagaat taattctcat gtttgacagc ttatcatcga ctgcacggtg caccaatgct    6060
tctggcgtca ggcagccatc ggaagctgtg gtatggctgt gcaggtcgta atcactgca     6120 taattcgtgt cgctcaaggc gcactcccgt tctggataat gttttttgcg ccgacatcat    6180
aacggttctg gcaaatattc tgaaatgagc tgttgacaat taatcatccg gctcgtataa    6240
tgtgtggaat tgtgagcgga taacaatttc acacaggaaa cagaccatga gggaagcgtt    6300
gatcgccgaa gtatcgactc aactatcaga ggtagttggc gtcatcgagc gccatctcga    6360
accgacgttg ctggccgtac atttgtacgg ctccgcagtg gatggcggcc tgaagccaca    6420
cagtgatatt gatttgctgg ttacggtgac cgtaaggctt gatgaaacaa cgcggcgagc    6480
tttgatcaac gaccttttgg aaacttcggc ttcccctgga gagagcgaga ttctccgcgc    6540
tgtagaagtc accattgttg tgcacgacga catcattccg tggcgttatc cagctaagcg    6600
cgaactgcaa tttggagaat ggcagcgcaa tgacattctt gcaggtatct tcgagccagc    6660
cacgatcgac attgatctgg ctatcttgct gacaaaagca agagaacata gcgttgcctt    6720
ggtaggtcca gcggcggagg aactctttga tccggttcct gaacaggatc tatttgaggc    6780
gctaaatgaa accttaacgc tatggaactc gccgcccgac tgggctggcg atgagcgaaa    6840
tgtagtgctt acgttgtccc gcatttggta cagcgcagta accggcaaaa tcgcgccgaa    6900
ggatgtcgct gccgactggg caatggagcg cctgccggcc cagtatcagc ccgtcatact    6960
```

```
tgaagctagg caggcttatc ttggacaaga agatcgcttg gcctcgcgcg cagatcagtt     7020
ggaagaattt gttcactacg tgaaaggcga gatcaccaaa gtagtcggca aataaagctc     7080
tagtggatcc ccgaggaatc ggcgtgagcg gtcgcaaacc atccggcccg gtacaaatcg     7140
gcgcggcgct gggtgatgac ctggtggaga agttgaaggc cgcgcaggcc gcccagcggc     7200
aacgcatcga ggcagaagca cgccccggtg aatcgtggca agcggccgct gatcgaatcc     7260
gcaaagaatc ccggcaaccg ccggcagccg gtgcgccgtc gattaggaag ccgcccaagg     7320
gcgacgagca accagatttt ttcgttccga tgctctatga cgtgggcacc cgcgatagtc     7380
gcagcatcat ggacgtggcc gttttccgtc tgtcgaagcg tgaccgacga gctggcgagg     7440
tgatccgcta cgagcttcca gacgggcacg tagaggtttc cgcagggccg gccggcatgg     7500
ccagtgtgtg ggattacgac ctggtactga tggcggtttc ccatctaacc gaatccatga     7560
accgataccg ggaagggaag ggagacaagc ccggccgcgt gttccgtcca cacgttgcgg     7620
acgtactcaa gttctgccgg cgagccgatg gcggaaagca gaaagacgac ctggtagaaa     7680
cctgcattcg gttaaacacc acgcacgttg ccatgcagcg tacgaagaag gccaagaacg     7740
gccgcctggt gacggtatcc gagggtgaag ccttgattag ccgctacaag atcgtaaaga     7800
gcgaaaccgg gcggccggag tacatcgaga tcgagctagc tgattggatg taccgcgaga     7860
tcacagaagg caagaacccg gacgtgctga cggttcaccc cgattacttt ttgatcgatc     7920
ccggcatcgg ccgttttctc taccgcctgg cacgccgcgc cgcaggcaag gcagaagcca     7980
gatggttgtt caagacgatc tacgaacgca gtggcagcgc cggagagttc aagaagttct     8040
gtttcaccgt gcgcaagctg atcgggtcaa atgacctgcc ggagtacgat ttgaaggagg     8100
aggcggggca ggctggcccg atcctagtca tgcgctaccg caacctgatc gagggcgaag     8160
catccgccgg ttcctaatgt acggagcaga tgctagggca aattgcccta gcagggaaa     8220 aaggtcgaaa aggtctcttt cctgtggata gcacgtacat tgggaaccca aagccgtaca     8280
ttgggaaccg gaacccgtac attgggaacc caaagccgta cattgggaac cggtcacaca     8340
tgtaagtgac tgatataaaa gagaaaaaag gcgattttc cgcctaaaac tctttaaaac      8400
ttattaaaac tcttaaaacc cgcctggcct gtgcataact gtctggccag cgcacagccg     8460
aagagctgca aaaagcgcct acccttcggt cgctgcgctc cctacgcccc gccgcttcgc     8520
gtcggcctat cgcggccgct ggccgctcaa aaatggctgg cctacggcca ggcaatctac     8580
cagggcgcgg acaagccgcg ccgtcgccac tcgaccgccg gcgctgaggt ctgcctcgtg     8640
aagaaggtgt tgctgactca taccaggcct gaatcgcccc atcatccagc cagaaagtga     8700
gggagccacg gttgatgaga gctttgttgt aggtggacca gttggtgatt ttgaactttt     8760
gctttgccac ggaacggtct gcgttgtcgg gaagatgcgt gatctgatcc ttcaactcag     8820
caaaagttcg atttattcaa caaagccgcc gtcccgtcaa gtcagcgtaa tgctctgcca     8880
gtgttacaac caattaacca attctgatta gaaaaactca tcgagcatca aatgaaactg     8940
caatttattc atatcaggat tatcaatacc atattttga aaaagccgtt tctgtaatga     9000
aggagaaaac tcaccgaggc agttccatag gatggcaaga tcctggtatc ggtctgcgat     9060
tccgactcgt ccaacatcaa tacaacctat taatttcccc tcgtcaaaaa taaggttatc     9120
aagtgagaaa tcaccatgag tgacgactga atccggtgag aatggcaaaa gctctgcatt     9180
aatgaatcgg ccaacgcgcg gggagaggcg gtttgcgtat tgggcgctct tccgcttcct     9240
cgctcactga ctcgctgcgc tcggtcgttc ggctgcggcg agcggtatca gctcactcaa     9300
aggcggtaat acggttatcc acagaatcag gggataacgc aggaaagaac atgtgagcaa     9360
```

| | | |
|---|---|---|
| aaggccagca | aaaggccagg aaccgtaaaa aggccgcgtt gctggcgttt ttccataggc | 9420 |
| tccgccccc | tgacgagcat cacaaaaatc gacgctcaag tcagaggtgg cgaaacccga | 9480 |
| caggactata | aagataccag gcgtttcccc ctggaagctc cctcgtgcgc tctcctgttc | 9540 |
| cgaccctgcc | gcttaccgga tacctgtccg cctttctccc ttcgggaagc gtggcgcttt | 9600 |
| ctcatagctc | acgctgtagg tatctcagtt cggtgtaggt cgttcgctcc aagctgggct | 9660 |
| gtgtgcacga | accccccgtt cagcccgacc gctgcgcctt atccggtaac tatcgtcttg | 9720 |
| agtccaaccc | ggtaagacac gacttatcgc cactggcagc agccactggt aacaggatta | 9780 |
| gcagagcgag | gtatgtaggc ggtgctacag agttcttgaa gtggtggcct aactacggct | 9840 |
| acactagaag | aacagtattt ggtatctgcg ctctgctgaa gccagttacc ttcggaaaaa | 9900 |
| gagttggtag | ctcttgatcc ggcaaacaaa ccaccgctgg tagcggtggt ttttttgttt | 9960 |
| gcaagcagca | gattacgcgc agaaaaaaag gatctcaaga agatcctttg atcttttcta | 10020 |
| cggggtctga | cgctcagtgg aacgaaaact cacgttaagg gattttggtc atgagatta | 10079 |

<210> SEQ ID NO 34
<211> LENGTH: 10904
<212> TYPE: DNA
<213> ORGANISM: Artificial
<220> FEATURE:
<223> OTHER INFORMATION: vector sequence comprising coding sequence of
      BvFT1
<220> FEATURE:
<221> NAME/KEY: misc_feature
<222> LOCATION: (2076)..(2615)
<223> OTHER INFORMATION: nucleotide sequence encoding BvFT1 inserted
      into the vector

<400> SEQUENCE: 34

| | | |
|---|---|---|
| attcctgtgg | ttggcatgca catacaaatg gacgaacgga taaaccttt cacgcccttt | 60 |
| taaatatccg | attattctaa taaacgctct tttctcttag gtttacccgc caatatatcc | 120 |
| tgtcaaacac | tgatagttta aactgaaggc gggaaacgac aatctgatca tgagcggaga | 180 |
| attaagggag | tcacgttatg accccgccg atgacgcggg acaagccgtt ttacgtttgg | 240 |
| aactgacaga | accgcaacgc tgcaggaatt ggccgcagcg gccatttaaa tcaattgggc | 300 |
| gcgccgaatt | cgagctcggt acaagcttgg gaccccggac ccgatccgga gccaagtctc | 360 |
| ataaacgcca | ttgtggaaga aagtcttgag ttggtggtaa tgtaacagag tagtaagaac | 420 |
| agagaagaga | gagagtgtga gatacatgaa ttgtcgggca acaaaaatcc tgaacatctt | 480 |
| attttagcaa | agagaaagag ttccgagtct gtagcagaag agtgaggaga aatttaagct | 540 |
| cttggacttg | tgaattgttc cgcctcttga atacttcttc aatcctcata tattcttctt | 600 |
| ctatgttacc | tgaaaaccgg catttaatct cgcgggttta ttccggttca acattttttt | 660 |
| tgttttgagt | tattatctgg gcttaataac gcaggcctga aataaattca aggcccaact | 720 |
| gttttttttt | ttaagaagtt gctgttaaaa aaaaaaaag ggaattaaca acaacaacaa | 780 |
| aaaagataa | agaaaataat aacaattact ttaattgtag actaaaaaa catagatttt | 840 |
| atcatgaaaa | aaagagaaaa gaaataaaa cttggatcaa aaaaaaaca tacagatctt | 900 |
| ctaattatta | acttttctta aaaattaggt ccttttcccc aacaattagg tttagagttt | 960 |
| tggaattaaa | ccaaaaagat tgttctaaaa aatactcaaa tttggtagat aagtttcctt | 1020 |
| attttaatta | gtcaatggta gatacttttt tttcttttct ttattagagt agattagaat | 1080 |
| cttttatgcc | aagtattgat aaattaaatc aagaagataa actatcataa tcaacatgaa | 1140 |
| attaaaagaa | aaatctcata tatagtatta gtattctcta tatatattat gattgcttat | 1200 |

```
tcttaatggg ttgggttaac caagacatag tcttaatgga aagaatcttt tttgaacttt   1260
ttccttattg attaaattct tctatagaaa agaaagaaat tatttgagga aaagtatata   1320
caaaaagaaa aatagaaaaa tgtcagtgaa gcagatgtaa tggatgacct aatccaacca   1380
ccaccatagg atgtttctac ttgagtcggt cttttaaaaa cgcacggtgg aaaatatgac   1440
acgtatcata tgattccttc ctttagtttc gtgataataa tcctcaactg atatcttcct   1500 tttttttgttt tggctaaaga tattttattc tcattaatag aaaagacggt tttgggcttt   1560
tggtttgcga tataaagaag accttcgtgt ggaagataat aattcatcct ttcgtctttt   1620
tctgactctt caatctctcc caaagcctaa agcgatctct gcaaatctct cgcgactctc   1680
tctttcaagg tatattttct gattcttttt gttttttgatt cgtatctgat ctccaatttt   1740
tgttatgtgg attattgaat ctttttgtata aattgctttt gacaatattg ttcgtttcgt   1800
caatccagct tctaaatttt gtcctgatta ctaagatatc gattcgtagt gtttacatct   1860
gtgtaatttc ttgcttgatt gtgaaattag gattttcaag gacgatctat tcaattttg   1920 tgttttcttt gttcgattct ctctgttttta ggtttcttat gtttagatcc gtttctcttt   1980
ggtgttgttt tgatttctct tacggctttt gatttggtat atgttcgctg attggtttct   2040
acttgttcta ttgttttatt tcaggtggat ccaccatgcc tagaacatca gcaagtgcgc   2100
caagagatcc attagtatta ggtggagtta ttggtgatgt tttagagcca ttcgaaagat   2160
ccgtcactct caaaatcagc tttaacaata gaaatgttaa taatggagga gattttaggc   2220
catcacaagt tgttaaccaa cctagggtcg aagtcggagg tgatgacctt aggacttgct   2280
ataccttggt aatggtagat ccagatgctc ctagcccaag taacccgcat caaagagagt   2340
acttgcactg gttggtgact gatattcccg gaaccacaag tgcatcattt ggagaagaga   2400
ttgtttacta tgaaaaccca cgaccctcaa cggggataca tcgatttgta tttgcattgt   2460
ttcggcaatt gggaaggcaa actgtaaatg ctccacaaca acgccaaaat tttaatacaa   2520
gagactttgc tgaactctac aatcttggct tgcctgttgc tgctgtatat ttcaattgcc   2580
aaagggaggg aggctgtggt ggaaggaggt tttaggagct ccgcggcgcc gatcgttcaa   2640
acatttggca ataaagtttc ttaagattga atcctgttgc cggtcttgcg atgattatca   2700
tataatttct gttgaattac gttaagcatg taataattaa catgtaatgc atgacgttat   2760
ttatgagatg ggttttttatg attagagtcc cgcaattata catttaatac gcgatagaaa   2820
acaaaatata gcgcgcaaac taggataaat tatcgcgcgc ggtgtcatct atgttactag   2880
atcggaccgg gtaccgagct cgagactagc tacaggccaa attcgctctt agccgtacaa   2940
tattactcac cggtgcgatg ccccccatcg taggtgaagg tggaaattaa tgatccatct   3000
tgagaccaca ggcccacaac agctaccagt ttcctcaagg gtccaccaaa aacgtaagcg   3060
cttacgtaca tggtcgataa gaaaaggcaa tttgtagatg ttaacatcca acgtcgcttt   3120
cagggatccc gaattccaag cttggaattc gggatcctac aggccaaatt cgctcttagc   3180
cgtacaatat tactcaccgg tgcgatgccc ccatcgtag gtgaaggtgg aaattaatga   3240
tccatcttga ccacaggcc cacaacagc taccagtttc ctcaagggtc caccaaaaac   3300
gtaagcgctt acgtacatgg tcgataagaa aaggcaattt gtagatgtta acatccaacg   3360
tcgctttcag gatcccgaa ttccaagctt ggaattcggg atcctacagg ccaaattcgc   3420
tcttagccgt acaatattac tcaccggtgc gatgcccccc atcgtaggtg aaggtggaaa   3480
ttaatgatcc atcttgagac cacaggccca caacagctac cagtttcctc aagggtccac   3540
caaaaacgta agcgcttacg tacatggtcg ataagaaaag gcaatttgta gatgttaaca   3600
```

```
tccaacgtcg ctttcaggga tcccgaattc caagcttggg ctgcaggtca atcccattgc    3660
ttttgaagca gctcaacatt gatctctttc tcgagggaga ttttcaaat cagtgcgcaa     3720 gacgtgacgt aagtatccga gtcagttttt attttctac taatttggtc gtttatttcg    3780
gcgtgtagga catggcaacc gggcctgaat tcgcgggta ttctgtttct attccaactt    3840
tttcttgatc cgcagccatt aacgactttt gaatagatac gctgacacgc caagcctcgc    3900
tagtcaaaag tgtaccaaac aacgctttac agcaagaacg gaatgcgcgt gacgctcgcg    3960
gtgacgccat ttcgccttt cagaaatgga taaatagcct tgcttcctat tatatcttcc     4020
caaattacca atacattaca ctagcatctg aatttcataa ccaatctcga tacaccaaat    4080
cgagatcccc gatcatgcaa aaactcatta actcagtgca aaactatgcc tggggcagca    4140
aaacggcgtt gactgaactt tatggtatgg aaaatccgtc cagccagccg atggccgagc    4200
tgtggatggg cgcacatccg aaaagcagtt cacgagtgca gaatgccgcc ggagatatcg    4260
tttcactgcg tgatgtgatt gagagtgata atcgactct gctcggagag gccgttgcca     4320
aacgctttgg cgaactgcct ttcctgttca aagtattatg cgcagcacag ccactctcca    4380
ttcaggttca tccaaacaaa cacaattctg aaatcggttt tgccaaagaa aatgccgcag    4440
gtatcccgat ggatgccgcc gagcgtaact ataaagatcc taaccacaag ccggagctgg    4500
tttttgcgct gacgccttc cttgcgatga acgcgtttcg tgaattttcc gagattgtct     4560
ccctactcca gccggtcgca ggtgcacatc cggcgattgc tcacttttta caacagcctg    4620
atgccgaacg tttaagcgaa ctgttcgcca gcctgttgaa tatgcagggt gaagaaaaat    4680
cccgcgcgct ggcgatttta aaatcggccc tcgatagcca gcaggtgaa ccgtggcaaa     4740 cgattcgttt aatttctgaa ttttacccgg aagacagcgg tctgttctcc ccgctattgc    4800
tgaatgtggt gaaattgaac cctggcgaag cgatgttcct gttcgctgaa acaccgcacg    4860
cttacctgca aggcgtggcg ctggaagtga tggcaaactc cgataacgtg ctgcgtgcgg    4920
gtctgacgcc taaatacatt gatattccgg aactggttgc caatgtgaaa ttcgaagcca    4980
aaccggctaa ccagttgttg acccagccgg tgaaacaagg tgcagaactg gacttcccga    5040
ttccagtgga tgattttgcc ttctcgctgc atgaccttag tgataaagaa accaccatta    5100
gccagcagag tgccgccatt ttgttctgcg tcgaaggcga tgcaacgttg tggaaaggtt    5160
ctcagcagtt acagcttaaa ccgggtgaat cagcgtttat tgccgccaac gaatcaccgg    5220
tgactgtcaa aggccacggc cgtttagcgc gtgtttacaa caagctgtaa gagcttactg    5280
aaaaaattaa catctcttgc taagctggga gctcgatccg tcgacctgca gatcgttcaa    5340
acatttggca ataaagtttc ttaagattga atcctgttgc cggtcttgcg atgattatca    5400
tataatttct gttgaattac gttaagcatg taataattaa catgtaatgc atgacgttat    5460
ttatgagatg ggtttttatg attagagtcc cgcaattata catttaatac gcgatagaaa    5520
acaaaatata gcgcgcaaac taggataaat tatcgcgcgc ggtgtcatct atgttactag    5580
atctgtagcc ctgcaggaaa tttaccggtg cccgggcggc cagcatggcc gtatccgcaa    5640
tgtgttatta agttgtctaa gcgtcaattt gtttacacca caatatatcc tgccaccagc    5700
cagccaacag ctccccgacc ggcagctcgg cacaaaatca ccactcgata caggcagccc    5760
atcagaatta attctcatgt ttgacagctt atcatcgact gcacggtgca ccaatgcttc    5820
tggcgtcagg cagccatcgg aagctgtggt atggctgtgc aggtcgtaaa tcactgcata    5880
attcgtgtcg ctcaaggcgc actcccgttc tggataatgt ttttgcgcc gacatcataa     5940 cggttctggc aaatattctg aaatgagctg ttgacaatta atcatccggc tcgtataatg    6000
```

```
tgtggaattg tgagcggata acaatttcac acaggaaaca gaccatgagg gaagcgttga   6060
tcgccgaagt atcgactcaa ctatcagagg tagttggcgt catcgagcgc catctcgaac   6120
cgacgttgct ggccgtacat ttgtacggct ccgcagtgga tggcggcctg aagccacaca   6180
gtgatattga tttgctggtt acggtgaccg taaggcttga tgaaacaacg cggcgagctt   6240
tgatcaacga ccttttggaa acttcggctt cccctggaga gagcgagatt ctccgcgctg   6300
tagaagtcac cattgttgtg cacgacgaca tcattccgtg gcgttatcca gctaagcgcg   6360
aactgcaatt tggagaatgg cagcgcaatg acattcttgc aggtatcttc gagccagcca   6420
cgatcgacat tgatctggct atcttgctga caaaagcaag agaacatagc gttgccttgg   6480
taggtccagc ggcggaggaa ctctttgatc cggttcctga acaggatcta tttgaggcgc   6540
taaatgaaac cttaacgcta tggaactcgc cgcccgactg ggctggcgat gagcgaaatg   6600
tagtgcttac gttgtcccgc atttggtaca gcgcagtaac cggcaaaatc gcgccgaagg   6660
atgtcgctgc cgactgggca atggagcgcc tgccggccca gtatcagccc gtcatacttg   6720
aagctaggca ggcttatctt ggacaagaag atcgcttggc ctcgcgcgca gatcagttgg   6780
aagaatttgt tcactacgtg aaaggcgaga tcaccaaagt agtcggcaaa taaagctcta   6840
gtggatctcc gtaccgggga atctggctcg cggcggacgc acgacgccgg ggcgagacca   6900
taggcgatcc cctaaatcaa tagtagctgt aacctcgaag cgtttcactt gtaacaacga   6960
ttgagaattt ttgtcataaa attgaaatac ttggttcgca tttttgtcat ccgcggtcag   7020
ccgcaattct gacgaactgc ccatttagct ggagatgatt gtacatcctt cacgtgaaaa   7080
tttctcaagc gctgtgaaca agggttcaga ttttagattg aaaggtgagc cgttgaaaca   7140
cgttcttctt gtcgatgacg acgtcgctat gcggcatctt attattgaat accttacgat   7200
ccacgccttc aaagtgaccg cggtagccga cagcacccag ttcacaagag tactctcttc   7260
cgcgacggtc gatgtcgtgg ttgttgatct agatttaggt cgtgaagatg ggctcgagat   7320
cgttcgtaat ctggcggcaa agtctgatat tccaatcata attatcagtg gcgaccgcct   7380
tgaggagacg gataaagttg ttgcactcga gctaggagca agtgattta tcgctaagcc   7440 gttcagtatc agagagtttc tagcacgcat tcgggttgcc ttgcgcgtgc gccccaacgt   7500
tgtccgctcc aaagaccgac ggtcttttg ttttactgac tggacactta atctcaggca   7560
acgtcgcttg atgtccgaag ctggcggtga ggtgaaactt acggcaggtg agttcaatct   7620
tctcctcgcg ttttagaga aaccccgcga cgttctatcg cgcgagcaac ttctcattgc   7680
cagtcgagta cgcgacgagg aggtttatga caggagtata gatgttctca ttttgaggct   7740
gcgccgcaaa cttgaggcag atccgtcaag ccctcaactg ataaaaacag caagaggtgc   7800
cggttatttc tttgacgcgg acgtgcaggt ttcgcacggg gggacgatgg cagcctgagc   7860
caattcccag atccccgagg aatcggcgtg agcggtcgca aaccatccgg cccggtacaa   7920
atcggcgcgg cgctgggtga tgacctggtg gagaagttga aggccgcgca ggccgcccag   7980
cggcaacgca tcgaggcaga agcacgcccc ggtgaatcgt ggcaagcggc cgctgatcga   8040
atccgcaaag aatcccggca accgccggca gccggtgcgc cgtcgattag gaagccgccc   8100
aagggcgacg agcaaccaga ttttttcgtt ccgatgctct atgacgtggg caccgcgat   8160 agtcgcagca tcatggacgt ggccgttttc cgtctgtcga agcgtgaccg acgagctggc   8220
gaggtgatcc gctacgagct tccagacggg cacgtagagg tttccgcagg gccggccggc   8280
atggccagtg tgtgggatta cgacctggta ctgatggcgg tttcccatct aaccgaatcc   8340
atgaaccgat accgggaagg gaagggagac aagcccggcc gcgtgttccg tccacacgtt   8400
```

```
gcggacgtac tcaagttctg ccggcgagcc gatggcggaa agcagaaaga cgacctggta    8460
gaaacctgca ttcggttaaa caccacgcac gttgccatgc agcgtacgaa gaaggccaag    8520
aacggccgcc tggtgacggt atccgagggt gaagccttga ttagccgcta caagatcgta    8580
aagagcgaaa ccgggcggcc ggagtacatc gagatcgagc tagctgattg gatgtaccgc    8640
gagatcacag aaggcaagaa cccggacgtg ctgacggttc accccgatta cttttttgatc   8700
gatcccggca tcggccgttt tctctaccgc ctggcacgcc gcgccgcagg caaggcagaa    8760
gccagatggt tgttcaagac gatctacgaa cgcagtggca gcgccggaga gttcaagaag    8820
ttctgtttca ccgtgcgcaa gctgatcggg tcaaatgacc tgccggagta cgatttgaag    8880
gaggaggcgg ggcaggctgg cccgatccta gtcatgcgct accgcaacct gatcgagggc    8940
gaagcatccg ccggttccta atgtacggag cagatgctag ggcaaattgc cctagcaggg    9000
gaaaaaggtc gaaaaggtct cttttcctgtg gatagcacgt acattgggaa cccaaagccg    9060
tacattggga accggaaccc gtacattggg aacccaaagc cgtacattgg gaaccggtca    9120
cacatgtaag tgactgatat aaaagagaaa aaaggcgatt tttccgccta aaactcttta    9180
aaacttatta aaactcttaa aacccgcctg gcctgtgcat aactgtctgg ccagcgcaca    9240
gccgaagagc tgcaaaaagc gcctacccctt cggtcgctgc gctccctacg ccccgccgct   9300
tcgcgtcggc ctatcgcggc cgctggccgc tcaaaaatgg ctggcctacg gccaggcaat    9360
ctaccagggc gcggacaagc cgcgccgtcg ccactcgacc gccggcgctg aggtctgcct    9420
cgtgaagaag gtgttgctga ctcataccag gcctgaatcg ccccatcatc cagccagaaa    9480
gtgagggagc cacggttgat gagagctttg ttgtaggtgg accagttggt gattttgaac    9540
ttttgctttg ccacggaacg gtctgcgttg tcgggaagat gcgtgatctg atccttcaac    9600
tcagcaaaag ttcgatttat tcaacaaagc cgccgtcccg tcaagtcagc gtaatgctct    9660
gccagtgtta caaccaatta accaattctg attagaaaaa ctcatcgagc atcaaatgaa    9720
actgcaattt attcatatca ggattatcaa taccatattt ttgaaaaagc cgtttctgta    9780
atgaaggaga aaactcaccg aggcagttcc ataggatggc aagatcctgg tatcggtctg    9840
cgattccgac tcgtccaaca tcaatacaac ctattaattt cccctcgtca aaataaggt    9900
tatcaagtga gaaatcacca tgagtgacga ctgaatccgg tgagaatggc aaaagctctg    9960
cattaatgaa tcggccaacg cgcggggaga ggcggtttgc gtattgggcg ctcttccgct   10020
tcctcgctca ctgactcgct gcgctcggtc gttcggctgc ggcgagcggt atcagctcac   10080
tcaaaggcgg taatacggtt atccacagaa tcagggata acgcaggaaa gaacatgtga   10140
gcaaaaggcc agcaaaaggc caggaaccgt aaaaaggccg cgttgctggc gtttttccat   10200
aggctccgcc cccctgacga gcatcacaaa aatcgacgct caagtcagag gtggcgaaac   10260
ccgacaggac tataaagata ccaggcgttt ccccctggaa gctccctcgt gcgctctcct   10320
gttccgaccc tgccgcttac cggatacctg tccgcctttc tcccttcggg aagcgtggcg   10380
ctttctcata gctcacgctg taggtatctc agttcggtgt aggtcgttcg ctccaagctg   10440
ggctgtgtgc acgaacccccc gttcagccc gaccgctgcg ccttatccgg taactatcgt   10500
cttgagtcca acccggtaag acacgactta tcgccactgg cagcagccac tggtaacagg   10560
attagcagag cgaggtatgt aggcggtgct acagagttct tgaagtggtg gcctaactac   10620
ggctacacta gaagaacagt atttggtatc tgcgctctgc tgaagccagt taccttcgga   10680
aaaagagttg gtagctcttg atccggcaaa caaaccaccg ctggtagcgg tggtttttt    10740
gtttgcaagc agcagattac gcgcagaaaa aaaggatctc aagaagatcc tttgatcttt   10800
```

-continued

```
tctacggggt ctgacgctca gtggaacgaa aactcacgtt aagggatttt ggtcatgaga    10860
ttatcaaaaa ggatcttcac ctagatcctt ttgatccgga atta                    10904
```

<210> SEQ ID NO 35
<211> LENGTH: 46
<212> TYPE: DNA
<213> ORGANISM: Artificial
<220> FEATURE:
<223> OTHER INFORMATION: oligonucleotide sequence
<220> FEATURE:
<221> NAME/KEY: misc_feature
<222> LOCATION: (46)..(46)
<223> OTHER INFORMATION: n is a, c, g, or t

<400> SEQUENCE: 35

```
gcgagcacag aattaatacg actcactata ggttttttttt ttttvn                  46
```

<210> SEQ ID NO 36
<211> LENGTH: 23
<212> TYPE: DNA
<213> ORGANISM: Artificial
<220> FEATURE:
<223> OTHER INFORMATION: oligonucleotide primer

<400> SEQUENCE: 36

```
gcgagcacag aattaatacg act                                            23
```

<210> SEQ ID NO 37
<211> LENGTH: 32
<212> TYPE: DNA
<213> ORGANISM: Artificial
<220> FEATURE:
<223> OTHER INFORMATION: oligonucleotide primer

<400> SEQUENCE: 37

```
cgcggatccg aattaatacg actcactata gg                                  32
```

<210> SEQ ID NO 38
<211> LENGTH: 35
<212> TYPE: DNA
<213> ORGANISM: Artificial
<220> FEATURE:
<223> OTHER INFORMATION: oligonucleotide primer

<400> SEQUENCE: 38

```
ctatggatcc gcaagcgtta agttcattga aatgg                               35
```

<210> SEQ ID NO 39
<211> LENGTH: 45
<212> TYPE: DNA
<213> ORGANISM: Artificial
<220> FEATURE:
<223> OTHER INFORMATION: oligonucleotide primer

<400> SEQUENCE: 39

```
gtagaagcag aaacttacct agaagagatt gtttactatg aaaac                    45
```

<210> SEQ ID NO 40
<211> LENGTH: 28
<212> TYPE: DNA
<213> ORGANISM: Artificial
<220> FEATURE:
<223> OTHER INFORMATION: oligonucleotide primer

<400> SEQUENCE: 40

```
atccaaccgc ggacctgcac atcaacaa                                       28
```

<210> SEQ ID NO 41
<211> LENGTH: 40
<212> TYPE: DNA
<213> ORGANISM: Artificial
<220> FEATURE:
<223> OTHER INFORMATION: oligonucleotide primer

<400> SEQUENCE: 41
catagtaaac aatctcttct aggtaagttt ctgcttctac          40

<210> SEQ ID NO 42
<211> LENGTH: 32
<212> TYPE: DNA
<213> ORGANISM: Artificial
<220> FEATURE:
<223> OTHER INFORMATION: oligonucleotide primer

<400> SEQUENCE: 42
taaatccgcg gagaagagat tgtttactat ga                  32

<210> SEQ ID NO 43
<211> LENGTH: 44
<212> TYPE: DNA
<213> ORGANISM: Artificial
<220> FEATURE:
<223> OTHER INFORMATION: oligonucleotide primer

<400> SEQUENCE: 43
ctatttgtcg acgcaagcgt taagttcatt gaaatggaga ggtg      44

<210> SEQ ID NO 44
<211> LENGTH: 35
<212> TYPE: DNA
<213> ORGANISM: Artificial
<220> FEATURE:
<223> OTHER INFORMATION: oligonucleotide primer

<400> SEQUENCE: 44
ctatggatcc gcatttaata aaatctcttt caatg                35

<210> SEQ ID NO 45
<211> LENGTH: 41
<212> TYPE: DNA
<213> ORGANISM: Artificial
<220> FEATURE:
<223> OTHER INFORMATION: oligonucleotide primer

<400> SEQUENCE: 45
gtagaagcag aaacttacct gccaagaagt tgtctgctat g         41

<210> SEQ ID NO 46
<211> LENGTH: 41
<212> TYPE: DNA
<213> ORGANISM: Artificial
<220> FEATURE:
<223> OTHER INFORMATION: oligonucleotide primer

<400> SEQUENCE: 46
catagcagac aacttcttgg caggtaagtt tctgcttcta c         41

<210> SEQ ID NO 47
<211> LENGTH: 32
<212> TYPE: DNA
<213> ORGANISM: Artificial
<220> FEATURE:
<223> OTHER INFORMATION: oligonucleotide primer

```
<400> SEQUENCE: 47
taaatccgcg ggccaagaag ttgtctgcta tg                                    32

<210> SEQ ID NO 48
<211> LENGTH: 33
<212> TYPE: DNA
<213> ORGANISM: Artificial
<220> FEATURE:
<223> OTHER INFORMATION: oligonucleotide primer

<400> SEQUENCE: 48
ctatttgtcg acgcatttaa taaaatctct ttc                                   33

<210> SEQ ID NO 49
<211> LENGTH: 8
<212> TYPE: PRT
<213> ORGANISM: Beta vulgaris
<220> FEATURE:
<221> NAME/KEY: MISC_FEATURE
<222> LOCATION: (1)..(8)
<223> OTHER INFORMATION: represents amino acid residues 51 to 58

<400> SEQUENCE: 49

Lys Pro Arg Val Glu Ile Gly Gly
1               5

<210> SEQ ID NO 50
<211> LENGTH: 9
<212> TYPE: PRT
<213> ORGANISM: Beta vulgaris

<400> SEQUENCE: 50

Leu Val Thr Asp Ile Pro Ala Thr Thr
1               5

<210> SEQ ID NO 51
<211> LENGTH: 18
<212> TYPE: DNA
<213> ORGANISM: Artificial
<220> FEATURE:
<223> OTHER INFORMATION: oligonucleotide primer

<400> SEQUENCE: 51
ccgggtgaat cagcgttt                                                    18

<210> SEQ ID NO 52
<211> LENGTH: 18
<212> TYPE: DNA
<213> ORGANISM: Artificial
<220> FEATURE:
<223> OTHER INFORMATION: oligonucleotide primer

<400> SEQUENCE: 52
gccgtggcct ttgacagt                                                    18

<210> SEQ ID NO 53
<211> LENGTH: 10800
<212> TYPE: DNA
<213> ORGANISM: Artificial
<220> FEATURE:
<223> OTHER INFORMATION: vector sequence comprising the PMI selectable
      marker gene downstream of the pOp6 promoter in combination with
      the gene cassette for constitutive expression of LhG4Ato under to
      the control of Ubi3 promoter

<400> SEQUENCE: 53
```

```
gtttacccgc caatatatcc tgtcaaacac tgatagttta aactgaaggc gggaaacgac      60
aatctgatca tgagcggaga attaagggag tcacgttatg accccgccg atgacgcggg      120 acaagccgtt ttacgtttgg aactgacaga accgcaacgc tgcaggaatt ggccgcagcg     180
gccatttaaa tcaattgggc gcgccgaatt cgagctcaag aaatctagaa agaagaaagg     240
gaagagaaag aattgtgagc gctcacaatt gaaagactag aaagaagaaa gggaagagaa     300
agaattgtga gcgctcacaa ttgaaagact agaaagaaga agggaagag aaagaattgt      360 gagcgctcac aattgaaaga ctagaaagaa gaagggaag agaaagaatt gtgagcgctc     420
acaattgaaa gactagaaag aagaaaggga agagaaagaa ttgtgagcgc tcacaattga     480
aagactagaa agaagaaagg gaagagaaag aattgtgagc gctcacaatt gaaagactag     540
tggatcgatc ttcgcaagac ccttcctcta tataaggaag ttcatttcat tggagagga     600 cacgctgaag ctagacgcgc gtattttac aacaattacc aacaacaaca caaacaaca      660 acaacattac attttacatt ctacaactac agctagcaag cttgtcgacc tcgaggggg      720 gcccggtacc cggggatccc cgatcatgca aaaactcatt aactcagtgc aaaactatgc     780
ctggggcagc aaaacggcgt tgactgaact ttatggtatg aaaatccgt ccagccagcc      840 gatggccgag ctgtggatgg gcgcacatcc gaaaagcagt tcacgagtgc agaatgccgc     900
cggagatatc gtttcactgc gtgatgtgat tgagagtgat aaatcgactc tgctcggaga     960
ggccgttgcc aaacgctttg gcgaactgcc tttcctgttc aaagtattat gcgcagcaca    1020
gccactctcc attcaggttc atccaaacaa acacaattct gaaatcggtt ttgccaaaga    1080
aaatgccgca ggtatcccga tggatccgc cgagcgtaac tataaagatc ctaaccacaa    1140 gccgagctg gttttgcgc tgacgccttt ccttgcgatg aacgcgtttc gtgaattttc      1200
cgagattgtc tccctactcc agccggtcgc aggtgcacat ccggcgattg ctcactttt    1260 acaacagcct gatgccgaac gtttaagcga actgttcgcc agcctgttga atatgcaggg    1320
tgaagaaaaa tcccgcgcgc tggcgatttt aaaatcggcc ctcgatagcc agcagggtga    1380
accgtggcaa acgattcgtt taatttctga attttacccg gaagacagcg gtctgttctc    1440
cccgctattg ctgaatgtgg tgaaattgaa ccctggcgaa gcgatgttcc tgttcgctga    1500
aacaccgcac gcttacctgc aaggcgtggc gctggaagtg atggcaaact ccgataacgt    1560
gctgcgtgcg ggtctgacgc taaatacat tgatattccg gaactggttg ccaatgtgaa    1620
attcgaagcc aaaccggcta accagttgtt gacccagccg gtgaaacaag gtgcagaact    1680
ggacttcccg attccagtgg atgattttgc cttctcgctg catgaccta gtgataaaga    1740 aaccaccatt agccagcaga gtgccgccat tttgttctgc gtcgaaggcg atgcaacgtt    1800
gtggaaaggt tctcagcagt tacagcttaa accgggtgaa tcagcgttta ttgccgccaa    1860
cgaatcaccg gtgactgtca aaggccacgg ccgtttagcg cgtgtttaca caagctgta    1920 agagcttact gaaaaaatta acatctcttg ctaagctggg agctcgtcga cggcatgccc    1980
gctgaaatca ccagtctctc tctacaaatc tatctctctc tataataatg tgtgagtagt    2040
tcccagataa gggaattagg gttcttatag gttcgctc atgtgttgag catataagaa    2100
acccttagta gttatttgta tttgtaaaat acttctatca ataaaatttc taattcctaa    2160
aaccaaaatc caggggtacg atctcgacca tggtgatcac tgcaggcatg caagcttcgt    2220
acgttaatta acgtacgaag cttctagag atccgtccgg atttggagcc aagtctcata    2280
aacgccattg tggaagaaag tcttgagttg gtggtaatgt aacagagtag taagaacaga    2340
gaagagagag agtgtgagat acatgaattg tcgggcaaca aaaatcctga acatcttatt    2400
```

```
ttagcaaaga gaaagagttc cgagtctgta gcagaagagt gaggagaaat ttaagctctt      2460
ggacttgtga attgttccgc ctcttgaata cttcttcaat cctcatatat tcttcttcta      2520
tgttacctga aaaccggcat ttaatctcgc gggtttattc cggttcaaca tttttttgt       2580 tttgagttat tatctgggct taataacgca ggcctgaaat aaattcaagg cccaactgtt      2640
ttttttttta agaagttgct gttaaaaaaa aaaaaggga attaacaaca acaacaaaaa       2700
aagataaaga aaataataac aattacttta attgtagact aaaaaaacat agattttatc      2760
atgaaaaaaa gagaaaagaa ataaaaactt ggatcaaaaa aaaaacatac agatcttcta      2820
attattaact tttcttaaaa attaggtcct ttttcccaac aattaggttt agagttttgg      2880
aattaaacca aaaagattgt tctaaaaaat actcaaattt ggtagataag tttccttatt      2940
ttaattagtc aatggtagat acttttttt ctttctttta ttagagtaga ttagaatctt       3000
ttatgccaag tattgataaa ttaaatcaag aagataaact atcataatca acatgaaatt      3060
aaaagaaaaa tctcatatat agtattagta ttctctatat atattatgat tgcttattct      3120
taatgggttg ggttaaccaa gacatagtct taatggaaag aatctttttt gaacttttc       3180 cttattgatt aaattcttct atagaaaaga aagaaattat ttgaggaaaa gtatatacaa      3240
aaagaaaaat agaaaaatgt cagtgaagca gatgtaatgg atgacctaat ccaaccacca      3300
ccataggatg tctctacttg agtcggtctt ttaaaaacgc acggtggaaa atatgacacg      3360
tatcatatga ttccttcctt tagtttcgtg ataataatcc tcaactgata tcttcctttt      3420
tttgttttgg ctaaagatat tttattctca ttaatagaaa agacggtttt gggcttttgg     3480
tttgcgatat aaagaagacc ttcgtgtgga agataataat tcatcctttc gtcttttct       3540 gactcttcaa tctctcccaa agcctaaagc gatctctgca aatctctcgc gactctctct      3600
ttggatccat tatgaaaccg gtaacgttat acgacgtcgc tgaatacgcc ggcgtttctc      3660
atcaaaccgt ttctagagtg gttaaccagg cttcacatgt tagcgctaaa acccgggaaa      3720
aagttgaagc tgccatggct gagctcaact acatcccgaa ccgtgttgcg cagcagctgg      3780
ctggtaaaca aagcttgctg atcggtgtcg cgacctcgag cttggccctg cacgcgccgt      3840
cgcaaattgt cgcggcgatt aaatctcgcg ccgatcaact gggtgccagc gtggtggtgt      3900
cgatggtaga acgaagcggc gtcgaagcct gtaaagcggc ggtgcacaat cttctcgcgc      3960
aacgcgtcag tgggctgatc attaactatc cgctggatga ccaggatgcc attgctgtgg      4020
aagctgcctg cactaatgtt ccggcgttat ttcttgatgt ctctgaccag acacccatca      4080
acagtattat tttctcccat gaagacggta cgcgactggg cgtggagcat ctggtcgcat      4140
tgggtcacca gcaaatcgcg ctgttagcgg gcccattaag ttctgtctcg gcgcgtctgc      4200
gtctggctgc ctggcataaa tatctcactc gcaatcaaat tcagccgata gcggaacggg      4260
aaggcgactg gagtgccatg tccggttttc aacaaccat gcaaatgctg aatgagggca      4320
tcgttcccac tgcgatgctg gttgccaacg atcagatggc gctgggcgca atgcgcgcca      4380
ttaccgagtc cgggctgcgc gttggtgcgg atatctcggt agtgggatac gacgataccg      4440
aagacagctc atgttatatc ccgccgttaa ccaccatcaa acaggatttt cgcctgctgg      4500
ggcaaaccag cgtggaccgc ttgctgcaac tctctcaggg ccaggcggtg aagggcaatc      4560
agctgttgcc cgtctcactg gtgaaaagaa aaaccactag tggatcggaa ttcgctaact      4620
tcaaccagtc cggaaacatc gctgattctt ccttgagctt cactttcact aactcttcta      4680
acggacctaa cctatcacc actcagacca actctcaggc tcttagccag ccaatcgcta      4740
gctctaacgt gcacgacaac ttcatgaaca acgagatcac tgctagcaag atcgatgatg      4800
```

```
gtaacaattc taagcctctt agcccaggat ggactgatca gactgcttac aacgcattcg   4860
gtatcactac cggtatgttc aacaccacta ccatggacga tgtgtacaac tacctcttcg   4920
acgatgagga tactccacct aaccctaaga aggagtgagg atgtcgacct gcagagatcg   4980
ttcaaacatt tggcaataaa gtttcttaag attgaatcct gttgccggtc ttgcgatgat   5040
tatcatctaa tttctgttga attacgttaa gcatgtaata attaacatgt aatgcatgac   5100
gttatttatg agatgggttt ttatgattag agtcccgcaa ttatacattt aatacgcgat   5160
agaaaacaaa atatagcgcg caaactagga taaattatcg cgcgcggtgt catctatgtt   5220
actagatcgg gaattgggta ccgaattcac tggccgtcgt tttacaacgt cgtgactggg   5280
aaaaccctgg cgttacccaa cttaatcgcc ttgcagcaca tcccccttc gccagctggc    5340
gtaatagcga agaggcccgc accgatcgcc cttcccaaca gttgcgcagc ctgaatggcg   5400
aatggcgggc ggccagcatg gccgtatccg caatgtgtta ttaagttgtc taagcgtcaa   5460
tttgtttaca ccacaatata tcctgccacc agccagccaa cagctccccg accggcagct   5520
cggcacaaaa tcaccactcg atacaggcag cccatcagaa ttaattctca tgtttgacag   5580
cttatcatcg actgcacggt gcaccaatgc ttctggcgtc aggcagccat cggaagctgt   5640
ggtatggctg tgcaggtcgt aaatcactgc ataattcgtg tcgctcaagg cgcactcccg   5700
ttctggataa tgttttttgc gccgacatca taacggttct ggcaaatatt ctgaaatgag   5760
ctgttgacaa ttaatcatcc ggctcgtata atgtgtggaa ttgtgagcgg ataacaattt   5820
cacacaggaa acagaccatg agggaagcgt tgatcgccga agtatcgact caactatcag   5880
aggtagttgg cgtcatcgag cgccatctcg aaccgacgtt gctggccgta catttgtacg   5940
gctccgcagt ggatggcggc ctgaagccac acagtgatat tgatttgctg gttacggtga   6000
ccgtaaggct tgatgaaaca acgcggcgag ctttgatcaa cgaccttttg gaaacttcgg   6060
cttcccctgg agagagcgag attctccgcg ctgtagaagt caccattgtt gtgcacgacg   6120
acatcattcc gtggcgttat ccagctaagc gcgaactgca atttggagaa tggcagcgca   6180
atgacattct tgcaggtatc ttcgagccag ccacgatcga cattgatctg ctatcttgc    6240
tgacaaaagc aagagaacat agcgttgcct tggtaggtcc agcggcggag gaactctttg   6300
atccggttcc tgaacaggat ctatttgagg cgctaaatga aaccttaacg ctatggaact   6360
cgccgcccga ctgggctggc gatgagcgaa atgtagtgct tacgttgtcc cgcatttggt   6420
acagcgcagt aaccggcaaa atcgcgccga aggatgtcgc tgccgactgg gcaatggagc   6480
gcctgccggc ccagtatcag cccgtcatac ttgaagctag caggcttat cttggacaag    6540
aagatcgctt ggcctcgcgc gcagatcagt tggaagaatt tgttcactac gtgaaaggcg   6600
agatcaccaa agtagtcggc aaataaagct ctagtggatc tccgtacccc cggggatct    6660
ggctcgcggc ggacgcacga cgccggggcg agaccatagg cgatctccta aatcaatagt   6720
agctgtaacc tcgaagcgtt tcacttgtaa caacgattga aattttgt cataaaattg     6780
aaatacttgg ttcgcatttt tgtcatccgc ggtcagccgc aattctgacg aactgcccat   6840
ttagctggag atgattgtac atccttcacg tgaaatttc tcaagcgctg tgaacaaggg    6900
ttcagatttt agattgaaag gtgagccgtt gaaacacgtt cttcttgtcg atgacgacgt   6960
cgctatgcgg catcttatta ttgaataccrt acgatccac gccttcaaag tgaccgcggt    7020
agccgacagc acccagttca caagagtact ctcttccgcg acggtcgatg tcgtggttgt   7080
tgatctaaat ttaggtcgtg aagatgggct cgagatcgtt cgtaatctgg cggcaaagtc   7140
tgatattcca atcataatta tcagtggcga ccgccttgag gagacggata aagttgttgc   7200
```

```
actcgagcta ggagcaagtg attttatcgc taagccgttc agtatcagag agtttctagc    7260
acgcattcgg gttgccttgc gcgtgcgccc aacgttgtc cgctccaaag accgacggtc     7320
tttttgtttt actgactgga cacttaatct caggcaacgt cgcttgatgt ccgaagctgg    7380
cggtgaggtg aaacttacgg caggtgagtt caatcttctc ctcgcgtttt tagagaaacc    7440
ccgcgacgtt ctatcgcgcg agcaacttct cattgccagt cgagtacgcg acgaggaggt    7500
ttatgacagg agtatagatg ttctcatttt gaggctgcgc cgcaaacttg aggcagatcc    7560
gtcaagccct caactgataa aaacagcaag aggtgccggt tatttctttg acgcggacgt    7620
gcaggtttcg cacggggga cgatggcagc ctgagccaat tcccagatcc ccgaggaatc     7680
ggcgtgagcg gtcgcaaacc atccggcccg gtacaaatcg gcgcggcgct gggtgatgac    7740
ctggtggaga agttgaaggc cgcgcaggcc gcccagcggc aacgcatcga ggcagaagca    7800
cgccccggtg aatcgtggca agcggccgct gatcgaatcc gcaaagaatc ccggcaaccg    7860
ccggcagccg gtgcgccgtc gattaggaag ccgcccaagg gcgacgagca accagatttt    7920
ttcgttccga tgctctatga cgtgggcacc cgcgatagtc gcagcatcat ggacgtggcc    7980
gttttccgtc tgtcgaagcg tgaccgacga gctggcgagg tgatccgcta cgagcttcca    8040
gacgggcacg tagaggtttc cgcagggccg gccggcatgg ccagtgtgtg ggattacgac    8100
ctggtactga tggcggtttc ccatctaacc gaatccatga accgataccg ggaagggaag    8160
ggagacaagc ccggccgcgt gttccgtcca cacgttgcgg acgtactcaa gttctgccgg    8220
cgagccgatg gcgaaagca gaaagacgac ctggtagaaa cctgcattcg gttaaacacc     8280
acgcacgttg ccatgcagcg tacgaagaag gccaagaacg gccgcctggt gacggtatcc    8340
gagggtgaag ccttgattag ccgctacaag atcgtaaaga gcgaaaccgg gcggccggag    8400
tacatcgaga tcgagctagc tgattggatg taccgcgaga tcacagaagg caagaacccg    8460
gacgtgctga cggttcaccc cgattacttt ttgatcgatc ccggcatcgg ccgttttctc    8520
taccgcctgg cacgccgcgc cgcaggcaag gcagaagcca gatggttgtt caagacgatc    8580
tacgaacgca gtggcagcgc cggagagttc aagaagttct gtttcaccgt gcgcaagctg    8640
atcgggtcaa atgacctgcc ggagtacgat ttgaaggagg aggcggggca ggctggcccg    8700
atcctagtca tgcgctaccg caacctgatc gagggcgaag catccgccgg ttcctaatgt    8760
acggagcaga tgctagggca aattgcccta gcaggggaaa aaggtcgaaa aggtctcttt    8820
cctgtggata gcacgtacat tgggaaccca aagccgtaca ttgggaaccg gaacccgtac    8880
attgggaacc caaagccgta cattgggaac cggtcacaca tgtaagtgac tgatataaaa    8940
gagaaaaag gcgatttttc cgcctaaaac tctttaaaac ttattaaaac tcttaaaacc     9000
cgcctggcct gtgcataact gtctggccag cgcacagccg aagagctgca aaaagcgcct    9060
acccttcggt cgctgcgctc cctacgcccc gccgcttcgc gtcggcctat cgcggccgct    9120
ggccgctcaa aaatggctgg cctacggcca ggcaatctac cagggcgcgg acaagccgcg    9180
ccgtcgccac tcgaccgccg gcgctgaggt ctgcctcgtg aagaaggtgt tgctgactca    9240
taccaggcct gaatcgcccc atcatccagc cagaaagtga gggagccacg gttgatgaga    9300
gctttgttgt aggtggacca gttggtgatt ttgaactttt gctttgccac ggaacggtct    9360
gcgttgtcgg gaagatgcgt gatctgatcc ttcaactcag caaagttcg atttattcaa     9420
caaagccgcc gtcccgtcaa gtcagcgtaa tgctctgcca gtgttacaac caattaacca    9480
attctgatta gaaaaactca tcgagcatca aatgaaactg caatttattc atatcaggat    9540
tatcaatacc atatttttga aaagccgttt tctgtaatga aggagaaaac tcaccgaggc    9600
```

```
agttccatag gatggcaaga tcctggtatc ggtctgcgat tccgactcgt ccaacatcaa    9660
tacaacctat taatttcccc tcgtcaaaaa taaggttatc aagtgagaaa tcaccatgag    9720
tgacgactga atccggtgag aatggcaaaa gctctgcatt aatgaatcgg ccaacgcgcg    9780
gggagaggcg gtttgcgtat tgggcgctct tccgcttcct cgctcactga ctcgctgcgc    9840
tcggtcgttc ggctgcggcg agcggtatca gctcactcaa aggcggtaat acggttatcc    9900
acagaatcag gggataacgc aggaaagaac atgtgagcaa aaggccagca aaaggccagg    9960
aaccgtaaaa aggccgcgtt gctggcgttt tccataggc tccgccccc tgacgagcat    10020 cacaaaaatc gacgctcaag tcagaggtgg cgaaacccga caggactata agataccagg    10080
gcgtttcccc ctggaagctc cctcgtgcgc tctcctgttc cgaccctgcc gcttaccgga    10140
tacctgtccg cctttctccc ttcgggaagc gtggcgcttt ctcatagctc acgctgtagg    10200
tatctcagtt cggtgtaggt cgttcgctcc aagctgggct gtgtgcacga accccccgtt    10260
cagcccgacc gctgcgcctt atccggtaac tatcgtcttg agtccaaccc ggtaagacac    10320
gacttatcgc cactggcagc agccactggt aacaggatta gcagagcgag gtatgtaggc    10380
ggtgctacag agttcttgaa gtggtggcct aactacggct acactagaag aacagtattt    10440
ggtatctgcg ctctgctgaa gccagttacc ttcggaaaaa gagttggtag ctcttgatcc    10500
ggcaaacaaa ccaccgctgg tagcggtggt ttttttgttt gcaagcagca gattacgcgc    10560
agaaaaaaag gatctcaaga agatcctttg atcttttcta cggggtctga cgctcagtgg    10620
aacgaaaact cacgttaagg gattttggtc atgagattat caaaaaggat cttcacctag    10680
atccttttga tccggaatta attcctgtgg ttggcatgca catacaaatg gacgaacgga    10740 taaaccttt cacgcccttt taaatatccg attattctaa taaacgctct tttctcttag    10800
```

<210> SEQ ID NO 54
<211> LENGTH: 9478
<212> TYPE: DNA
<213> ORGANISM: Artificial
<220> FEATURE:
<223> OTHER INFORMATION: vector sequence comprising an expression
      cassette comprising the inverted repeat of exon 4 of BvFT2
      downstream of the pOp6 promoter fragment and combined with the PMI
      selectable marker gene under the control of the SuperMAS promoter

<400> SEQUENCE: 54

```
attcctgtgg ttggcatgca catacaaatg gacgaacgga taaaccttt cacgcccttt      60 taaatatccg attattctaa taaacgctct tttctcttag gtttaccgc caatatatcc     120 tgtcaaacac tgatagttta aactggcact agcctaacgg tgttgactaa ctaggccgct     180
tccctaatta gctaaccatg gcccgggact gaggcgcgcc gggaccgggt accgagctcg     240
agactagcta caggccaaat tcgctcttag ccgtacaata ttactcaccg gtgcgatgcc     300
ccccatcgta ggtgaaggtg gaaattaatg atccatcttg agaccacagg cccacaacag     360
ctaccagttt cctcaagggt ccaccaaaaa cgtaagcgct tacgtacatg gtcgataaga     420
aaaggcaatt tgtagatgtt aacatccaac gtcgctttca gggatcccga attccaagct     480
tggaattcgg gatcctacag gccaaattcg ctcttagccg tacaatatta ctcaccggtg     540
cgatgccccc catcgtaggt gaaggtggaa attaatgatc catcttgaga ccacaggccc     600
acaacagcta ccagtttcct caagggtcca ccaaaaacgt aagcgcttac gtacatggtc     660
gataagaaaa ggcaatttgt agatgttaac atccaacgtc gctttcaggg atcccgaatt     720
ccaagcttgg aattcgggat cctacaggcc aaattcgctc ttagccgtac aatattactc     780
accggtgcga tgcccccat cgtaggtgaa ggtggaaatt aatgatccat cttgagacca     840
```

```
caggcccaca acagctacca gtttcctcaa gggtccacca aaaacgtaag cgcttacgta      900
catggtcgat aagaaaaggc aatttgtaga tgttaacatc aacgtcgct ttcagggatc       960
ccgaattcca agcttgggct gcaggtcaat cccattgctt ttgaagcagc tcaacattga     1020
tctctttctc gagggagatt tttcaaatca gtgcgcaaga cgtgacgtaa gtatccgagt    1080
cagtttttat ttttctacta atttggtcgt ttatttcggc gtgtaggaca tggcaaccgg    1140
gcctgaattt cgcgggtatt ctgtttctat tccaactttt tcttgatccg cagccattaa    1200
cgacttttga atagatacgc tgacacgcca agcctcgcta gtcaaaagtg taccaaacaa    1260
cgctttacag caagaacgga atgcgcgtga cgctcgcggt gacgccattt cgccttttca    1320
gaaatggata aatagccttg cttcctatta tatcttccca aattaccaat acattacact    1380
agcatctgaa tttcataacc aatctcgata caccaaatcg atatcccga tcatgcaaaa     1440
actcattaac tcagtgcaaa actatgcctg gggcagcaaa acggcgttga ctgaacttta    1500
tggtatggaa aatccgtcca gccagccgat ggccgagctg tggatgggcg cacatccgaa    1560
aagcagttca cgagtgcaga atgccgccgg agatatcgtt tcactgcgtg atgtgattga    1620
gagtgataaa tcgactctgc tcggagaggc cgttgccaaa cgctttggcg aactgccttt    1680
cctgttcaaa gtattatgcg cagcacagcc actctccatt caggttcatc caaacaaaca    1740
caattctgaa atcggttttg ccaaagaaaa tgccgcaggt atcccgatgg atgccgccga    1800
gcgtaactat aaagatccta accacaagcc ggagctggtt tttgcgctga cgcctttcct    1860
tgcgatgaac gcgtttcgtg aattttccga gattgtctcc ctactccagc cggtcgcagg    1920
tgcacatccg gcgattgctc acttttttaca acagcctgat gccgaacgtt taagcgaact    1980
gttcgccagc ctgttgaata tgcagggtga agaaaaatcc cgcgcgctgg cgattttaaa    2040
atcggccctc gatagccagc agggtgaacc gtggcaaacg attcgtttaa tttctgaatt    2100
ttacccggaa gacagcggtc tgttctcccc gctattgctg aatgtggtga aattgaaccc    2160
tggcgaagcg atgttcctgt cgctgaaac accgcacgct tacctgcaag gcgtggcgct    2220
ggaagtgatg gcaaactccg ataacgtgct gcgtgcgggt ctgacgccta aatacattga    2280
tattccggaa ctggttgcca atgtgaaatt cgaagccaaa ccggctaacc agttgttgac    2340
ccagccggtg aaacaaggtg cagaactgga cttcccgatt ccagtggatg attttgcctt    2400
ctcgctgcat gaccttagtg ataaagaaac caccattagc cagcagagtg ccgccatttt    2460
gttctgcgtc gaaggcgatg caacgttgtg gaaaggttct cagcagttac agcttaaacc    2520
gggtgaatca gcgtttattg ccgccaacga atcaccggtg actgtcaaag gccacggccg    2580
tttagcgcgt gtttcaaaca agctgtaaga gcttactgaa aaaattaaca tctcttgcta    2640
agctgggagc tcgatccgtc gacgcatgcc cgctgaaatc accgtctct ctctacaaat     2700
ctatctctct ctataataat gtgtgagtag ttcccagata agggaattag ggttcttata    2760
gggtttcgct catgtgttga gcatataaga aacccttagt atgtatttgt atttgtaaaa    2820
tacttctatc aataaaattt ctaattccta aaaccaaaat ccaggggtac gatctcgatt    2880
taaataatat tcggaccgtg tacagatcta gtaacataga tgcaccgcg cgcgataatt    2940
tatcctagtt tgcgcgctat atttttgtttt ctatcgcgta ttaaatgtat aattgcggga    3000
ctctaatcat aaaaacccat ctcataaata acgtcatgca ttcatgtta attattacat    3060
gcttaacgta attcaacaga aattatatga taatcatcgc aagaccggca acaggattca    3120
atcttaagaa actttattgc caaatgtttg aacgatctgc aggtcgacgc atttaataaa    3180
atctctttca atgtagaaag aaagagaagt gtagtaaatt tacaaccttc ttccaccaga    3240
```

```
gcctccttcc ctctgacaat tgaaatagac agcagcaaca ggcaaaccaa ggttgtaaag    3300
ttcagcaaaa tctctagtgt tgaagttttg acgccaccct ggtgcataaa cagtttgtct    3360
tcccaattgt ctaaacaaca caagtatgaa tcgatgtatt ccaactgatg gtcttggatt    3420
ttcatagcag acaacttctt ggcccgcgga cctgcacatc aacaaatttt ggtcatatat    3480
tagaaaagtt ataaattaaa atatacacac ttataaacta cagaaaagca attgctatat    3540
actacattct tttattttga aaaaaatatt tgaaatatta tattactact aattaatgat    3600
aattattata tatatatcaa aggtagaagc agaaacttac ctgccaagag ttgtctgcta    3660
tgaaaatcca agaccatcag ttggaataca tcgattcata cttgtgttgt ttagacaatt    3720
gggaagacaa actgtttatg caccagggtg gcgtcaaaac ttcaacacta gagattttgc    3780
tgaactttac aaccttggtt tgcctgttgc tgctgtctat ttcaattgtc agagggaagg    3840
aggctctggt ggaagaaggt tgcaaattta ctacacttct cttctttct acattgaaag     3900 agattttatt aaatgcggat cctgtagttg tagaatgtaa aatgtaatgt tgttgttgtt    3960
tgttgttgtt gttggtaatt gttgtaaaaa tacgcgcgtc tagcttcagc gtgtcctctc    4020
caaatgaaat gaacttcctt atatagagga agggtcttgc gaagatcgat ccactagtct    4080
ttcaattgtg agcgctcaca attctttctc ttccctttct tcttcctgca ggcccgggtt    4140
agtccatggc taattagcta acggccagga tcgccgcgtg agcctttagc aactagctag    4200
attaattaac gcaatctgtt attaagttgt ctaagcgtca atttgtttac accacaatat    4260
atcctgccac cagccagcca acagctcccc gaccggcagc tcggcacaaa atcaccactc    4320
gatacaggca gcccatcaga attaattctc atgtttgaca gcttatcatc gactgcacgg    4380
tgcaccaatg cttctggcgt caggcagcca tcggaagctg tggtatggct gtgcaggtcg    4440
taaatcactg cataattcgt gtcgctcaag gcgcactccc gttctggata atgttttttg    4500
cgccgacatc ataacggttc tggcaaatat tctgaaatga gctgttgaca attaatcatc    4560
cggctcgtat aatgtgtgga attgtgagcg gataacaatt tcacacagga aacagaccat    4620
gagggaagcg ttgatcgccg aagtatcgac tcaactatca gaggtagttg gcgtcatcga    4680
gcgccatctc gaaccgacgt tgctggccgt acatttgtac ggctccgcag tggatggcgg    4740
cctgaagcca cacagtgata ttgatttgct ggttacggtg accgtaaggc ttgatgaaac    4800
aacgcggcga gctttgatca cgaccttttt ggaaacttcg gcttcccctg gagagagcga    4860
gattctccgc gctgtagaag tcaccattgt tgtgcacgac gacatcattc cgtggcgtta    4920
tccagctaag cgcgaactgc aatttggaga atggcagcgc aatgacattc ttgcaggtat    4980
cttcgagcca gccacgatcg acattgatct ggctatcttg ctgacaaaag caagagaaca    5040
tagcgttgcc ttggtaggtc cagcggcgga ggaactcttt gatccggttc ctgaacagga    5100
tctatttgag gcgctaaatg aaaccttaac gctatggaac tcgccgcccg actgggctgg    5160
cgatgagcga aatgtagtgc ttacgttgtc ccgcatttgg tacagcgcag taaccggcaa    5220
aatcgcgccg aaggatgtcg ctgccgactg ggcaatggag cgcctgccgg cccagtatca    5280
gcccgtcata cttgaagcta ggcaggctta tcttggacaa gaagatcgct tggcctcgcg    5340
cgcagatcag ttggaagaat tgttcactac gtgaaaggc gagatcacca agtagtcgg     5400 caaataaagc tctagtggat ctccgtaccc agggatctgg ctcgcggcgg acgcacgacg    5460
ccggggcgag accataggcg atctcctaaa tcaatagtag ctgtaacctc gaagcgtttc    5520
acttgtaaca acgattgaga attttgtca taaaattgaa atacttggtt cgcatttttg     5580
tcatccgcgg tcagccgcaa ttctgacgaa ctgcccattt agctggagat gattgtacat    5640
```

```
ccttcacgtg aaaatttctc aagcgctgtg aacaagggtt cagattttag attgaaaggt   5700
gagccgttga aacacgttct tcttgtcgat gacgacgtcg ctatgcggca tcttattatt   5760 gaataccttä cgatccacgc cttcaaagtg accgcggtag ccgacagcac ccagttcaca   5820
agagtactct cttccgcgac ggtcgatgtc gtggttgttg atctagattt aggtcgtgaa   5880
gatgggctcg agatcgttcg taatctggcg gcaaagtctg atattccaat cataattatc   5940
agtggcgacc gccttgagga gacggataaa gttgttgcac tcgagctagg agcaagtgat   6000
tttatcgcta agccgttcag tatcagagag tttctagcac gcattcgggt tgccttgcgc   6060
gtgcgcccca acgttgtccg ctccaaagac cgacggtctt tttgttttac tgactggaca   6120
cttaatctca ggcaacgtcg cttgatgtcc gaagctggcg gtgaggtgaa acttacggca   6180
ggtgagttca atcttctcct cgcgttttta gagaaacccc gcgacgttct atcgcgcgag   6240
caacttctca ttgccagtcg agtacgcgac gaggaggttt atgacaggag tatagatgtt   6300
ctcattttga ggctgcgccg caaacttgag gcagatccgt caagccctca actgataaaa   6360
acagcaagag gtgccggtta tttctttgac gcggacgtgc aggtttcgca cgggggacg    6420 atggcagcct gagccaattc ccagatcccc gaggaatcgg cgtgagcggt cgcaaaccat   6480
ccggcccggt acaaatcggc gcggcgctgg gtgatgacct ggtggagaag ttgaaggccg   6540
cgcaggccgc ccagcggcaa cgcatcgagg cagaagcacg ccccggtgaa tcgtggcaag   6600
cggccgctga tcgaatccgc aaagaatccc ggcaaccgcc ggcagccggt gcgccgtcga   6660
ttaggaagcc gcccaagggc gacgagcaac cagatttttt cgttccgatg ctctatgacg   6720
tgggcacccg cgatagtcgc agcatcatgg acgtggccgt tttccgtctg tcgaagcgtg   6780
accgacgagc tggcgaggtg atccgctacg agcttccaga cgggcacgta gaggtttccg   6840
cagggccggc cggcatggcc agtgtgtggg attacgacct ggtactgatg gcggtttccc   6900
atctaaccga atccatgaac cgataccggg aagggaaggg agacaagccc ggccgcgtgt   6960
tccgtccaca cgttgcggac gtactcaagt tctgccggcg agccgatggc ggaaagcaga   7020
aagacgacct ggtagaaacc tgcattcggt taaacaccac gcacgttgcc atgcagcgta   7080
cgaagaaggc caagaacggc cgcctggtga cggtatccga gggtgaagcc ttgattagcc   7140
gctacaagat cgtaaagagc gaaaccgggc ggccggagta catcgagatc gagctggctg   7200
attggatgta ccgcgagatc acagaaggca agaacccgga cgtgctgacg gttcaccccg   7260
attacttttt gatcgatccc ggcatcggcc gttttctcta ccgcctggca cgccgcgccg   7320
caggcaaggc agaagccaga tggttgttca agacgatcta cgaacgcagt ggcagcgccg   7380
gagagttcaa gaagttctgt ttcaccgtgc gcaagctgat cgggtcaaat gacctgccgg   7440
agtacgattt gaaggaggag gcggggcagg ctggcccgat cctagtcatg cgctaccgca   7500
acctgatcga gggcgaagca tccgccggtt cctaatgtac ggagcagatg ctagggcaaa   7560
ttgccctagc aggggaaaaa ggtcgaaaag gtctctttcc tgtggatagc acgtacattg   7620
ggaacccaaa gccgtacatt gggaaccgga acccgtacat tgggaaccca aagccgtaca   7680
ttgggaaccg gtcacacatg taagtgactg atataaaaga gaaaaaggc gattttccg    7740 cctaaaactc tttaaaactt attaaaactc ttaaaacccg cctggcctgt gcataactgt   7800
ctggccagca cacagccgaa gagctgcaaa aagcgcctac ccttcggtcg ctgcgctccc   7860
tacgccccgc cgcttcgcgt cggcctatcg cggccgctgg ccgctcaaaa atggctggcc   7920 tacgccagg caatctacca gggcgcggac aagccgcgcc gtcgccactc gaccgccggc   7980
gctgaggtct gcctcgtgaa gaaggtgttg ctgactcata ccaggcctga atcgccccat   8040
```

```
catccagcca gaaagtgagg gagccacggt tgatgagagc tttgttgtag gtggaccagt    8100
tggtgatttt gaacttttgc tttgccacgg aacggtctgc gttgtcggga agatgcgtga    8160
tctgatcctt caactcagca aaagttcgat ttattcaaca aagccgccgt cccgtcaagt    8220
cagcgtaatg ctctgccagt gttacaacca attaaccaat tctgattaga aaaactcatc    8280
gagcatcaaa tgaaactgca atttattcat atcaggatta tcaataccat attttgaaa     8340 aagccgtttc tgtaatgaag gagaaaactc accgaggcag ttccatagga tggcaagatc    8400
ctggtatcgg tctgcgattc cgactcgtcc aacatcaata caacctatta atttcccctc    8460
gtcaaaaata aggttatcaa gtgagaaatc accatgagtg acgactgaat ccggtgagaa    8520
tggcaaaagc tctgcattaa tgaatcggcc aacgcgcggg gagaggcggt ttgcgtattg    8580
ggcgctcttc cgcttcctcg ctcactgact cgctgcgctc ggtcgttcgg ctgcggcgag    8640
cggtatcagc tcactcaaag gcggtaatac ggttatccac agaatcaggg gataacgcag    8700
gaaagaacat gtgagcaaaa ggccagcaaa aggccaggaa ccgtaaaaag gccgcgttgc    8760
tggcgttttt ccataggctc cgcccccctg acgagcatca caaaaatcga cgctcaagtc    8820
agaggtggcg aaacccgaca ggactataaa gataccaggc gtttccccct ggaagctccc    8880
tcgtgcgctc tcctgttccg accctgccgc ttaccggata cctgtccgcc tttctccctt    8940
cgggaagcgt ggcgctttct catagctcac gctgtaggta tctcagttcg gtgtaggtcg    9000
ttcgctccaa gctgggctgt gtgcacgaac cccccgttca gcccgaccgc tgcgccttat    9060
ccggtaacta tcgtcttgag tccaacccgg taagacacga cttatcgcca ctggcagcag    9120
ccactggtaa caggattagc agagcgaggt atgtaggcgg tgctacagag ttcttgaagt    9180
ggtggcctaa ctacggctac actagaagaa cagtatttgg tatctgcgct ctgctgaagc    9240
cagttacctt cggaaaaaga gttggtagct cttgatccgg caaacaaacc accgctggta    9300
gcggtggttt ttttgtttgc aagcagcaga ttacgcgcag aaaaaaagga tctcaagaag    9360
atcctttgat cttttctacg ggtctgacg ctcagtggaa cgaaaactca cgttaaggga     9420
ttttggtcat gagattatca aaaaggatct cacctagat ccttttgatc cggaatta       9478
```

<210> SEQ ID NO 55
<211> LENGTH: 9270
<212> TYPE: DNA
<213> ORGANISM: Artificial
<220> FEATURE:
<223> OTHER INFORMATION: vector sequence comprising an expression
      cassette comprising the coding sequence of BvFT1 downstream of the
      pOp6 promoter fragment and combined with the PMI selectable marker
      gene under the control of the SuperMAS promoter

<400> SEQUENCE: 55

```
attcctgtgg ttggcatgca catacaaatg gacgaacgga taaacctttt cacgcccttt      60
taaatatccg attattctaa taaacgctct tttctcttag gttacccgc caatatatcc      120 tgtcaaacac tgatagttta aactggcact agcctaacgg tgttgactaa ctaggccgct     180
tccctaatta gctaaccatg gcccgggact gaggcgcgcc gggaccgggt accgagctcg     240
agactagcta caggccaaat tcgctcttag ccgtacaata ttactcaccg gtgcgatgcc     300
ccccatcgta ggtgaaggtg gaaattaatg atccatcttg agaccacagg cccacaacag    360
ctaccagttt cctcaagggt ccaccaaaaa cgtaagcgct tacgtacatg gtcgataaga    420
aaaggcaatt tgtagatgtt aacatccaac gtcgctttca gggatcccga attccaagct    480
tggaattcgg gatcctacag gccaaattcg ctcttagccg tacaatatta ctcaccggtg    540
```

```
cgatgccccc catcgtaggt gaaggtggaa attaatgatc catcttgaga ccacaggccc      600
acaacagcta ccagtttcct caagggtcca ccaaaaacgt aagcgcttac gtacatggtc      660
gataagaaaa ggcaatttgt agatgttaac atccaacgtc gctttcaggg atcccgaatt      720
ccaagcttgg aattcgggat cctacaggcc aaattcgctc ttagccgtac aatattactc      780
accggtgcga tgccccccat cgtaggtgaa ggtggaaatt aatgatccat cttgagacca      840
caggcccaca acagctacca gtttcctcaa gggtccacca aaaacgtaag cgcttacgta      900
catggtcgat aagaaaggc aatttgtaga tgttaacatc caacgtcgct tcagggatc       960 ccgaattcca gcttgggct gcaggtcaat cccattgctt tgaagcagc tcaacattga      1020 tctctttctc gagggagatt tttcaaatca gtgcgcaaga cgtgacgtaa gtatccgagt     1080 cagttttat ttttctacta atttggtcgt ttatttcggc gtgtaggaca tggcaaccgg     1140
gcctgaattt cgcgggtatt ctgtttctat tccaactttt tcttgatccg cagccattaa     1200
cgacttttga atagatacgc tgacacgcca agcctcgcta gtcaaaagtg taccaaacaa     1260
cgctttacag caagaacgga atgcgcgtga cgctcgcggt gacgccattt cgccttttca     1320
gaaatggata aatagccttg cttcctatta tatcttccca aattaccaat acattacact     1380
agcatctgaa tttcataacc aatctcgata caccaaatcg atccccga tcatgcaaaa      1440 actcattaac tcagtgcaaa actatgcctg gggcagcaaa acggcgttga ctgaacttta     1500
tggtatggaa aatccgtcca gccagccgat ggccgagctg tggatgggcg cacatccgaa     1560
aagcagttca cgagtgcaga atgccgccgg agatatcgtt tcactgcgtg atgtgattga     1620
gagtgataaa tcgactctgc tcggagaggc cgttgccaaa cgctttggcg aactgccttt     1680
cctgttcaaa gtattatgcg cagcacagcc actctccatt caggttcatc caaacaaaca     1740
caattctgaa atcggttttg ccaaagaaaa tgccgcaggt atcccgatgg atgccgccga     1800
gcgtaactat aaagatccta accacaagcc ggagctggtt tttgcgctga cgcctttcct     1860
tgcgatgaac gcgtttcgtg aattttccga gattgtctcc ctactccagc cggtcgcagg     1920
tgcacatccg gcgattgctc actttttaca acagcctgat gccgaacgtt taagcgaact     1980
gttcgccagc ctgttgaata tgcagggtga agaaaaatcc cgcgcgctgg cgattttaaa     2040
atcggccctc gatagccagc agggtgaacc gtggcaaacg attcgtttaa tttctgaatt     2100
ttacccggaa gacagcggtc tgttctcccc gctattgctg aatgtggtga aattgaaccc     2160
tggcgaagcg atgttcctgt cgctgaaac accgcacgct tacctgcaag gcgtggcgct     2220
ggaagtgatg gcaaactccg ataacgtgct gcgtgcgggt ctgacgccta atacattga     2280 tattccggaa ctggttgcca atgtgaaatt cgaagccaaa ccggctaacc agttgttgac     2340
ccagccggtg aaacaaggtg cagaactgga cttcccgatt ccagtggatg attttgcctt     2400
ctcgctgcat gaccttagtg ataaagaaac caccattagc cagcagagtg ccgccatttt     2460
gttctgcgtc gaaggcgatg caacgttgtg gaaaggttct cagcagttac agcttaaacc     2520
gggtgaatca gcgtttattg ccgccaacga atcaccggtg actgtcaaag gccacggccg     2580
tttagcgcgt gtttacaaca agctgtaaga gcttactgaa aaaattaaca tctcttgcta     2640
agctgggagc tcgatccgtc gacgcatgcc cgctgaaatc accagtctct ctctacaaat     2700
ctatctctct ctataataat gtgtgagtag ttcccagata agggaattag ggttcttata     2760
gggtttcgct catgtgttga gcatataaga aacccttagt atgtatttgt atttgtaaaa     2820
tacttctatc aataaaattt ctaattccta aaaccaaat ccaggggtac gatctcgatt      2880
taaataatat tcggaccgtg tacagatcta gtaacataga tgcaccgcg cgcgataatt      2940
```

```
tatcctagtt tgcgcgctat attttgtttt ctatcgcgta ttaaatgtat aattgcggga    3000
ctctaatcat aaaaacccat ctcataaata acgtcatgca ttacatgtta attattacat    3060
gcttaacgta attcaacaga aattatatga taatcatcgc aagaccggca acaggattca    3120
atcttaagaa actttattgc caaatgtttg aacgatctgc aggtcgacct aaaacctcct    3180
tccaccacag cctccctccc tttggcaatt gaaatataca gcagcaacag gcaagccaag    3240
attgtagagt tcagcaaagt ctcttgtatt aaaattttgg cgttgttgtg gagcatttac    3300
agtttgcctt cccaattgcc gaaacaatgc aaatacaaat cgatgtatcc ccgttgaggg    3360
tcgtgggttt tcatagtaaa caatctcttc tccaaatgat gcacttgtgg ttccgggaat    3420
atcagtcacc aaccagtgca agtactctct tgatgcggg ttacttgggc taggagcatc    3480
tggatctacc attaccaagg tatagcaagt cctaaggtca tcacctccga cttcgaccct    3540
aggttggtta acaacttgtg atggcctaaa atctcctcca ttattaacat ttctattgtt    3600
aaagctgatt tgagagtga cggatctttc gaatggctct aaaacatcac caataactcc    3660
acctaatact aatggatctc ttggcgcact tgctgatgtt ctaggcatgg atcctgtagt    3720
tgtagaatgt aaaatgtaat gttgttgttg tttgttgttg ttgttggtaa ttgttgtaaa    3780
aatacgcgcg tctagcttca gcgtgtcctc tccaaatgaa atgaacttcc ttatatagag    3840
gaagggtctt gcgaagatcg atccactagt ctttcaattg tgagcgctca caattctttc    3900
tcttcccttt cttcttcctg caggcccggg ttagtccatg gctaattagc taacggccag    3960
gatcgccgcg tgagccttta gcaactagct agattaatta acgcaatctg ttattaagtt    4020
gtctaagcgt caatttgttt acaccacaat atatcctgcc accagccagc caacagctcc    4080
ccgaccggca gctcggcaca aaatcaccac tcgatacagg cagcccatca gaattaattc    4140
tcatgtttga cagcttatca tcgactgcac ggtgcaccaa tgcttctggc gtcaggcagc    4200
catcggaagc tgtggtatgg ctgtgcaggt cgtaaatcac tgcataattc gtgtcgctca    4260
aggcgcactc ccgttctgga taatgttttt tgcgccgaca tcataacggt tctggcaaat    4320
attctgaaat gagctgttga caattaatca tccggctcgt ataatgtgtg gaattgtgag    4380
cggataacaa tttcacacag gaaacagacc atgagggaag cgttgatcgc cgaagtatcg    4440
actcaactat cagaggtagt tggcgtcatc gagcgccatc tcgaaccgac gttgctggcc    4500
gtacatttgt acggctccgc agtggatggc ggcctgaagc cacacagtga tattgatttg    4560
ctggttacgg tgaccgtaag gcttgatgaa acaacgcggc gagctttgat caacgacctt    4620
ttggaaactt cggcttcccc tggagagagc gagattctcc gcgctgtaga agtcaccatt    4680
gttgtgcacg acgacatcat tccgtggcgt tatccagcta agcgcgaact gcaatttgga    4740
gaatggcagc gcaatgacat tcttgcaggt atcttcgagc cagccacgat cgacattgat    4800
ctggctatct tgctgacaaa agcaagagaa catagcgttg ccttggtagg tccagcggcg    4860
gaggaactct ttgatccggt tcctgaacag gatctatttg aggcgctaaa tgaaacctta    4920
acgctatgga actcgccgcc cgactgggct ggcgatgagc gaaatgtagt gcttacgttg    4980
tcccgcattt ggtacagcgc agtaaccggc aaaatcgcgc cgaaggatgt cgctgccgac    5040
tgggcaatgg agcgcctgcc ggcccagtat cagcccgtca tacttgaagc taggcaggct    5100
tatcttggac aagaagatcg cttggcctcg cgcgcagatc agttggaaga atttgttcac    5160
tacgtgaaag gcgagatcac caaagtagtc ggcaaataaa gctctagtgg atctccgtac    5220
ccagggatct ggctcgcggc ggacgcacga cgccggggcg agaccatagg cgatctccta    5280
aatcaatagt agctgtaacc tcgaagcgtt tcacttgtaa caacgattga gaattttgt     5340
```

```
cataaaattg aaatacttgg ttcgcatttt tgtcatccgc ggtcagccgc aattctgacg    5400
aactgcccat ttagctggag atgattgtac atccttcacg tgaaaatttc tcaagcgctg    5460
tgaacaaggg ttcagatttt agattgaaag gtgagccgtt gaaacacgtt cttcttgtcg    5520
atgacgacgt cgctatgcgg catcttatta ttgaatacct tacgatccac gccttcaaag    5580
tgaccgcggt agccgacagc acccagttca aagagtact  ctcttccgcg acggtcgatg    5640
tcgtggttgt tgatctagat ttaggtcgtg aagatgggct cgagatcgtt cgtaatctgg    5700
cggcaaagtc tgatattcca atcataatta tcagtggcga ccgccttgag gagacggata    5760
aagttgttgc actcgagcta ggagcaagtg attttatcgc taagccgttc agtatcagag    5820
agtttctagc acgcattcgg gttgccttgc gcgtgcgccc caacgttgtc cgctccaaag    5880
accgacggtc ttttgtttt  actgactgga cacttaatct caggcaacgt cgcttgatgt    5940
ccgaagctgg cggtgaggtg aaacttacgg caggtgagtt caatcttctc ctcgcgtttt    6000
tagagaaacc ccgcgacgtt ctatcgcgcg agcaacttct cattgccagt cgagtacgcg    6060
acgaggaggt ttatgacagg agtatagatg ttctcatttt gaggctgcgc cgcaaacttg    6120
aggcagatcc gtcaagccct caactgataa aaacagcaag aggtgccggt tatttctttg    6180
acgcggacgt gcaggtttcg cacgggggga cgatggcagc ctgagccaat tcccagatcc    6240
ccgaggaatc ggcgtgagcg gtcgcaaacc atccggcccg gtacaaatcg gcgcggcgct    6300
gggtgatgac ctggtggaga agttgaaggc cgcgcaggcc gcccagcggc aacgcatcga    6360
ggcagaagca cgccccggtg aatcgtggca agcggccgct gatcgaatcc gcaaagaatc    6420
ccggcaaccg ccggcagccg gtgcgccgtc gattaggaag ccgcccaagg gcgacgagca    6480
accagatttt ttcgttccga tgctctatga cgtgggcacc cgcgatagtc gcagcatcat    6540
ggacgtggcc gttttccgtc tgtcgaagcg tgaccgacga gctggcgagg tgatccgcta    6600
cgagcttcca gacgggcacg tagaggtttc gcgcaggccg gccggcatgg ccagtgtgtg    6660
ggattacgac ctggtactga tggcggtttc ccatctaacc gaatccatga accgataccg    6720
ggaagggaag ggagacaagc ccggccgcgt gttccgtcca cacgttgcgg acgtactcaa    6780
gttctgccgg cgagccgatg gcggaaagca gaaagacgac ctggtagaaa cctgcattcg    6840
gttaaacacc acgcacgttg ccatgcagcg tacgaagaag gccaagaacg gccgcctggt    6900
gacggtatcc gagggtgaag ccttgattag ccgctacaag atcgtaaaga gcgaaaccgg    6960
gcggccggag tacatcgaga tcgagctggc tgattggatg taccgcgaga tcacagaagg    7020
caagaacccg gacgtgctga cggttcaccc cgattacttt ttgatcgatc ccggcatcgg    7080
ccgttttctc taccgcctgg cacgccgcgc cgcaggcaag gcagaagcca gatggttgtt    7140
caagacgatc tacgaacgca gtggcagcgc cggagagttc aagaagttct gtttcaccgt    7200
gcgcaagctg atcgggtcaa atgacctgcc ggagtacgat ttgaaggagg aggcggggca    7260
ggctggcccg atcctagtca tgcgctaccg caacctgatc gagggcgaag catccgccgg    7320
ttcctaatgt acgagcagat gctagggca  aattgcccta gcagggaaa  aaggtcgaaa    7380 aggtctcttt cctgtggata gcacgtacat tgggaaccca aagccgtaca ttggaaccg     7440 gaacccgtac attgggaacc caaagccgta cattgggaac cggtcacaca tgtaagtgac    7500
tgatataaaa gagaaaaaag gcgattttc  cgcctaaaac tctttaaaac ttattaaaac    7560
tcttaaaacc cgcctggcct gtgcataact gtctggccag cgcacagccg aagagctgca    7620
aaaagcgcct acccttcggt cgctgcgctc cctacgcccc gccgcttcgc gtcggcctat    7680
cgcggccgct ggccgctcaa aaatggctgg cctacggcca ggcaatctac cagggcgcgg    7740
```

```
acaagccgcg ccgtcgccac tcgaccgccg gcgctgaggt ctgcctcgtg aagaaggtgt   7800
tgctgactca taccaggcct gaatcgcccc atcatccagc cagaaagtga gggagccacg   7860
gttgatgaga gctttgttgt aggtggacca gttggtgatt ttgaacttttt gctttgccac   7920 ggaacggtct gcgttgtcgg gaagatgcgt gatctgatcc ttcaactcag caaaagttcg   7980
atttattcaa caaagccgcc gtcccgtcaa gtcagcgtaa tgctctgcca gtgttacaac   8040
caattaacca attctgatta gaaaaactca tcgagcatca aatgaaactg caatttattc   8100
atatcaggat tatcaatacc atattttttga aaaagccgtt tctgtaatga aggagaaaac   8160
tcaccgaggc agttccatag gatggcaaga tcctggtatc ggtctgcgat tccgactcgt   8220
ccaacatcaa tacaacctat taatttcccc tcgtcaaaaa taaggttatc aagtgagaaa   8280
tcaccatgag tgacgactga atccggtgag aatggcaaaa gctctgcatt aatgaatcgg   8340
ccaacgcgcg gggagaggcg gtttgcgtat tgggcgctct tccgcttcct cgctcactga   8400
ctcgctgcgc tcggtcgttc ggctgcggcg agcggtatca gctcactcaa aggcggtaat   8460
acggttatcc acagaatcag gggataacgc aggaaagaac atgtgagcaa aaggccagca   8520
aaaggccagg aaccgtaaaa aggccgcgtt gctggcgttt ttccataggc tccgcccccc   8580
tgacgagcat cacaaaaatc gacgctcaag tcagaggtgg cgaaacccga caggactata   8640
aagataccag gcgtttcccc ctggaagctc cctcgtgcgc tctcctgttc cgaccctgcc   8700
gcttaccgga tacctgtccg cctttctccc ttcgggaagc gtggcgcttt ctcatagctc   8760
acgctgtagg tatctcagtt cggtgtaggt cgttcgctcc aagctgggct gtgtgcacga   8820
accccccgtt cagcccgacc gctgcgcctt atccggtaac tatcgtcttg agtccaaccc   8880
ggtaagacac gacttatcgc cactggcagc agccactggt aacaggatta gcagagcgag   8940
gtatgtaggc ggtgctacag agttcttgaa gtggtggcct aactacggct acactagaag   9000
aacagtattt ggtatctgcg ctctgctgaa gccagttacc ttcggaaaaa gagttggtag   9060
ctcttgatcc ggcaaacaaa ccaccgctgg tagcggtggt ttttttgttt gcaagcagca   9120
gattacgcgc agaaaaaaag gatctcaaga agatcctttg atcttttcta cggggtctga   9180
cgctcagtgg aacgaaaact cacgttaagg gattttggtc atgagattat caaaaaggat   9240
cttcacctag atccttttga tccggaatta                                     9270
```

The invention claimed is:

1. An isolated polypeptide encoded by the isolated nucleic acid sequence as set forth in SEQ ID NO: 5 or 6.

2. An isolated polypeptide comprising the amino acid sequence of SEQ ID NO: 7.

3. A chimeric construct comprising the isolated nucleic acid sequence as set forth in SEQ ID NO: 5 or 6, wherein the isolated nucleic acid sequence is under the control of regulatory elements, wherein said regulatory elements are functional in plants.

4. The chimeric construct of claim 3, further comprising a selection marker gene which allows discrimination between transformed and non-transformed plant material in a selection process.

5. The chimeric construct of claim 3, wherein said chimeric construct is provided
   a) for transgenic downregulation or suppression of expression of the endogenous BvFT2 gene in a sugar beet plant: or
   b) for transgenic upregulation of expression of the endogenous BvFT1 gene in a sugar beet plant.

6. The chimeric construct of claim 5, wherein said nucleotide sequence encoding the BvFT1 gene has a nucleotide sequence as set forth in SEQ ID NO: 6.

7. The chimeric construct of claim 5, wherein the chimeric construct comprises a nucleotide sequence as depicted by nucleotides 2076 to 2615 of SEQ ID NO: 34.

8. The chimeric construct of claim 7, wherein the chimeric construct comprises the nucleotide sequence as depicted in SEQ ID NO: 34.

9. The chimeric construct of claim 5, wherein SEQ ID NO: 5 or 6 is operatively linked to a constitutive promoter.

10. A plant transformation vector and/or plant expression vector comprising the chimeric construct of claim 3.

11. The expression vector of claim 10, wherein said expression vector comprises the chimeric construct having the nucleic acid sequence as set forth in SEQ ID NO: 34.

12. A transgenic sugar beet plant, plant part, plant tissue, plant cell or seed in which the expression of the endogenous BvFT1 gene is modulated by expression of the chimeric construct of claim 5.

13. The transgenic sugar beet plant, plant part, plant tissue, plant cell or seed of claim 12, comprising nucleic acid sequence SEQ ID NO: 5 or 6, wherein said endogenous BvFT1 has been upregulated and said transgenic sugar beet plant, plant part, plant tissue, plant cell or seed exhibits a phenotype of non-bolting.

14. A transgenic sugar beet plant produced from cells, tissues or seeds of claim 12.

15. A root or a progeny of a transgenic sugar beet plant produced from cells, tissues or seeds of claim 12.

16. The plant parts of claim 12 wherein plant parts are selected from the group consisting of embryos, microspores, anthers, zygotes, protoplasts, ovary, ovules, pollen, taproots, cotyledons, extracts or biological samples.

17. A method comprising the step of transforming a sugar beet plant cell, wherein transforming comprises a transformation vector further comprising the chimeric construct of claim 3.

18. A method comprising the step of transforming a sugar beet plant cell, wherein transforming comprises a transformation vector further comprising the chimeric construct of claim 3.

19. A method for producing sugar wherein the sugar beet plant, plant part, plant tissue, or plant cell of claim 12 are processed to produce sugar.

20. A sugar beet plant, plant part, plant tissue, plant cell or seed comprising the chimeric construct of claim 3.

* * * * *